US008722084B2

(12) United States Patent
Akiyama et al.

(10) Patent No.: US 8,722,084 B2
(45) Date of Patent: *May 13, 2014

(54) CONTROLLED RELEASE PREPARATION

(75) Inventors: Yohko Akiyama, Osaka (JP); Takashi Kurasawa, Osaka (JP); Hiroto Bando, Osaka (JP); Naoki Nagahara, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/832,683

(22) Filed: Jul. 8, 2010

(65) Prior Publication Data
US 2010/0278911 A1 Nov. 4, 2010

Related U.S. Application Data

(63) Continuation of application No. 10/531,069, filed as application No. PCT/JP03/13155 on Oct. 15, 2003, now Pat. No. 7,790,755.

(30) Foreign Application Priority Data

Oct. 16, 2002 (JP) .................................. 2002-301876
Mar. 12, 2003 (JP) .................................. 2003-066336

(51) Int. Cl.
*A61K 9/62* (2006.01)

(52) U.S. Cl.
USPC ........................................................ 424/461

(58) Field of Classification Search
USPC ........................................................ 424/461
See application file for complete search history.

(56) References Cited

U.S. PATENT DOCUMENTS

| | | | |
|---|---|---|---|
| 4,649,043 A | 3/1987 | Urquhart et al. |
| 4,690,822 A | 9/1987 | Uemura et al. |
| 4,794,001 A | 12/1988 | Mehta et al. |
| 4,871,549 A | 10/1989 | Ueda et al. |
| 4,980,170 A | 12/1990 | Schneider et al. |
| 5,026,560 A | 6/1991 | Makino et al. |
| 5,045,321 A | 9/1991 | Makino et al. |
| 5,093,132 A | 3/1992 | Makino et al. |
| 5,229,131 A | 7/1993 | Amidon et al. |
| 5,229,134 A | 7/1993 | Mention et al. |
| 5,229,135 A | 7/1993 | Philippon et al. |
| 5,264,223 A | 11/1993 | Yamamoto et al. |
| 5,326,570 A | 7/1994 | Rudnie et al. |
| 5,470,584 A | 11/1995 | Hendrickson et al. |
| 5,567,441 A | 10/1996 | Chen |
| 5,651,983 A | 7/1997 | Kelm et al. |
| 5,656,290 A | 8/1997 | Kelm et al. |
| 5,814,338 A | 9/1998 | Veronesi |
| 5,817,338 A | 10/1998 | Bergstrand et al. |
| 5,840,737 A | 11/1998 | Phillips |
| 5,885,616 A | 3/1999 | Hsiao et al. |
| 5,914,132 A | 6/1999 | Kelm et al. |
| 5,945,123 A | 8/1999 | Hermelin et al. |
| 5,945,124 A | 8/1999 | Sachs et al. |
| 5,972,389 A | 10/1999 | Shell et al. |
| 6,077,541 A | 6/2000 | Chen et al. |
| 6,132,771 A | 10/2000 | Depui et al. |
| 6,156,340 A | 12/2000 | Adeyeye et al. |
| 6,159,499 A | 12/2000 | Seth |
| 6,162,463 A | 12/2000 | Lippa |
| 6,214,379 B1 | 4/2001 | Hermelin et al. |
| 6,228,398 B1 | 5/2001 | Devane et al. |
| 6,274,173 B1 | 8/2001 | Sachs et al. |
| 6,277,412 B1 | 8/2001 | Otterbeck et al. |
| 6,306,435 B1 | 10/2001 | Chen et al. |
| 6,328,994 B1 | 12/2001 | Shimizu et al. |
| 6,365,148 B1 | 4/2002 | Kim et al. |
| 6,372,254 B1 | 4/2002 | Ting et al. |
| 6,391,342 B1 | 5/2002 | Henriksen et al. |
| 6,419,954 B1 | 7/2002 | Chu et al. |
| 6,436,441 B1 | 8/2002 | Sako et al. |
| 6,500,457 B1 | 12/2002 | Midha et al. |
| 6,605,303 B1 | 8/2003 | Karehill et al. |
| 6,610,323 B1 | 8/2003 | Lundberg et al. |
| 6,635,276 B1 | 10/2003 | Von Falkenhausen |
| 2001/0008900 A1 | 7/2001 | Cederberg et al. |
| 2001/0020039 A1 | 9/2001 | Qiu et al. |
| 2001/0046964 A1 | 11/2001 | Percel et al. |

(Continued)

FOREIGN PATENT DOCUMENTS

| | | |
|---|---|---|
| CA | 2 320 963 | 8/1999 |
| CA | 2 403 670 | 8/2002 |

(Continued)

OTHER PUBLICATIONS

Vanderhoff et al. "Proton pump inhibitors: An update". *American Family Physician*, vol. 66, No. 2, pp. 273-270, Jul. 15, 2002.

Huang et al. "Pharmacological and pharmacodynamic essentials of $H_2$-receptor antagonists and proton pump inhibitors for the practicing physician". *Best Practice & Research Clinical Gastroenterology*, vol. 15, No. 3, pp. 355-370, 2001.

Katz et al. "Gastro-oesphageal reflux associated with nocturnal gastric acid breakthrough on proton pump inhibitors". *Aliment Pharmacol Ther*, vol. 12, pp. 1231-1234, 1998.

Tytgat. "Shortcomings on the first-generation proton pump inhibitors". *Eur J Gastroenterol Hepatol*, vol. 13, Supplement 1, S29-S33, May 2001.

Tytgat. "Medical therapy of gastroesophageal reflux disease" as published in *Gastroesophageal Reflux Disease* pp. 295-297, 2001.

Yamada et al. "Evaluation of gastrointestinal transit controlled-beagle dog as a suitable animal model for bioavailability testing of sustained-released acetaminophen dosage form". *International Journal of Pharmaceutics*, vol. 119, pp. 1-10, 1995.

(Continued)

*Primary Examiner* — Adam C Milligan
(74) *Attorney, Agent, or Firm* — Hamre, Schumann, Mueller & Larson, P.C.

(57) ABSTRACT

A controlled release preparation wherein the release of active ingredient is controlled, which releases an active ingredient for an extended period of time by staying or slowly migrating in the gastrointestinal tract, is provided by means such as capsulating a tablet, granule or fine granule wherein the release of active ingredient is controlled and a gel-forming polymer. Said tablet, granule or fine granule has a release-controlled coating-layer formed on a core particle containing an active ingredient.

11 Claims, No Drawings

(56) References Cited

U.S. PATENT DOCUMENTS

| | | |
|---|---|---|
| 2002/0034541 A1 | 3/2002 | Valducci |
| 2002/0042433 A1 | 4/2002 | Yelle et al. |
| 2002/0076435 A1 | 6/2002 | Hao et al. |
| 2002/0142034 A1 | 10/2002 | Shimizu et al. |
| 2002/0172727 A1 | 11/2002 | Valducci |
| 2002/0192282 A1 | 12/2002 | Beckert et al. |
| 2003/0152627 A1 | 8/2003 | Beckert et al. |
| 2004/0029924 A1 | 2/2004 | Sirca |
| 2008/0234352 A1 | 9/2008 | Fischer et al. |
| 2008/0292701 A1 | 11/2008 | Shimizu et al. |
| 2011/0081412 A1 | 4/2011 | Shimizu et al. |

FOREIGN PATENT DOCUMENTS

| | | | |
|---|---|---|---|
| DE | 19801811 | 7/1999 | |
| EP | 0 247 983 | 12/1987 | |
| EP | 0 546 593 | 6/1993 | |
| EP | 0 629 398 | 12/1994 | |
| EP | 0 960 620 | 12/1999 | |
| EP | 1 004 305 | 5/2000 | |
| EP | 1 064 938 | 1/2001 | |
| EP | 1 086 694 | 3/2001 | |
| ES | 2 052 697 | 7/1994 | |
| JP | 63-10719 | 1/1988 | |
| JP | 9-188617 | 7/1997 | |
| JP | 2000-119181 | 4/2000 | |
| JP | 2000-302681 | 10/2000 | |
| JP | 2000-344660 | 12/2000 | |
| JP | 2001-501642 | 2/2001 | |
| JP | 2001-502333 | 2/2001 | |
| JP | 2001-507359 | 6/2001 | |
| JP | 2001-526211 | 12/2001 | |
| JP | 2002-80398 | 3/2002 | |
| JP | 2002-114779 | 4/2002 | |
| WO | WO 95/01783 | 1/1995 | |
| WO | WO 96/01623 | 1/1996 | |
| WO | WO 96/01624 | 1/1996 | |
| WO | WO 96/36322 | 11/1996 | |
| WO | WO 97/02020 | 1/1997 | |
| WO | WO 97/02261 | 1/1997 | |
| WO | WO 97/25064 | 7/1997 | |
| WO | WO 97/25065 | 7/1997 | |
| WO | WO 97/25066 | 7/1997 | |
| WO | WO 97/32573 | 9/1997 | |
| WO | WO 98/29095 | 7/1998 | |
| WO | WO 98/50019 | 11/1998 | |
| WO | WO 99/32091 | 1/1999 | |
| WO | WO 99/29303 | 6/1999 | |
| WO | WO 99/32091 | 7/1999 | |
| WO | WO 99/32093 | * 7/1999 | A61K 9/26 |
| WO | WO 99/38513 | 8/1999 | |
| WO | WO 99/51208 | 10/1999 | |
| WO | WO 00/06132 | 2/2000 | |
| WO | WO 00/09092 | 2/2000 | |
| WO | WO 01/13890 | 3/2001 | |
| WO | WO 01/13898 | 3/2001 | |
| WO | WO 01/13898 A2 | 3/2001 | |
| WO | WO 01/24777 | 4/2001 | |
| WO | WO 01/24780 | 4/2001 | |
| WO | WO 01/37808 | 5/2001 | |
| WO | WO 01/66094 | 9/2001 | |
| WO | WO 01/80824 | 11/2001 | |
| WO | WO 01/89483 | 11/2001 | |
| WO | WO 02/17887 | 3/2002 | |
| WO | WO 02/26210 | 4/2002 | |
| WO | WO 02/32427 | 4/2002 | |
| WO | WO 02/060415 | 8/2002 | |
| WO | WO 03/061584 | 7/2003 | |
| WO | WO 03/103638 | 12/2003 | |
| WO | WO 2004/035020 | 4/2004 | |
| WO | WO 2004/045580 | 6/2004 | |
| WO | WO 2004/062577 | 7/2004 | |

OTHER PUBLICATIONS

PIL for Omeprazole (approved Sep. 14, 1989).
PIL for Pantoprazole (approved Feb. 2, 2000).
PIL for Lansoprazole (approved May 10, 1995).
Sachs et al. The pharmacology of the gastic acid pump: the H+, K+ ATPase. *Annual Review of Pharmacology and Toxicology*, vol. 35, pp. 277-305, 1995.
Uwe-Peterson. "Comparison of different proton pump inhibitors" as published in *Proton Pump Inhibitors*. pp. 144-157, 1999.
Wolfe et al. "Acid suppression: Optimizing therapy for gastroduodenal ulcer healing, gastroesophageal reflux disease, and stress-related erosive syndrome". *Journal of Gastroenterology*, vol. 118, S9-S31, 2000.
Saitoh et al. "Intrgastric acidity and circadian rhythm". *Biomed Pharmacother*, vol. 55, pp. 138-141, 2001.
Kost et al. "Responsive polymeric delivery systems" *Advanced Drug Delivery Reviews*, vol. 46, pp. 125-148, 2001.
Khan et al. "A ph-dependent colon targeted oral drug delivery system using methacrylic acid copolymers". *Journal of Controlled Release*, vol. 58, pp. 215-222, 1999.
Xue et al. "Bedtime $h_2$ blockers improve nocturnal gastric acid control in GERD patients on proton pump inhibitors". *Ailment Pharmacol Ther*, vol. 15, pp. 1351-1356, 2001.
Katz et al. "Gastric acidity and acid breakthrough with twice-daily omeprazole and lansoprazol". *Ailment Pharmacol Ther*, vol. 14, pp. 709-714, 2000.
"Application of Acrylic Resin in Pharmaceutical Formulation", *Progress in Pharmaceutical Sciences*, 1992, vol. 16, No. 1 and partial English translation.
Intellectual Property Office of New Zealand, "Examination Report of New Zealand Patent Application 552591" dated May 22, 2007.
Katz et al. "Gastro-oesphageal reflux associated with nocturnal gastric acid breakthrough on proton pump inhibitors". *Aliment Pharmacol Ther*, vol. 12, pp. 1231-1234, 1998.
Sachs et al. The pharmacology of the gastic acid pump: the H+, K+ ATPase. *Annual Review of Pharmacology and Toxicology*. vol. 35, pp. 277-305, 1995.
Bauer et al.: "Pharmazeutische Technologies"; Ed. 5, Stuttgart Jena Lubeck Ulm, Govi-Verlag Frankfurt, pp. 331-332 (1997).
Wilding et al.: "Targeting of Drugs and Vaccines to the Gut"; Pharmac. Ther. vol. 62, pp. 97-124 (1994).
Khan et al.: "A pH-dependent colon targeted oral drug delivery system using methacrylic acid copolymers"; Journal of Controlled Release vol. 58, pp. 215-222 (1999).
Fell: "Targeting of drugs and delivery systems to specific sites in the gastrointestinal tract"; J. Anat., vol. 189, pp. 517-519 (1996).
Schreier: "Drug Targeting Technology, Physocal• Chemical• Biological Methods"; vol. 115, pp. 1-49 (2001).
Tarcha: "Polymers for Controlled Drug Delivery"; CRC Press, pp. 40-66 (1991).
Vanderhoff et al.: "Proton Pump Inhibitors: An Update"; American Family Physician, vol. 66, No. 2, pp. 273-280 (Jul. 15, 2002).
Huber et al.: "Review article: the continuing development of proton pump inhibitors with particular reference to pantoprazole"; Aliment Pharmacol Ther, vol. 9, pp. 363-378 (1995).

* cited by examiner

US 8,722,084 B2

CONTROLLED RELEASE PREPARATION

This application is a continuation of U.S. Ser. No. 10/531,069 filed Apr. 11, 2005, now U.S. Pat. No. 7,790,755 which is a U.S. National Stage application of International No. PCT/JP2003/013155, filed Oct. 15, 2003, which applications are incorporated herein by reference.

TECHNICAL FIELD

The present invention relates to a controlled release preparation, in particular a capsule comprising a tablet, granule or fine granule wherein the release of active ingredient is controlled and a gel-forming polymer which delays the migration speed in the gastrointestinal tract.

BACKGROUND ART

An oral formulation is a dosage form which is used most frequently among pharmaceutical agents. Lots of preparations for oral administration wherein the drug efficacy thereof is sustained with the administration of once or twice a day have been developed from the viewpoint of improving QOL in these years. The compound having a kinetics of sustained drug efficacy with the administration of once or twice a day is tried to synthesize in the synthetic stage of compound itself, while quite a lot of attempts to modify the kinetics are made with designing controlled release preparation by contriving formulation. As the dosage form of oral controlled release preparation, various release-controlled systems such as a release control by a release-controlled coating-layer or a diffusion control of compound by a matrix, a release control of compound by erosion of matrix (base material), a pH-dependent release control of compound and a time-dependent release control wherein the compound is released after a certain lag time, are developed and applied. It is considered that a further extension of sustainability becomes possible by combining the above-mentioned release-controlled system with a control of migration speed in the gastrointestinal tract.

The preparation containing a medicament having an acid-labile property as an active ingredient such as a benzimidazole compound having a proton pump inhibitor (hereinafter sometimes referred to as PPI) action needs to be enteric-coated. That is, a composition containing a benzimidazole compound having a proton pump inhibitor action is needed to disintegrate rapidly in the small intestine, so the composition is preferred to formulate into a granule or fine granule which has a broader surface area than a tablet and is easy to disintegrate or dissolve rapidly. In the case of a tablet, it is desirable to reduce the size of tablet (for example, see JP-A 62-277322).

After administered orally, the tablet, granule or fine granule migrates through gastrointestinal tract with releasing an active ingredient to stomach, duodenum, jejunum, ileum and colon sequentially. And in the meantime, the active ingredient is absorbed at the each absorption site. A controlled release preparation is designed to control the absorption by delaying the release of active ingredient in some way. It is considered that a further extension of sustainability becomes possible by combining a release-controlled system with a function to control the migration speed in gastrointestinal tract such as adherability, floatability etc. These prior arts are disclosed in WO 01/89483, JP-A 2001-526213, U.S. Pat. No. 6,274,173, U.S. Pat. No. 6,093,734, U.S. Pat. No. 4,045,563, U.S. Pat. No. 4,686,230, U.S. Pat. No. 4,873,337, U.S. Pat. No. 4,965,269, U.S. Pat. No. 5,021,433 and the like.

DISCLOSURE OF INVENTION

Object of the Invention

An object of the present invention is to provide a controlled release preparation wherein the release of active ingredient of drug is controlled, which releases an active ingredient for an extended period of time with staying or slowly migrating in the gastrointestinal tract.

SUMMARY OF THE INVENTION

That is, the present invention provides:
(1) A capsule comprising a tablet, granule or fine granule wherein the release of active ingredient is controlled and a gel-forming polymer;
(2) The capsule according to the above-mentioned (1), wherein the release of active ingredient is controlled by a release-controlled coating-layer formed on a core particle containing an active ingredient;
(3) The capsule according to the above-mentioned (2), wherein the release-controlled coating-layer contains a pH-dependently soluble polymer;
(4) The capsule according to the above-mentioned (2), wherein the release-controlled coating-layer is a diffusion-controlled layer;
(5) The capsule according to the above-mentioned (1), wherein the release of active ingredient is controlled by dispersing an active ingredient into a release-controlled matrix composing tablet, granule or fine granule;
(6) The capsule according to the above-mentioned (3) or (4), wherein the tablet, granule or fine granule in which the release of active ingredient is controlled has a disintegrant layer containing disintegrant formed on the core particle containing an active ingredient and a release-controlled coating-layer formed on said disintegrant layer, and the release of active ingredient is initiated after a certain lag time;
(7) The capsule according to any one of the above-mentioned (3) to (6), wherein the tablet, granule or fine granule in which the release of active ingredient is controlled is coated with a gel-forming polymer;
(8) The capsule according to the above-mentioned (7) which further contains a gel-forming polymer;
(9) The capsule according to any one of the above-mentioned (1) to (7), which comprises two kinds of tablet, granule or fine granule having different release properties of active ingredient;
(10) The capsule according to the above-mentioned (9), which comprises a tablet, granule or fine granule having an enteric coat that releases an active ingredient at the pH of about 5.5 and a tablet, granule or fine granule having a release-controlled coating-layer that releases an active ingredient at the pH of about 6.0 or above;
(11) The capsule according to the above-mentioned (1), (7) or (8), wherein the gel-forming polymer is a polymer whose viscosity of 5% aqueous solution is about 3,000 mPa·s or more at 25° C.;
(12) The capsule according to the above-mentioned (1), (7) or (8), wherein the gel-forming polymer is a polymer having molecular weight of 400,000 to 10,000,000;
(13) The capsule according to any one of the above-mentioned (2) to (4) or (6), wherein the release-controlled coating-layer is a layer containing one or more kinds of polymeric substances selected from the group consisting of hydroxypropylmethyl cellulose phthalate, cellulose acetate phthalate, carboxymethylethyl cellulose, methyl methacrylate-methacrylic acid copolymer, methacrylic acid-ethyl acrylate copolymer, ethyl acrylate-methyl methacrylate-trimethylammoniumethyl methacrylate chloride copolymer, methyl methacrylate-ethyl acrylate copolymer, methacrylic acid-methyl acrylate-methyl methacrylate copolymer, hydroxypropyl cellulose acetate succinate and polyvinyl acetate phthalate;

(14) The capsule according to the above-mentioned (13), wherein the release-controlled coating-layer is comprised of 2 or more kinds of layers;

(15) The capsule according to the above-mentioned (1), wherein the release-controlled granule or fine granule has a particle size of about 100-1,500 μm;

(16) The capsule according to the above-mentioned (1), wherein the active ingredient is a proton pump inhibitor (PPI);

(17) The capsule according to (16), wherein the PPI is an imidazole compound represented by the formula (I'):

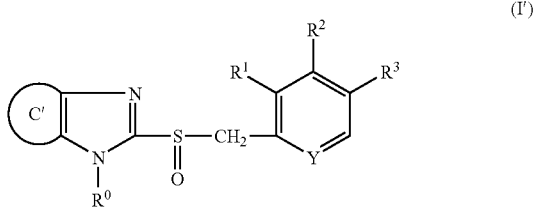

wherein ring C' is an optionally substituted benzene ring or an optionally substituted aromatic monocyclic heterocyclic ring, $R^0$ is a hydrogen atom, an optionally substituted aralkyl group, acyl group or acyloxy group, $R^1$, $R^2$ and $R^3$ are the same or different and are a hydrogen atom, an optionally substituted alkyl group, an optionally substituted alkoxy group or an optionally substituted amino group, and Y represents a nitrogen atom or CH; or a salt thereof or an optically active isomer thereof;

(18) The capsule according to the above-mentioned (17), wherein the imidazole compound is lansoprazole;

(19) The capsule according to the above-mentioned (17), wherein PPI is an optically active R-isomer of lansoprazole;

(20) The capsule according to any one of the above-mentioned (1), (7) or (8), wherein the gel-forming polymer is one or more kinds of substances selected from the group consisting of polyethylene oxide (PEO, molecular weight: 400,000-10,000,000), hydroxypropylmethyl cellulose (HPMC), carboxymethyl cellulose (CMC-Na), hydroxypropyl cellulose (HPC), hydroxyethyl cellulose and carboxyvinyl polymer;

(21) The capsule according to any one of the above-mentioned (1), (7) or (8), wherein the gel-forming polymer is polyethylene oxide (molecular weight: 400,000-10,000,000);

(22) The capsule according to the above-mentioned (1) or (8), wherein the gel-forming polymer is added as a powder, fine granule or granule;

(23) The capsule according to the above-mentioned (3), wherein the pH-dependently soluble polymer is methyl methacrylate-methacrylic acid copolymer;

(24) A tablet, granule or fine granule wherein the release of active ingredient is controlled, said tablet, granule or fine granule comprising a core particle containing an imidazole compound represented by the formula (I'):

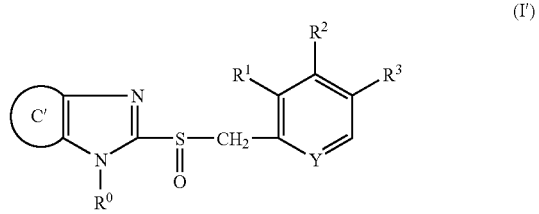

wherein ring C' is an optionally substituted benzene ring or an optionally substituted aromatic monocyclic heterocyclic ring, $R^0$ is a hydrogen atom, an optionally substituted aralkyl group, acyl group or acyloxy group, $R^1$, $R^2$ and $R^3$ are the same or different and are a hydrogen atom, an optionally substituted alkyl group, an optionally substituted alkoxy group or an optionally substituted amino group, and Y represents a nitrogen atom or CH; or a salt thereof or an optically active isomer thereof as an active ingredient, and a pH-dependently soluble release-controlled coating-layer which comprises one kind of polymeric substance or a mixture of two or more kinds of polymeric substances having different release properties selected from the group consisting of hydroxypropylmethyl cellulose phthalate, cellulose acetate phthalate, carboxymethylethyl cellulose, methyl methacrylate-methacrylic acid copolymer, methacrylic acid-ethyl acrylate copolymer, methacrylic acid-methyl acrylate-methyl methacrylate copolymer, hydroxypropyl cellulose acetate succinate, polyvinyl acetate phthalate and shellac, and said polymeric substance is soluble in the pH range of 6.0 to 7.5;

(25) The tablet, granule or fine granule according to the above-mentioned (24), wherein the pH-dependently soluble release-controlled coating-layer is formed on an intermediate layer which is formed on a core particle;

(26) The capsule comprising the tablet, granule or fine granule according to the above-mentioned (24);

(27) The capsule comprising the tablet, granule or fine granule according to the above-mentioned (24) and an enteric-coated tablet, granule or fine granule containing a compound represented by the formula (I');

(28) The tablet, granule or fine granule according to the above-mentioned (24), wherein the active ingredient is lansoprazole;

(29) The tablet, granule or fine granule according to the above-mentioned (24), wherein the active ingredient is an optically active R-isomer of lansoprazole;

(30) The tablet, granule or fine granule according to the above-mentioned (24), wherein the active ingredient is an optically active S-isomer of lansoprazole;

(31) The tablet, granule or fine granule according to the above-mentioned (24), wherein the active ingredient is a derivative of lansoprazole;

(32) The tablet, granule or fine granule according to the above-mentioned (24), wherein the active ingredient is a derivative of optically active R-isomer of lansoprazole;

(33) The tablet, granule or fine granule according to any one of the above-mentioned (24), (25) or (28) to (32), comprising having an enteric coat on the core particle containing an active ingredient, a disintegrant layer containing disintegrant on said enteric coat and a release-controlled coating-layer on said disintegrant layer;

(34) The tablet, granule or fine granule according to any one of the above-mentioned (28) to (33), which is coated with a gel-forming polymer;

(35) An extended release capsule comprising the tablet, granule or fine granule according to any one of the above-mentioned (28) to (32) and a gel-forming polymer;

(36) A tablet, granule or fine granule according to the above-mentioned (24) wherein the release of active ingredient is controlled by two or more kinds of release-controlled coating-layers, and the outermost release-controlled coating-layer is soluble at higher pH than the inner release-controlled coating-layer;

(37) The tablet, granule or fine granule according to the above-mentioned (36), wherein the inner release-controlled coating-layer is soluble in the pH range of 6.0-7.0 and the outermost release-controlled coating-layer is soluble at the pH of 7.0 or above;

(38) The tablet, granule or fine granule according to the above-mentioned (36), wherein the inner release-controlled coating-layer is soluble in the pH range of 6.5-7.0 and the outermost release-controlled coating-layer is soluble at the pH of 7.0 or above;

(39) The tablet, granule or fine granule according to the above-mentioned (36), wherein the thickness of the outermost release-controlled coating-layer is 100 μm or less;

(40) The granule or fine granule according to the above-mentioned (36), wherein the release-controlled granule or fine granule has a particle size of about 100-1,500 μm;

(41) A capsule comprising
(i) a tablet, granule or fine granule in which the release of active ingredient is controlled; said tablet, granule or fine granule comprises
a core particle containing an imidazole compound represented by the formula (I'):

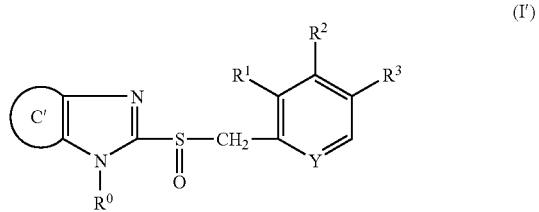

wherein ring C' is an optionally substituted benzene ring or an optionally substituted aromatic monocyclic heterocyclic ring, $R^0$ is a hydrogen atom, an optionally substituted aralkyl group, acyl group or acyloxy group, $R^1$, $R^2$ and $R^3$ are the same or different and are a hydrogen atom, an optionally substituted alkyl group, an optionally substituted alkoxy group or an optionally substituted amino group, and Y represents a nitrogen atom or CH; or a salt thereof or an optically active isomer thereof as an active ingredient, and
a pH-dependently soluble release-controlled coating-layer which comprises one kind of polymeric substance or a mixture of two or more kinds of polymeric substances having different release properties selected from the group consisting of hydroxypropylmethyl cellulose phthalate, cellulose acetate phthalate, carboxymethylethyl cellulose, methyl methacrylate-methacrylic acid copolymer, methacrylic acid-ethyl acrylate copolymer, methacrylic acid-methyl acrylate-methyl methacrylate copolymer, hydroxypropyl cellulose acetate succinate, polyvinyl acetate phthalate and shellac; said polymeric substance is soluble in the pH range of 6.0 to 7.5, and
(ii) a tablet, granule or fine granule comprising a core particle containing an active ingredient and enteric coat which is dissolved, thereby an active ingredient being released in the pH range of no less than 5.0, nor more than 6.0;

(42) The capsule according to the above-mentioned (41), wherein the pH-dependently soluble release-controlled coating-layer is formed on an intermediate layer which is formed on the core particle containing an active ingredient;

(43) The capsule according to the above-mentioned (41), wherein the active ingredient is lansoprazole;

(44) The capsule according to the above-mentioned (41), wherein the active ingredient is an optically active R-isomer of lansoprazole;

(45) The capsule according to the above-mentioned (41), wherein the active ingredient is an optically active S-isomer of lansoprazole;

(46) The capsule according to the above-mentioned (41), wherein the core particle containing an active ingredient contains a stabilizer of basic inorganic salt;

(47) The capsule according to the above-mentioned (41), wherein the pH-dependently soluble release-controlled coating-layer of the tablet, granule or fine granule in which the release of an active ingredient is controlled is a layer soluble in the pH range of no less than 6.5, nor more than 7.0;

(48) The capsule according to the above-mentioned (47), wherein the pH-dependently soluble release-controlled coating-layer contains a mixture of two or more kinds of methyl methacrylate-methacrylic acid copolymers having different release properties; and

(49) The capsule according to the above-mentioned (41), which further contains a gel-forming polymer.

DETAILED DESCRIPTION OF THE INVENTION

The present invention relates to a pharmaceutical composition containing a tablet, granule or fine granule wherein the release of active ingredients is controlled, or a pharmaceutical composition containing these tablet, granule or fine granule and a gel-forming polymer which delays digestive tract migration speed. The pharmaceutical composition of the present invention may be these tablet, granule or fine granule itself, or a form of a mixture of a tablet, granule or fine granule and a gel-forming polymer, or a capsule filled in capsule, but a capsule is preferred in particular. It has been cleared that the persistence of blood levels after oral administration is remarkably prolonged by these combinations.

The release control of active ingredient in "a tablet, granule or fine granule wherein the release of active ingredient is controlled" of the present invention is performed by coating the active ingredient in a tablet, granule or fine granule with a layer controlling the release of active ingredient, or by dispersing the active ingredient in release-controlled matrices. Further, the "tablet, granule or fine granule wherein the release of active ingredient is controlled" of the present invention include also a tablet, granule or fine granule which is coated with a usual enteric coat which is dissolved at a pH of about 5.5, and tablets containing these granules or fine granules.

On the other hand, when the "release-controlled coating-layer" is mentioned in the present specification, it indicates a coating-layer having a function of further delaying or extending the release of active ingredient, such as a pH-dependently soluble layer which is dissolved at a higher pH region than a usual enteric coating which is dissolved at a pH of about 5.5, and a diffusion-controlled layer whose layer itself is not dissolved and which releases an active ingredient through pores which are formed in the layer. It does not include a usual enteric coat and layer which is dissolved at a pH of about 5.5, rapidly dissolved in the intestinal juice and release an active ingredient. Further, the pH mentioned here means a pH of the Mcilvaine solution or Clark-Lubs solution. Hereinafter, the pH of a pH-dependently soluble layer means the pH of these solutions.

The coating-layer of the "release-controlled coating-layer" includes coating layers in a film form and those having larger thickness. Also, the coating-layer includes not only a coating-layer which entirely coats the inner core or layer but also the coating layers in which a part of the inner core or layer is not covered but most of the inner core or layer is coated (coating-layer which covers at least about 80% or more of the surface of the inner core or layer, and preferably covers the surface entirely).

The absorption from the digestive tract of the active ingredient from the pharmaceutical composition of the present invention is controlled by two kind of systems utilizing (1) a release control of active ingredient by a controlled release tablet, granule or fine granule and (2) retentive prolongation in the digestive tract of a tablet, granule or fine granule by a gel-forming polymer, or their combinations. Among the pharmaceutical composition of the present invention, the composition containing a gel-forming polymer forms adhesive gels by rapidly absorbing water by the gel-forming polymer in the digestive tract when orally administrated, and the tablet, granule or fine granule is retained on the surface of gels or in the gels to be gradually migrated through the digestive tract. The release of active ingredient is controlled in the meanwhile, the active ingredient is released continuously or in a pulsatile manner from the tablet, granule or fine granule by a controlled system, and as a result, the incidences of prolonged absorption and drug efficacy are attained.

The above-mentioned system enabling the persistence of therapeutic effective levels by controlling the release over a long time has advantages of therapeutic effectiveness at a low dose and reduction of side effects caused by initial rise of blood level and the like, as well as the reduction of administration times.

The gel-forming polymer may be a polymer which rapidly forms highly viscous gels by contacting with water and prolongs the retention time in the digestive tract. Such gel-forming polymer is preferably a polymer having a viscosity of about 3000 mPa·s or more for 5% aqueous solution at 25° C. Further, the gel-forming polymer is preferably a polymer usually having a molecular weight of about 400000 to 10000000 in general. As the gel-forming polymer, powder, granular or fine granular polymer is preferable for producing formulations. The gel-forming polymer includes a polyethylene oxide (PEO, for example, Polyox WSR 303 (molecular weight: 7000000), Polyox WSR Coagulant (molecular weight: 5000000), Polyox WSR 301 (molecular weight: 4000000), Polyox WSR N-60K (molecular weight: 2000000), and Polyox WSR 205 (molecular weight: 600000); manufactured by Dow Chemical Co., Ltd.), hydroxypropyl methylcellulose (HPMC, Metlose 90SH10000, Metlose 90SH50000, and Metlose 90SH30000; manufactured by Shin-Etsu Chemical Co., Ltd.), carboxymethylcellulose (CMC-Na, Sanlose F-1000MC), hydroxypropyl cellulose (HPC, for example, HPC-H, manufactured by Nippon Soda Co., Ltd.), hydroxyethyl cellulose (HEC), carboxyvinyl polymer (HIVISWAKO (R) 103, 104 and 105 manufactured by Wako Pure Chemical Industries Ltd.; CARBOPOL 943 manufactured by Goodrich Co., Ltd.), chitosan, sodium alginate, pectin and the like. These may be used alone or as a mixture of at least 2 or more of powders by mixing at an appropriate proportion. In particular, PEO, HPMC, HPC, CMC-Na, carboxyvinyl polymer and the like are preferably used as a gel-forming polymer.

One preferable form of a tablet, granule or fine granule wherein the release of active ingredient is controlled includes a tablet, granule or fine granule wherein a core particle containing at least one active ingredient is coated with a release-controlled coating-layer and a tablet containing these granules or fine granules. In order to prepare such core-possessing tablet, granule or fine granule, as a core particle can be used the tablet, granule or fine granule wherein an active ingredient is coated on a core which is an inactive carrier such as NONPAREIL (NONPAREIL-101 (particle diameter: 850-710, 710-500, and 500-355), NONPAREIL-103 (particle diameter: 850-710, 710-500, and 500-355), NONPAREIL-105 (particle diameter: 710-500, 500-355 and 300-180); manufactured by Freund Industrial Co., Ltd.) and Celphere (CP-507 (particle diameter: 500-710), and CP-305 (particle diameter: 300-500); manufactured by Asahi Kasei Corporation); or the tablet prepared by using these granules or fine granules; or the particle obtained by granulation using an active ingredient and an excipient usually used for formulation. For example, they can be produced by the method disclosed in JP-A 63-301816. For example, when a core particle is prepared by coating an active ingredient on a core of an inactive carrier, core particles containing an active ingredient can be produced by wet granulation, using, for example, a centrifugal fluid-bed granulator (CF-mini, CF-360, manufactured by Freund Industrial Co., Ltd.) or a centrifugal fluidized coating granulator (POWREX MP-10), or the like. Further, coating may be carried out by dusting an active ingredient while adding a solution containing a binder and the like on the core of an inactive carrier with spray and the like. The production apparatuses are not limited and for example, it is preferable in the latter coating to produce them using a centrifugal fluid-bed granulator and the like. An active ingredient may be coated at two steps by carrying out the coating using the above-mentioned two apparatuses in combination. When an inactive carrier core is not used, a core particle can be produced by granulating excipient such as lactose, white sugar, mannitol, corn starch and crystalline cellulose and an active ingredient, using binders such as hydroxypropyl methylcellulose, hydroxypropyl cellulose, methyl cellulose, a polyvinyl alcohol, Macrogol, Pullronic F68, gum arabic, gelatin and starch, if necessary, adding disintegrants such as sodium carboxymethyl cellulose, calcium carboxymethyl cellulose, sodium cross carboxymethyl cellulose (Ac-Di-Sol, manufactured by FMC International Co., Ltd.), polyvinyl pyrrolidone and low substituted hydroxypropyl cellulose, with a stirring granulator, a wet extruding granulator, a fluidized bed granulator and the like.

Particles having desired sizes can be obtained by sieving the granules or fine granules obtained. The core particle may be prepared by dry granulation with a roller compactor and the like. Particles having a particle size of 50 μm to 5 mm, preferably 100 μm to 3 mm and more preferably 100 μm to 2 mm are used.

The active ingredient-containing core particle thus obtained may be further coated to provide an intermediate coating layer, and the particle may be used as a core particle. It is preferable from the viewpoint of improving the stability of drugs that the intermediate coating layer is provided to intercept the direct contact of active ingredient-containing core particle with the release-controlled coating-layer when the active ingredient is an unstable drug against an acid, such as PPI and the like, etc. The intermediate coating layer may be formed by a plural number of layers.

The coating materials for the intermediate coating layer include those obtained by appropriately compounding polymeric materials such as low substituted hydroxypropyl cellulose, hydroxypropyl cellulose, hydroxypropyl methylcellulose (for example, TC-5 and the like), polyvinylpyrrolidone, polyvinyl alcohol, methylcellulose and hydroxyethyl methylcellulose with saccharides such as sucrose [purified sucrose (pulverized (powdered sugar), not pulverized) and the like], starch saccharide such as corn starch, lactose, sugar alcohol (D-mannitol, erythritol and the like). Excipients (for example, masking agents (titanium oxide and the like) and antistatic agents (titanium oxide, talc and the like) may be suitably added to the intermediate coating layer for the preparations mentioned below, if necessary.

The coating amount of the intermediate coating layer is usually about 0.02 part by weight to about 1.5 parts by weight based on 1 part by weight of granules containing an active ingredient, and preferably about 0.05 part by weight to about 1 part by weight. The coating can be carried out by conventional methods. For example, preferably, the components of the intermediate coating layer are diluted with purified water and sprayed to coat in liquid form. Then, it is preferable to carry out the coating while spraying a binder such as hydroxypropyl cellulose.

As the controlled release tablet, granule or fine granule contained in the pharmaceutical composition of the present invention, it is preferable to coat the above-mentioned core particle with a coating material which is pH-dependently dissolved/eluted to control the release, and to prepare the tablet, granule or fine granule having a release-controlled coating-layer, or the tablet containing these controlled release granules or fine granules. Herein, the "pH-dependently" means that the coating material is dissolved/eluted under the circumstances of more than a certain pH value to release an active ingredient. A usual enteric coat is eluted at a pH of about 5.5 to initiate the release of drug, while the coating material of the present invention is preferably a substance which is dissolved at a higher pH (preferably a pH of 6.0 or above and 7.5 or below, and more preferably a pH of 6.5 or above and below 7.2) and controls more favorably the release of drug in the stomach.

As a coating material for controlling pH-dependently the release of medical active ingredient, polymers such as hydroxypropyl methylcellulose phthalate (HP-55, HP-50 manufactured by Shin-Etsu Chemical Co., Ltd.), cellulose acetate phthalate, carboxymethyl ethylcellulose (CMEC manufactured by Freund Industrial Co., Ltd.), methyl methacrylate-methacrylic acid copolymer (Eudragit L100 (methacrylic acid copolymer L) or Eudragit S100 (methacrylic acid copolymer S); manufactured by Rohm Co.), methacrylic acid-ethyl acrylate copolymer (Eudragit L100-55 (dried methacrylic acid copolymer LD) or Eudragit L30D-55 (methacrylic acid copolymer LD); manufactured by Rohm Co.), methacrylic acid-methyl acrylate-methyl methacrylate copolymer (Eudragit FS30D manufactured by Rohm Co.), hydroxypropyl cellulose acetate succinate (HPMCAS manufactured by Shin-Etsu Chemical Co., Ltd.), polyvinyl acetate phthalate and shellac are used. The tablet, granule or fine granule may be those having two or more kinds of release-controlled coating-layers which have different release properties of active ingredient. The polymer as the above-mentioned coating material may be used alone or at least 2 or more kinds of the polymers may be used to coat in combination, or at least 2 or more kinds of the polymers may be coated sequentially to prepare multi-layers. It is desirable that the coating material is used alone or, if necessary, in combination so that the polymer is dissolved preferably at a pH of 6.0 or above, more preferably at a pH of 6.5 or above, and further more preferably at a pH of 6.75 or above. Further, more desirably, a polymer soluble at a pH of 6.0 or above and a polymer soluble at a pH of 7.0 or above are used in combination, and furthermore desirably, a polymer soluble at a pH of 6.0 or above and a polymer soluble at a pH of 7.0 or above are used in combination at a ratio of 1:0.5 to 1:5.

Further, plasticizers such as a polyethylene glycol, dibutyl sebacate, diethyl phthalate, triacetin and triethyl citrate, stabilizers and the like may be used for coating, if necessary. The amount of coating material is 5% to 200% based on the core particle, preferably 20% to 100% and more preferably 30% to 60%. The rate of elution of active ingredient from the active ingredient release-controlled tablet, granule or fine granule thus obtained is desirably 10% or less for 5 hours in a solution of pH 6.0, and 5% or less for one hour and 60% or more for 8 hours in a solution of pH 6.8.

The controlled release tablet, granule or fine granule (hereinafter, sometimes referred to simply as a controlled release granule) may be a tablet, granule or fine granule wherein a material which becomes viscous by contact with water, such as polyethylene oxide (PEO, for example, Polyox WSR 303 (molecular weight: 7000000), Polyox WSR Coagulant (molecular weight: 5000000), Polyox WSR 301 (molecular weight: 4000000), Polyox WSR N-60K (molecular weight: 2000000), and Polyox WSR 205 (molecular weight: 600000); manufactured by Dow Chemical Co., Ltd.), hydroxypropyl methylcellulose (HPMC, Metlose 90SH10000, Metlose 90SH50000, Metlose 90SH30000; manufactured by Shin-Etsu Chemical Co., Ltd.), carboxymethyl cellulose (CMC-Na, Sanlose F-1000MC), hydroxypropyl cellulose (HPC, for example, HPC-H manufactured by Nippon Soda Co., Ltd.), hydroxyethyl cellulose (HEC), carboxyvinyl polymer (HI-VISWAKO (R) 103, 104, 105: manufactured by Wako Pure Chemical Industries Ltd.; CARBOPOL 943 manufactured by Goodrich Co., Ltd.), chitosan, sodium alginate and pectin, is coated on the active ingredient release-controlled tablet, granule or fine granule thus obtained.

The controlled release granule may be a form in which the core particle containing an active ingredient is coated with a diffusion-controlled layer having an action of controlling the release of active ingredient by diffusion. The materials for these diffusion-controlled layer include ethyl acrylate-methyl methacrylate-trimethylammoniumethyl methacrylate chloride copolymer (Eudragit RS (aminoalkyl methacrylate copolymer RS) or Eudragit RL (aminoalkyl methacrylate copolymer RL); manufactured by Rohm Co.), methyl methacrylate-ethyl acrylate copolymer (Eudragit NE30D manufactured by Rohm Co.), ethyl cellulose and the like. Further, these materials for layer may be mixed at an appropriate ratio, and can be used by mixing with hydrophilic pore forming substances such as HPMC, HPC, carboxyvinyl polymer, polyethylene glycol 6000, lactose, mannitol and organic acid at a fixed ratio.

Further, in order to prepare the tablet, granule or fine granule wherein the release of active ingredient is controlled to initiate after a fixed lag time, a disintegrant layer is provided between the core particle containing an active ingredient and the release-controlled coating-layer by coating a swelling substance such as a disintegrant previously before coating the above-mentioned diffusion-controlled layer. For example, preferably, a swelling substance such as cross carmelose sodium (Ac-Di-Sol, manufactured by FMC International Co.), carmelose calcium (ECG 505, manufactured by Gotoku Chemicals Co.), CROSSPOVIDON (ISP Inc.) and low substituted hydroxypropyl cellulose (L-HPC manufactured by Shin-Etsu Chemical Co., Ltd.) is primarily coated on a core particle, and then the resulting coated particle is secondarily coated with a diffusion-controlled layer which is prepared by mixing at a fixed ratio one or more kinds of polymers selected from ethyl acrylate-methyl methacrylate-trimethylammoniummethyl methacrylate chloride copolymer (Eudragit RS or Eudragit RL; manufactured by Rohm Co.), methyl methacrylate-ethyl acrylate copolymer (Eudragit NE30D manufactured by Rohm Co.), ethyl cellulose and the like; with hydrophilic pore forming substances such as HPMC, HPC, carboxyvinyl polymer, polyethylene glycol 6000, lactose, mannitol and an organic acid. The secondary coating material may be enteric polymers which release pH-dependently an active ingredient, such as hydroxypropyl methylcellulose phthalate (HP-55, HP-50; manufactured by Shin-Etsu Chemical Co., Ltd.), cellulose acetate phthalate, carboxymethyl ethylcellulose (CMEC; manufactured by Freund Industrial Co., Ltd.), methyl methacrylate-methacrylic acid copolymer (Eudragit L100 (methacrylic acid copolymer L) or Eudragit 5100 (methacrylic acid copolymer S); manufactured by Rohm Co.), methacrylic acid-ethyl acrylate copolymer (Eudragit L100-55 (dried methacrylic acid copolymer LD) or Eudragit L30D-55 (methacrylic acid copolymer LD); manufactured by Rohm Co.), methacrylic acid-methyl acrylate-methyl methacrylate copolymer (Eudragit FS30D; manufactured by Rohm Co.), hydroxypropyl cellulose acetate succinate (HPMCAS; manufactured by Shin-Etsu Chemical Co., Ltd.), polyvinyl acetate and shellac. The amount of coating material is 1% to 200% based on the core particle, preferably 20% to 100% and more preferably 30% to 60%.

Plasticizers such as polyethylene glycol, dibutyl sebacate, diethyl phthalate, triacetin and triethyl citrate, stabilizers and the like may be used for coating, if necessary. The controlled release tablet, granule or fine granule may be a tablet, granule or fine granule wherein a material which becomes viscous by contact with water, such as polyethylene oxide (PEO, for example, Polyox WSR 303 (molecular weight: 7000000), Polyox WSR Coagulant (molecular weight: 5000000), Polyox WSR 301 (molecular weight: 4000000), Polyox WSR N-60K (molecular weight: 2000000), and Polyox WSR 205 (molecular weight: 600000); manufactured by Dow Chemical Co., Ltd.), hydroxypropyl methylcellulose (HPMC, Metlose 90SH10000, Metlose 90SH50000, Metlose 90SH30000; manufactured by Shin-Etsu Chemical Co., Ltd.), carboxymethyl cellulose (CMC-Na, Sanlose F-1000MC), hydroxypropyl cellulose (HPC, for example, HPC-H manufactured by Nippon Soda Co., Ltd.), hydroxyethyl cellulose (HEC), carboxyvinyl polymer (HIVISWAKO (R) 103, 104, 105: manufactured by Wako Pure Chemical Industries Ltd.; CARBOPOL 943 manufactured by Goodrich Co., Ltd.), chitosan, sodium alginate and pectin, is coated on the active ingredient release-controlled tablet, granule or fine granule thus obtained.

In the tablet, granule or fine granule having 2 or more kinds of release-controlled coating-layers having different release properties of active ingredient, a layer containing an active ingredient may be set up between said release-controlled coating-layers. A form of these multi-layer structure containing an active ingredient between release-controlled coating-layers includes a tablet, granule or fine granule which is prepared by coating an active ingredient on the tablet, granule or fine granule wherein the release of active ingredient is controlled by the release-controlled coating-layer of the present invention, followed by further coating with the release-controlled coating-layer of the present invention.

Another form of the tablet, granule or fine granule wherein the release of at least one of the active ingredients is controlled may be a tablet, granule or fine granule in which the active ingredients are dispersed in a release-controlled matrix. These controlled release tablet, granule or fine granule can be produced by homogeneously dispersing the active ingredients into hydrophobic carriers such as waxes such as hardened castor oil, hardened rape seed oil, stearic acid and stearyl alcohol, and polyglycerin fatty acid ester. The matrix is a composition in which the active ingredients are homogeneously dispersed in a carrier. If necessary, excipients such as lactose, mannitol, corn starch and crystalline cellulose which are usually used for preparation of a drug may be dispersed with the active ingredients. Further, powders of polyoxyethylene oxide, cross-linked acrylic acid polymer (HI-VISWAKO (R) 103, 104 and 105, CARBOPOL), HPMC, HPC, chitosan and the like which form viscous gels by contact with water may be dispersed into the matrix together with the active ingredients and excipients.

As the preparation method, they can be prepared by methods such as spray dry, spray chilling and melt granulation.

The controlled release tablet, granule or fine granule may be a tablet, granule or fine granule wherein a material which becomes viscous by contact with water, such as polyethylene oxide (PEO, for example, Polyox WSR 303 (molecular weight: 7000000), Polyox WSR Coagulant (molecular weight: 5000000), Polyox WSR 301 (molecular weight: 4000000), Polyox WSR N-60K (molecular weight: 2000000), and Polyox WSR 205 (molecular weight: 600000); manufactured by Dow Chemical Co., Ltd.), hydroxypropyl methylcellulose (HPMC, Metlose 90SH10000, Metlose 90SH50000, Metlose 90SH30000; manufactured by Shin-Etsu Chemical Co., Ltd.), carboxymethyl cellulose (CMC-Na, Sanlose F-1000MC), hydroxypropyl cellulose (HPC, for example, HPC-H manufactured by Nippon Soda Co., Ltd.), hydroxyethyl cellulose (HEC), carboxyvinyl polymer (HI-VISWAKO (R) 103, 104, 105: manufactured by Wako Pure Chemical Industries Ltd.; CARBOPOL 943 manufactured by Goodrich Co., Ltd.), chitosan, sodium alginate and pectin, is coated on the active ingredient release-controlled tablet, granule or fine granule thus obtained. These materials which become viscous by contact with water may be coexisted in one preparation such as a capsule and the like as well as using for coat.

The tablet, granule or fine granule of the present invention wherein the release of active ingredient is controlled may be a form having the above-mentioned various kinds of release-controlled coating-layers, release-controlled matrixes and the like in combination.

As the size of tablet, granule or fine granule wherein the release of active ingredient is controlled, particles having a particle size of 50 μm to 5 mm, preferably 100 μm to 3 mm and more preferably 100 μm to 2 mm are used. Granules or fine granules having a particle size of about 100 μm to 1500 μm are most preferred.

Further, additives such as excipients for providing preparations (for example, glucose, fructose, lactose, sucrose, D-mannitol, erythritol, multitol, trehalose, sorbitol, corn starch, potato starch, wheat starch, rice starch, crystalline cellulose, silicic acid anhydride, calcium metaphosphorate, sedimented calcium carbonate, calcium silicate, and the like), binders (for example, hydroxypropyl cellulose, hydroxypropyl methylcellulose, polyvinyl pyrrolidone, methyl cellulose, polyvinyl alcohol, carboxymethyl cellulose sodium, partial a starch, a starch, sodium alginate, pullulan, gum arabic powder, gelatin and the like), disintegrants (for example, low substituted hydroxypropyl cellulose, carmelose, carmelose calcium, carboxymethylstarch sodium, cross carmelose sodium, crosspovidon, hydroxypropylstarch and the like), flavoring agents (for example, citric acid, ascorbic acid, tartaric acid, malic acid, aspartame, acesulfam potassium, thaumatin, saccharin sodium, glycyirrhizin dipotassium, sodium glutamate, sodium 5'-inosinate, sodium 5'-guanylate and the like), surfactants (for example, polysolvate (polysolvate 80 and the like), polyoxyethylene-polyoxypropylene copolymer, sodium laurylsulfate and the like), perfumes (for example, lemon oil, orange oil, menthol, peppermint oil and the like), lubricants (for example, magnesium stearate, sucrose fatty acid eater, sodium stearylfumarate, stearic acid, talc, polyethylene glycol and the like), colorants (for example, titanium oxide, edible Yellow No. 5, edible Blue No. 2, iron (III) oxide, yellow iron (III) oxide, and the like), antioxidants (for example, sodium ascorbate, L-cysteine, sodium bisulfate, and the like), masking agents (for example, titanium oxide and the like), and antistatic agents (for example, talc, titanium oxide and the like) can be used.

The particle diameter of raw materials used here are not particularly limited, and particles having a diameter of about 500 μm or less are preferred from the viewpoint of productivity and dosing.

The tablet, granule or fine granule thus obtained may be administrated as it is by mixing with a digestive tract retentive gel-forming polymer, or can be formulated as a capsule by filling in capsules. The amount of the gel-forming polymer being retentive in the digestive tract is 0.1% to 100% relative to the controlled release tablet, granule or fine granule, preferably 2% to 50%, more preferably 10% to 40%, and further more preferably 10% to 35%.

The pharmaceutical composition of the present invention thus obtained is a composition having a extended activity of drug by a release-controlled system wherein therapeutic effect is revealed for at least 6 hours, preferably 8 hours, more preferably 12 hours and further preferably 16 hours.

The active ingredients are not particularly limited, and can be applied irrespective of the region of drug efficacy. Exemplified are anti-inflammatory drugs such as indomethacin and acetaminophen, analgesics such as morphine, cardiovascular agonists such as diazepam and diltiazepam, anti-histamines such as chlorophenylamine maleate, antitumors such as fluorouracil and aclarubicin, narcotics such as midazolam, antihemostasis agents such as ephedrine, diuretics such as hydrochlorothiazide and furosemide, bronchodilators such as theophyline, antitussives such as codeine, antiarrythmic agents such as quinidine and dizoxin, antidiabetics such as tolbutamide, pioglitazone and troglitazone, vitamins such as ascorbic acid, anticonvulsants such as phenitoin, local anesthetics such as lidocaine, adrenocortical hormones such as hydrocortisone, drugs effective for central nerve such as eisai, hypolipidemic drugs such as pravastatin, antibiotics such as amoxicillin and cephalexin, digestive tract exitomotory agents such as mosapride and cisapride, H2 blockers such as famotidine, ranitidine and cimetidine which are the remedies of gastritis, symptomatic gastroesophageal reflux disease, and gastric and duodenal ulcers, and benzimidazole proton pump inhibitors (PPI) represented by lansoprazole and optically active isomers thereof (R-isomer and S-isomer, preferably R-isomer (hereinafter, occasionally referred to as Compound A)), omeprazole and optically active isomers thereof (S-isomer: S omeprazole), rabeprazole and optically active isomers thereof, pantoprazole and optically active isomers thereof and the like, and imidazopyridine PPI represented by tenatoprazole and the like.

According to the present invention, the preparations which contain, as an active ingredient, a PPI such as acid-labile imidazole compounds represented by the following general formula (I') such as lansoprazole and optically active isomers thereof, in particular, acid-labile benzimidazole compounds represented by the following formula (I), and relatively acid-stable imidazole compound derivatives (prodrug type PPI) represented by the following general formula (II) or (III) or salts thereof or optically active isomers thereof have an excellent sustainability of drug efficacy. As a result, dosing compliance is also improved and therapeutic effect is increased.

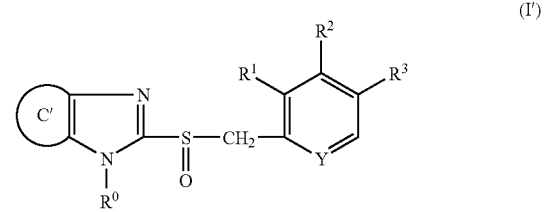

Wherein ring C' indicates a benzene ring optionally having a substituent group or an aromatic monocyclic heterocyclic ring optionally having a substituent group; $R^0$ indicates a hydrogen atom, an aralkyl group optionally having substituent group, an acyl group or an acyloxy group; $R^1$, $R^2$ and $R^3$ are the same or different and indicate a hydrogen atom, an alkyl group optionally having a substituent group, an alkoxy group optionally having a substituent group or an amino group optionally having a substituent group, respectively; and Y indicates a nitrogen atom or CH.

Among the compounds represented by the above-mentioned formula (I'), the compound in which the ring C' is a benzene ring optionally having a substituent group is particularly represented by the following formula (I).

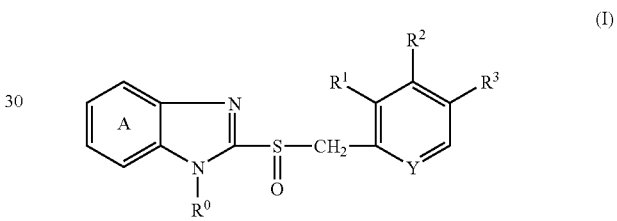

Namely, in the formula (I), ring A indicates a benzene ring optionally having a substituent group, and $R^0$, $R^1$, $R^2$, $R^3$ and Y have the same meaning as in the above-mentioned formula (I').

In the above-mentioned formula (I), the preferable compound is a compound wherein ring A is a benzene ring which may have a substituent group selected from a halogen atom, an optionally halogenated $C_{1-4}$ alkyl group, an optionally halogenated $C_{1-4}$ alkoxy group and a 5- or 6-membered heterocyclic group; $R^0$ is a hydrogen atom, an optionally substituted aralkyl group, an acyl group or an acyloxy group; $R^1$ is a $C_{1-6}$ alkyl group, a $C_{1-6}$ alkoxy group, a $C_{1-6}$ alkoxy group or a di-$C_{1-6}$ alkylamino group; $R^2$ is a hydrogen atom, a $C_{1-6}$ alkoxy-$C_{1-6}$ alkoxy group, or an optionally halogenated $C_{1-6}$ alkoxy group; $R^3$ is a hydrogen atom or a $C_{1-6}$ alkyl group, and Y is a nitrogen atom.

In particular, the preferable compound is a compound represented by the formula (Ia);

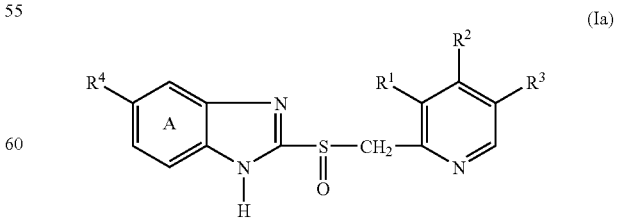

wherein $R^1$ indicates a $C_{1-3}$ alkyl group or a $C_{1-3}$ alkoxy group; $R^2$ indicates a $C_{1-3}$ alkoxy group which may be halogenated or may be substituted with a $C_{1-3}$ alkoxy group; $R^3$ indicates a hydrogen atom or a $C_{1-3}$ alkyl group, and $R^4$ indicates a hydrogen atom, an optionally halogenated $C_{1-3}$ alkoxy group or a pyrrolyl group (for example, 1-, 2- or 3-pyrrolyl group).

In the formula (Ia), the compound wherein $R^1$ is a $C_{1-3}$ alkyl group; $R^2$ is an optionally halogenated $C_{1-3}$ alkoxy group; $R^3$ is a hydrogen atom and $R^4$ is a hydrogen atom or an optionally halogenated $C_{1-3}$ alkoxy group is particularly preferred.

In the compound represented by the above-mentioned formula (I) (hereinafter, referred to as Compound (I)), the "substituent group" of the "benzene ring optionally having a substituent group" represented by ring A includes, for example, a halogen atom, a nitro group, an alkyl group optionally having a substituent group, a hydroxy group, an alkoxy group optionally having a substituent group, an aryl group, an aryloxy group, a carboxy group, an acyl group, an acyloxy group, a 5- to 10-membered heterocyclic group and the like. The benzene ring may be substituted with about 1 to 3 of these substituent groups. When the number of substituents is 2 or more, each substituent groups may be the same or different. Among these substituent groups, a halogen atom, an alkyl group optionally having a substituent group, an alkoxy group optionally having a substituent group and the like are preferred.

The halogen atom includes fluorine, chlorine, bromine atom and the like. Among these, fluorine is preferred.

As the "alkyl group" of the "alkyl group optionally having a substituent group", for example, a alkyl group (for example, a methyl, ethyl, propyl, isopropyl, butyl, isobutyl, sec-butyl, tert-butyl, pentyl, hexyl, heptyl group and the like) is exemplified. As the "substituent group" of the "alkyl group optionally having a substituent group", for example, a halogen atom, a hydroxy group, a $C_{1-6}$ alkoxy group (for example, methoxy, ethoxy, propoxy, butoxy and the like), a $C_{1-6}$ alkoxy-carbonyl group (for example, methoxycarbonyl, ethoxycarbonyl, propoxycarbonyl and the like), a carbamoyl group and the like can be exemplified, and the number of these substituent groups may be about 1 to 3. When the number of substituent group is 2 or more, each substituent groups may be the same or different.

The "alkoxy group" of the "alkoxy group optionally having a substituent group" includes, for example, a $C_{1-6}$ alkoxy group (for example, methoxy, ethoxy, propoxy, isopropoxy, butoxy, isobutoxy, pentoxy and the like) and the like. The "substituent group" of the "alkoxy group optionally having a substituent group" are exemplified by those for the above-mentioned "substituent group" of the "alkyl group optionally having a substituent group", and the number of the substituent group is the same.

The "aryl group" include, for example, a $C_{6-14}$ aryl group (for example, a phenyl, 1-naphthyl, 2-naphthyl, biphenyl, 2-anthryl group and the like) and the like.

The "aryloxy group" includes, for example, a $C_{6-14}$ aryloxy group (for example, a phenyloxy, 1-naphthyloxy, 2-naphthyloxy and the like) and the like.

The "acyl group" includes, for example, a formyl, alkylcarbonyl, alkoxycarbonyl, carbamoyl, alkylcarbamoyl, alkylsulfinyl, alkylsulfonyl group and the like.

The "alkylcarbonyl group" includes, a $C_{1-6}$ alkyl-carbonyl group (for example, acetyl, propionyl group and the like) and the like.

The "alkoxycarbonyl group" includes, for example, a $C_{1-6}$ alkoxy-carbonyl group (for example, a methoxycarbonyl, ethoxycarbonyl, propoxycarbonyl, butoxycarbonyl group and the like) and the like.

The "alkylcarbamoyl group" include, a N—$C_{1-6}$ alkyl-carbamoyl group (for example, methylcarbamoyl, ethylcarbamoyl group and the like), a. N,N-di$C_{1-6}$ alkyl-carbamoyl group (for example, N,N-dimethylcarbamoyl, N,N-diethylcarbamoyl group and the like), and the like.

The "alkylsulfinyl group" includes, for example, a $C_{1-7}$ alkylsulfinyl group (for example, a methylsulfinyl, ethylsulfinyl, propylsulfinyl, isopropylsulfinyl group and the like) and the like.

The "alkylsulfonyl group" includes, for example, a $C_{1-7}$ alkylsulfonyl group (for example, a methylsulfonyl, ethylsulfonyl, propylsulfonyl, isopropylsulfonyl group and the like) and the like.

The "acyloxy group" includes, for example, an alkylcarbonyloxy group, an alkoxycarbonyloxy group, a carbamoyloxy group, an alkylcarbamoyloxy group, an alkylsulfinyloxy group, an alkylsulfonyloxy group and the like.

The "alkylcarbonyloxy group" includes, a $C_{1-6}$ alkyl-carbonyloxy group (for example, acetyloxy, propionyloxy group and the like) and the like.

The "alkoxycarbonyloxy group" includes, for example, a $C_{1-6}$ alkoxy-carbonyloxy group (for example, methoxycarbonyloxy, ethoxycarbonyloxy, propoxycarbonyloxy, butoxycarbonyloxy group and the like) and the like.

The "alkylcarbamoyloxy group" includes, a $C_{1-6}$ alkyl-carbamoyloxy group (for example, methylcarbamoyloxy, ethylcarbamoyloxy group and the like) and the like.

The "alkylsulfinyloxy group" includes, for example, a $C_{1-7}$ alkylsulfinyloxy group (for example, methylsulfinyloxy, ethylsulfinyloxy, propylsulfinyloxy, isopropylsulfinyloxy group and the like) and the like.

The "alkylsulfonyloxy group" includes, for example, a $C_{1-7}$ alkylsulfonyloxy group (for example, methylsulfonyloxy, ethylsulfonyloxy, propylsulfonyloxy, isopropylsulfonyloxy group and the like) and the like.

The 5- to 10-membered heterocyclic group include, for example, a 5- to 10-membered (preferably 5- or 6-membered) heterocyclic group which contains one or more (for example, one to three) hetero atoms selected from a nitrogen atom, a sulfur atom and an oxygen atom in addition to a carbon atom. Specific example includes 2- or 3-thienyl group, 2-, 3- or 4-pyridyl group, 2- or 3-furyl group, 1-, 2- or 3-pyrrolyl group, 2-, 3-, 4-, 5- or 8-quinolyl group, 1-, 3-, 4- or 5-isoquinolyl group, 1-, 2- or 3-indolyl group. Among these, 5- or 6-membered heterocyclic groups such as 1-, 2- or 3-pyrrolyl groups are preferred.

Ring A is preferably a benzene ring which may have 1 or 2 substituent groups selected from a halogen atom, an optionally halogenated $C_{1-4}$ alkyl group, an optionally halogenated $C_{1-4}$ alkoxy-group and 5- or 6-membered heterocyclic group.

In the above-mentioned formula (I'), the "aromatic monocyclic heterocyclic ring" of the "optionally substituted aromatic monocyclic heterocyclic ring" represented by ring C' includes, for example, 5- to 6-membered aromatic monocyclic heterocyclic rings such as furan, thiophene, pyrrole, oxazole, isoxazole, thiazole, isothiazole, imidazole, pyrazole, 1,2,3-oxadiazole, 1,2,4-oxadiazole, 1,3,4-oxadiazole, furazane, 1,2,3-thiadiazole, 1,2,4-thiadiazole, 1,3,4-thiadiazole, 1,2,3-triazole, 1,2,4-triazole, tetrazole, pyridine, pyridazine, pyrimidine, pyrazine and triazine. As the "aromatic monocyclic heterocyclic ring" represented by ring C', "a benzene ring which may have a substituent group" represented by the above-mentioned ring A and "a pyridine ring optionally having a substituent group" are particularly preferred. The "pyridine ring optionally having a substituent group" represented by ring C' may have 1 to 4 of the same substituent groups as those exemplified with respect to the "benzene ring which may have a substituent group" represented by the above-mentioned ring A at substitutable positions.

The position wherein "aromatic monocyclic heterocyclic ring" of the "aromatic monocyclic heterocyclic ring optionally having a substituent group" is condensed with an imidazole moiety is not specifically limited.

In the above-mentioned formula (I') or (I), the "aralkyl group" of the "aralkyl group optionally having a substituent group" represented by $R^0$ includes, for example, a $C_{7-16}$ aralkyl group (for example, $C_{6-10}$ aryl$C_{1-6}$ alkyl group such as benzyl and phenethyl and the like) and the like. Examples of the "substituent group" of the "aralkyl group optionally having a substituent group" include the same groups as those exemplified with respect to the "substituent group" of the above-mentioned "alkyl group optionally having a substituent group", and the number of the substituent groups is 1 to about 4. When the number of the substituent group is 2 or more, each substituent groups may be the same or different.

The "acyl group" represented by $R^0$ includes, for example, the "acyl group" described as the substituent group of the above-mentioned ring A.

The "acyloxy group" represented by $R^0$ includes, for example, the "acyloxy group" described as the substituent group of the above-mentioned ring A.

The preferable $R^0$ is a hydrogen atom.

In the above-mentioned formula (I') or (I), the "alkyl group optionally having a substituent group" represented by $R^1$, $R^2$ or $R^3$ includes the "alkyl group optionally having a substituent group" described as the substituent group of the above-mentioned ring A.

The "alkoxy group optionally having a substituent group" represented by $R^1$, $R^2$ or $R^3$ includes the "alkoxy group optionally having a substituent group" described as the substituent group of the above-mentioned ring A.

The "amino group optionally having a substituent group" represented by $R^0$, $R^2$ or $R^3$ includes, for example, an amino group, a mono-$C_{1-6}$ alkylamino group (for example, methylamino, ethylamino and the like), a mono-$C_{6-14}$ arylamino group (for example, phenylamino, 1-naphthylamino, 2-naphthylamino and the like), a di-$C_{1-6}$ alkylamino group (for example, dimethylamino, diethylamino and the like), a di-$C_{6-14}$ arylamino group (for example, diphenylamino and the like) and the like.

The preferable $R^1$ is a $C_{1-6}$ alkyl group, a $C_{1-6}$ alkoxy group, a $C_{1-6}$ alkoxy-$C_{1-6}$ alkoxy group and a di-$C_{1-6}$ alkylamino group. Further preferable $R^2$ is a $C_{1-3}$ alkyl group or a $C_{1-3}$ alkoxy group.

The preferable $R^2$ is a hydrogen atom, a $C_{1-6}$ alkoxy-$C_{1-6}$ alkoxy group or an optionally halogenated $C_{1-6}$ alkoxy group. Further preferable $R^3$ is a $C_{1-3}$ alkoxy group which may be optionally halogenated or may be optionally substituted with a $C_{1-3}$ alkoxy group.

The preferable $R^3$ is a hydrogen atom or a $C_{1-6}$ alkyl group. Further preferable $R^3$ is a hydrogen atom or a $C_{1-3}$ alkyl group (in particular, a hydrogen atom).

The preferable Y is a nitrogen atom.

As the specific example of the compound (I), the following compounds are exemplified.

2-[[[3-methyl-4-(2,2,2-trifluoroethoxy)-2-pyridinyl]methyl]sulfinyl]-1H-benzimidazole (lansoprazole), 2-[[(3,5-dimethyl-4-methoxy-2-pyridinyl)methyl]sulfinyl]-5-methoxy-1H-benzimidazole, 2-[[[4-(3-methoxypropoxy)-3-methyl-2-pyridinyl]methyl]sulfinyl]-1H-benzimidazole sodium salt, 5-difluoromethoxy-2-[[(3,4-dimethoxy-2-pyridinyl)methyl]sulfinyl]-1H-benzimidazole and the like.

Among these compounds, lansoprazole, namely 2-[[[3-methyl-4-(2,2,2-trifluoroethoxy)-2-pyridinyl]methyl]sulfinyl]-1H-benzimidazole is preferable in particular.

The present invention is preferably applied to the PPI of imidazopyridine compound in addition to the PPI of the above-mentioned benzimidazole compound. As the PPI of the imidazopyridine compound, for example, tenatoprazole is exemplified.

Further, the above-mentioned compound (I) and compound (I') including the imidazopyridine compound may be racemic, and optically active compounds such as R-isomer and S-isomer. For example, the optically active compounds such as optically active compound of lansoprazole, that is, (R)-2-[[[3-methyl-4-(2,2,2-trifluoroethoxy)-2-pyridinyl]methyl]sulfinyl]-1H-benzimidazole and (S)-2-[[[3-methyl-4-(2,2,2-trifluoroethoxy)-2-pyridinyl]methyl]sulfinyl]-1H-benzimidazole are preferable for the present invention in particular. Further, for lansoprazole, lansoprazole R-isomer and lansoprazole S-isomer, crystals are usually preferred, but since they are stabilized by preparation itself as described later and stabilized by compounding a basic inorganic salt and further providing an intermediate layer, those being amorphous as well as crystalline can be also used.

The salt of compound (I') and compound (I) is preferably a pharmacologically acceptable salt, and for example, a salt with an inorganic base, a salt with an organic base, a salt with a basic amino acid and the like are mentioned.

The preferable salt with an inorganic base includes, for example, alkali metal salts such as sodium salt and potassium salt; alkali earth metal salts such as calcium salt and magnesium salt; ammonium salt and the like.

The preferable example of the salt with an organic base includes, for example, salts with an alkylamine (trimethylamine, triethylamine and the like), a heterocyclic amine (pyridine, picoline and the like), an alkanolamine (ethanolamine, diethanolamine, triethanolamine and the like), dicyclohexylamine, N,N'-dibenzylethylenediamine and the like.

The preferable example of the salt with a basic amino acid includes, for example, salts with arginine, lysine, ornithine and the like.

Among these salts, an alkali metal salt and an alkali earth metal salt are preferred. A sodium salt is preferred particularly.

The compound (I') or (I) can be produced by known methods, and are produced by methods disclosed in, for example, JP-A 61-50978, U.S. Pat. No. 4,628,098, JP-A 10-195068, WO 98/21201, JP-A 52-62275, JP-A 54-141783 and the like, or analogous methods thereto. Further, the optically active compound (I) can be obtained by optical resolution methods (a fractional recrystallization method, a chiral column method, a diastereomer method, a method using microorganism or enzyme, and the like) and an asymmetric oxidation method, etc. Further, lansoprazole R-isomer can be produced according to production methods described in, for example, WO 00-78745, WO 01/83473 and the like.

The benzimidazole compound having antitumor activity used in the present invention is preferably lansoprazole, omeprazole, rabeprazole, pantoprazole, leminoprazole, tenatoprazole (TU-199) and the like, or optically active compounds thereof and pharmacologically acceptable salts thereof. Lansoprazole or an optically active compound thereof, in particular R-isomer is preferred. Lansoprazole or an optically active compound thereof, in particular R-isomer is preferably in a form of crystal, but may be an amorphous form. Further, they are also suitably applied to the prodrug of these PPIs.

Examples of these preferable prodrugs include the compound represented by the following general formula (II) and (III) in addition to the prodrug which is included in compound (I) or (I').

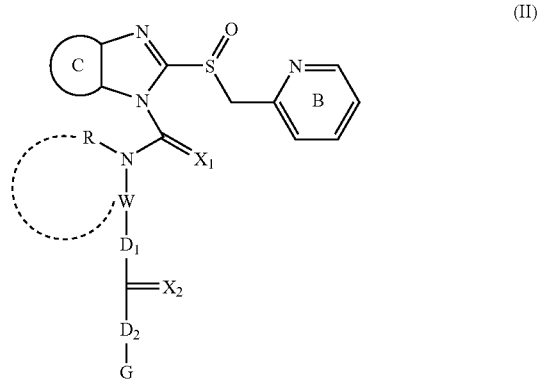

(II)

In the compound represented by the above formula (II) (hereinafter, referred to as compound (II)), ring B designates a "pyridine ring optionally having substituents".

The pyridine ring of the "pyridine ring optionally having substituents" represented by ring B may have 1 to 4 substituents at substitutable positions thereof. As the substituent, for example, a halogen atom (e.g., fluorine, chlorine, bromine, iodine etc.), a hydrocarbon group optionally having substituents (e.g., alkyl group having 1 to 6 carbon atoms such as methyl group, ethyl group, n-propyl group etc., and the like), an amino group optionally having substituents (e.g., amino; amino group mono- or di-substituted by alkyl group having 1 to 6 carbon atoms, such as methylamino, dimethylamino, ethylamino, diethylamino group etc., and the like), an amide group (e.g., $C_{1-3}$ acylamino group such as formamide, acetamide etc., and the like), a lower alkoxy group optionally having substituents (e.g., alkoxy group having 1 to 6 carbon atoms such as methoxy, ethoxy, 2,2,2-trifluoroethoxy, 3-methoxypropoxy group and the like), a lower alkylenedioxy group (e.g., $C_{1-3}$ alkylenedioxy group such as methylenedioxy, ethylenedioxy etc., and the like) and the like can be mentioned.

As the substituent, which is the substituent of the "pyridine ring optionally having substituents" represented by ring B can have, for example, a halogen atom (e.g., fluorine, chlorine, bromine, iodine etc.), a lower alkyl group (e.g., alkyl group having 1 to 6 carbon atoms such as methyl, ethyl, propyl group and the like), a lower alkenyl group (e.g., alkenyl group having 2 to 6 carbon atoms such as vinyl, allyl group and the like), a lower alkynyl group (e.g., alkynyl group having 2 to 6 carbon atoms such as ethynyl, propargyl group and the like), a cycloalkyl group (e.g., cycloalkyl group having 3 to 8 carbon atoms such as cyclopropyl, cyclobutyl, cyclopentyl, cyclohexyl group and the like), a lower alkoxy group (e.g., alkoxy group having 1 to 6 carbon atoms such as methoxy, ethoxy group and the like), a nitro group, a cyano group, a hydroxy group, a thiol group, a carboxyl group, a lower alkanoyl group (e.g., formyl; $C_1$-$C_6$ alkyl-carbonyl group, such as acetyl, propionyl, butyryl group and the like), a lower alkanoyloxy group (e.g., formyloxy; $C_1$-$C_6$ alkyl-carbonyloxy group, such as acetyloxy, propionyloxy group and the like), a lower alkoxycarbonyl group (e.g., $C_1$-$C_6$ alkoxy-carbonyl group, such as methoxycarbonyl, ethoxycarbonyl, propoxycarbonyl group and the like), an aralkyloxycarbonyl group (e.g., $C_7$-$C_{11}$ aralkyloxy-carbonyl group, such as benzyloxycarbonyl group and the like), an aryl group (e.g., aryl group having 6 to 14 carbon atoms such as phenyl, naphthyl group and the like), an aryloxy group (e.g., aryloxy group having 6 to 14 carbon atoms such as phenyloxy, naphthyloxy group and the like), an arylcarbonyl group (e.g., $C_6$-$C_{14}$ aryl-carbonyl group, such as benzoyl, naphthoyl group and the like), an arylcarbonyloxy group (e.g., $C_6$-$C_{14}$ aryl-carbonyloxy group, such as benzoyloxy, naphthoyloxy group and the like), a carbamoyl group optionally having substituents (e.g., carbamoyl; carbamoyl group mono- or di-substituted by alkyl group having 1 to 6 carbon atoms, such as methylcarbamoyl, dimethylcarbamoyl group etc., and the like), an amino group optionally having substituents (e.g., amino; amino group mono- or di-substituted by alkyl group having 1 to 6 carbon atoms, such as methylamino, dimethylamino, ethylamino, diethylamino group etc., and the like) and the like, can be mentioned, wherein the number of substituents and the position of the substitution are not particularly limited.

While the number of substituents and the position of substitution of the "pyridine ring optionally having substituents" represented by ring B are not particularly limited, 1 to 3 substituents mentioned above preferably substitute any of the 3-, 4- and 5-positions of the pyridine ring.

As the "pyridine ring optionally having substituents" represented by ring B, 3-methyl-4-(2,2,2-trifluoroethoxy)-2-pyridyl is preferable.

In the present invention, ring C represents a "benzene ring optionally having substituents" or an "aromatic monocyclic heterocycle optionally having substituents", which is condensed with an imidazole part. Of these, the former is preferable.

The benzene ring of the "benzene ring optionally having substituents" represented by ring C may have 1 to 4 substituents at substitutable positions thereof. As the substituent, for example, a halogen atom (e.g., fluorine, chlorine, bromine, iodine etc.), a hydrocarbon group optionally having substituents (e.g., alkyl group having 1 to 6 carbon atoms selected from methyl group, ethyl group, n-propyl group etc., and the like), an amino group optionally having substituents (e.g., amino; amino group mono- or di-substituted by alkyl group having 1 to 6 carbon atoms, such as methylamino, dimethylamino, ethylamino, diethylamino group etc., and the like), an amide group (e.g., $C_{1-3}$ acylamino group such as formamide, acetamide etc., and the like), a lower alkoxy group optionally having substituents (e.g., alkoxy group having 1 to 6 carbon atoms, such as methoxy, ethoxy, difluoromethoxy group etc., and the like), a lower alkylenedioxy group (e.g., $C_{1-3}$ alkylenedioxy group such as methylenedioxy, ethylenedioxy etc., and the like), and the like can be mentioned.

As the substituent, which is the substituent of the "benzene ring optionally having substituents" represented by ring C can have, for example, a halogen atom (e.g., fluorine, chlorine, bromine, iodine etc.), a lower alkyl group (e.g., alkyl group having 1 to 6 carbon atoms such as methyl, ethyl, propyl group and the like), a lower alkenyl group (e.g., alkenyl group having 2 to 6 carbon atoms such as vinyl, allyl group and the like), a lower alkynyl group (e.g., alkynyl group having 2 to 6 carbon atoms such as ethynyl, propargyl group and the like), a cycloalkyl group (e.g., cycloalkyl group having 3 to 8 carbon atoms such as cyclopropyl, cyclobutyl, cyclopentyl, cyclohexyl group and the like), a lower alkoxy group (e.g., alkoxy group having 1 to 6 carbon atoms such as methoxy, ethoxy group and the like), a nitro group, a cyano group, a hydroxy group, a thiol group, a carboxyl group, a lower alkanoyl group (e.g., formyl; $C_{1-6}$ alkyl-carbonyl group, such as acetyl, propionyl, butyryl group and the like), a lower alkanoyloxy group (e.g., formyloxy; $C_{1-6}$ alkyl-carbonyloxy group, such as acetyloxy, propionyloxy group and the like), a lower alkoxycarbonyl group (e.g., $C_{1-6}$ alkoxycarbonyl group, such as methoxycarbonyl, ethoxycarbonyl, propoxycarbonyl group and the like), an aralkyloxycarbonyl group (e.g., $C_{7-17}$ aralkyloxy-carbonyl group, such as benzyloxycarbonyl group and the like), an aryl group (e.g., aryl group having 6 to 14 carbon atoms such as phenyl, naphthyl group and the like), an aryloxy group (e.g., aryloxy group having 6 to 14 carbon atoms such as phenyloxy, naphthyloxy group and the like), an arylcarbonyl group (e.g., $C_{6-14}$ arylcarbonyl group, such as benzoyl, naphthoyl group and the like), an arylcarbonyloxy group (e.g., $C_{6-14}$ aryl-carbonyloxy group, such as benzoyloxy, naphthoyloxy group and the like), a carbamoyl group optionally having substituents (e.g., carbamoyl; carbamoyl group mono- or di-substituted by alkyl group having 1 to 6 carbon atoms such as methylcarbamoyl, dimethylcarbamoyl group etc., and the like), an amino group optionally having substituents (e.g., amino; amino group mono- or di-substituted by alkyl group having 1 to 6 carbon atoms such as methylamino, dimethylamino, ethylamino, diethylamino group etc., and the like) and the like can be mentioned, wherein the number of substituents and the position of the substitution are not particularly limited.

As the "benzene ring optionally having substituents" represented by ring C, a benzene ring is preferable.

As the "aromatic monocyclic heterocycle" of the "aromatic monocyclic heterocycle optionally having substituents" represented by ring C, for example, a 5- or 6-membered aromatic monocyclic heterocycle such as furan, thiophene, pyrrole, oxazole, isoxazole, thiazole, isothiazole, imidazole, pyrazole, 1,2,3-oxadiazole, 1,2,4-oxadiazole, 1,3,4-oxadiazole, furazan, 1,2,3-thiadiazole, 1,2,4-thiadiazole, 1,3,4-thiadiazole, 1,2,3-triazole, 1,2,4-triazole, tetraxole, pyridine, pyridazine, pyrimidine, pyrazine, triazine etc., and the like can be mentioned. As the "aromatic monocyclic heterocycle" represented by ring C, a pyridine ring is particularly preferable. It may have, at substitutable positions thereof, 1 to 4 substituents similar to those for the "benzene ring optionally having substituents" represented by ring C.

The position where the "aromatic monocyclic heterocycle" of the "aromatic monocyclic heterocycle optionally having substituents" is condensed with the imidazole part is not particularly limited.

In the present invention, $X_1$ and $X_2$ represent an oxygen atom and a sulfur atom, respectively. Both $X_1$ and $X_2$ preferably represent an oxygen atom.

In the present invention, W represents a "divalent chain hydrocarbon group optionally having substituents", or the formula:

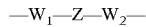
—$W_1$—Z—$W_2$— wherein $W_1$ and $W_2$ are each a "divalent chain hydrocarbon group" or a bond, and Z is a divalent group such as a "divalent hydrocarbon ring group optionally having substituents", a "divalent heterocyclic group optionally having substituents", an oxygen atom, $SO_n$ wherein n is 0, 1 or 2 or >N-E wherein E is a hydrogen atom, a hydrocarbon group optionally having substituents, a heterocyclic group optionally having substituents, a lower alkanoyl group, a lower alkoxycarbonyl group, an aralkyloxycarbonyl group, a thiocarbamoyl group, a lower alkylsulfinyl group, a lower alkylsulfonyl group, a sulfamoyl group, a mono-lower alkylsulfamoyl group, a di-lower alkylsulfamoyl group, an arylsulfamoyl group, an arylsulfinyl group, an arylsulfonyl group, an arylcarbonyl group, or a carbamoyl group optionally having substituents, when Z is an oxygen atom, $SO_n$ or >N-E, $W_1$ and $W_2$ are each a "divalent chain hydrocarbon group". Particularly, W is preferably a "divalent chain hydrocarbon group optionally having substituents".

As the "divalent chain hydrocarbon group" of the "divalent chain hydrocarbon group optionally having substituents" represented by W and "divalent chain hydrocarbon group" represented by $W_1$ and $W_2$, for example, $C_{1-6}$ alkylene group (e.g., methylene, ethylene, trimethylene etc.), a $C_{2-6}$ alkenylene group (e.g., ethenylene etc.), a $C_{2-6}$ alkynylene group (e.g., ethynylene etc.) and the like can be mentioned. The divalent chain hydrocarbon group for W may have 1 to 6 substituents similar to those for the "benzene ring optionally having substituents" represented by ring C at substitutable positions thereof.

As the "divalent chain hydrocarbon group" of the "divalent chain hydrocarbon group optionally having substituents" represented by W and "divalent chain hydrocarbon group" represented by $W_1$ and $W_2$, a methylene group and an ethylene group are preferable. As W, an ethylene group is particularly preferable. When Z is an oxygen atom, $SO_n$ or >N-E (n and E are as defined above), the "divalent chain hydrocarbon group" represented by $W_1$ is preferably a hydrocarbon group having 2 or more carbon atoms.

As the "hydrocarbon ring" of the "divalent hydrocarbon ring group optionally having substituents" represented by Z, for example, an alicyclic hydrocarbon ring, an aromatic hydrocarbon ring and the like can be mentioned, with preference given to one having 3 to 16 carbon atoms, which may have 1 to 4 substituents similar to those for the "benzene ring optionally having substituents" represented by ring C at substitutable positions thereof. As the hydrocarbon ring, for example, cycloalkane, cycloalkene, arene and the like are used.

As a cycloalkane in the "divalent hydrocarbon ring group optionally having substituents" represented by Z, for example, a lower cycloalkane and the like are preferable, and, for example, $C_{3-10}$ cyclcalkane such as cyclopropane, cyclobutane, cyclopentane, cyclohexane, cycloheptane, cyclooctane, bicyclo[2.2.1]heptane, adamantane etc., and the like are generally used.

As a cycloalkene in the "divalent hydrocarbon ring group optionally having substituents" represented by Z, for example, a lower cycloalkene is preferable, and, for example, $C_{4-9}$ cycloalkene such as cyclopropene, cyclobutene, cyclopentene, cyclohexene, cycloheptene, cyclooctene etc., and the like are generally used.

As an arene in the "divalent hydrocarbon ring group optionally having substituents" represented by Z, for example, a $C_{6-14}$ arene such as benzene, naphthalene, phenanthrene etc., and the like are preferable, and, for example, phenylene and the like are generally used.

As a heterocycle in the "divalent heterocyclic group optionally having substituents" represented by Z, a 5- to 12-membered "aromatic heterocycle" or "saturated or unsaturated non-aromatic heterocycle" containing, as ring-constituting atom (ring atom), 1 to 3 (preferably 1 or 2) kinds of at least 1 (preferably 1 to 4, more preferably 1 or 2) hetero atoms selected from oxygen atom, sulfur atom and nitrogen atom etc., and the like can be mentioned, which may have 1 to 4 substituents similar to those for the "benzene ring optionally having substituents" represented by ring C at substitutable positions thereof.

As an aromatic heterocycle in the "divalent heterocyclic group optionally having substituents" represented by Z, an aromatic monocyclic heterocycle, an aromatic fused heterocycle and the like can be mentioned.

As the "aromatic monocyclic heterocycle", for example, a 5- or 6-membered aromatic monocyclic heterocycle such as furan, thiophene, pyrrole, oxazole, isoxazole, thiazole, isothiazole, imidazole, pyrazole, 1,2,3-oxadiazole, 1,2,4-oxadiazole, 1,3,4-oxadiazole, furazan, 1,2,3-thiadiazole, 1,2,4-thiadiazole, 1,3,4-thiadiazole, 1,2,3-triazole, 1,2,4-triazole, tetrazole, pyridine, pyridazine, pyrimidine, pyrazine, triazine etc., and the like can be mentioned.

As the "aromatic fused heterocycle", for example, a 8- to 12-membered aromatic fused heterocycle such as benzofuran, isobenzofuran, benzothiophene, isobenzothiophene, indole, isoindole, 1H-indazole, benzimidazole, benzoxazole, 1,2-benzisoxazole, benzothiazole, 1,2-benzisothiazole, 1H-benzotriazole, quinoline, isoquinoline, cinnoline, quinazoline, quinoxaline, phthalazine, naphthyridine, purine, pteridine, carbazole, carboline, acridine, phenoxazine, phenothiazine, phenazine, phenoxathiin, thianthrene, phenanthridine, phenanthroline, indolizine, pyrrolo[1,2-b]pyridazine, pyrazolo[1,5-a]pyridine, imidazo[1,2-a]pyridine, imidazo[1,5-a]pyridine, imidazo[1,2-b]pyridazine, imidazo[1,2-a]pyrimidine, 1,2,4-triazolo[4,3-a]pyridine, 1,2,4-triazolo[4,3-b]pyridazine etc., and the like can be mentioned.

As a saturated or unsaturated non-aromatic heterocycle in the "divalent heterocyclic group optionally having substituents" represented by Z, for example, a 3- to 8-membered (preferably 5- or 6-membered) saturated or unsaturated (preferably saturated) non-aromatic heterocycle (aliphatic heterocycle) such as oxylane, azetidine, oxetane, thietane, pyrrolidine, tetrahydrofuran, tetrahydrothiophene, piperidine, tetrahydropyran, tetrahydrothiopyran, morpholine, thiomorpholine, piperazine, azepane, oxepane, thiene, oxazepane, thiazepane, azocane, oxocane, thiocane, oxazocane, thiazocane etc., and the like can be mentioned.

These may be oxo-substituted and may be, for example, 2-oxoazetidine, 2-oxopyrrolidine, 2-oxopiperidine, 2-oxazepane, 2-oxazocane, 2-oxotetrahydrofuran, 2-oxotetrahydropyran, 2-oxotetrahydrothiophene, 2-oxothiane, 2-oxopiperazine, 2-oxooxepane, 2-oxooxazepane, 2-oxothiepane, 2-oxothiazepane, 2-oxooxocane, 2-oxothiocane, 2-oxooxazocane, 2-oxothiazocane and the like.

The two bonds from the "hydrocarbon ring group" of the "divalent hydrocarbon ring group optionally having substituents" or the "heterocyclic group" of the "divalent heterocyclic group optionally having substituents" represented by Z may be present at any possible position.

The "hydrocarbon group optionally having substituents" and "heterocyclic group optionally having substituents" represented by E is as defined in the following.

As the "lower alkanoyl group" represented by E, for example, formyl, a $C_{1-6}$ alkyl-carbonyl group such as acetyl, propionyl, butyryl, isobutyryl etc., and the like can be used.

As the "lower alkoxycarbonyl group" represented by E, for example, a $C_{1-6}$ alkoxy-carbonyl group such as methoxycarbonyl, ethoxycarbonyl, propoxycarbonyl, butoxycarbonyl etc., and the like are used.

As the "aralkyloxycarbonyl" represented by E, for example, a $C_{7-11}$ aralkyloxy-carbonyl group such as benzyloxycarbonyl etc., and the like are used.

As the "lower alkylsulfinyl group" represented by E, for example, a $C_{1-6}$ alkylsulfinyl group such as methylsulfinyl, ethylsulfinyl etc., and the like are used.

As the "lower alkylsulfonyl group" represented by E, for example, a $C_{1-6}$ alkylsulfonyl group such as methylsulfonyl, ethylsulfonyl etc., and the like are used.

As the "mono-lower alkylsulfamoyl group" represented by E, for example, a mono-$C_{1-6}$ alkylsulfamoyl group such as methylsulfamoyl, ethylsulfamoyl etc., and the like are used.

As the "di-lower alkylsulfamoyl group" represented by E, for example, a di-$C_{1-6}$ alkylsulfamoyl group such as dimethylsulfamoyl, diethylsulfamoyl etc., and the like are used.

As the "arylsulfamoyl group" represented by E, for example, a $C_{6-10}$ arylsulfamoyl group such as phenylsulfamoyl, naphthylsulfamoyl etc., and the like are used.

As the "arylsulfinyl group" represented by E, for example, a $C_{6-10}$ arylsulfinyl group such as phenylsulfinyl, naphthylsulfinyl etc., and the like are used.

As the "arylsulfonyl group" represented by E, for example, a $C_{6-10}$ arylsulfonyl group such as phenylsulfonyl, naphthylsulfonyl etc., and the like are used.

As the "arylcarbonyl group" represented by E, for example, $C_{6-10}$ aryl-carbonyl group such as benzoyl, naphthoyl etc., and the like are used.

The "carbamoyl group optionally having substituents" represented by E is, for example, a group of the formula —$CONR_2R_3$ wherein $R_2$ and $R_3$ are each a hydrogen atom, a hydrocarbon group optionally having substituents or a heterocyclic group optionally having substituents, and in the formula —$CONR_2R_3$, $R_2$ and $R_3$ may form a ring together with the adjacent nitrogen atom, and the like.

In the present invention, R is a "hydrocarbon group optionally having substituents" or a "heterocyclic group optionally having substituents", and R can be bonded to W. Of these, a $C_{1-6}$ hydrocarbon group optionally having substituents is preferable and a lower ($C_{1-6}$) alkyl group is particularly preferable. The "hydrocarbon group optionally having substituents" and "heterocyclic group optionally having substituents" represented by R are as defined in the following. A detailed explanation of the case where R is bonded to W is given in the following.

In the present invention, $D_1$ and $D_2$ are each a bond, an oxygen atom, a sulfur atom or >$NR_1$, and in the formula, $R_1$ is a hydrogen atom or a hydrocarbon group optionally having substituents. However, the present invention excludes a case where $D_1$ and $D_2$ are both respectively a bond. Among others, each of $D_1$ and $D_2$ is preferably a bond or an oxygen atom, and particularly preferably, $D_1$ is an oxygen atom and $D_2$ is an oxygen atom or a bond. The "hydrocarbon group optionally having substituents" represented by $R_1$ is as defined in the following.

In the present invention, G is a "hydrocarbon group optionally having substituents" or a "heterocyclic group optionally having substituents". Of these, a $C_{1-6}$ hydrocarbon group optionally having substituents or a saturated heterocyclic group optionally having substituents, which contains, as ring-constituting atom, 1 to 4 hetero atoms selected from oxygen atom, sulfur atom and nitrogen atom is preferable. As G, among others, a hydrocarbon group optionally having substituents or a saturated oxygen-containing heterocyclic group optionally having substituents, which further contains, as ring-constituting atom, 1 to 3 hetero atoms selected from oxygen atom, sulfur atom and nitrogen atom is preferable. The "hydrocarbon group optionally having substituents" and "heterocyclic group optionally having substituents" represented by G are as defined in the following.

As the "hydrocarbon group" of the "hydrocarbon group optionally having substituents" represented by the above-mentioned E, R, $R_1$ and G, for example, a saturated or unsaturated aliphatic hydrocarbon group, a saturated or unsaturated alicyclic hydrocarbon group, a saturated or unsaturated alicyclic-aliphatic hydrocarbon group, an aromatic hydrocarbon group, an aromatic-saturated or unsaturated alicyclic hydrocarbon group and the like can be mentioned, with preference given to those having 1 to 16, more preferably 1 to 6, carbon atoms. Specific examples thereof include alkyl group, alkenyl group, alkynyl group, cycloalkyl group, cycloalkenyl group, cycloalkylalkyl group, cycloalkenylalkyl group, aryl group and arylalkyl group and the like.

For example, the "alkyl group" is preferably a lower alkyl group ($C_{1-6}$ alkyl group) and the like, and, for example, a $C_{1-6}$ alkyl group such as methyl, ethyl, propyl, isopropyl, butyl, isobutyl, sec-butyl, tert-butyl, pentyl, 1-ethylpropyl, hexyl etc., and the like are generally used. For R, a lower alkyl group ($C_{1-6}$ alkyl group) is preferable, particularly a methyl group is preferable.

For example, the "alkenyl group" is preferably a lower alkenyl group and the like, and, for example, a $C_{2-7}$ alkenyl group such as vinyl, 1-propenyl, allyl, isopropenyl, butenyl, isobutenyl, 2,2-dimethyl-pent-4-enyl etc., and the like are generally used.

For example, the "alkynyl group" is preferably a lower alkynyl group and the like, and, for example, a $C_{2-6}$ alkynyl group such as ethynyl, propargyl, 1-propynyl etc., and the like are generally used.

For example, the "cycloalkyl group" is preferably a lower cycloalkyl group and the like, and, for example, a $C_{3-10}$ cycloalkyl group such as cyclopropyl, cyclobutyl, cyclopentyl, cyclohexyl, cycloheptyl, cyclooctyl, bicyclo[2.2.1]heptanyl and adamantyl etc., and the like are generally used.

For example, the "cycloalkenyl group" is preferably a lower cycloalkenyl group, and, for example, a $C_{3-10}$ cycloalkenyl group such as cydlopropenyl, cyclobutenyl, cyclopentenyl, cyclohexenyl, cycloheptenyl, cyclooctenyl, bicyclo[2.2.1]hept-5-en-2-yl etc., and the like are generally used.

For example, the "cycloalkylalkyl group." is preferably a lower cycloalkylalkyl group, and, for example, a $C_{4-9}$ cycloalkylalkyl group such as cyclopropylmethyl, cyclopropylethyl, cyclobutylmethyl, cyclopentylmethyl, cyclohexylmethyl and cyclohexylethyl etc., and the like are generally used.

For example, the "cycloalkenylalkyl group" is preferably a lower cycloalkenylalkyl group, and, for example, $C_{4-9}$ cycloalkenylalkyl such as cyclopentenylmethyl, cyclohexenylmethyl, cyclohexenylethyl, cyclohexenylpropyl, cycloheptenylmethyl, cycloheptenylethyl and bicyclo[2.2.1]hept-5-en-2-ylmethyl etc., and the like are generally used.

For example, the "aryl group" is preferably a $C_{6-14}$ aryl group such as phenyl, 1-naphthyl, 2-naphthyl, biphenylyl, 2-anthryl etc., and the like, and, for example, phenyl group and the like are generally used.

The "arylalkyl group" contains, as the aryl moiety, the "aryl group" defined above, and as the alkyl moiety, the "alkyl group" defined above. Of these, for example, a $C_{6-14}$ aryl-$C_{1-6}$ alkyl group is preferable, and, for example, benzyl, phenethyl and the like are generally used.

As the substituent that the "hydrocarbon group" of the "hydrocarbon group optionally having substituents" represented by the above-mentioned E, R, $R_1$ and G may have, for example, a halogen atom (e.g., fluorine, chlorine, bromine, iodine etc.), a nitro group, a cyano group, a hydroxy group, a thiol group, a sulfo group, a sulphino group, a phosphono group, an optionally halogenated lower alkyl group (e.g., $C_{1-6}$ alkyl such as methyl, ethyl, propyl, isopropyl, butyl, isobutyl, sec-butyl, tert-butyl, pentyl, 1-ethylpropyl, hexyl and the like, a mono-, di- or tri-halogeno-$C_{1-6}$ alkyl group such as chloromethyl, dichloromethyl, trichloromethyl, fluoromethyl, difluoromethyl, trifluoromethyl, 2-bromoethyl, 2,2,2-trifluoroethyl, pentafluoroethyl, 3,3,3-trifluoropropyl, 4,4,4-trifluorobutyl, 5,5,5-trifluoropentyl, 6,6,6-trifluorohexyl etc., and the like), an oxo group, an amidino group, an imino group, an alkylenedioxy group (e.g., $C_{1-3}$ alkylenedioxy group such as methylenedioxy, ethylenedioxy etc., and the like), a lower alkoxy group (e.g., $C_{1-6}$ alkoxy group such as methoxy, ethoxy, propoxy, isopropoxy, butoxy, isobutoxy, pentyloxy, hexyloxy etc., and the like), an optionally halogenated lower alkoxy group (e.g., a mono-, di- or tri-halogeno-$C_{1-6}$ alkoxy group such as chloromethyloxy, dichloromethyloxy, trichloromethyloxy, fluoromethyloxy, difluoromethyloxy, trifluoromethyloxy, 2-bromoethyloxy, 2,2,2-trifluoroethyloxy, pentafluoroethyloxy, 3,3,3-trifluoropropyloxy, 4,4,4-trifluorobutyloxy, 5,5,5-trifluoropentyloxy, 6,6,6-trifluorohexyloxy etc., and the like), a lower alkylthio group (e.g., a $C_{1-6}$ alkylthio group such as methylthio, ethylthio, propylthio, isopropylthio, butylthio, isobutylthio, pentylthio, hexylthio etc., and the like), a carboxyl group, a lower alkanoyl group (e.g., formyl; a $C_{1-6}$ alkyl-carbonyl group such as acetyl, propionyl, butyryl, isobutyryl etc., and the like), a lower alkanoyloxy group (e.g., formyloxy; a $C_{1-6}$ alkyl-carbonyloxy group such as acetyloxy, propionyloxy, butyryloxy, isobutyryloxy etc., and the like), a lower alkoxy-carbonyl group (e.g., a $C_{1-6}$ alkoxy-carbonyl group such as methoxycarbonyl, ethoxycarbonyl, propoxycarbonyl, butoxycarbonyl etc., and the like), aralkyloxycarbonyl group (e.g., a $C_{7-11}$ aralkyloxy-carbonyl group such as benzyloxycarbonyl etc., and the like), a thiocarbamoyl group, a lower alkylsulfinyl group (e.g., a $C_{1-6}$ alkylsulfinyl group such as methylsulfinyl, ethylsulfinyl etc., and the like), a lower alkylsulfonyl group (e.g., a alkylsulfonyl group such as methylsulfonyl, ethylsulfonyl etc., and the like), a sulfamoyl group, a mono-lower alkylsulfamoyl group (e.g., a mono-$C_{1-6}$ alkylsulfamoyl group such as methylsulfamoyl, ethylsulfamoyl etc., and the like), di-lower alkylsulfamoyl group (e.g., a di-$C_{1-6}$ alkylsulfamoyl group such as dimethylsulfamoyl, diethylsulfamoyl etc., and the like), an arylsulfamoyl group (e.g., a $C_{6-10}$ arylsulfamoyl group such as phenylsulfamoyl, naphthylsulfamoyl etc., and the like), an aryl group (e.g., a $C_{6-10}$ aryl group such as phenyl, naphthyl etc., and the like), an aryloxy group (e.g., a $C_{6-10}$ aryloxy group such as phenyloxy, naphthyloxy etc., and the like), an arylthio group (e.g., a $C_{6-10}$ arylthio group such as phenylthio, naphthylthio etc., and the like), an arylsulfinyl group (e.g., a $C_{6-10}$ arylsulfinyl group such as phenylsulfinyl, naphthylsulfinyl etc., and the like), an arylsulfonyl group (e.g., a $C_{6-10}$ arylsulfonyl group such as phenylsulfonyl, naphthylsulfonyl etc., and the like), an arylcarbonyl group (e.g., a $C_{6-10}$ aryl-carbonyl group such as benzoyl, naphthoyl etc., and the like), an arylcarbonyloxy group (e.g., a $C_{6-10}$ aryl-carbonyloxy group such as benzoyloxy, naphthoyloxy etc., and the like), an optionally halogenated lower alkylcarbonylamino group (e.g., an optionally halogenated $C_{1-6}$ alkyl-carbonylamino group such as acetylamino, trifluoroacetylamino etc., and the like), a carbamoyl group optionally having substituents (e.g., a group of the formula —$CONR_2R_3$ wherein $R_2$ and $R_3$ are each a hydrogen atom, a hydrocarbon group optionally having substituents or a heterocyclic group optionally having substituents and in the formula —$CONR_2R_3$, $R_2$ and $R_3$ may form a ring together with the adjacent nitrogen atom), an amino group optionally having substituents (e.g., a group of the formula —$NR_2R_3$ wherein $R_2$ and $R_3$ are as defined above and in the formula —$NR_2R_3$, $R_2$ and $R_3$ may form a ring together with the adjacent nitrogen atom), a ureido group optionally having substituents (e.g., a group of the formula —$NHCONR_2R_3$ wherein $R_2$ and $R_3$ are as defined above and in the formula —$NHCONR_2R_3$, $R_2$ and $R_3$ may form a ring together with the adjacent nitrogen atom), a carboxamide group optionally having substituents (e.g., a group of the formula —$NR_2COR_3$ wherein $R_2$ and $R_3$ are as defined above), a sulfonamide group optionally having substituents (e.g., a group of the formula —$NR_2SO_2R_3$ wherein $R_2$ and $R_3$ are as defined above), a heterocyclic group optionally having substituents (as defined for $R_2$ and $R_3$) and the like are used.

As the "hydrocarbon group" of the "hydrocarbon group optionally having substituents" for $R_2$ and $R_3$, for example, a lower alkyl group (e.g., alkyl group having 1 to 6 carbon atoms such as methyl, ethyl, propyl group and the like), a lower alkenyl group (e.g., alkenyl group having 2 to 6 carbon atoms such as vinyl, allyl group and the like), a lower alkynyl group (e.g., alkynyl group having 2 to 6 carbon atoms such as ethynyl, propargyl group and the like), a cycloalkyl group (e.g., cycloalkyl group having 3 to 8 carbon atoms such as cyclopropyl, cyclobutyl, cyclopentyl, cyclohexyl group and the like), a cycloalkenyl group (e.g., cycloalkenyl group having 3 to 8 carbon atoms such as cyclobutenyl, cyclopentenyl, cyclohexenyl group and the like), a cycloalkylalkyl group (e.g., $C_3$-$C_8$ cycloalkyl —$C_1$-$C_6$ alkyl group, such as cyclopropylmethyl, cyclobutylmethyl, cyclopentylmethyl, cyclohexylmethyl group and the like), a cycloalkenylalkyl group (e.g., $C_3$-$C_8$ cycloalkenyl —$C_1$-$C_6$ alkyl group, such as cyclobutenylmethyl, cyclopentenylmethyl, cyclohexenylmethyl group and the like), an aryl group (e.g., aryl group having 6 to 14 carbon atoms such as phenyl, naphthyl group and the like), an arylalkyl group (e.g., $C_6$-$C_{14}$ aryl —$C_1$-$C_6$ alkyl group, such as benzyl, naphthylmethyl group and the like) and the like can be mentioned.

As the "heterocyclic group" of the "heterocyclic group optionally having substituents" represented by $R_2$ and $R_3$, a 5- to 12-membered monocyclic or fused heterocyclic group containing 1 or 2 kinds of 1 to 4 hetero atoms selected from nitrogen atom, sulfur atom and oxygen atom such as pyridyl, pyrrolidinyl, piperazinyl, piperidinyl, 2-oxazepinyl, furyl, decahydroisoquinolyl, quinolyl, indolyl, isoquinolyl, thienyl, imidazolyl, morpholinyl etc., and the like can be mentioned. As the substituent for the "hydrocarbon group optionally having substituents" and "heterocyclic group optionally having substituents" for $R_2$ and $R_3$, for example, a halogen atom (e.g., fluorine, chlorine, bromine, iodine etc.), a lower alkyl group (e.g., alkyl group having 1 to 6 carbon atoms such as methyl, ethyl, propyl group and the like), a lower alkenyl group (e.g., alkenyl group having 2 to 6 carbon atoms such as vinyl, allyl group and the like), a lower alkynyl group (e.g., alkynyl group having 2 to 6 carbon atoms such as ethynyl, propargyl group and the like), a cycloalkyl group (e.g., cycloalkyl group having 3 to 8 carbon atoms such as cyclopropyl, cyclobutyl, cyclopentyl, cyclohexyl group and the like), a lower alkoxy group (e.g., alkoxy group having 1 to 6 carbon atoms such as methoxy, ethoxy group and the like), a nitro group, a cyano group, a hydroxy group, a thiol group, a carboxyl group, a lower alkanoyl group (e.g., formyl; $C_{1-6}$ alkyl-carbonyl group, such as acetyl, propionyl, butyryl group and the like), a lower alkanoyloxy group (e.g., formyloxy; $C_{1-6}$ alkyl-carbonyloxy group, such as acetyloxy, propionyloxy group and the like), a lower alkoxycarbonyl group (e.g., $C_{1-6}$ alkoxy-carbonyl group, such as methoxycarbonyl, ethoxycarbonyl, propoxycarbonyl group and the like), an aralkyloxycarbonyl group (e.g., $C_{7-17}$ aralkyloxy-carbonyl group, such as benzyloxycarbonyl group and the like), an aryl group (e.g., $C_{6-14}$ aryl group, such as phenyl, naphthyl group and the like), an aryloxy group (e.g., $C_{6-14}$ aryloxy group having, such as phenyloxy, naphthyloxy group and the like), an arylcarbonyl group (e.g., $C_{6-14}$ aryl-carbonyl group, such as benzoyl, naphthoyl group and the like), an arylcarbonyloxy group (e.g., $C_{6-14}$ aryl-carbonyloxy group, such as benzoyloxy, naphthoyloxy group and the like), a carbamoyl group optionally having substituents (e.g., carbamoyl; carbamoyl group mono- or di-substituted by alkyl group having 1 to 6 carbon atoms such as methylcarbamoyl, dimethylcarbamoyl group etc., and the like), an amino group optionally having substituents (e.g., amino; amino group mono- or di-substituted by alkyl group having 1 to 6 carbon atoms such as methylamino, dimethylamino, ethylamino, diethylamino group etc., and the like) and the like can be mentioned. The number and the position of the substitutions are not particularly limited.

As the ring formed by $R_2$ and $R_3$ together with the adjacent nitrogen atom, for example, pyrrolidine, piperidine, homopiperidine, morpholine, piperazine, tetrahydroquinoline, tetrahydroisoquinoline and the like can be mentioned.

The "hydrocarbon group" of the "hydrocarbon group optionally having substituents" represented by the above-mentioned E, R, $R_1$ and G may have 1 to 5, preferably 1 to 3, the aforementioned substituent at substitutable positions of the hydrocarbon group, wherein, when the number of substituents is not less than 2, each substituents are the same or different.

As the "heterocyclic group" of the "heterocyclic group optionally having substituents" represented by the above-mentioned E, R and G, a 5- to 12-membered aromatic heterocyclic group and saturated or unsaturated non-aromatic heterocyclic group containing, as ring-constituting atom (ring atom), 1 to 3 (preferably 1 or 2) kinds of at least 1. (preferably 1 to 4, more preferably 1 to 3) hetero atoms selected from oxygen atom, sulfur atom and nitrogen atom and the like can be mentioned. As the mentioned above, as the "heterocyclic group" of the "heterocyclic group optionally having substituents" represented by G, a saturated oxygen-containing heterocyclic group containing, as ring atoms, 1 to 4, more preferably 1 to 3, hetero atoms selected from oxygen atom, sulfur atom and nitrogen atom etc., and the like are preferable, particularly a 5- to 12-membered saturated oxygen-containing heterocyclic group and the like are preferable.

As the "aromatic heterocyclic group", an aromatic monocyclic heterocyclic group, an aromatic fused heterocyclic group and the like can be mentioned.

As the "aromatic monocyclic heterocyclic group", for example, a 5- or 6-membered aromatic monocyclic heterocyclic group such as furyl, thienyl, pyrrolyl, oxazolyl, isooxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl etc., and the like can be mentioned.

As the "aromatic fused heterocyclic group", for example, a 8- to 12-membered aromatic fused heterocyclic group (preferably a heterocyclic group wherein the aforementioned 5- or 6-membered aromatic monocyclic heterocyclic group is condensed with a benzene ring, or a heterocyclic group wherein the same or different two heterocyclic groups of the aforementioned 5- or 6-membered aromatic monocyclic heterocyclic group are condensed), such as benzofuranyl, isobenzofuranyl, benzothienyl, isobenzothienyl, indolyl, isoindolyl, 1H-indazolyl, benzimidazolyl, benzoxazolyl, 1,2-benzoisoxazolyl, benzothiazolyl, 1,2-benzoisothiazolyl, 1H-benzotriazolyl, quinolyl, isoquinolyl, cinnolinyl, quinazolinyl, quinoxalinyl, phthalazinyl, naphthylidinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl etc., and the like can be mentioned.

As the "saturated or unsaturated non-aromatic heterocyclic group", for example, a 3- to 8-membered (preferably 5- or 6-membered) saturated or unsaturated (preferably saturated) non-aromatic heterocyclic group (aliphatic heterocyclic group) such as oxylanyl, azetidinyl, oxetanyl, thietanyl, pyrrolidinyl, tetrahydrofuryl, thiolanyl, piperidinyl, tetrahydropyranyl, thianyl, morpholinyl, thiomorpholinyl, piperazinyl, azepanyl, oxepanyl, thiepanyl, oxazepanyl, thiazepanyl, azocanyl, oxocanyl, thiocanyl, oxazocanyl, thiazocanyl and the like can be mentioned. These may be oxo-substituted and examples thereof include 2-oxoazetidinyl, 2-oxopyrrolidinyl, 2-oxopiperidinyl, 2-oxazepanyl, 2-oxazocanyl, 2-oxotetrahydrofuryl, 2-oxotetrahydropyranyl, 2-oxothiolanyl, 2-oxothianyl, 2-oxopiperazinyl, 2-oxooxepanyl, 2-oxooxazepanyl, 2-oxothiepanyl, 2-oxothiazepanyl, 2-oxooxocanyl, 2-oxothiocanyl, 2-oxooxazocanyl, 2-oxothiazocanyl and the like. A 5-membered non-aromatic heterocyclic group such as 2-oxopyrrolidinyl and the like is preferable.

As the substituent that the "heterocyclic group" of the "heterocyclic group optionally having substituents" represented by the above-mentioned E, R and G may have, for example, those similar to the "substituent" of the "hydrocarbon group optionally having substituents" represented by the aforementioned E, R, $R_1$ and G and the like are used.

The "heterocyclic group" of the "heterocyclic group optionally having substituents" represented by E, R and G may each have 1 to 5, preferably 1 to 3, substituents mentioned above at substitutable positions of the heterocyclic group, and when the number of substituents is two or more, the substituents are the same or different.

The bond between R and W in the compound of the present invention is explained below. When R and W are bonded, the position of the bond between R and W is not particularly limited as long as R and W can be bonded. The bondable position of R is the position where the "hydrocarbon group" and "substituent" of the "hydrocarbon group optionally having substituents" defined above for R can be bonded, and the position where the "heterocyclic group" and "substituent" of the "heterocyclic group optionally having substituents" defined above for R can be bonded.

As the bondable position of W, a bondable position of the "divalent chain hydrocarbon group" of the "divalent chain hydrocarbon group optionally having substituents" defined above for W, a bondable position of the "divalent chain hydrocarbon group" defined above for $W_1$ and $W_2$, a bondable position of the "hydrocarbon ring" of the "hydrocarbon ring optionally having substituents" defined above for ring Z, and a bondable position of the "heterocyclic group" of the "heterocyclic group optionally having substituents" defined above for ring Z can be mentioned.

R and W can be bonded at the bondable position thereof and can form a ring together with the adjacent nitrogen atom. As such ring, for example, a saturated nitrogen-containing ring (e.g., azetidine, pyrrolidine, piperidine, homopiperidine etc.), an unsaturated nitrogen-containing ring (e.g., tetrahydropyridine etc.), an aromatic nitrogen-containing ring (e.g., pyrrole etc.), a hetero ring (e.g., piperazine, morpholine etc.) containing, besides the nitrogen atom to which R and W are adjacent, at least one hetero atom selected from the group consisting of nitrogen, oxygen and sulfur, a fused ring (e.g., indole, indoline, isoindole, isoindoline, tetrahydroquinoline, tetrahydroisoquinoline etc.) and the like can be mentioned. Of these, a 4- to 7-membered ring is preferable.

The ring formed by R and W, which are bonded at each bondable position thereof, together with the adjacent nitrogen atom may have 1 to 4 substituents at substitutable positions thereof. When the number of substituents is 2 or more, the substituents are the same or different. As the substituent, the substituents of the "hydrocarbon group optionally having substituents" and "heterocyclic group optionally having substituents" defined for R, and the substituents of the "divalent chain hydrocarbon group optionally having substituents" defined for W can be mentioned. Specifically, a halogen atom (e.g., fluorine, chlorine, bromine, iodine etc.), a $C_{1-6}$ alkyl group such as methyl, ethyl, propyl, isopropyl, butyl, isobutyl, sec-butyl, tert-butyl, pentyl, 1-ethylpropyl, hexyl etc., and the like can be mentioned.

By the bond between R and W, for example,

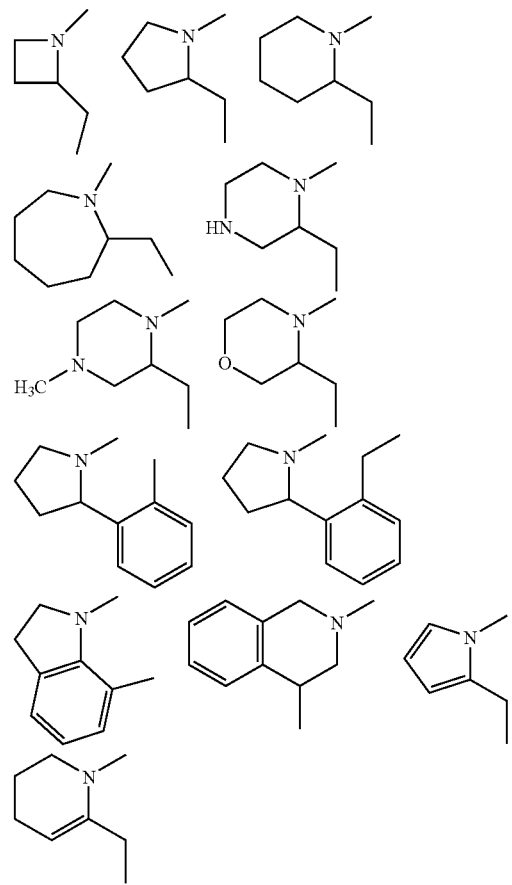

and the like are formed, but the ring is not limited to these. These may have substituents as defined above, and it would be understood for those of ordinary skill in the art that they may also have an isomer.

In the present invention, X represents a leaving group, such as a halogen atom, a benzotriazolyl group, a (2,5-dioxypyrrolidin-1-yl)oxy group and the like. Of these, a halogen atom such as fluorine, chlorine, bromine, iodine and the like is preferable, and chlorine is particularly preferable.

In the present invention, M represents a hydrogen atom, a metal cation or a quaternary ammonium ion.

In the present invention, the "metal cation" is exemplified by alkali metal ion (e.g., $Na^+$, $K^+$, $Li^+$, $Cs^+$ and the like), with preference given to $Na^+$.

In the present invention, the "quaternary ammonium ion" is exemplified by tetramethylammonium ion, tetraethylammonium ion, tetrapropylammonium ion, tetrabutylammonium ion and the like, with preference given to tetrabutylammonium ion.

In the compound (II), a pharmacologically acceptable basic salt can be formed between an acidic group in a molecule and an inorganic base or an organic base etc, and a pharmacologically acceptable acid addition salt can be formed between a basic group in a molecule and an inorganic acid or an organic acid etc.

Examples of the inorganic basic salt of compound (II) include salt with alkali metal (e.g., sodium, potassium and the like), alkaline earth metal (e.g., calcium and the like), ammonia etc., and the like, and examples of the organic basic salt of compound (II) include salt with dimethylamine, triethylamine, piperazine, pyrrolidine, piperidine, 2-phenylethylamine, benzylamine, ethanolamine, diethanolamine, pyridine, collidine etc., and the like.

Examples of the acid addition salt of compound (II) include inorganic acid salt (e.g., hydrochloride, sulfate, hydrobromide, phosphate and the like), organic acid salt (e.g., acetate, trifluoroacetate, succinate, maleate, fumarate, propionate, citrate, tartrate, lactate, oxalate, methanesulfonate, p-toluenesulfonate and the like) and the like.

The compound (II) of the present invention encompasses hydrates. Examples of the "hydrate" include 0.5 hydrate –5.0 hydrate. Of these, 0.5 hydrate, 1.0 hydrate, 1.5 hydrate and 2.0 hydrate are preferable.

The compound (II) of the present invention encompasses racemates and optically active compounds. As the optically active compound, such compound wherein one enantiomer is in enantiomer excess (e.e.) of not less than 90% is preferable, more preferably in enantiomer excess of not less than 99%.

As an optically active form, an (R)-form represented by the formula:

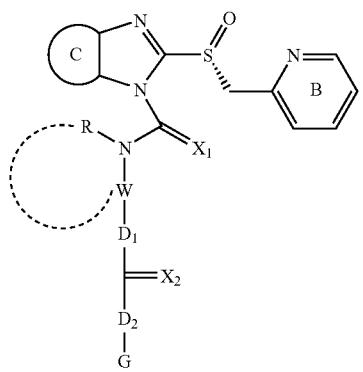

wherein each symbol is as defined above, is preferable. As the preferable compounds encompassed in compound (II), for example, the following specific compounds can be mentioned. That is,
2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl acetate,
2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl trimethylacetate,
2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl cyclohexanecarboxylate,
2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl benzoate,
2-[methyl[[2-[[[3-methyl-4-(2,2,2-trifluoroethoxy)-2-pyridyl]methyl]sulfinyl]-1H-benzimidazol-1-yl]carbonyl]amino]ethyl benzoate,
2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl 4-methoxybenzoate,
2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl 3-chlorobenzoate,
2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl 3,4-difluorobenzoate,
2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl 4-trifluoromethoxybenzoate,
2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl 4-fluorobenzoate,
2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl 3,4,5-trimethoxybenzoate,
2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl 2-pyridinecarboxylate,
2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl methoxyacetate,
ethyl 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate,
isopropyl 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate,
isopropyl 2-[methyl[[2-[[[3-methyl-4-(2,2,2-trifluoroethoxy)-2-pyridyl]methyl]sulfinyl]-1H-benzimidazol-1-yl]carbonyl]amino]ethyl carbonate,
benzyl 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate,
2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl tetrahydropyran-4-yl carbonate,
2-methoxyethyl 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate,
2-[ethyl[[(R)-2-[[[3-methyl-4-(2,2,2-trifluoroethoxy)-2-pyridyl]methyl]sulfinyl]-1H-benzimidazol-1-yl]carbonyl]amino]ethyl acetate,
2-[isopropyl[[(R)-2-[[[3-methyl-4-(2,2,2-trifluoroethoxy)-2-pyridyl]methyl]sulfinyl]-1H-benzimidazol-1-yl]carbonyl]amino]ethyl acetate,
ethyl 2-[isopropyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate,
2-[cyclohexyl[[(R)-2-[[[3-methyl-4-(2,2,2-trifluoroethoxy)-2-pyridyl]methyl]sulfinyl]-1H-benzimidazol-1-yl]carbonyl]amino]ethyl acetate,
2-[cyclohexyl[[(R)-2-[[[3-methyl-4-(2,2,2-trifluoroethoxy)-2-pyridyl]methyl]sulfinyl]-1H-benzimidazol-1-yl]carbonyl]amino]ethyl ethyl carbonate,
2-[[[(R)-2-[[[3-methyl-4-(2,2,2-trifluoroethoxy)-2-pyridyl]methyl]sulfinyl]-1H-benzimidazol-1-yl]carbonyl](phenyl)amino]ethyl acetate,
2-[[[2-[[[3-methyl-4-(2,2,2-trifluoroethoxy)-2-pyridyl]methyl]sulfinyl]-1H-benzimidazol-1-yl]carbonyl](phenyl)amino]ethyl acetate,
tert-butyl [2-[methyl[[(R)-2-[[[3-methyl-4-(2,2,2-trifluoroethoxy)-2-pyridyl]methyl]sulfinyl]-1H-benzimidazol-1-yl]carbonyl]amino]-3-pyridyl]methyl carbonate, 2-[methyl[[(R)-2-[[[3-methyl-4-(2,2,2-trifluoroethoxy)-2-pyridyl]methyl]sulfinyl]-1H-benzimidazol-1-yl]carbonyl]amino]benzyl acetate,
2-[[2-(acetyloxy)ethyl][[(R)-2-[[[3-methyl-4-(2,2,2-trifluoroethoxy)-2-pyridyl]methyl]sulfinyl]-1H-benzimidazol-1-yl]carbonyl]amino]ethyl acetate,
[(2S)-1-[[(R)-2-[[[3-methyl-4-(2,2,2-trifluoroethoxy)-2-pyridyl]methyl]sulfinyl]-1H-benzimidazol-1-yl]carbonyl]-2-pyrrolidinyl]methyl acetate,
ethyl[methyl[[(R)-2-[[[3-methyl-4-(2,2,2-trifluoroethoxy)-2-pyridyl]methyl]sulfinyl]-1H-benzimidazol-1-yl]carbonyl]amino]acetate,
2-[[[5-methoxy-2-[[(4-methoxy-3,5-dimethyl-2-pyridyl)methyl]sulfinyl]-1H-benzoimidazol-1-yl]carbonyl](methyl)amino]ethyl benzoate,
3-[methyl[[(R)-2-[[[3-methyl-4-(2,2,2-trifluoroethoxy)-2-pyridyl]methyl]sulfinyl]-1H-benzimidazol-1-yl]carbonyl]amino]propyl benzoate,
2-[methyl[[2-[[[3-methyl-4-(2,2,2-trifluoroethoxy)-2-pyridyl]methyl]sulfinyl]-1H-benzimidazol-1-yl]carbonyl]amino]ethyl tetrahydropyran-4-yl carbonate,
ethyl 2-[methyl[[2-[[[3-methyl-4-(2,2,2-trifluoroethoxy)-2-pyridyl]methyl]sulfinyl]-1H-benzimidazol-1-yl]carbonyl]amino]ethyl carbonate,
 ethyl 2-[methyl[[(S)-2-[[[3-methyl-4-(2,2,2-trifluoroethoxy)-2-pyridyl]methyl]sulfinyl]-1H-benzimidazol-1-yl]carbonyl]amino]ethyl carbonate,
ethyl 2-[[[5-methoxy-2-[[(4-methoxy-3,5-dimethyl-2-pyridyl)methyl]sulfinyl]-3H-imidazo[4,5-b]pyridin-3-yl]carbonyl](methyl)amino]ethyl carbonate,
2-[[[5-methoxy-2-[[(4-methoxy-3,5-dimethyl-2-pyridyl)methyl]sulfinyl]-3H-imidazo[4,5-b]pyridin-3-yl]carbonyl]methyl)amino]ethyl acetate,
2-[[[5-methoxy-2-[[(4-methoxy-3,5-dimethyl-2-pyridyl)methyl]sulfinyl]-3H-imidazo[4,5-b]pyridin-3-yl]carbonyl](phenyl)amino]ethyl acetate,
4-[methyl[[(R)-2-[[[3-methyl-4-(2,2,2-trifluoroethoxy)-2-pyridyl]methyl]sulfinyl]-1H-benzimidazol-1-yl]carbonyl]amino]butyl acetate,
ethyl 4-[methyl[[(R)-2-[[[3-methyl-4-(2,2,2-trifluoroethoxy)-2-pyridyl]methyl]sulfinyl]-1H-benzimidazol-1-yl]carbonyl]amino]butyl carbonate,
ethyl 3-[methyl[[(R)-2-[[[3-methyl-4-(2,2,2-trifluoroethoxy)-2-pyridyl]methyl]sulfinyl]-1H-benzimidazol-1-yl]carbonyl]amino]propyl carbonate,
3-[methyl[[(R)-2-[[[3-methyl-4-(2,2,2-trifluoroethoxy)-2-pyridyl]methyl]sulfinyl]-1H-benzimidazol-1-yl]carbonyl]amino]propyl acetate,
3-[methyl[[(R)-2-[[[3-methyl-4-(2,2,2-trifluoroethoxy)-2-pyridyl]methyl]sulfinyl]-1H-benzimidazol-1-yl]carbonyl]amino]propane-1,2-diyl diacetate,
diethyl 3-[methyl[[(R)-2-[[[3-methyl-4-(2,2,2-trifluoroethoxy)-2-pyridyl]methyl]sulfinyl]-1H-benzimidazol-1-yl]carbonyl]amino]propane-1,2-diyl biscarbonate,
2-[[[5-methoxy-2-[[(4-methoxy-3,5-dimethyl-2-pyridyl)methyl]sulfinyl]-3H-imidazo[4,5-b]pyridin-3-yl]carbonyl](methyl)amino]ethyl 3-chlorobenzoate,
2-[methyl[[2-[[[3-methyl-4-(2,2,2-trifluoroethoxy)-2-pyridyl]methyl]sulfinyl]-1H-benzimidazol-1-yl]carbonyl]amino]ethyl acetate,
2-ethoxyethyl 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate,
3-methoxypropyl 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate,
2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl N,N-dimethylglycinate,
S-[2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl]thioacetate,
ethyl 2-[2-[methyl[[(R)-2-[[[3-methyl-4-(2,2,2-trifluoroethoxy)-2-pyridyl]methyl]sulfinyl]-1H-benzimidazol-1-yl]carbonyl]amino]ethoxy]ethyl carbonate,
ethyl 2-[methyl[[2-[methyl[[(R)-2-[[[3-methyl-4-(2,2,2-trifluoroethoxy)-2-pyridyl]methyl]sulfinyl]-1H-benzimidazol-1-yl]carbonyl]amino]ethoxy]carbonyl]amino]ethyl carbonate,
ethyl 2-[[[5-methoxy-2-[[(4-methoxy-3,5-dimethyl-2-pyridyl)methyl]sulfinyl]-1H-benzimidazol-1-yl]carbonyl](methyl)amino]ethyl carbonate,
2-[[[5-methoxy-2-[[(4-methoxy-3,5-dimethyl-2-pyridyl)methyl]sulfinyl]-1H-benzimidazol-1-yl]carbonyl](phenyl)amino]ethyl acetate,
ethyl 2-[[[(S)-5-methoxy-2-[[(4-methoxy-3,5-dimethyl-2-pyridyl)methyl]sulfinyl]-1H-benzimidazol-1-yl]carbonyl](methyl)amino]ethyl carbonate,
ethyl 2-[[[2-[[[4-(3-methoxypropoxy)-3-methyl-2-pyridyl]methyl]sulfinyl]-1H-benzimidazol-1-yl]carbonyl](methyl)amino]ethyl carbonate,
2-[[[2-[[[4-(3-methoxypropoxy)-3-methyl-2-pyridyl]methyl]sulfinyl]-1H-benzimidazol-1-yl]carbonyl](phenyl)amino]ethyl acetate,
2-[[[5-(difluoromethoxy)-2-[[(3,4-dimethoxy-2-pyridyl)methyl]sulfinyl]-1H-benzimidazol-1-yl]carbonyl](methyl)amino]ethyl ethyl carbonate,
2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl 1-methylpiperidine-4-carboxylate,
2-[[4-(aminocarbonyl)phenyl][[(R)-2-[[[3-methyl-4-(2,2,2-trifluoroethoxy)-2-pyridyl]methyl]sulfinyl]-1H-benzimidazol-1-yl]carbonyl]amino]ethyl acetate,
2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl 1-methyl-4-piperidinyl carbonate,
2-[[4-(aminocarbonyl)phenyl][[2-[[[3-methyl-4-(2,2,2-trifluoroethoxy)-2-pyridyl]methyl]sulfinyl]-1H-benzimidazol-1-yl]carbonyl]amino]ethyl acetate,
(−)-ethyl 2-[[[5-methoxy-2-[[(4-methoxy-3,5-dimethyl-2-pyridyl)methyl]sulfinyl]-3H-imidazo[4,5-b]pyridin-3-yl]carbonyl]methyl)amino]ethyl carbonate and
(+)-ethyl 2-[[[5-methoxy-2-[[(4-methoxy-3,5-dimethyl-2-pyridyl)methyl]sulfinyl]-3H-imidazo[4,5-b]pyridin-3-yl]carbonyl](methyl)amino]ethyl carbonate, a salt thereof and the like can be mentioned.

Of these, the following compounds and salts thereof are preferable.

2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl acetate,
ethyl 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate,
2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl tetrahydropyran-4-yl carbonate,
2-[methyl[[2-[[[3-methyl-4-(2,2,2-trifluoroethoxy)-2-pyridyl]methyl]sulfinyl]-1H-benzimidazol-1-yl]carbonyl]amino]ethyl tetrahydropyran-4-yl carbonate,
ethyl 2-[methyl[[2-[[[3-methyl-4-(2,2,2-trifluoroethoxy)-2-pyridyl]methyl]sulfinyl]-1H-benzimidazol-1-yl]carbonyl]amino]ethyl carbonate, ethyl 2-[[[5-methoxy-2-[[(4-methoxy-3,5-dimethyl-2-pyridyl)methyl]sulfinyl]-3H-imidazo[4,5-b]pyridin-3-yl]carbonyl](methyl)amino]ethyl carbonate,
2-[[[5-methoxy-2-[[(4-methoxy-3,5-dimethyl-2-pyridyl)methyl]sulfinyl]-3H-imidazo[4,5-b]pyridin-3-yl]carbonyl](methyl)amino]ethyl acetate,
2-[methyl[[2-[[[3-methyl-4-(2,2,2-trifluoroethoxy)-2-pyridyl]methyl]sulfinyl]-1H-benzimidazol-1-yl]carbonyl]amino]ethyl acetate,
ethyl 2-[[[5-methoxy-2-[[(4-methoxy-3,5-dimethyl-2-pyridyl)methyl]sulfinyl]-1H-benzimidazol-1-yl]carbonyl]methyl)amino]ethyl carbonate,
ethyl 2-[[[(S)-5-methoxy-2-[[(4-methoxy-3,5-dimethyl-2-pyridyl)methyl]sulfinyl]-1H-benzimidazol-1-yl]carbonyl](methyl)amino]ethyl carbonate,
ethyl 2-[[[2-[[[4-(3-methoxypropoxy)-3-methyl-2-pyridyl]methyl]sulfinyl]-1H-benzimidazol-1-yl]carbonyl](methyl)amino]ethyl carbonate, and
2-[[[5-(difluoromethoxy)-2-[[(3,4-dimethoxy-2-pyridyl)methyl]sulfinyl]-1H-benzimidazol-1-yl]carbonyl](methyl)amino]ethyl ethyl carbonate.

The compound (II) can be produced by the following method A or B.

(Method A)

The compound (II) or a salt thereof can be obtained by condensation of compound (IV) or a salt thereof with compound (V) or a salt thereof in the presence or absence of a base. The salt of compound (IV) and the salt of compound (V) here are exemplified by the above-mentioned salts of compound (II). For example, acid addition salts such as inorganic acid salt (e.g., hydrochloride, sulfate, hydrobromide, phosphate and the like), organic acid salt (e.g., acetate, trifluoroacetate, succinate, maleate, fumarate, propionate, citrate, tartrate, lactate, oxalate, methanesulfonate, p-toluenesulfonate and the like), and the like can be mentioned.

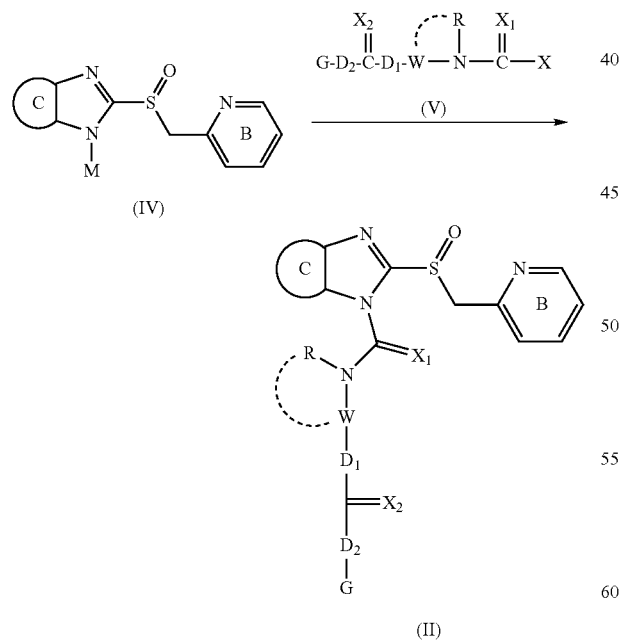

wherein each symbol is as defined above. The reaction of Method A is generally conducted in a solvent, and a solvent that does not inhibit the reaction of Method A is selected as appropriate. Examples of such solvent include ethers (e.g., dioxane, tetrahydrofuran, diethyl ether, tert-butyl methyl ether, diisopropyl ether, ethylene glycol dimethyl ether and the like), esters (e.g., ethyl formate, ethyl acetate, butyl acetate and the like), halogenated hydrocarbons (e.g., dichloromethane, chloroform, carbon tetrachloride, trichlene, 1,2-dichloroethane and the like), hydrocarbons (e.g., n-hexane, benzene, toluene and the like), amides (e.g., formamide, N,N-dimethylformamide, N,N-dimethylacetamide and the like), ketones (e.g., acetone, methyl ethyl ketone, methyl isobutyl ketone and the like), nitriles (e.g., acetonitrile, propionitrile and the like) and the like, as well as dimethyl sulfoxide, sulfolane, hexamethylphosphoramide, water and the like, which may be used alone or as a mixed solvent. The amount of the solvent to be used is not particularly limited as long as the reaction mixture can be stirred, which is generally 2- to 100-fold amount by weight, preferably 5- to 50-fold amount by weight, relative to 1 mole of compound (IV) or a salt thereof.

The amount of compound (IV) or a salt thereof to be used is generally 1-10 mole, preferably 1-3 mole, relative to 1 mole of compound (IV) or a salt thereof. The reaction of Method A is carried out within a temperature range of from about 0° C. to 100° C., preferably 20° C. to 80° C.

The reaction time of Method A varies depending on the kind of compounds (IV), (V) or a salt thereof and solvent, reaction temperature and the like, but it is generally 1 min. –96 hrs., preferably 1 min. –72 hrs., more preferably 15 min. –24 hrs.

The base in Method A is, for example, an inorganic base (e.g., sodium carbonate, potassium carbonate, calcium carbonate, sodium hydrogen carbonate etc.), a tertiary amine (e.g., triethylamine, tripropylamine, tributylamine, cyclohexyldimethylamine, pyridine, lutidine, γ-collidine, N,N-dimethylaniline, N-methylpiperidine, N-methylpyrrolidine, N-methylmorpholine, 4-dimethylaminopyridine and the like); alkylene oxides (e.g., propylene oxide, epichlorohydrin etc.) and the like. The amount of the base to be used is generally 1 mole –10 mole, preferably 1 mole –3 mole, relative to 1 mole of compound (V) or a salt thereof.

The compound (IV) or a salt thereof can be produced according to the method described in JP-A-61-50978, U.S. Pat. No. 4,628,098 and the like or a method similar thereto.

The compound (V) or a salt thereof can be produced according to a method known per se or a method analogous thereto. For example, when X is a chlorine atom, compound (V) can be obtained by reacting a compound represented by the formula (VII):

wherein each symbol is as defined above, or a salt thereof with phosgene, trichloromethyl chloroformate, bis(trichloromethyl)carbonate, thiophosgene and the like in the presence of an acid scavenger in a solvent (e.g., tetrahydrofuran, acetonitrile, dichloromethane etc.). Alternatively, compound (V) can be also obtained by treating ethylcarbamate, which is obtained by reacting compound (VII) or a salt thereof with ethyl chloroformate, with phosphorus oxychloride according to the method described in Synthetic Communications, vol. 17, p. 1887 (1987) or a method analogous thereto. As the salt of compound (VII), for example, acid addition salts such as inorganic acid salts (e.g., hydrochloride, sulfate, hydrobromide, phosphate etc.), organic acid salts (e.g., acetate, trifluoroacetate, succinate, maleate, fumarate, propionate, citrate, tartrate, lactate, oxalate, methanesulfonate, p-toluenesulfonate etc.), and the like can be mentioned.

As the acid scavenger used here, for example, inorganic bases (e.g., sodium carbonate, potassium carbonate, calcium carbonate, sodium hydrogen carbonate etc.), tertiary amine (e.g., triethylamine, tripropylamine, tributylamine, cyclohexyldimethylamine, pyridine, lutidine, γ-collidine, N,N-dimethylaniline, N-methylpiperidine, N-methylpyrrolidine, N-methylmorpholine, 4-dimethylaminopyridine etc.) and the like can be mentioned. The compound (VII) and a salt thereof can be produced according to a method known per se or a method analogous thereto. For example, when $D_1$ is other than a bond, compound (VII) can be obtained by condensing a compound represented by the formula (VIII):

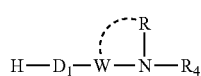

(VIII)

wherein $R_4$ is a hydrogen atom or nitrogen-protecting group, and other symbols are as defined above, or a salt thereof with carboxylic acid or thionic acid represented by the formula (IX):

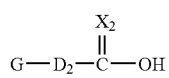

(IX)

wherein each symbol is as defined above, or a reactive derivative thereof (e.g., anhydride, halide etc.), or a salt thereof in a suitable solvent (e.g., ethyl acetate, tetrahydrofuran, dichloromethane, N,N-dimethylformamide etc., followed by deprotection as necessary. As the salt of compound (VIII), for example, acid addition salts such as inorganic acid salts (e.g., hydrochloride, sulfate, hydrobromide, phosphate etc.), organic acid salts (e.g., acetate, trifluoroacetate, succinate, maleate, fumarate, propionate, citrate, tartrate, lactate, oxalate, methanesulfonate, p-toluenesulfonate etc.) etc., and the like can be mentioned.

Alternatively, when $D_1$ is a bond, compound (VII) can be obtained by condensing carboxylic acid or thionic acid represented by the formula (X):

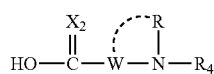

(X)

wherein each symbol is as defined above, or a reactive derivative thereof (e.g., anhydride, halide etc.), or a salt thereof with a compound represented by G-$D_2$-H in a suitable solvent (e.g., ethyl acetate, tetrahydrofuran, dichloromethane, N,N-dimethylformamide etc.), followed by deprotection, as necessary. As the salt of compound (X), for example, acid addition salts such as inorganic acid salts (e.g., hydrochloride, sulfate, hydrobromide, phosphate etc.), organic acid salts (e.g., acetate, trifluoroacetate, succinate, maleate, fumarate, propionate, citrate, tartrate, lactate, oxalate, methanesulfonate, p-toluenesulfonate etc.) and the like, salts with alkali metal (e.g., sodium, potassium etc.), alkaline earth metal (e.g., calcium etc.), ammonia etc., and the like, and for example, organic base such as dimethylamine, triethylamine, piperazine, pyrrolidine, piperidine, 2-phenylethylamine, benzylamine, ethanolamine, diethanolamine, pyridine, collidine etc., and the like can be mentioned.

As the protecting group represented by $R_4$ in the formula (VIII) and the formula (X), for example, a formyl group, a $C_{1-6}$ alkyl-carbonyl group (e.g., acetyl, ethylcarbonyl etc.), a benzyl group, a tert-butyloxycarbonyl group, a benzyloxycarbonyl group, an allyloxycarbonyl group, a $C_{7-10}$ aralkyl-carbonyl group (e.g., benzylcarbonyl etc.), a trityl group and the like are used. These groups may be substituted by 1 to 3 halogen atoms (e.g., fluorine, chlorine, bromine etc.), a nitro group and the like.

As a method for removing such protecting groups, a method known per se or a method analogous thereto is used, which is, for example, a method using an acid, a base, reduction, UV light, palladium acetate etc., and the like are used.
(Method B)

The compound (II) and a salt thereof can be obtained by subjecting compound (VI) or a salt thereof to oxidization reaction.

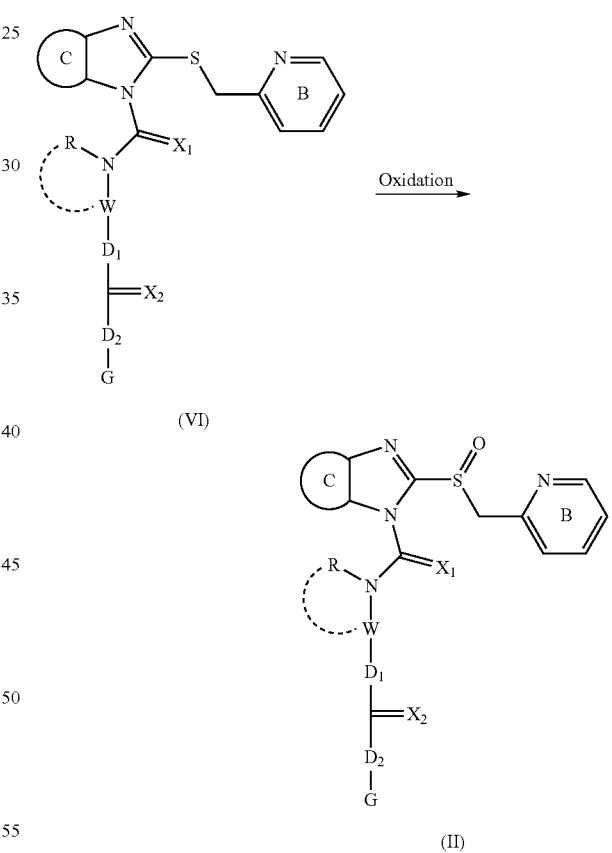

wherein each symbol is as defined above.

The reaction in Method B can be carried out using an oxidant such as nitric acid, hydrogen peroxide, peroxyacid, peroxyacid ester, ozone, dinitrogen tetraoxide, iodosobenzene, N-halosuccinimide, 1-chlorobenzotriazole, tert-butyl hypochlorite, diazabicyclo[2.2.2]octane-bromine complex, sodium metaperiodate, selenium dioxide, manganese dioxide, chromic acid, cerium ammonium nitrate, bromine, chlorine, sulfuryl chloride, magnesium monoperoxyphthalate and the like. The amount of the oxidant to be used is generally 0.5 mole −2 mole, preferably 0.8 mole −1.2 mole, per 1 mole of compound (VI) or a salt thereof. The oxidization may be carried out using the above-mentioned oxidant such as hydrogen peroxide and peroxyacids in the presence of a catalyst such as vanadium acetate, vanadium oxide acetylacetonate, titanium tetraisopropoxide and the like.

The reaction of Method B is generally carried out in a solvent inert to the above-mentioned oxidation reaction. Examples of the "inert solvent" include water, alcohols (e.g., methanol, ethanol, 1-propanol, 2-propanol etc.), ketones (e.g., acetone, methyl ethyl ketone etc.), nitriles (e.g., acetonitrile, propionitrile etc.), amides (e.g., formamide, N,N-dimethylformamide etc.), ethers (e.g., diethyl ether, tert-butyl methyl ether, diisopropyl ether, dioxane, tetrahydrofuran etc.), sulfoxides (e.g., dimethyl sulfoxide etc.) and polar solvents (e.g., sulfolane, hexamethylphosphoramide etc.), which may be used alone or as a mixed solvent thereof. The "inert solvent" is used in generally 1- to 100-fold amount by weight of compound (VI) or a salt thereof.

The reaction temperature is generally from −80° C. to 80° C., preferably from 0° C. to 30° C.

The reaction time is generally 1 min. −6 hrs., preferably 15 mins. −1 hr.

The compound (VI), which is a starting material in Method B, can be obtained by a reaction similar to that in Method A, by the use of, for example, a compound represented by the following formula (XI):

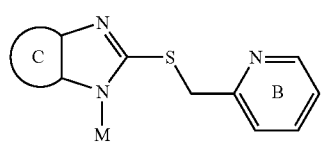

(XI)

wherein each symbol is as defined above, instead of compound (IV).

The compound (XI) can be synthesized according to the methods described in the following references or a method analogous thereto: JP-A-61-50978, JP-A-54-141783, JP-A-61-22079, JP-A-1-6270, JP-A-63-146882.

The salt of compound (VI) is exemplified by the above-mentioned salts of the compound (II), which are acid addition salts such as inorganic acid salt (e.g., hydrochloride, sulfate, hydrobromide, phosphate and the like), organic acid salt (e.g., acetate, trifluoroacetate, succinate, maleate, fumarate, propionate, citrate, tartrate, lactate, oxalate, methanesulfonate, p-toluenesulfonate and the like) and the like.

The compound (II) or a salt thereof obtained by the above-mentioned methods A or B can be isolated and purified from the reaction mixture by a separation means known per se (e.g., concentration, concentration under reduced pressure, solvent extraction, crystallization, recrystallization, phase transfer, chromatography and the like). Since compound (II) and a salt thereof obtained by the above-mentioned methods A or B encompass any isomers thereof, optically pure compound (II) and a salt thereof can be obtained by, for example, subjecting compound (II) or a salt thereof to optical resolution, or asymmetric oxidation of compound (VI) or a salt thereof.

The method of optical resolution includes methods known per se, such as a fractional recrystallization method, a chiral column method, a diastereomer method, and so forth. Asymmetric oxidation includes methods known per se, such as the method described in WO96/02535 and the like.

The "fractional recrystallization method" includes a method in which a salt is formed between a racemate and an optically active compound [e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine, etc.], which salt is separated by fractional recrystallization etc., and, if desired, subjected to a neutralization process to give a free optical isomer.

The "chiral column method" includes a method in which a racemate or a salt thereof is applied to a column for optical isomer separation (chiral column). In the case of liquid chromatography, for example, optical isomers are separated by adding a racemate to a chiral column such as ENANTIO-OVM (produced by Tosoh Corporation), the DAICEL CHIRAL series (produced by Daicel Corporation) and the like, and developing the racemate in water, a buffer (e.g., phosphate buffer), an organic solvent (e.g., hexane, ethanol, methanol, isopropanol, acetonitrile, trifluoroacetic acid, diethylamine, triethylamine, etc.), or a solvent mixture thereof. In the case of gas chromatography, for example, a chiral column such as CP-Chirasil-DeX CB (produced by GL Science) and the like is used to separate optical isomers.

The "diastereomer method" includes a method in which a racemate and an optically active reagent are reacted to give a diastereomeric mixture, which is then subjected to ordinary separation means (e.g., fractional recrystallization, chromatography, etc.) to obtain either diastereomer, which is subjected to a chemical reaction (e.g., acid hydrolysis, base hydrolysis, hydrogenolysis, etc.) to cut off the optically active reagent moiety, whereby the desired optical isomer is obtained. Said "optically active reagent" includes, for example, optically active organic acids such as MTPA [α-methoxy-α-(trifluoromethyl)phenylacetic acid], (−)-menthoxyacetic acid and the like, optically active alkoxymethyl halides such as (1R-endo)-2-(chloromethoxy)-1,3,3-trimethylbicyclo[2.2.1]heptane etc., and the like.

Further, a benzimidazole compound represented by the following general formula (III) or a salt thereof is also mentioned as the specific example of the above-mentioned prodrug.

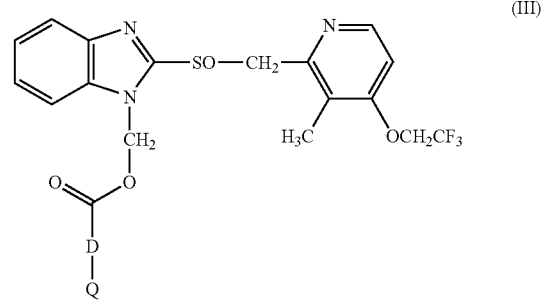

(III)

In the above-mentioned formula (III), D indicates an oxygen atom or a bond, and Q indicates a hydrocarbon group optionally having a substituent group.

The "hydrocarbon group" of the "hydrocarbon group optionally having a substituent group" represented by Q includes an aliphatic or aromatic hydrocarbon group, and an aliphatic hydrocarbon group mentioned here means a saturated or unsaturated, linear, branched or cyclic hydrocarbon group. The hydrocarbon group is preferably a hydrocarbon group having 1 to 14 carbon atoms, and for example, a $C_{1-6}$ alkyl group, a $C_{2-6}$ alkenyl group, a $C_{2-6}$ alkynyl group, a $C_{3-8}$ cycloalkyl group and a $C_{6-14}$ aryl group are exemplified. A $C_{1-6}$ alkyl group, a $C_{3-8}$ cycloalkyl group and a $C_{6-14}$ aryl group are preferred, and above all a $C_{1-6}$ alkyl group and a $C_{3-8}$ cycloalkyl group are more preferred.

The above-mentioned "alkyl group" is a linear or branched alkyl group, preferably an alkyl group having 1 to 6 carbon atoms ("$C_{1-6}$ alkyl group") and for example, methyl, ethyl, n-propyl, isopropyl, n-butyl, isobutyl, sec-butyl, tert-butyl, n-pentyl, isopentyl, neopentyl, 1-methylpropyl, n-hexyl, isohexyl, 1,1-dimethylbutyl, 2,2-dimethylbutyl, 3,3-dimethylbutyl, 3,3-dimethylpropyl, 2-ethylbutyl and the like are exemplified. An alkyl group having 1 to 4 carbon atoms is preferred. Among these, in Q, methyl, ethyl, isopropyl and tert-butyl are preferred, and tert-butyl is preferred particularly.

The above-mentioned "$C_{2-6}$ alkenyl group" is a linear or branched alkenyl group having 2 to 6 carbon atoms. Example thereof includes vinyl, n-propenyl, isopropenyl, n-butenyl, isobutenyl, sec-butenyl, tert-butenyl, n-pentenyl, isopentenyl, neopentenyl, 1-methylpropenyl, n-hexenyl, isohexenyl, 1,1-dimethylbutenyl, 2,2-dimethylbutenyl, 3,3-dimethylbutenyl, 3,3-dimethylpropenyl, 2-ethylbutenyl and the like. An alkenyl group having 2 to 4 carbon atoms is preferred and vinyl, n-propenyl and isopropenyl are preferred particularly.

The above-mentioned "$C_{2-6}$ alkinyl group" is a linear or branched alkinyl group having 2 to 6 carbon atoms. Example thereof includes ethynyl, n-propynyl (1-propynyl), isopropynyl (2-propynyl), n-butynyl, isobutynyl, sec-butynyl, tert-butynyl, n-pentynyl, isopentynyl, neopentynyl, 1-methylpropynyl, n-hexynyl, isohexynyl, 1,1-dimethylbutynyl, 2,2-dimethylbutynyl, 3,3-dimethylbutynyl, 3,3-dimethylpropynyl, 2-ethylbutynyl and the like. An alkynyl group having 2 to 3 carbon atoms is preferred and ethynyl, 1-propynyl and 2-propynyl are preferred particularly.

The above-mentioned "$C_{3-8}$ cycloalkyl group" is a cycloalkyl group having 3 to 8 carbon atoms. Example thereof includes cyclopropyl, cyclobutyl, cyclopentyl, cyclohexyl, cycloheptyl, cyclooctyl and the like. A cycloalkyl group having 5 to 7 carbon atoms is preferred and among them, cyclopentyl, cyclohexyl and cycloheptyl are preferred. Cyclohexyl is preferred particularly.

The above-mentioned "aryl group" is a monocyclic or condensed polycyclic aromatic hydrocarbon group, and preferably an aromatic hydrocarbon group having 6 to 14 carbon atoms ("$C_{6-14}$ aryl group"). Example thereof includes phenyl, naphthyl, anthryl, phenanthryl and acenaphthylenyl. An aromatic hydrocarbon group having 6 to 10 carbon atoms is preferred, and phenyl is particularly preferred in Q.

The above-mentioned "hydrocarbon group" may be substituted, and examples of the substituent group include, for example, a $C_{6-14}$ aryl group, a hydroxyl group, a halogen, an optionally halogenated $C_{1-6}$ alkoxy group, a $C_{7-12}$ aralkyloxy group, a $C_{1-5}$ alkoxy-carbonyl group, an optionally halogenated $C_{1-6}$ alkyl group, an amino group which may be substituted with a $C_{1-6}$ alkyl group, and the like.

Examples of the substituent group in the "alkyl group optionally having a substituent group" include, for example, an aryl group, a hydroxyl group, a halogen, an alkoxy group which may be substituted with 1 to 5 halogens, a $C_{7-12}$ aralkyloxy group, a $C_{1-5}$ alkoxy-carbonyl group, and the like. The number of said substituent group is 1 to 5 and preferably 1 to 3.

Examples of the substituent group in the "aryl group optionally having a substituent group" include a halogen, an alkyl group which may be substituted with 1 to 5 halogens, an aryl group, a hydroxyl group, an alkoxy group aralkyloxy group, a $C_{1-5}$ alkoxy-carbonyl group, and the like. The number of said substituent group is 1 to 5 and preferably 1 to 3.

The above-mentioned "$C_{1-6}$ alkyl group", "$C_{2-6}$ alkenyl group" and "$C_{2-6}$ alkinyl group" may be substituted, and examples of the substituent group include (i) a $C_{6-14}$ aryl group, (ii) a hydroxyl group, (iii) a halogen, (iv) an optionally halogenated $C_{1-6}$ alkoxy group, (v) a $C_{7-12}$ aralkyloxy group, (vi) a $C_{1-5}$ alkoxy-carbonyl group, (vii) an acylamino group, (viii) an amino group which may be substituted with a $C_{1-6}$ alkyl group, and the like, and among these, (i) to (vii) are preferred. The number of said substituent group is 1 to 5 and preferably 1 to 3.

The above-mentioned "$C_{3-8}$ cycloalkyl group" and "$C_{6-14}$ aryl group" may be substituted, and examples of the substituent group include (i) a $C_{6-14}$ aryl group, (ii) a hydroxyl group, (iii) a halogen, (iv) an optionally halogenated $C_{1-6}$ alkoxy group, (v) a $C_{7-12}$ aralkyloxy group, (vi) a $C_{1-5}$ alkoxy-carbonyl group, (vii) a $C_{1-6}$ alkyl group which may be substituted with halogen, (viii) an amino group which may be substituted with a $C_{1-6}$ alkyl group, and the like, and among these, (i) to (vii) are preferred particularly. The number of said substituent group is 1 to 5 and preferably 1 to 3.

In the formula (III), Q is preferably a $C_{1-6}$ alkyl group, a $C_{2-6}$ alkenyl group and a $C_{2-6}$ alkinyl group, which may have a substituent group selected from a group consisting of (i) a $C_{6-14}$ aryl group, (ii) a hydroxyl group, (iii) a halogen, (iv) an optionally halogenated $C_{1-6}$ alkoxy group, (v) a $C_{7-12}$ aralkyloxy group, (vi) a $C_{1-6}$ alkoxy-carbonyl group and (vii) an acylamino group, or a $C_{3-8}$ cycloalkyl group or a $C_{6-14}$ aryl group, which may have a substituent selected from the group consisting of (i) a $C_{6-14}$ aryl group, (ii) a hydroxyl group, (iii) a halogen, (iv) an optionally halogenated $C_{1-6}$ alkoxy group, (v) a $C_{7-12}$ aralkyloxy group, (vi) a $C_{1-5}$ alkoxy-carbonyl group, and (vii) an optionally halogenated $C_{1-6}$ alkyl group.

Q is more preferably (1) a $C_{1-6}$ alkyl group which may have 1 to 5 substituent groups selected from the group consisting of (i) a $C_{6-14}$ aryl group, (ii) a hydroxyl group, (iii) a halogen, (iv) a $C_{1-6}$ alkoxy group which may be substituted with 1 to 5 halogens, (v) a $C_{7-12}$ aralkyloxy group and (vi) a $C_{1-6}$ alkoxy-carbonyl group, or (2) a $C_{6-14}$ aryl group which may have 1 to 5 substituent groups selected from the group consisting of (i) a halogen, (ii) a $C_{1-6}$ alkyl group which may be substituted with 1 to 5 halogens, (iii) a $C_{6-14}$ aryl group, (iv) a hydroxyl group, (v) a $C_{1-6}$ alkoxy group which may be substituted with 1 to 5 halogens, (vi) a $C_{7-12}$ aralkyloxy group and (vii) a $C_{1-5}$ alkoxy-carbonyl group.

Q is further more preferably a $C_{1-6}$ alkyl group which may have a substituent group selected from the group consisting of (i) a $C_{6-14}$ aryl group, (ii) a hydroxyl group, (iii) a halogen, (iv) an optionally halogenated $C_{1-6}$ alkoxy group, (v) a $C_{7-12}$ aralkyloxy group, (vi) a $C_{1-5}$ alkoxy-carbonyl group and (vii) an acylamino group; or a $C_{3-8}$ cycloalkyl group or a $C_{6-14}$ aryl group, which may have a substituent group selected from the group consisting of (i) a $C_{6-14}$ aryl group, (ii) a hydroxyl group, (iii) a halogen, (iv) an optionally halogenated $C_{1-6}$ alkoxy group, (v) a $C_{7-12}$ aralkyloxy group, (vi) a $C_{1-5}$ alkoxy-carbonyl group and (vii) an optionally halogenated $C_{1-6}$ alkyl group.

Among these, Q is preferably a $C_{1-6}$ alkyl group which may be substituted with a $C_{6-14}$ aryl group or a $C_{6-14}$ aryl group, and Q is preferably phenyl group, methyl or tert-butyl group in particular.

In compound (III), an acidic group in the molecule can form a pharmacologically acceptable base salt with an inorganic salt or an organic salt or the like, and a basic group in the molecule can form a pharmacologically acceptable acid additive salt with an inorganic salt or an organic salt or the like.

One preferable form of compound (III) of the present invention includes a compound wherein D is a bond and Q is an alkyl group optionally having a substituent group or an aryl group optionally having a substituent group.

Examples of the inorganic base salt of compound (III) include, for example, salts with an alkali metal (for example, sodium, potassium and the like), an alkali earth metal (for example, calcium and the like), ammonia and the like, and Examples of the organic base salt of compound (III) include, for example, salts with dimethylamine, triethylamine, piperazine, pyrrolidine, piperidine, 2-phenylethylamine, benzylamine, ethanolamine, diethanolamine, pyridine, collidine and the like.

The acid additive salt of compound (III) includes, for example, inorganic acid salts (for example, hydrochloride, sulfate, hydrobromide, phosphate and the like), organic acid salts (for example, acetate, trifluoroacetate, succinate, maleate, fumarate, propionate, citrate, tartarate, lactate, oxalate, methanesulfoante, p-toluenesulfoante, and the like), etc.

The compound (III) of the present invention includes a hydrate. Said "hydrate" includes a 0.5 hydrate to 5.0 hydrates. Among these, 0.5 hydrate, 1.0 hydrate, 1.5 hydrates and 2.0 hydrates are preferred.

The compound (III) of the present invention includes a racemic compound and an optically active compound. As the optically active compound, such compound wherein one enantiomer is in enantiomer excess (e.e.) of not less than 90% is preferable, more preferably in enantiomer excess of not less than 99%. As an optically active form, an (R)-isomer represented by the formula:

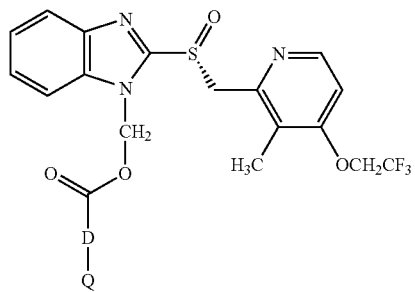

wherein each symbol is as defined above, is preferable.

The compound (III) can be produced by known methods per se, and are produced by the methods disclosed in, for example, JP-A 2002-187890, WO 02/30920 and the like, or analogous methods thereto. Further, the optically active compound (III) can be obtained by optical resolution methods (a fractional recrystallization method, a chiral column method, a diastereomer method, a method using microorganism or enzyme, and the like) and an asymmetric oxidation method, etc. As the PPI of other benzimidazole derivative, the present invention can be applied to the compound disclosed in WO 03/27098.

Although the compounding amounts of the active ingredient represented by the general formulae (I'), (I), (II) and (III) used in the present invention differ depending on the kinds and doses of the active ingredient, the amounts are, for example, about 1% by weight to about 60% by weight based on the total amount of tablets or granules of the present invention, preferably about 1% by weight to about 50% by weight and further preferably about 8% by weight to about 40% by weight. When the active ingredient is a benzimidazole compound PPI, in particular lansoprazole, the amount is about 8% by weight to about 40% by weight.

In case of capsules containing the imidazole PPI, especially benzimidazole PPI represented by the general formula (I') or (I) such as lansoprazole or an optically active compound thereof (R-isomer and the like) and the imidazole derivative PPI represented by the formula (II) and (III), 2 kinds or more of a tablet, granule or fine granule having different behavior of release (for example, 2 kinds of granules such as granules wherein the active ingredient is released comparatively quickly and granules wherein the active ingredient is released with prolonged time) may be filled in combination, using release-controlled coating-layers which have different release properties and conditions respectively. Further, 2 kinds of these release-controlled coating-layers may be stacked in 2 or more layers in the respective granules or fine granules. The preparation which enhances blood levels at a more earlier stage after administration to reveal drug efficacy and then sustain the drug efficacy by the expression of the drug efficacy of the release-controlled granule can be provided, by preparing a preparation (preferably a capsule) which contains a granule having an intermediate layer on the core particle containing the above-mentioned active ingredient and only one layer of enteric coat on said intermediate layer (accordingly, among the above-mentioned release-controlled granule or fine granule by the present invention, the granule in which the release of active ingredient is comparatively rapid), in addition to a tablet, granule or fine granule having the release-controlled coating-layers of the present invention and the digestive tract retentive gel-forming polymer; or by administering capsules containing a tablet, granule or fine granule having the release control layer of the present invention and the digestive tract retentive gel-forming polymer, together with a preparation containing only granules having a usual enteric coat. Further, when the tablet (in this case, small size tablet is preferable); granule or fine granule to be filled has an enough release-controlling function, the capsules of the present invention may not always contain the gel-forming polymer. Capsules may be prepared using only the release-controlled tablet, granule or fine granule, or by combining the release-controlled tablet, granule or fine granule with a fast-releasing type granule having only enteric coat. In case of such combined preparations and combined administration, there can be prepared the preparations by which the blood level is preferably enhanced at a more earlier stage to achieve drug efficacy and to reach the first maximal blood level, and then the second maximal blood level is reached by the release of active ingredient from granules in which the release was controlled, that is, two peaks are expressed. Further, the controlled release preparation such as the above-mentioned controlled release capsule of the present invention and a usual capsule wherein the active ingredient is comparatively released quickly may be administered at the same time or at an interval. A high blood level of active ingredient can be maintained over a long time by such combined administration.

Usual enteric-coated Granules can be produced, for example, according to the method described in JP-A 63-301826. Further, it is preferable to prepare a stabilized preparation according to the method described in JP-A 62-277322.

Further, the granule which contains lansoprazole or optically active form thereof and the like at a higher concentration and is sufficiently stabilized can be produced as follow. Namely, there are produced the granules having an active ingredient layer, an intermediate layer formed on said active ingredient layer and an enteric coated layer formed on said intermediate layer, wherein said active ingredient layer contains about 10% by weight to about 40% by weight of lansoprazole and the like based on the total amount of the granule and a basic inorganic salt as a stabilizer and average particle diameter is about 600 µm to about 2500 µm, using known granulation methods such as a fluid-bed granulation method (for example, a centrifugal fluid-bed granulation method), a fluidized granulation method and a stirring granulation method (for example, a fluid-bed fluidized granulation method).

Specifically, the active ingredient layer can be obtained, for example, by coating a core particle with a dusting powder containing the imidazole PPI, a basic metal salt, an excipient, a disintegrant and the like while spraying a binding solution such as hydroxypropylcellulose and the like on the core particle. As said core particle, for example, Nonpareil prepared by coating sucrose (75 parts by weight) with corn starch (25 parts by weight) by a known method per se, a spherical core granule using crystalline cellulose and the like are exemplified. Further, a core granule itself may be the above-mentioned active ingredient of drug. The average particle size of said granules is 14 to 80 mesh in general.

As the core, a spherically granulated product of sucrose and starch, a spherically granulated product of crystalline cellulose, a spherically granulated product of crystalline cellulose and lactose and the like are exemplified.

The ratio of coating layer relative to the core can be selected within a range of being able to control the elution property of active ingredient and the particle size of granules. For example, it is usually about 0.2 part by weight to about 5 parts by weight based on 1 part by weight of core, and preferably about 0.1 part by weight to about 5 parts by weight.

Then, the intermediate layer is formed on the active ingredient layer obtained by a conventional method. For example, the component of the intermediate layer is diluted with purified water and the like, and the mixture is sprayed in liquid form to coat the active ingredient layer. At this time, it is preferable to coat the layer while spraying a binding agent such as hydroxypropylcellulose. Examples of the intermediate layer include, for example, a layer in which sugars such as sucrose (purified white sugar (those pulverized (powder sugar) and those not pulverized) and the like), starch sugar such as corn starch, lactose, honey and sugar alcohol (D-mannitol, erythritol and the like) are appropriately compounded with polymeric base materials such as low substituted hydroxypropylcellulose, hydroxypropylcellulose, hydroxypropyl methylcellulose (for example, TC-5 and the like), polyvinyl pyrrolidone, polyvinyl alcohol, methylcellulose and hydroxyethyl methylcellulose. Excipients (for example, masking agent (titanium oxide and the like)) and antistatic agents (titanium oxide, talc and the like) which are added to prepare a preparation may be further appropriately added in the intermediate coating layer, if necessary.

The coat amount of the intermediate coating layer is usually, for example, about 0.02 part by weight to about 1.5 parts by weight based on 1 part by weight of granules containing the benzimidazole PPI, and preferably about 0.05 part by weight to about 1 part by weight.

Further, the granules which contain lansoprazole and the like at a high concentration and are sufficiently stabilized can be produced by forming a enteric coated layer on the intermediate coating layer by a conventional method. As the component of the enteric coated layer, for example, sustained release base materials such as aqueous enteric polymer base materials such as cellulose acetate phthalate (CAP), hydroxypropyl methylcellulose phthalate, hydroxymethylcellulose acetate succinate, ethyl acrylate-methyl methacrylate-trimethylammoniumethyl methacrylate chloride copolymer (Eudragit RS or RL; manufactured by Rohm Co.), methyl methacrylate-ethyl acrylate copolymer (Eudragit NE30D; manufactured by Rohm Co.), carboxymethyl ethylcellulose and shellac; plasticizers such as water-soluble polymer, triethyl citrate, polyethylene glycol (polyethylene glycol 6000 (trade name: Macrogol 6000, and the like), acetylated monoglyceride, triacetin and castor oil are used. These may be used alone or by mixing 2 kinds or more.

The coat amount of the enteric coated layer is about 10% by weight to about 70% by weight based on the total amount of granules before enteric coating, preferably about 10% by weight to about 50% by weight and more preferably about 15% by weight to about 30% by weight.

In case of a tablet, for example, the benzimidazole compound, an excipient, a binding agent, a disintegrant, a lubricant and the like are mixed to directly produce tables by compression, or the granules which is produced in same manner as the above-mentioned granules can be compressed into tablet. Further, alternatively, 2 layered tablets may be prepared with a commercially available multilayer tablet machine using the granulated granules.

Among the preparations of the present invention, preparations containing the PPI of benzimidazole compound represented by the general formula (I') such as lansoprazole and optically active form thereof, above all benzimidazole PPI compound represented by the general formula (I), and the PPI of a prodrug-type imidazole compound derivative (in particular, a compound represented by the above-mentioned general formula (II) and (III) and an optically active compound thereof) have superior anti-ulcer effect, gastric juice secretion suppressing effect, mucosa protective effect, anti-Helicobacter pylori effect and the like in vivo, and are useful as a medicine because of low toxicity. In particular, since the imidazole compound represented by the above-mentioned general formula (II) is stable to an acid, it is unnecessary to prepare an enteric preparation for oral administration, the cost of preparing enteric preparations is reduced, and the patients with weak deglutition, in particular, aged people and children are easily dosed because the size of the preparations becomes small. Further, since the absorption is faster than enteric preparations, gastric juice secretion suppressing effect is rapidly expressed, and since it is gradually converted to its original compound in vivo, it has a sustainability and is useful as anti-ulcer agents and the like. The PPI compound of compound (I') of the present invention or a salt thereof is less toxic, and can be orally or parenterally (for example, local, rectal, vein administration) and safely administered as it is or as a pharmaceutical composition by mixing with a pharmacologically acceptable carrier according to a known method per se, that is, for example, as a preparation such as a tablet (including sugar coated tablet and film coated tablet), powder, granule, capsule (including soft capsule), intraoral disintegrating tablet, liquid, injection, suppository, sustained-release agent and liniment.

The tablet, granule or fine granule of the present invention can be orally administrated to mammals (for example, human, monkey, sheep, horse, dog, cat, rabbit, mouse and the like) for the treatment and prevention of digestive ulcer (for example, gastric ulcer, duodenum ulcer, marginal ulcer and the like), Zollinger-Ellison syndrome, gastritis, reflux esophagitis, Symptomatic Gastroesophageal Reflux Disease (symptomatic GERD) with no esophagitis, NUD (Non Ulcer Dyspepsia), gastric cancer (including gastric cancer accompanied with the production promotion of interleukin-1β caused by gene polymorphism of interleukin-1), gastric MALT lymphoma and the like; the eradication of Helicobacter pylori, the suppression of upper digestive tract hemorrhage caused by the digestive ulcer, acute stress ulcer and hemorrhagic gastritis; the suppression of upper digestive tract hemorrhage caused by invasive stress (stress caused by major operation which requires intensive management after operation and by cerebro-vascular accident, head lesion, multiorgan disorder and wide range burn which require intensive care), and the treatment and prevention of ulcer caused by non steroid anti-inflammatories; the treatment and prevention of hyperchylia and ulcers caused by stress after operation, etc. The granules and capsules of the present invention may be used in combination with other active ingredients (for example, 1 to 3 active ingredients) for the eradication of Helicobacter pylori and the like.

Examples of the "other active ingredients" include, for example, an antibacterial such as an anti-Helicobacter pylori active substance, an imidazole compound and a quinolone compound, and bismuth salts. In particular, pharmaceuticals obtained by combining the granules and capsules of the present invention with the antibacterials are preferable. Among these, the combination with an antibacterial such as an anti-Helicobacter pylori active substance and an imidazole compound is preferable. Examples of the anti-Helicobacter pylori active substance include, for example, penicillin antibiotic (for example, amoxicillin, benzylpenicillin, piperacillin, mecillinam and the like), cephem antibiotic (for example, cefixime, cephachlor and the like), macrolide antibiotic (for example, erythromycin antibiotic such as erythromycin and clarithromycin), tetracycline antibiotic (for example, tetracycline, minocycline, streptomycin and the like), aminoglycoside antibiotic (for example, gentamicin, amikacin and the like), imipenem etc. In particular, penicillin antibiotic, macrolide antibiotic and the like are preferred.

Examples of the "imidazole compound" include, for example, metronidazole, miconazole and the like. Examples of the "bismuth salt" include, for example, there are mentioned bismuth acetate, bismuth citrate and the like. The antibacterial of "quinolone compound" is also preferable, and for example, ofloxacin, ciproxacin and the like are exemplified. In particular, it is preferable to use the granules and capsules of the present invention together with penicillin antibiotic (for example, amoxicillin and the like) and/or erythromycin antibiotic (for example, clarithromycin and the like) for the eradication of Helicobacter pylori.

Further, for example, in case of lansoprazole, capsules containing 15 mg of crystalline lansoprazole have been often filled in No. 3 capsules, and capsules containing 30 mg have been often filled in No. 1 capsules. However, the granules containing an active ingredient at high concentration are unexpectedly obtained by providing an intermediate coating layer, compounding a basic inorganic salt stabilizer and further controlling the particle size of granules without damaging the stability of the active ingredient and preparation. Thus, since the amount of components other than the active ingredient can be reduced, capsules containing 15 mg can be miniaturized to No. 4 to No. 5 capsules and capsules containing 30 mg can be miniaturized to No. 3 to No. 5 capsules.

Further, No. 1 to No. 3 capsule can be also used for the capsule containing 60 mg.

Further, in case of the optically active compound of lansoprazole, No. 3 to No. 5 capsule, No. 2 to No. 4 capsule and No. 1 to No. 3 capsule can be used for the capsule containing 30 mg, 40 mg and 60 mg respectively.

For example, since the capsule containing 60 mg of lansoprazole or lansoprazole R-isomer contains the active ingredient at high concentration and the capsule is miniaturized, it is easy to take and suitable for treatment of acid excessive secretion symptom including Zollinger-Ellison syndrome in particular.

Dose per day differs depending on the extent of symptom, age for administration objective, sexuality, body weight, timing of administration, interval, the kind of active ingredient and the like, and are not specifically limited. For example, when the drug is orally administered to adults (60 kg) as an anti-ulcer agent, the dose is about 0.5 to 1500 mg/day and preferably about 5 to 150 mg/day as active ingredient. These preparations containing these benzimidazole or imidazole compound may be divided to administer once a day or 2 to 3 times a day.

Further, the form of package may be also stabilized in order to improve the stability of the solid preparation of the present invention at storage or transportation. For example, the stabilization of the capsule preparation containing the benzimidazole or imidazole compound of the present invention can be improved by using package form such as package suppressing the permeation of oxygen and moisture, package replaced with gas (namely, package replaced with gas other than oxygen), vacuum package and package enclosed with a deoxidizer. The stabilization is improved by reducing oxygen amount with which the solid preparation is directly brought in contact, using these package forms. When a deoxidizer is enclosed, the pharmaceutical solid preparation is packed with an oxygen permeating material, and then another packing may be carried out together with the package.

EXAMPLES

The present invention is explained in detail in the following by referring to Reference Examples, Synthetic Examples, Examples and Experiment Examples. The present invention is not limited by the Examples.

The corn starch, hydroxypropyl cellulose (HPC-L), polyethylene glycol 6000 and titanium oxide used in the following Examples of Preparation are the conformed materials to the 14th revised Japanese Pharmacopoeia.

In the following Reference Examples and Synthetic Examples, room temperature means about 15-30° C.

$^1$H-NMR spectra were determined with CDCl$_3$, DMSO-d$_6$ and CD$_3$OD as the solvent using Varian Gemini-200 and Mercury-300; data are shown in chemical shift δ (ppm) from the internal standard tetramethylsilane.

Other symbols in the present specification mean the following.
s: singlet
d: doublet
t: triplet
q: quartet
m: multiplet
br: broad
bs: broad singlet
bm: broad multiplet
J: coupling constant Reference Example 1 tert-Butyl 2-hydroxyethyl(methyl)carbamate

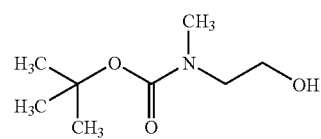

To a mixture of 2-(methylamino)ethanol (30.04 g) and ethyl acetate (90 mL) was dropwise added a mixture of di-tert-butyl dicarbonate (87.30 g) and ethyl acetate (10 mL) under ice-cooling. After stirring at room temperature for 2 hrs., the mixture was concentrated under reduced pressure. The residue was dissolved in ethyl acetate (150 mL), washed with water (100 mL) and dried over anhydrous magnesium sulfate. Concentration under reduced pressure gave the title compound (66.19 g) as a colorless oil.

$^1$H-NMR(CDCl$_3$): 1.47 (9H, s), 2.92 (3H, s), 3.40 (2H, t, J=5.1 Hz), 3.72-3.80 (2H, m).

Reference Example 2

2-(Methylamino)ethyl acetate hydrochloride

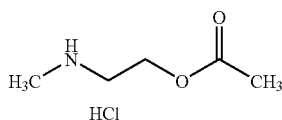

To a mixture of 2-(methylamino)ethanol (1.50 g) and ethyl acetate (20 mL) was added di-tert-butyl dicarbonate (4.37 g) under ice-cooling. After stirring under ice-cooling for 1.5 hrs., acetic anhydride (2.08 mL), pyridine (1.78 mL) and 4-dimethylaminopyridine (0.12 g) were added. After stirring at room temperature for 2 hrs., ethyl acetate (50 mL) was added to the reaction mixture, and the mixture was washed with water (50 mL), a 5% aqueous citric acid solution (50 mL) and saturated brine (50 mL). After drying over anhydrous magnesium sulfate, the mixture was concentrated under reduced pressure. To the residue was added a 4N hydrogen chloride-ethyl acetate solution (20 mL), and the mixture was stirred at room temperature for 2 hrs. Diethyl ether (10 mL) was added, and the precipitated solid was collected by filtration. The solid was dried under reduced pressure to give the title compound (2.93 g) as a white solid.

$^1$H-NMR(DMSO-d$_6$): 2.07 (3H, s), 2.53 (3H, s), 3.12-3.17 (2H, m), 4.24-4.30 (2H, m), 9.29 (2H, br).

Reference Example 3

2-(Methylamino)ethyl trimethylacetate hydrochloride

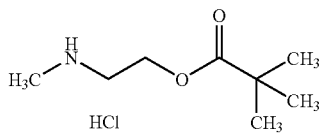

To a mixture of tert-butyl hydroxyethyl(methyl)carbamate (1.75 g) obtained in Reference Example 1 and ethyl acetate (15 mL) was added triethylamine (1.67 mL) and a mixture of trimethylacetyl chloride (1.35 mL), and ethyl acetate (5 mL) was dropwise added. After stirring at room temperature for 2 hrs., pyridine (1.62 mL) was added, and the mixture was stirred overnight at room temperature. Ethyl acetate (50 mL) was added to the reaction mixture, and the mixture was washed with water (50 mL), a 5% aqueous citric acid solution (50 mL) and saturated brine (50 mL), and dried over anhydrous magnesium sulfate. After concentration under reduced pressure, a 4N hydrogen chloride-ethyl acetate solution (10 mL) was added to the residue. After stirring at room temperature for 2 hrs., diethyl ether (10 mL) was added, and the precipitated solid was collected by filtration. The solid was dried under reduced pressure to give the title compound (1.65 g) as a white solid.

$^1$H-NMR(DMSO-d$_6$): 1.18 (9H, s), 2.56 (3H, s), 3.17 (2H, t, J=10.5 Hz), 4.22-4.28 (2H, m), 9.19 (2H, br).

Reference Example 4

2-(Methylamino)ethyl cyclohexanecarboxylate hydrochloride

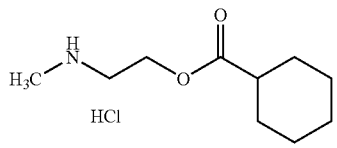

To a mixture of tert-butyl 2-hydroxyethyl(methyl)carbamate (1.75 g) obtained in Reference Example 1 and ethyl acetate (20 mL) were added pyridine (0.97 mL) and 4-dimethylaminopyridine (catalytic amount), and cyclohexanecarbonyl chloride (1.60 mL) was dropwise added.

After stirring at room temperature for 2 hrs., pyridine (0.65 mL) and cyclohexanecarbonyl chloride (0.58 mL) were added, and the mixture was stirred overnight at room temperature. Ethyl acetate (50 mL) was added to the reaction mixture, and the mixture was washed with water (50 mL), a 5% aqueous citric acid solution (50 mL) and saturated brine (50 mL), and dried over anhydrous magnesium sulfate. After concentration under reduced pressure, a 4N hydrogen chloride-ethyl acetate solution (10 mL) was added to the residue. After stirring at room temperature for 2 hrs., diethyl ether (10 mL) was added, and the precipitated solid was collected by filtration. The solid was dried under reduced pressure to give the title compound (1.88 g) as a white solid.

$^1$H-NMR(DMSO-d$_6$): 1.10-1.45 (5H, m), 1.54-1.73 (3H, m), 1.83-1.93 (2H, m), 2.29-2.42 (1H, m), 2.54 (3H, s), 3.12-3.18 (2H, m), 4.23-4.29 (2H, m), 9.23 (2H, br).

Reference Example 5

2-(Methylamino)ethyl benzoate hydrochloride

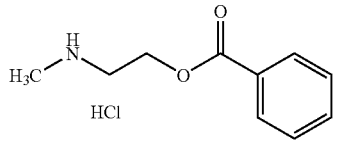

To a mixture of 2-(methylamino)ethanol (30.04 g) and ethyl acetate (90 mL) was dropwise added a mixture of di-tert-butyl Bicarbonate (87.30 g) and ethyl acetate (10 mL) under ice-cooling. After stirring at room temperature for 1 hr., benzoyl chloride (61.8 g) and pyridine (38.8 mL) were added under ice-cooling. After stirring at room temperature for 1 hr., a solid was filtered off. The solid was washed with ethyl acetate (100 mL) and the filtrate and the washing were combined, which was washed with water (100 mL) and saturated brine (100 mL). After drying over anhydrous magnesium sulfate, the mixture was concentrated under reduced pressure. The residue was dissolved in ethyl acetate (100 mL), a 4N hydrogen chloride-ethyl acetate solution (200 mL) was added, and the mixture was stirred at room temperature for 30 min. Diethyl ether (100 mL) was added and a solid was collected by filtration. The solid was washed twice with ethyl acetate (100 mL) and dried under reduced pressure at 60° C. to give the title compound (57.4 g) as a white solid.

$^1$H-NMR(DMSO-$d_6$): 2.62 (3H, s), 3.32 (2H, m), 4.53 (2H, t, J=9.9 Hz), 7.51-7.57 (2H, m), 7.68 (1H, m), 8.11 (2H, d, J=7.8 Hz), 9.26 (2H, bs).

Reference Example 6

2-(Methylamino)ethyl 4-methoxybenzoate hydrochloride

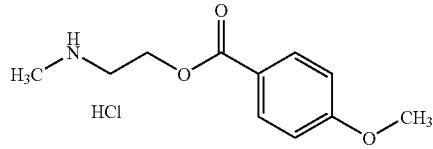

To a mixture of tert-butyl 2-hydroxyethyl(methyl)carbamate (1.75 g) obtained in Reference Example 1 and ethyl acetate (10 mL) were added 4-methoxybenzoyl chloride (1.88 g) and pyridine (0.97 mL). After stirring at room temperature for 14 hrs., 4-methoxybenzoyl chloride (0.70 g) and pyridine (0.97 mL) were added and the mixture was stirred at room temperature for 1 hr. Ethyl acetate (80 mL) was added to the reaction mixture, and the mixture was washed with water (20 mL), a saturated aqueous sodium hydrogen carbonate solution (20 mL) and water (20 mL), and dried over anhydrous magnesium sulfate. After concentration under reduced pressure, the residue was dissolved in ethyl acetate (10 mL), and a 4N hydrogen chloride-ethyl acetate solution (10 mL) was added. After stirring at room temperature for 1 hr., diethyl ether (20 mL) was added, and the precipitated solid was collected by filtration. The solid was washed twice with ethyl acetate (15 mL) and dried under reduced pressure at 60° C. to give the title compound (1.99 g) as a white solid.

$^1$H-NMR(DMSO-$d_6$): 2.62 (3H, s), 3.32 (2H, m), 4.48 (2H, t, J=5.0 Hz), 7.07 (2H, d, J=8.7 Hz), 8.06 (2H, d, J=8.7 Hz), 9.04 (2H, bs).

Reference Example 7

2-(Methylamino)ethyl 3-chlorobenzoate hydrochloride

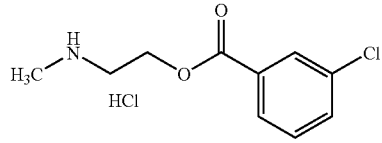

To a mixture of tert-butyl 2-hydroxyethyl(methyl)carbamate (1.75 g) obtained in Reference Example 1 and ethyl acetate (10 mL) were added 3-chlorobenzoyl chloride (1.92 g) and pyridine (0.97 mL). After stirring at room temperature for 1 hr., the mixture was stirred at 60° C. for 6 hrs. Ethyl acetate (80 mL) was added to the reaction mixture, and the mixture was washed with water (20 mL), a saturated aqueous sodium hydrogen carbonate solution (20 mL) and water (20 mL), and dried over anhydrous magnesium sulfate. After concentration under reduced pressure, a 4N hydrogen chloride-ethyl acetate solution (10 mL) was added to the residue. After stirring at room temperature for 22 hrs., diethyl ether (15 mL) was added, and the precipitated solid was collected by filtration.

The solid was washed twice with ethyl acetate (15 mL) and dried under reduced pressure at 60° C. to give the title compound (2.01 g) as a white solid.

$^1$H-NMR(DMSO-$d_6$): 2.63 (3H, s), 3.32 (2H, m), 4.53 (2H, t, J=4.9 Hz), 7.60 (1H, t, J=8.0 Hz), 7.78 (1H, d, J=8.0 Hz), 8.05 (1H, d, J=8.0 Hz), 8.15 (1H, s), 9.07 (2H, bs).

Reference Example 8

2-(Methylamino)ethyl 3,4-difluorobenzoate hydrochloride

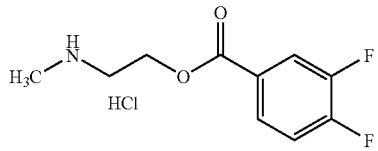

To a mixture of tert-butyl 2-hydroxyethyl(methyl)carbamate (1.75 g) obtained in Reference Example 1 and ethyl acetate (10 mL) were added 3,4-difluorobenzoyl chloride (1.77 g) and pyridine (0.97 mL). After stirring at room temperature for 3 days, ethyl acetate (80 mL) was added to the reaction mixture. The mixture was washed with water (20 mL), a saturated aqueous sodium hydrogen carbonate solution (20 mL) and water (20 mL), and dried over anhydrous magnesium sulfate. After concentration under reduced pressure, a 4N hydrogen chloride-ethyl acetate solution (10 mL) was added to the residue. After stirring at room temperature for 4 hrs, the mixture was concentrated under reduced pressure. The residue was washed with ethyl acetate (15 mL), and dried under reduced pressure at 60° C. to give the title compound (2.05 g) as a white solid.

$^1$H-NMR(DMSO-$d_6$): 2.62 (3H, s), 3.32 (2H, m), 4.53 (2H, t, J=5.0 Hz), 7.64 (1H, m), 8.00 (1H, m), 8.25 (1H, m), 9.25 (2H, bs).

Reference Example 9

2-(Methylamino)ethyl 4-trifluoromethoxybenzoate hydrochloride

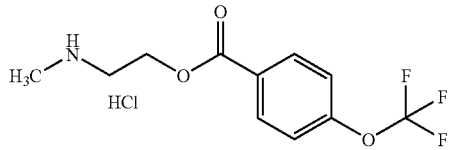 [SMILES: CNCCOC(=O)c1ccc(OC(F)(F)F)cc1 ; Cl]

To a mixture of tert-butyl 2-hydroxyethyl(methyl)carbamate (1.30 g) obtained in Reference Example 1 and ethyl acetate (10 mL) were added 4-trifluoromethoxybenzoyl chloride (1.83 g) and pyridine (0.72 mL). The mixture was stirred at 60° C. for 25 hrs. Ethyl acetate (60 mL) was added to the reaction mixture, and the mixture was washed with water (30 mL), a saturated aqueous sodium hydrogen carbonate solution (20 mL) and water (20 mL), and dried over anhydrous magnesium sulfate. After concentration under reduced pressure, a 4N hydrogen chloride-ethyl acetate solution (10 mL) was added to the residue. After stirring at room temperature for 14.5 hrs., the mixture was concentrated under reduced pressure. The residue was washed twice with ethyl acetate (15 mL), and dried under reduced pressure at 60° C. to give the title compound (1.83 g) as a white solid.

$^1$H-NMR(DMSO-$d_6$): 2.63 (3H, s), 3.31 (2H, m), 4.54 (2H, t, J=4.9 Hz), 7.55 (2H, d, J=8.5 Hz), 8.24 (2H, d, J=8.5 Hz), 9.02 (2H, bs).

Reference Example 10

2-(Methylamino)ethyl 4-fluorobenzoate hydrochloride

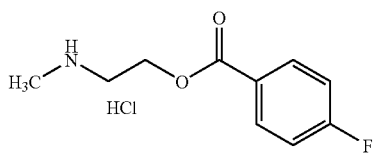

To a mixture of tert-butyl 2-hydroxyethyl(methyl)carbamate (1.75 g) obtained in Reference Example 1 and ethyl acetate (10 mL) were added 4-fluorobenzoyl chloride (1.74 g) and pyridine (0.97 mL). The mixture was stirred at room temperature for 6.5 hrs. Ethyl acetate (80 mL) was added to the reaction mixture, and the mixture was washed with water (30 mL), a saturated aqueous sodium hydrogen carbonate solution (30 mL), water (30 mL) and saturated brine (30 mL), and dried over anhydrous magnesium sulfate. After concentration under reduced pressure, a 4N hydrogen chloride-ethyl acetate solution (10 mL) was added to the residue. After stirring at room temperature for 1 hr., the precipitated solid was collected by filtration. The solid was washed twice with ethyl acetate (15 mL) and dried under reduced pressure at 60° C. to give the title compound (1.89 g) as a white solid.

$^1$H-NMR(DMSO-$d_6$): 2.62 (3H, s), 3.32 (2H, m), 4.52 (2H, t, J=4.9 Hz), 7.34-7.44 (2H, m), 8.16-8.24 (2H, m), 9.18 (2H, bs).

Reference Example 11

2-(Methylamino)ethyl 3,4,5-trimethoxybenzoate hydrochloride

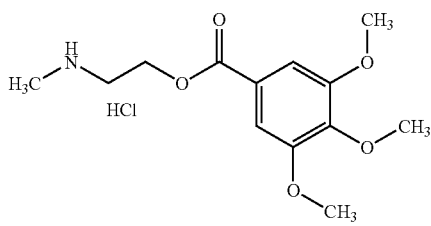

To a mixture of tert-butyl 2-hydroxyethyl(methyl)carbamate (1.75 g) obtained in Reference Example 1 and ethyl acetate (10 mL) were added 3,4,5-trimethoxybenzoyl chloride (2.54 g) and pyridine (0.97 mL). After stirring at 60° C. for 14 hrs., 3,4,5-trimethoxybenzoyl chloride (1.30 g), pyridine (0.97 mL) and ethyl acetate (10 mL) were added, and the mixture was stirred at 60° C. for 24 hrs. The reaction mixture was filtered and ethyl acetate (50 mL) and water (30 mL) were added to the filtrate. After partitioning, ethyl acetate layer was washed with 1N hydrochloric acid (30 mL), water (30 mL), an aqueous copper (II) sulfate solution (30 mL), water (30 mL) and saturated brine (30 mL), and dried over anhydrous magnesium sulfate. After concentration under reduced pressure, the residue was purified by silica gel column chromatography (eluted with ethyl acetate:hexane=1:1). A 4N hydrogen chloride-ethyl acetate solution (10 mL) was added to the purified product. After stirring at room temperature for 4 hrs, the mixture was concentrated under reduced pressure. Toluene (10 mL) was added, and the mixture was concentrated under reduced pressure. The residue was suspended in ethyl acetate, and the solid was filtrated. After washing with ethyl acetate (15 mL), the solid was dried under reduced pressure to give the title compound (1.79 g) as a white solid.

$^1$H-NMR(DMSO-$d_6$): 2.61 (3H, s), 3.28-3.35 (2H, m), 3.74 (3H, s), 3.87 (6H, s), 4.48-4.54 (2H, m), 7.40 (2H, s), 9.43 (2H, br).

Reference Example 12

2-(Methylamino)ethyl 2-pyridinecarboxylate dihydrochloride

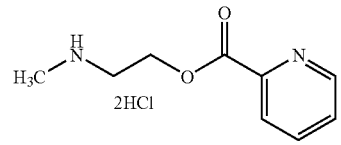

To a solution (100 mL) of tert-butyl 2-hydroxyethyl(methyl)carbamate (1.75 g) obtained in Reference Example 1, 2-pyridinecarbonyl chloride hydrochloride (2.67 g), pyridine (1.21 mL) and 4-dimethylaminopyridine (0.122 g) in tetrahydrofuran was dropwise added triethylamine (2.09 mL) under ice-cooling, and the mixture was stirred at room temperature for 6 hrs. Water (200 mL) was added to the reaction mixture and the mixture was extracted with ethyl acetate (150 mL). The organic layer was washed successively with a 5% aqueous copper (II) sulfate solution (100 mL), water (100 mL) and saturated brine (100 mL), dried over anhydrous sodium sulfate and evaporated under reduced pressure. The residue was dissolved in ethyl acetate (50 mL) and ethanol (100 mL), and a 4N hydrogen chloride-ethyl acetate solution (15 mL) was added. The mixture was stirred at room temperature for 1 hr. The precipitated solid was collected by filtration, washed twice with ethyl acetate (100 mL), and dried under reduced pressure at 60° C. to give the title compound (1.08 g) as a white solid.

$^1$H-NMR(DMSO-$d_6$): 2.62 (3H, t, J=5.4 Hz), 3.35 (2H, m), 4.63 (2H, t, J=5.0 Hz), 5.26 (1H, bs), 7.77-7.84 (1H, m), 8.14-8.18 (1H, m), 8.36-8.40 (1H, m), 8.70-8.90 (1H, m), 9.48 (2H, br).

Reference Example 13

2-(Methylamino)ethyl methoxyacetate

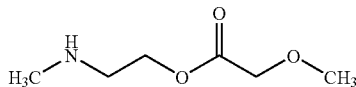

To a mixture of tert-butyl 2-hydroxyethyl (methyl)carbamate (1.75 g) obtained in Reference Example 1 and ethyl acetate (10 mL) were added methoxyacetyl chloride (1.20 g) and pyridine (0.97 mL). After stirring at room temperature for 3 hrs., ethyl acetate (70 mL) was added to the reaction mixture. The mixture was washed with water (20 mL), a saturated aqueous sodium hydrogen carbonate solution (20 mL) and water (20 mL), and dried over anhydrous magnesium sulfate. After concentration under reduced pressure, the residue was dissolved in ethyl acetate (5 mL), and a 4N hydrogen chloride-ethyl acetate solution (10 mL) was added. After stirring at room temperature for 1 hr., the mixture was concentrated under reduced pressure. Water (60 mL) and diethyl ether (30 mL) were added to the residue. After stirring, the aqueous layer was separated and taken. The aqueous layer was basified with sodium hydrogen carbonate and extracted twice with ethyl acetate (40 mL). The ethyl acetate layer was dried over anhydrous magnesium sulfate and concentrated under reduced pressure to give the title compound (1.00 g) as a colorless oil.

$^1$H-NMR(CDCl$_3$): 2.40 (1H, bs), 3.06 (3H, s), 3.44 (3H, s), 3.57 (2H, t, J=5.1 Hz), 3.75-3.82 (2H, m), 4.13 (2H, s).

Reference Example 14

Ethyl 2-(methylamino)ethyl carbonate hydrochloride

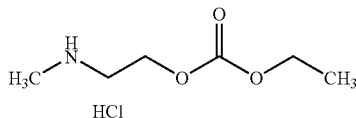

To a mixture of tert-butyl 2-hydroxyethyl(methyl)carbamate (1.75 g) obtained in Reference Example 1 and ethyl acetate (20 mL) were added pyridine (0.97 mL) and 4-dimethylaminopyridine (catalytic amount), and ethyl chlorocarbonate (1.25 mL) was dropwise added. The mixture was stirred overnight at room temperature and ethyl acetate (50 mL) was added. The mixture was washed with water (50 mL), a 5% aqueous citric acid solution (50 mL) and saturated brine (50 mL), and dried over anhydrous magnesium sulfate. After concentration under reduced pressure, a 4N hydrogen chloride-ethyl acetate solution (10 mL) was added to the residue. After stirring at room temperature for 2 hrs., diethyl ether (10 mL) was added, and the precipitated solid was collected by filtration. The solid was dried under reduced pressure to give the title compound (1.66 g) as a white solid.

$^1$H-NMR(DMSO-$d_6$): 1.23 (3H, t, J=7.1 Hz), 2.54 (3H, s), 3.16-3.22 (2H, m), 4.15 (2H, q, J=7.1 Hz), 4.32-4.37 (2H, m), 9.25 (2H, br).

Reference Example 15

Isopropyl 2-(methylamino)ethyl carbonate hydrochloride

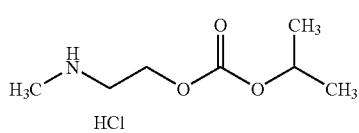

To a mixture of tert-butyl 2-hydroxyethyl(methyl)carbamate (3.50 g) obtained in Reference Example 1 and ethyl acetate (20 mL) were added isopropyl chlorocarbonate (1.35 g) and pyridine (1.94 mL) under ice-cooling. After stirring under ice-cooling for 3.5 hrs., isopropyl chlorocarbonate (1.84 g) was added, and the mixture was stirred at room temperature for 2.5 hrs. Ethyl acetate (120 mL) was added to the reaction mixture, and the mixture was washed with water (50 mL) and saturated brine (50 mL), and dried over anhydrous magnesium sulfate. After concentration under reduced pressure, a 4N hydrogen chloride-ethyl acetate solution (10 mL) was added to the residue. After stirring at room temperature for 2 hrs., the precipitated solid was collected by filtration. The solid was washed with ethyl acetate (15 mL), and dried under reduced pressure at 60° C. to give the title compound (1.38 g) as a white solid.

$^1$H-NMR(DMSO-$d_6$): 1.25 (6H, d, J=6.2 Hz), 2.56 (3H, s), 3.20 (2H, t, J=5.1 Hz), 4.32 (2H, t, J=5.1 Hz), 4.80 (1H, m), 8.95 (2H, bs).

Reference Example 16

Benzyl 2-(methylamino)ethyl carbonate hydrochloride

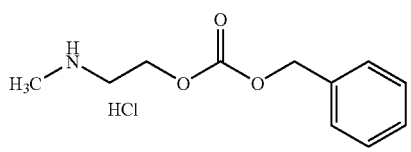

To a mixture of tert-butyl 2-hydroxyethyl(methyl)carbamate (1.75 g) obtained in Reference Example 1 and ethyl acetate (20 mL) were added pyridine (0.97 mL) and 4-dimethylaminopyridine (catalytic amount), and benzyl chlorocarbonate (1.57 mL) was dropwise added. After stirring at room temperature for 2 hrs., pyridine (0.65 mL) and benzyl chlorocarbonate (1.28 mL) were added. After stirring at room temperature for 5 days, pyridine (0.81 mL) was added under ice-cooling and a solution (5 mL) of benzyl chlorocarbonate (1.43 mL) in ethyl acetate was dropwise added slowly. After stirring at room temperature for 2 hrs., ethyl acetate (50 mL) was added to the mixture, washed with water (50 mL), a 5% aqueous citric acid solution (50 mL) and saturated brine (50 mL), and dried over anhydrous magnesium sulfate. After concentration under reduced pressure, a 4N hydrogen chloride-ethyl acetate solution (10 mL) was added to the residue.

After stirring at room temperature for 2 hrs., diethyl ether (10 mL) was added, and the precipitated solid was collected by filtration. The solid was dried under reduced pressure to give the title compound (1.99 g) as a white solid.

$^1$H-NMR(DMSO-$d_6$): 2.55 (3H, s), 3.21 (2H, t, J=5.1 Hz), 4.37 (2H, t, J=5.1 Hz), 5.18 (2H, s), 7.30-7.50 (5H, m), 9.07 (2H, br).

Reference Example 17

2-(Methylamino)ethyl tetrahydropyran-4-yl carbonate hydrochloride

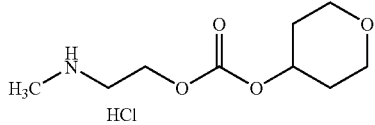

To a solution (40 mL) of bis(trichloromethyl)carbonate (2.97 g) in tetrahydrofuran was dropwise added a solution (10 mL) of pyridine (2.43 mL) in tetrahydrofuran under ice-cooling. After stirring under ice-cooling for 10 min., a solution (20 mL) of tetrahydropyran-4-ol (1.91 g) in tetrahydrofuran was dropwise added slowly. After stirring at room temperature for 2 hrs., the mixture was concentrated under reduced pressure, and ethyl acetate (50 mL) and water (50 mL) were added to the residue. The ethyl acetate layer was separated and taken, washed with 0.2N hydrochloric acid (20 mL) and saturated brine (50 mL), and dried over anhydrous magnesium sulfate. Concentration under reduced pressure gave tetrahydropyran-4-yl chlorocarbonate (1.53 g). To a mixture of tert-butyl 2-hydroxyethyl(methyl)carbamate (1.40 g) obtained in Reference Example 1 and tetrahydrofuran (20 mL) was added pyridine (0.78 mL), and a solution (10 mL) of tetrahydropyran-4-yl chlorocarbonate (1.53 g) obtained above in tetrahydrofuran was dropwise added, and the mixture was stirred overnight at room temperature. After concentration of the reaction mixture under reduced pressure, water (50 mL) was added, the mixture was extracted with ethyl acetate (50 mL). The residue was washed with a 5% aqueous citric acid solution (50 mL) and saturated brine (50 mL), and dried over anhydrous magnesium sulfate. After concentration under reduced pressure, the residue was purified by silica gel column chromatography (eluted with ethyl acetate:hexane=4:1, then 3:2). The obtained colorless oil (2.03 g) was dissolved in diethyl ether (2 mL), and a 4N hydrogen chloride-ethyl acetate solution (5 mL) was added. After stirring at room temperature for 30 min., diethyl ether (10 mL) was added and the mixture was stirred overnight. The precipitated solid was collected by filtration and dried under reduced pressure to give the title compound (1.20 g) as a white solid.

$^1$H-NMR(DMSO-$d_6$): 1.50-1.65 (2H, m), 1.87-1.98 (2H, m), 2.54 (3H, s), 3.20 (2H, m), 3.40-3.50 (2H, m), 3.74-3.83 (2H, m), 4.36 (2H, t, J=5.1 Hz), 4.72-4.83 (1H, m), 9.32 (2H, br).

Reference Example 18

2-Methoxyethyl 2-(methylamino)ethyl carbonate hydrochloride

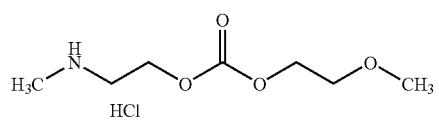

To a mixture of tert-butyl 2-hydroxyethyl(methyl)carbamate (1.75 g) obtained in Reference Example 1 and ethyl acetate (20 mL) was added pyridine (1.62 mL) and a solution (5 mL) of 2-methoxyethyl chlorocarbonate (2.77 g) in ethyl acetate was dropwise added slowly, and the mixture was stirred overnight at room temperature. After concentration of the reaction mixture under reduced pressure, water (50 mL) was added, the mixture was extracted with ethyl acetate (50 mL). The mixture was washed with 5% aqueous citric acid solution (50 mL) and saturated brine (50 mL), and dried over anhydrous magnesium sulfate. After concentration under reduced pressure, the residue was dissolved in diethyl ether (2 mL), and a 4N hydrogen chloride-ethyl acetate solution (5 mL) was added. After stirring at room temperature for 30 min., diethyl ether (10 mL) was added, and the mixture was stirred overnight. The precipitated solid was collected by filtration, and dried under reduced pressure to give the title compound (1.56 g) as a white solid.

$^1$H-NMR(DMSO-$d_6$): 2.54 (3H, s), 3.19 (2H, m), 3.26 (3H, s), 3.52-3.57 (2H, m), 4.20-4.25 (2H, m), 4.33-4.39 (2H, m), 9.26 (2H, br).

Reference Example 19 tert-Butyl ethyl(2-hydroxyethyl)carbamate

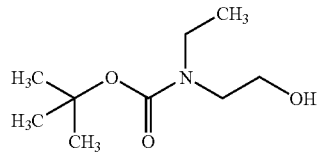

To a mixture of 2-(ethylamino)ethanol (8.91 g) and ethyl acetate (100 mL) was added di-tert-butyl dicarbonate (21.8 g) under ice-cooling. After stirring at room temperature for 3 days, the mixture was washed with saturated brine (100 mL), and dried over anhydrous magnesium sulfate. Concentration under reduced pressure gave the title compound (19.0 g) as a colorless oil.

$^1$H-NMR(CDCl$_3$): 1.11 (3H, t, J=7.0 Hz), 1.47 (9H, s), 3.27 (2H, q, J=7.0 Hz), 3.37 (2H, t, J=5.2 Hz), 3.73 (2H, q, J=5.2 Hz).

Reference Example 20

2-(Ethylamino)ethyl acetate hydrochloride

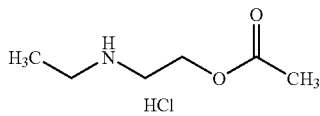

To a mixture of tert-butyl ethyl(2-hydroxyethyl)carbamate (1.89 g) obtained in Reference Example 19 and ethyl acetate (20 mL) were added acetic anhydride (1.04 mL), pyridine (0.89 mL) and 4-dimethylaminopyridine (0.061 g). After stirring at room temperature for 3 hrs., ethyl acetate (50 mL) was added, and the mixture was washed with water (50 mL), a 5% aqueous citric acid solution (50 mL) and saturated brine (50 mL). After drying over anhydrous magnesium sulfate, the mixture was concentrated under reduced pressure. A 4N hydrogen chloride-ethyl acetate solution (10 mL) was added to the residue, and the mixture was stirred at room temperature for 1 hr. Ethyl acetate (10 mL) and diethyl ether (20 mL) were added, and the precipitated solid was collected by filtration. The solid was dried under reduced pressure to give the title compound (1.54 g) as a white solid.

$^1$H-NMR(DMSO-d$_6$): 1.22 (3H, t, J=7.3 Hz), 2.07 (3H, s), 2.95 (2H, q, J=7.3 Hz), 3.15 (2H, t, J=5.3 Hz), 4.24-4.30 (2H, m), 9.17 (2H, br).

Reference Example 21

Tert-Butyl 2-hydroxyethyl(isopropyl)carbamate

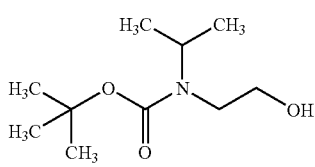

To a solution (30 mL) of 2-(isopropylamino)ethanol (10.0 g) in tetrahydrofuran was added di-tert-butyl dicarbonate (22.2 g), and the mixture was stirred at room temperature for 1 hr. The reaction mixture was concentrated under reduced pressure and water (100 mL) was added to the residue. The mixture was extracted with ethyl acetate (200 mL). The ethyl acetate layer was washed with saturated brine (100 mL), dried over anhydrous sodium sulfate and concentrated under reduced pressure to give the title compound (21.21 g) as a colorless oil.

$^1$H-NMR(CDCl$_3$): 1.12 (6H, d, J=6.6 Hz), 3.30 (2H, t, J=5.0 Hz), 3.71 (2H, t, J=5.0 Hz), 3.80-4.30 (1H, m).

Reference Example 22

2-(Isopropylamino)ethyl acetate hydrochloride

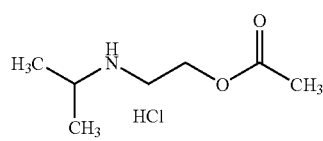

To a solution (15 mL) of tert-butyl 2-hydroxyethyl(isopropyl)carbamate (5.0 g) obtained in Reference Example 21 in tetrahydrofuran were added pyridine (6.0 mL) and acetic anhydride (2.79 mL) and the mixture was stirred at room temperature for 18 hrs. The reaction mixture was concentrated under reduced pressure, water (50 mL) was added to the residue, and the mixture was extracted with ethyl acetate (100 mL). The ethyl acetate layer was washed with a 5% aqueous citric acid solution (50 mL) and saturated brine (50 mL), dried over anhydrous sodium sulfate and concentrated under reduced pressure. The obtained colorless oil was dissolved in a 4N hydrogen chloride-ethyl acetate solution (10 mL), and the mixture was stirred at room temperature for 1 hr. The precipitated solid was collected by filtration, and dried under reduced pressure to give the title compound (3.14 g) as a colorless solid.

$^1$H-NMR(DMSO-d$_6$): 1.25 (6H, d, J=6.6 Hz), 2.08 (3H, s), 3.10-3.40 (3H, m), 4.29 (2H, t, J=6.0 Hz), 9.11 (2H, br).

Reference Example 23

Ethyl 2-(isopropylamino)ethyl carbonate hydrochloride

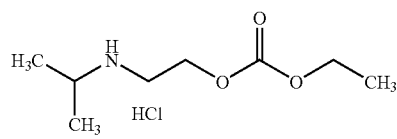

To a solution (15 mL) of tert-butyl 2-hydroxyethyl(isopropyl)carbamate (5.0 g) obtained in Reference Example 21 in tetrahydrofuran were added pyridine (6.0 mL) and ethyl chlorocarbonate (2.81 mL) and the mixture was stirred at room temperature for 18 hrs. The reaction mixture was concentrated under reduced pressure, and water (50 mL) was added to the residue, and the mixture was extracted with ethyl acetate (100 mL). The ethyl acetate layer was washed with a 5% aqueous citric acid solution (50 mL) and saturated brine (50 mL), dried over anhydrous sodium sulfate and the mixture was concentrated under reduced pressure. The obtained colorless oil was dissolved in a 4N hydrogen chloride-ethyl acetate solution (10 mL), and the mixture was stirred at room temperature for 1 hr. The precipitated solid was collected by filtration and dried under reduced pressure to give the title compound (3.34 g) as a colorless solid.

$^1$H-NMR(DMSO-d$_6$): 1.20-1.30 (9H, m), 3.10-3.40 (3H, m), 4.17 (2H, q, J=7.4 Hz), 4.37 (2H, t, J=5.6 Hz), 9.13 (2H, br).

Reference Example 24 tert-Butyl cyclohexyl(2-hydroxyethyl)carbamate

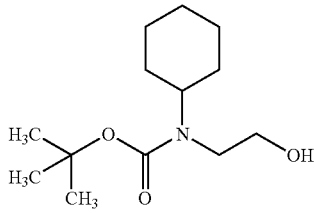

To a solution (200 mL) of 2-(cyclohexylamino)ethanol (14.3 g) in ethanol was dropwise added di-tert-butyl dicarbonate (21.8 g). After stirring at room temperature for 2 days, the mixture was concentrated under reduced pressure. The residue was dissolved in ethyl acetate (200 mL), washed with water (100 mL) and saturated brine (100 mL), and dried over anhydrous sodium sulfate. Concentration under reduced pressure gave the title compound (24.2 g) as a colorless oil.

$^1$H-NMR(CDCl$_3$): 1.26-1.39 (4H, m), 1.47 (9H, s), 1.61-1.81 (6H, m), 3.30-3.40 (2H, m), 3.69 (2H, t, J=5.4 Hz), 3.66-3.90 (2H, br).

Reference Example 25

2-(Cyclohexylamino)ethyl acetate hydrochloride

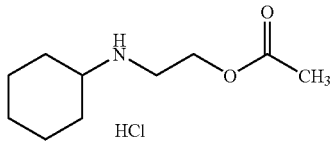

To a solution (50 mL) of tert-butyl cyclohexyl(2-hydroxyethyl)carbamate (2.43 g) obtained in Reference Example 24 in tetrahydrofuran were added pyridine (1.05 mL), acetic anhydride (1.23 mL) and 4-dimethylaminopyridine (0.122 g) under ice-cooling, and the mixture was stirred at room temperature for 12 hrs. Ethyl acetate (100 mL) was added to the reaction mixture and the mixture was washed successively with a saturated aqueous sodium hydrogen carbonate solution (100 mL), a 5% aqueous copper (II) sulfate solution (100 mL) and saturated brine (100 mL), and dried over anhydrous sodium sulfate. The mixture was concentrated under reduced pressure. The residue was dissolved in ethyl acetate (15 mL), and a 4N hydrogen chloride-ethyl acetate solution (15 mL) was added. After stirring at room temperature for 3 hrs., diisopropyl ether (20 mL) was added, and the precipitated solid was collected by filtration to give the title compound (1.78 g) as a white solid.

$^1$H-NMR(DMSO-d$_6$): 1.05-2.03 (10H, m), 2.07 (3H, s), 2.90-3.10 (1H, m), 3.17 (2H, t, J=5.2 Hz), 4.29 (2H, t, J=5.2 Hz), 9.19 (2H, br).

Reference Example 26

2-(Cyclohexylamino)ethyl ethyl carbonate hydrochloride

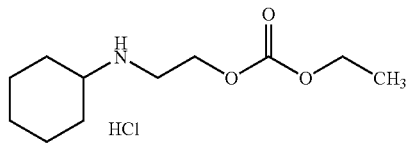

To a solution (50 mL) of tert-butyl cyclohexyl(2-hydroxyethyl)carbamate (2.43 g) obtained in Reference Example 24 in tetrahydrofuran were added pyridine (1.45 mL), ethyl chlorocarbonate (1.71 mL) and 4-dimethylaminopyridine (0.122 g) under ice-cooling, and the mixture was stirred at room temperature for 15 hrs. Ethyl acetate (100 mL) was added to the reaction mixture, and the mixture was washed successively with a saturated aqueous sodium hydrogen carbonate solution (100 mL), a 5% aqueous copper (II) sulfate solution (100 mL), water (100 mL) and saturated brine (100 mL), and dried over an hydrous sodium sulfate. The mixture was concentrated under reduced pressure and the residue was dissolved in ethyl acetate (15 mL). A 4N hydrogen chloride-ethyl acetate solution (15 mL) was added. After stirring at room temperature for 3 hrs., diisopropyl ether (20 mL) was added, and the precipitated solid was collected by filtration to give the title compound (2.12 g) as a white solid.

$^1$H-NMR(DMSO-d$_6$): 1.01-2.08 (10H, m), 1.23 (3H, t, J=7.0 Hz), 2.90-3.10 (1H, m), 3.21 (2H, t, J=5.2 Hz), 4.16 (2H, q, J=7.0 Hz), 4.39 (2H, t, J=5.2 Hz), 9.27 (2H, br).

Reference Example 27

2-Anilinoethyl acetate hydrochloride

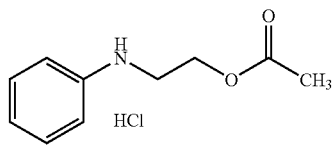

To a solution (700 mL) of 2-anilinoethanol (137 g) in tetrahydrofuran were added pyridine (97.1 mL), acetic anhydride (113.2 mL) and 4-dimethylaminopyridine (12.22 g) under ice-cooling, and the mixture was stirred at room temperature for 20 hrs. Ethyl acetate (1 L) was added to the reaction mixture and the mixture was washed successively with water (1 L), a saturated aqueous sodium hydrogen carbonate solution (1 L), a 5% aqueous copper (II) sulfate solution (1 L) and saturated brine (1 L), dried over anhydrous sodium sulfate, and evaporated under reduced pressure. To a solution of the obtained residue in ethyl acetate (700 mL) was added a 4N hydrogen chloride-ethyl acetate solution (250 mL) under ice-cooling, and the precipitated solid was collected by filtration to give the title compound (156 g) as a white solid.

$^1$H-NMR(CD$_3$OD): 2.11 (3H, s), 3.71-3.76 (2H, m), 4.32-4.37 (2H, m), 7.49-7.64 (5H, m).

Reference Example 28 tert-Butyl [2-(methylamino)-3-pyridyl]methyl carbonate

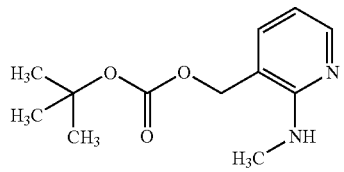 [SMILES: CNc1ncccc1COC(=O)OC(C)(C)C]

To a solution (50 mL) of [2-(methylamino)-3-pyridyl]methanol (2 g: synthesized according to the method described in WO 01/32652) in tetrahydrofuran were added di-tert-butyl dicarbonate (3.48 g) and 4-dimethylaminopyridine (0.18 g) and the mixture was refluxed for 1 hr. Water (30 mL) was added to the reaction mixture and extracted with ethyl acetate (50 mL). The obtained organic layer was washed with saturated brine (50 mL), and dried over anhydrous sodium sulfate. The residue obtained by concentration under reduced pressure was purified by flash silica gel column chromatography (eluted with ethyl acetate:hexane=1:5) to give the title compound (1.51 g) as a white solid.

$^1$H-NMR(CDCl$_3$): 1.49 (9H, s), 3.02 (3H, d, J=4.8 Hz), 4.99 (2H, s), 5.00 (1H, bs), 6.55 (1H, dd, J=7.0, 5.0 Hz), 7.37 (1H, dd, J=7.0, 1.8 Hz), 8.16 (1H, dd, J=5.0, 1.8 Hz).

Reference Example 29

2-(Methylamino)benzyl acetate

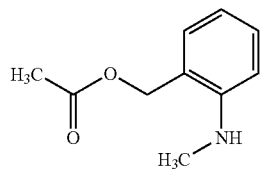

To a solution (50 mL) of [2-(methylamino)phenyl]methanol (1.37 g: synthesized according to the method described in WO 01/32652) in tetrahydrofuran were added pyridine (1.05 mL), acetic anhydride (1.23 mL) and 4-dimethylaminopyridine (0.18 g), and the mixture was stirred at room temperature for 8 hrs. Water (100 mL) was added to the reaction mixture, and the mixture was extracted with ethyl acetate (100 mL). The organic layer was washed successively with a 5% aqueous copper (II) sulfate solution (50 mL), a saturated aqueous sodium hydrogen carbonate solution (50 mL) and saturated brine (50 mL), and dried over anhydrous sodium sulfate. The solvent was evaporated under reduced pressure and the obtained residue was purified by flash silica gel column chromatography (eluted with ethyl acetate:hexane=1:5, then 1:3) to give the title compound (0.38 g) as a white solid.

$^1$H-NMR(CDCl$_3$): 2.08 (3H, s), 2.87 (3H, s), 4.40 (1H, br), 5.08 (2H, s), 6.64-6.74 (2H, m), 7.17-7.32 (2H, m).

Reference Example 30

2-[(2-Acetyloxyethyl)amino]ethyl acetate hydrochloride

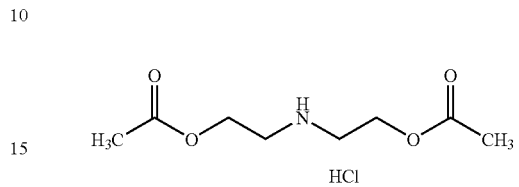

To a mixture of 2,2'-iminodiethanol (2.10 g) and ethyl acetate (20 mL) was added di-tert-butyl dicarbonate (4.37 g) under ice-cooling. After stirring for 1.5 hrs. under ice-cooling, acetic anhydride (2.08 mL), pyridine (1.78 mL) and 4-dimethylaminopyridine (0.12 g) were added. After stirring at room temperature for 2 hrs., ethyl acetate (50 mL) was added to the reaction mixture and the mixture was washed with water (50 mL), a 5% aqueous citric acid solution (50 mL) and saturated brine (50 mL). After drying over anhydrous magnesium sulfate, the mixture was concentrated under reduced pressure. A 4N hydrogen chloride-ethyl acetate solution (20 mL) was added to the residue, and the mixture was stirred at room temperature for 2 hrs. Diethyl ether (10 mL) was added, and the precipitated solid was collected by filtration. The solid was dried under reduced pressure to give the title compound (6.18 g) as a white solid.

$^1$H-NMR(DMSO-d$_6$): 2.07 (6H, s), 3.23 (4H, t, J=5.3 Hz), 4.27-4.33 (4H, m), 9.40 (2H, br).

Reference Example 31

(S)-2-Pyrrolidinylmethyl acetate hydrochloride

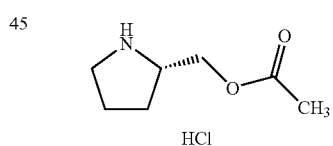

To a mixture of (S)-2-pyrrolidinylmethanol (1.01 g) and ethyl acetate (10 mL) was added di-tert-butyl dicarbonate (2.18 g) under ice-cooling. After stirring for 1 hr. under ice-cooling, acetic anhydride (1.04 mL), pyridine (0.89 mL) and 4-dimethylaminopyridine (0.061 g) were added. After stirring at room temperature for 1 hr., ethyl acetate (50 mL) was added to the reaction mixture, and the mixture was washed with water (50 mL), a 5% aqueous citric acid solution (50 mL) and saturated brine (50 mL). After drying over anhydrous magnesium sulfate, the mixture was concentrated under reduced pressure. A 4N hydrogen chloride-ethyl acetate solution (10 mL) was added to the residue, and the mixture was stirred at room temperature for 1 hr. Diethyl ether (10 mL) was added and the precipitated solid was collected by filtration. The solid was dried under reduced pressure to give the title compound (1.68 g) as a pale-brown solid.

$^1$H-NMR(DMSO-$d_6$): 1.56-2.10 (4H, m), 2.06 (3H, s), 3.05-3.24 (2H, m), 3.63-3.68 (1H, m), 4.15 (1H, dd, J=11.8, 8.1 Hz), 4.26 (1H, dd, J=11.8, 4.1 Hz), 9.21 (1H, br), 9.87 (1H, br).

Reference Example 32

3-(Methylamino)propyl benzoate hydrochloride

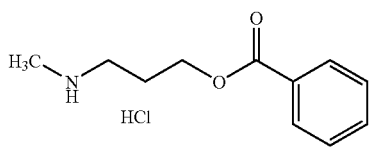

To a mixture of 3-amino-1-propanol (0.75 g) and ethyl acetate (2.25 mL) was added a solution (0.25 mL) of di-tert-butyl dicarbonate (2.18 g) in ethyl acetate under ice-cooling. After stirring at room temperature for 21.5 hrs., benzoyl chloride (1.30 mL), pyridine (0.98 mL) and 4-dimethylaminopyridine (0.012 g) were added. After stirring at room temperature for 5 hrs., ethyl acetate (32.5 mL) was added to the reaction mixture, and the mixture was washed with water (12.5 mL) and saturated brine (12.5 mL). After drying over anhydrous magnesium sulfate, the mixture was concentrated under reduced pressure. The residue was dissolved in N,N-dimethylformamide (20 mL), and methyl iodide (5 mL) was added. 60% sodium hydride (0.4 g) was added under ice-cooling. After stirring at room temperature for 3 hrs., the reaction mixture was poured into an ice-cooled aqueous ammonium chloride solution (60 mL). The mixture was extracted with diethyl ether (80 mL) and washed with saturated brine (30 mL). After drying over anhydrous magnesium sulfate, the mixture was concentrated under reduced pressure. The residue was purified by silica gel column chromatography (ethyl acetate:hexane=2:1, then ethyl acetate, then acetone:ethyl acetate=1:9) to give 3-[(tert-butoxycarbonyl)(methyl)amino]propyl benzoate (2.52 g) as a colorless oil. A 4N hydrogen chloride-ethyl acetate solution (10 mL) was added, and the mixture was stirred at room temperature for 1 hr. After concentration under reduced pressure, ethyl acetate (10 mL) was added to the residue and the precipitated solid was collected by filtration. After washing with diethyl ether (10 mL), the solid was dried under reduced pressure to give the title compound (1.73 g) as a colorless solid.

$^1$H-NMR(DMSO-$d_6$): 2.02-2.16 (2H, m), 2.56 (3H, s), 3.05 (2H, t, J=7.3 Hz), 4.35 (2H, t, J=6.1 Hz), 7.51 (2H, m), 7.65-7.73 (1H, m), 8.01 (2H, d, J=7.2 Hz), 8.95 (2H, br).

Reference Example 33

2-[(Ethoxycarbonyl)(methyl)amino]ethyl ethyl carbonate

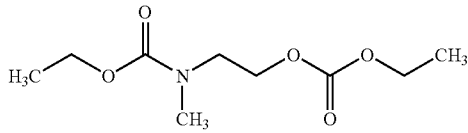

To a solution (1000 mL) of 2-(methylamino)ethanol (100 g) in ethyl acetate was added pyridine (222 mL), ethyl chlorocarbonate (240 mL) was dropwise added over 2 hr. under ice-cooling. After the completion of the dropwise addition, the reaction mixture was stirred at room temperature for 18 hrs. Water (300 mL) was added, and the ethyl acetate layer was separated and washed with 1N hydrochloric acid (200 mL) and saturated brine (200 mL). After drying over anhydrous sodium sulfate, the mixture was concentrated under reduced pressure, and the residue was evaporated under reduced pressure to give the title compound (180 g) as a colorless fraction having a boiling point of 95-100° C. (pressure: 0.1-0.2 mmHg).

$^1$H-NMR(CDCl$_3$): 1.20-1.40 (6H, m), 2.97 (3H, s), 3.50-3.60 (2H, m), 4.05-4.35 (6H, m).

Reference Example 34

2-[(Chlorocarbonyl)(methyl)amino]ethyl ethyl carbonate

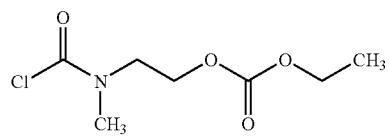

To a solution (1500 mL) of 2-[(ethoxycarbonyl)(methyl) amino]ethyl ethyl carbonate (150 g) obtained in Reference Example 33 in acetonitrile was added phosphorus oxychloride (200 mL), and the mixture was refluxed for 4 days. The reaction mixture was concentrated under reduced pressure and the residue was added to a mixture of water (500 mL)-ice (700 g)-ethyl acetate (300 mL) by portions with stirring. After stirring for 1 min., saturated brine (500 mL) was added, and the mixture was extracted with ethyl acetate (500 mL). The ethyl acetate layer was washed successively with saturated brine (300 mL), a saturated aqueous sodium hydrogen carbonate solution (300 mL) and saturated brine (300 mL), dried over anhydrous sodium sulfate and concentrated under reduced pressure. The residue was evaporated under reduced pressure to give the title compound (77 g) as a colorless fraction having a boiling point of 100-105° C. (pressure: 0.1-0.2 mmHg).

$^1$H-NMR(CDCl$_3$): 1.33 (3H, t, J=7.2 Hz), 3.12 (3H×0.4,s), 3.22 (3H×0.6,s), 3.68 (2H×0.6,t, J=4.8 Hz), 3.78 (2H×0.4,t, J=4.8 Hz), 4.23 (2H, q, J=7.2 Hz), 4.30-4.40 (2H, m).

Reference Example 35 tert-Butyl 4-hydroxybutylcarbamate

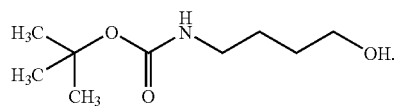

To a mixture of 4-aminobutanol (3.57 g) and ethyl acetate (9 mL) was dropwise added a mixture of di-tert-butyl dicarbonate (8.73 g) and ethyl acetate (1 mL) under ice-cooling. After stirring at room temperature for 24 hrs., the mixture was concentrated under reduced pressure. The residue was dissolved in ethyl acetate (200 mL), and the mixture was washed with water (50 mL), 1N hydrochloric acid (40 mL), water (30 mL) and saturated brine (30 mL) and dried over anhydrous magnesium sulfate. Concentration under reduced pressure gave the title compound (7.54 g) as a colorless oil.

$^1$H-NMR(CDCl$_3$): 1.44 (9H, s), 1.47-1.61 (4H, m), 3.07-3.22 (2H, m), 3.61-3.76 (2H, m), 4.62 (1H, bs).

Reference Example 36

4-[(tert-Butoxycarbonyl)amino]butyl acetate

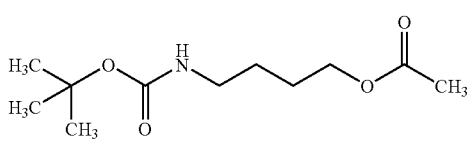 [SMILES: CC(=O)OCCCCNC(=O)OC(C)(C)C]

To a mixture of tert-butyl 4-hydroxybutylcarbamate (3.83 g) obtained in Reference Example 35 and ethyl acetate (20 mL) were added pyridine (1.80 mL) and acetic anhydride (2.27 g), and the mixture was stirred at room temperature for 19 hrs. Ethyl acetate (100 mL) was added to the reaction mixture, and the mixture was washed with water (50 mL), an aqueous copper sulfate solution (30 mL), water (30 mL) and saturated brine (30 mL) and dried over anhydrous magnesium sulfate. Concentration under reduced pressure gave the title compound (4.55 g) as a colorless oil.

$^1$H-NMR(CDCl$_3$): 1.44 (9H, s), 1.51-1.69 (4H, m), 2.05 (3H, s), 3.15 (2H, m), 4.07 (2H, t, J=6.5 Hz), 4.55 (1H, bs).

Reference Example 37

4-(Methylamino)butyl.acetate hydrochloride

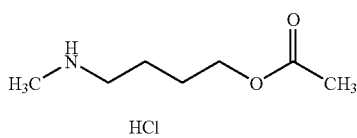

To a solution (20 mL) of 4-[(tert-butoxycarbonyl)amino] butyl acetate (4.50 g) obtained in Reference Example 36 and methyl iodide (4.85 mL) in N,N-dimethylformamide was added sodium hydride (60% in oil, 0.94 g) under ice-cooling. After stirring at room temperature for 4 hrs., the reaction mixture was poured into an ice-aqueous ammonium chloride solution. The mixture was extracted with diethyl ether (120 mL), and the diethyl ether layer was washed with saturated brine (30 mL) and dried over anhydrous magnesium sulfate. After concentration under reduced pressure, the residue was purified by silica gel column chromatography (eluted with ethyl acetate:hexane=1:9). To the purified product was added a 4N hydrogen chloride-ethyl acetate solution (20 mL), and the mixture was stirred at room temperature for 2 hrs. Diethyl ether (40 mL) was added, and the precipitated solid was collected by filtration. The solid was dried under reduced pressure to give the title compound (2.28 g) as a white solid.

$^1$H-NMR(DMSO-d$_6$): 1.58-1.70 (4H, m), 2.01 (3H, s), 2.50 (3H, s), 2.82-2.90 (2H, m), 4.00 (2H, t, J=6.0 Hz), 8.90 (2H, br).

Reference Example 38

4-[(tert-Butoxycarbonyl)amino]butyl ethyl carbonate

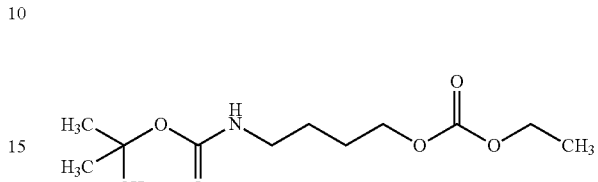

To a mixture of tert-butyl 4-hydroxybutylcarbamate (3.71 g) obtained in Reference Example 35 and ethyl acetate (20 mL) were added pyridine (1.71 mL) and ethyl chlorocarbonate (2.55 g) under ice-cooling, and the mixture was stirred at room temperature for 24 hrs. Ethyl acetate (100 mL) was added to the reaction mixture, and the mixture was washed with water (50 mL), an aqueous copper sulfate solution (30 ml), water (30 mL) and saturated brine (30 mL) and dried over anhydrous magnesium sulfate. Concentration under reduced pressure gave the title compound (4.92 g) as a colorless oil.

$^1$H-NMR(CDCl$_3$): 1.31 (3H, t, J=7.1 Hz), 1.44 (9H, s), 1.46-1.80 (4H, m), 3.15 (2H, m), 4.11-4.25 (4H, m), 4.54 (1H, bs).

Reference Example 39

Ethyl 4-(methylamino)butyl carbonate hydrochloride

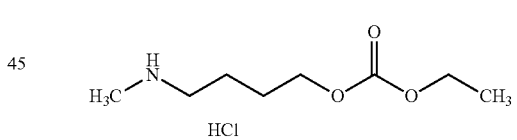

To a solution (20 mL) of 4-[(tert-butoxycarbonyl)amino] butyl ethyl carbonate (4.90 g) obtained in Reference Example 38 and methyl iodide (4.67 mL) in N,N-dimethylformamide was added sodium hydride (60% in oil, 0.90 g) under ice-cooling. After stirring at room temperature for 6 hrs., the reaction mixture was poured into an ice-aqueous ammonium chloride solution, and extracted with diethyl ether (120 mL). The diethyl ether layer was washed with saturated brine (30 mL) and dried over anhydrous magnesium sulfate. After concentration under reduced pressure, the residue was purified by silica gel column chromatography (eluted with ethyl acetate: hexane=1:9). To the purified product was added a 4N hydrogen chloride-ethyl acetate solution (20 mL), and the mixture was stirred at room temperature for 2 hrs. Diethyl ether (40 mL) was added, and the precipitated solid was collected by filtration. The solid was dried under reduced pressure to give the title compound (2.86 g) as a white solid.

¹H-NMR(DMSO-d₆): 1.21 (3H, t, J=7.1 Hz), 1.51-1.73 (4H, m), 2.50 (3H, s), 2.82-2.94 (2H, m), 4.05-4.15 (4H, m), 8.88 (2H, br).

Reference Example 40 tert-Butyl 3-hydroxypropylcarbamate

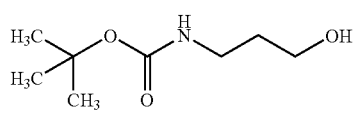

To a mixture of 3-aminopropanol (7.51 g) and ethyl acetate (30 mL) was dropwise added a mixture of di-tert-butyl dicarbonate (21.8 g) and ethyl acetate (3 mL) under ice-cooling. After stirring at room temperature for 22 hrs., the mixture was concentrated under reduced pressure.

The residue was dissolved in ethyl acetate (200 mL), washed with water (80 mL), 1N hydrochloric acid (60 mL), water (50 mL) and saturated brine (50 mL), and dried over anhydrous sodium sulfate. Concentration under reduced pressure gave the title compound (16.01 g) as a colorless oil.

¹H-NMR(CDCl₃): 1.45 (9H, s), 1.62-1.70 (2H, m), 3.24 (2H, q, J=6.6 Hz), 3.66 (2H, q, J=5.1 Hz), 4.73 (1H, bs).

Reference Example 41

3-[(tert-Butoxycarbonyl)amino]propyl acetate

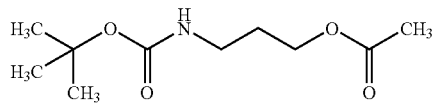

To a mixture of tert-butyl 3-hydroxypropylcarbamate (8.00 g) obtained in Reference Example 40 and ethyl acetate (50 mL) were added pyridine (4.06 mL) and acetic anhydride (5.13 g), and the mixture was stirred at room temperature for 21 hrs. Ethyl acetate (200 mL) was added to the reaction mixture, and the mixture was washed with water (100 mL), an aqueous copper sulfate solution (40 mL), water (60 mL) and saturated brine (60 mL), and dried over anhydrous sodium sulfate. Concentration under reduced pressure gave the title compound (8.34 g) as a colorless oil.

¹H-NMR(CDCl₃): 1.44 (9H, s), 1.77-1.86 (2H, m), 2.06 (3H, s), 3.20 (2H, q, J=6.3 Hz), 4.12 (2H, t, J=6.3 Hz), 4.67 (1H, bs).

Reference Example 42

3-(Methylamino)propyl acetate hydrochloride

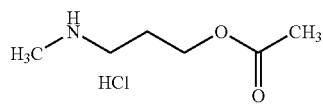

To a solution (80 mL) of 3-[(tert-butoxycarbonyl)amino]propyl acetate (17.28 g) obtained in Reference Example 41 and methyl iodide (19.8 mL) in N,N-dimethylformamide was added sodium hydride (60% in oil, 3.82 g) under ice-cooling. After stirring at room temperature for 15 hrs., the reaction mixture was poured into an ice-aqueous ammonium chloride solution and extracted with diethyl ether (300 mL). The diethyl ether layer was washed with saturated brine (100 mL), and dried over anhydrous sodium sulfate. After concentration under reduced pressure, the residue was purified by silica gel column chromatography (eluted with ethyl acetate:hexane=1:8). To the purified product was added a 4N hydrogen chloride-ethyl acetate solution (40 mL), and the mixture was stirred at room temperature for 2 hrs. Diethyl ether (100 mL) was added, and the precipitated solid was collected by filtration. The solid was dried under reduced pressure to give the title compound (2.93 g) as a white solid.

¹H-NMR(DMSO-d₆): 1.85-1.97 (2H, m), 2.02 (3H, s), 2.50 (3H, s), 2.87-2.96 (2H, m), 4.06 (2H, t, J=6.3 Hz), 8.87 (2H, br).

Reference Example 43

3-[(tert-Butoxycarbonyl)amino]propyl ethyl carbonate

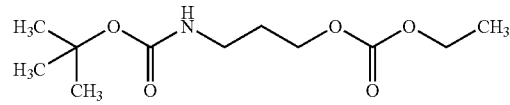 [SMILES: CCOC(=O)OCCCNC(=O)OC(C)(C)C]

To a mixture of tert-butyl 3-hydroxypropylcarbamate (8.00 g) obtained in Reference Example 40 and ethyl acetate (50 mL) were added pyridine (4.06 mL) and ethyl chlorocarbonate (5.95 g) under ice-cooling, and the mixture was stirred at room temperature for 24 hrs. Ethyl acetate (100 mL) was added to the reaction mixture, and the mixture was washed with water (50 mL), an aqueous copper sulfate solution (30 mL), water (30 mL) and saturated brine (30 mL), and dried over anhydrous sodium sulfate. Concentration under reduced pressure gave the title compound (9.31 g) as a colorless oil.

¹H-NMR(CDCl₃): 1.31 (3H, t, J=7.1 Hz), 1.44 (9H, s), 1.82-1.90 (2H, m), 3.22 (2H, t, J=6.3 Hz), 4.15-4.23 (4H, m), 4.68 (1H, bs).

Reference Example 44

Ethyl 3-(methylamino)propyl carbonate hydrochloride

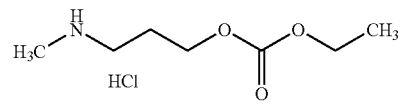

To a solution (40 mL) of 3-[(tert-butoxycarbonyl)amino]propyl ethyl carbonate (9.31 g) obtained in Reference Example 43 and methyl iodide (9.00 mL) in N,N-dimethylformamide was added sodium hydride (60% in oil, 1.82 g) under ice-cooling. After stirring at room temperature for 12 hrs., the reaction mixture was poured into an ice-aqueous ammonium chloride solution and the mixture was extracted with diethyl ether (200 mL). The diethyl ether layer was washed with saturated brine (100 mL), and dried over anhydrous sodium sulfate. After concentration under reduced pressure, the residue was purified by silica gel column chromatography (eluted with ethyl acetate:hexane=1:8). To the purified product was added a 4N hydrogen chloride-ethyl acetate solution (40 mL), and the mixture was stirred at room temperature for 2 hrs. Diethyl ether (200 mL) was added, and the precipitated solid was collected by filtration. The solid was dried under reduced pressure to give the title compound (4.98 g) as a white solid.

$^1$H-NMR(DMSO-$d_6$): 1.21 (3H, t, J=7.1 Hz), 1.91-2.00 (2H, m), 2.50 (3H, s), 2.88-2.98 (2H, m), 4.08-4.16 (4H, m), 8.90 (2H, br).

Reference Example 45 tert-Butyl(2,3-dihydroxypropyl)methylcarbamate

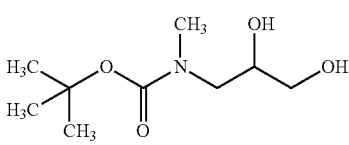

To a mixture of 3-(methylamino)-1,2-propanediol (24.5 g) and ethyl acetate (50 mL) was dropwise added a mixture of di-tert-butyl dicarbonate (51.4 g) and ethyl acetate (10 mL) under ice-cooling. After stirring at room temperature for 15 hrs., the mixture was concentrated under reduced pressure. The residue was dissolved in ethyl acetate (150 mL), and the solution was washed with water (80 mL), 1N hydrochloric acid (60 mL), water (50 mL) and saturated brine (50 mL), and dried over anhydrous sodium sulfate. Concentration under reduced pressure gave the title compound (26.9 g) as a colorless oil.

$^1$H-NMR(CDCl$_3$): 1.47 (9H, s), 2.92 (3H, s), 3.20-3.36 (2H, m), 3.41 (2H, bs), 3.50-3.62 (2H, m), 3.73-3.88 (1H, m).

Reference Example 46

3-(Methylamino)propane-1,2-diyl diacetate hydrochloride

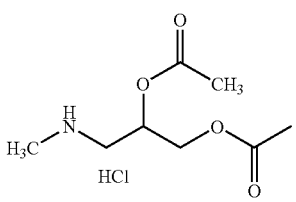

To a mixture of tert-butyl (2,3-dihydroxypropyl)methylcarbamate (10.26 g) obtained in Reference Example 45 and ethyl acetate (50 mL) were added pyridine (10.11 mL) and acetic anhydride (12.76 g), and the mixture was stirred at room temperature for 24 hrs. Ethyl acetate (300 mL) was added to the reaction mixture, and the mixture was washed with water (150 mL), an aqueous copper sulfate solution (100 mL), water (100 mL) and saturated brine (100 mL), and dried over anhydrous sodium sulfate. After concentration under reduced pressure, the residue was purified by silica gel column chromatography (eluted with ethyl acetate:hexane=1:8). To the purified product was added a 4N hydrogen chloride-ethyl acetate solution (40 mL), and the mixture was stirred at room temperature for 3 hrs. Diethyl ether (100 mL) was added, and the precipitated solid was collected by filtration. The solid was dried under reduced pressure to give the title compound (2.76 g) as a white solid.

$^1$H-NMR(DMSO-$d_6$): 2.03 (3H, s), 2.07 (3H, s), 2.55 (3H, s), 3.18-3.22 (2H, m), 4.09-4.28 (2H, m), 5.20-5.27 (1H, m), 9.01 (2H, br).

Reference Example 47

Diethyl 3-(methylamino)propane-1,2-diyl biscarbonate hydrochloride

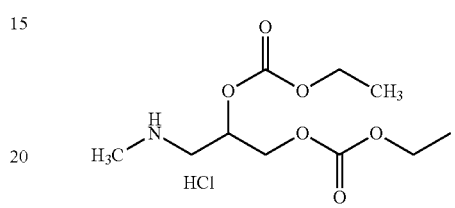

To a mixture of tert-butyl (2,3-dihydroxypropyl)methylcarbamate (15.53 g) obtained in Reference Example 45 and ethyl acetate (100 mL) were added pyridine (18.35 mL) and ethyl chlorocarbonate (24.62 g) under ice-cooling, and the mixture was stirred at room temperature for 96 hrs. Ethyl acetate (300 mL) was added to the reaction mixture, and the mixture was washed with water (150 mL), an aqueous copper sulfate solution (100 mL), water (100 mL) and saturated brine (100 mL), and dried over anhydrous sodium sulfate. After concentration under reduced pressure, the residue was purified by silica gel column chromatography (eluted with ethyl acetate:hexane=1:6). To the purified product was added a 4N hydrogen chloride-ethyl acetate solution (80 mL), and the mixture was stirred at room temperature for 3 hrs. Diethyl ether (200 mL) was added, and the precipitated solid was collected by filtration. The solid was dried under reduced pressure to give the title compound (5.93 g) as a white solid.

$^1$H-NMR(DMSO-$d_6$): 1.20-1.28 (6H, m), 2.57 (3H, s), 3.12-3.28 (2H, m), 4.10-4.43 (6H, m), 5.13-5.22 (1H, m), 9.14 (2H, br).

Reference Example 48

2-Ethoxyethyl 2-(methylamino)ethyl carbonate hydrochloride

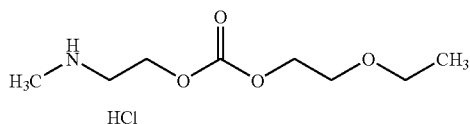

To a solution (20 mL) of bis(trichloromethyl)carbonate (2.97 g) in tetrahydrofuran was dropwise added a solution (10 mL) of 2-ethoxyethanol (1.80 g) in tetrahydrofuran under ice-cooling. Then a solution (10 mL) of pyridine (2.43 mL) in tetrahydrofuran was added dropwise, and the mixture was stirred at room temperature for 2 hrs. The reaction mixture was concentrated under reduced pressure and water (50 mL) was added to the residue. The mixture was extracted with ethyl acetate (50 mL). The ethyl acetate layer was washed with 0.2N hydrochloric acid (20 mL) and saturated brine (50 mL), dried over anhydrous magnesium sulfate, and concentrated under reduced pressure to give 2-ethoxyethyl chlorocarbonate (1.29 g). A solution (15 mL) of tert-butyl 2-hydroxyethyl(methyl)carbamate (1.23 g) obtained in Reference Example 1 in tetrahydrofuran was added pyridine (0.68 mL), and a solution (5 mL) of 2-ethoxyethyl chlorocarbonate obtained above in tetrahydrofuran was dropwise added to the mixture, and the mixture was stirred at room temperature for 3 days. After concentration of the reaction mixture under reduced pressure, water (50 mL) was added thereto and the mixture was extracted with ethyl acetate (50 mL). The ethyl acetate layer was washed with a 5% aqueous citric acid solution (50 mL) and saturated brine (50 mL), dried over anhydrous magnesium sulfate. The mixture was concentrated under reduced pressure and the residue was purified by silica gel column chromatography (eluted with ethyl acetate:hexane=1:5, then 2:3). The purified product (1.60 g) was dissolved in diethyl ether (3 mL) and a 4N hydrogen chloride-ethyl acetate solution (3 mL) was added. The mixture was stirred overnight at room temperature, and the precipitated solid was collected by filtration and dried under reduced pressure to give the title compound (0.94 g) as a white solid.

$^1$H-NMR(DMSO-$d_6$): 1.10 (3H, t, J=7.0 Hz), 2.57 (3H, s), 3.25 (2H, m), 3.44 (2H, q, J=7.0 Hz), 3.56-3.60 (2H, m), 4.19-4.24 (2H, m), 4.30-4.37 (2H, m), 8.79 (2H, br).

Reference Example 49

3-Methoxypropyl 2-(methylamino)ethyl carbonate hydrochloride

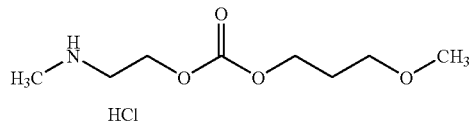

To a mixture of lithium aluminum hydride (2.85 g) and diethyl ether (100 mL) was dropwise added slowly a solution (50 mL) of methyl 3-methoxypropanoate (11.8 g) in tetrahydrofuran under ice-cooling. After stirring at room temperature for 1 hr., the mixture was again ice-cooled and water (3 mL) and a 10% aqueous sodium hydroxide solution (3 mL) were dropwise added. The mixture was allowed to reach room temperature, and water (9 mL) was dropwise added. The mixture was stirred for a while. The precipitate was filtered off and the filtrate was concentrated under reduced pressure to give 3-methoxypropanol (7.64 g) as a colorless oil.

$^1$H-NMR(CDCl$_3$): 1.83 (2H,quintet, J=5.8 Hz), 2.43 (1H, t, J=5.3 Hz), 3.36 (3H, s), 3.57 (2H, t, J=6.0 Hz), 3.77 (2H, q, J=5.5 Hz).

To a solution (50 mL) of bis(trichloromethyl)carbonate (4.45 g) in tetrahydrofuran was dropwise added N-ethyldiisopropylamine (5.75 mL) under ice-cooling. After stirring for a while, a solution (15 mL) of 3-methoxypropanol (2.70 g) obtained above in tetrahydrofuran was dropwise added. The mixture was stirred for 30 min. under ice-cooling and at room temperature for 1 day. After concentration of the reaction mixture under reduced pressure, diluted hydrochloric acid (50 mL) was added to the residue, and the mixture was extracted with ethyl acetate (80 mL). The ethyl acetate layer was washed with 0.2N hydrochloric acid (30 mL) and saturated brine (30 mL), dried over anhydrous magnesium sulfate and concentrated under reduced pressure to give 3-methoxypropyl chlorocarbonate (4.39 g). To a solution (20 mL) of tert-butyl 2-hydroxyethyl(methyl)carbamate (1.75 g) obtained in Reference Example 1 in tetrahydrofuran was added pyridine (0.97 mL) and a solution (5 mL) of a 3-methoxypropyl chlorocarbonate (1.83 g) obtained above in tetrahydrofuran was dropwise added, and the mixture was stirred at room temperature for 2 hrs. A solution (5 mL) of pyridine (0.65 mL) and 3-methoxypropyl chlorocarbonate (1.22 g) in tetrahydrofuran was added and the mixture was further stirred for 1 hr. The reaction mixture was concentrated under reduced pressure and water (50 mL) was added to the residue. The mixture was extracted with ethyl acetate (80 mL), and the ethyl acetate layer was washed with a 5% aqueous citric acid solution (50 mL) and saturated brine (50 mL), dried over anhydrous magnesium sulfate and concentrated under reduced pressure. The residue was purified by silica gel column chromatography (eluted with ethyl acetate:hexane=1:9, then 3:7). The purified product (3.40 g) was dissolved in diethyl ether (5 mL) and a 4N hydrogen chloride-ethyl acetate solution (5 mL) was added. The mixture was stirred overnight at room temperature and the reaction mixture was concentrated under reduced pressure. Diethyl ether was added for crystallization to give the title compound (2.06 g) as a colorless solid.

$^1$H-NMR(DMSO-$d_6$): 1.78-1.90 (2H, m), 2.54 (3H, s), 3.15-3.25 (2H, m), 3.23 (3H, s), 3.33-3.42 (2H, m), 4.16 (2H, t, J=6.0 Hz), 4.36 (2H, t, J=6.0 Hz), 9.27 (2H, br).

Reference Example 50

2-(Methylamino)ethyl N,N-dimethylglycinate dihydrochloride

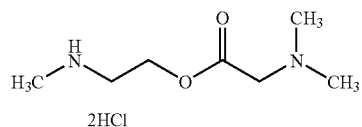

A mixture of tert-butyl 2-hydroxyethyl(methyl)carbamate (3.50 g) obtained in Reference Example 1, N,N-dimethylglycine hydrochloride (5.29 g), 1-ethyl-3-[3-(dimethylamino)propyl]carbodiimide hydrochloride (7.67 g), triethylamine (5.58 mL), 4-dimethylaminopyridine (1.22 g) and N,N-dimethylformamide (50 mL) was stirred overnight at room temperature. The reaction mixture was concentrated under reduced pressure and a saturated aqueous sodium hydrogen carbonate solution (50 mL) was added to the residue. The mixture was extracted with ethyl acetate (100 mL). The ethyl acetate layer was washed with saturated brine (50 mL), dried over anhydrous magnesium sulfate and concentrated under reduced pressure. The residue was purified by silica gel column chromatography (eluted with methanol:ethyl acetate=5:95, then 20:80). 1N Hydrochloric acid (24 mL) was added to the purified product (2.46 g), and the mixture was stirred overnight at room temperature. The reaction mixture was concentrated under reduced pressure to give the title compound (2.14 g) as a colorless solid.

$^1$H-NMR(DMSO-d$_6$): 2.52 (3H, s), 2.85 (6H, s), 3.20 (2H, m), 4.30 (2H, s), 4.43-4.49 (2H, m), 9.60 (2H, br), 10.81 (1H, br).

Reference Example 51

S-[2-(Methylamino)ethyl]thioacetate hydrochloride

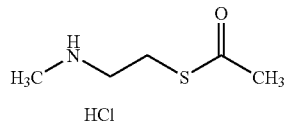

To a solution (50 mL) of tert-butyl 2-hydroxyethyl(methyl)carbamate (3.50 g) obtained in Reference Example 1, thioacetic acid (1.72 mL) and triphenylphosphine (7.87 g) in tetrahydrofuran was dropwise added slowly a solution (10 mL) of diisopropyl azodicarboxylate (5.91 mL) in tetrahydrofuran under ice-cooling. The mixture was stirred under ice-cooling for 1 hr. and at room temperature for 2 hrs. The reaction mixture was again ice-cooled and a solution (10 mL) of triphenylphosphine (7.87 g) and diisopropyl azodicarboxylate (5.91 mL) in tetrahydrofuran was added. The mixture was stirred under ice-cooling for 30 min. Thioacetic acid (1.14 mL) was added and the mixture was stirred under ice-cooling for 30 min. and at room temperature overnight. The reaction mixture was concentrated under reduced pressure and hexane and diisopropyl ether were added to the residue. The precipitate was filtered off and the filtrate was concentrated under reduced pressure. This step was repeated and a saturated aqueous sodium hydrogen carbonate solution (50 mL) was added. The mixture was extracted with ethyl acetate (100 mL). The ethyl acetate layer was washed with saturated brine (50 mL), dried over anhydrous magnesium sulfate and concentrated under reduced pressure. The residue was purified by silica gel column chromatography (eluted with ethyl acetate:hexane=5:95, and then 15:85). A 4N hydrogen chloride-ethyl acetate solution (10 mL) was added to the purified product (4.47 g) and the mixture was stirred overnight at room temperature. The reaction mixture was concentrated under reduced pressure and ethyl acetate and diethyl ether were added to the residue for crystallization to give the title compound (1.79 g) as a pale-yellow solid.

$^1$H-NMR(DMSO-d$_6$): 2.38 (3H, s), 2.52 (3H, s), 2.96-3.08 (2H, m), 3.12-3.20 (2H, m), 9.35 (2H, br).

Reference Example 52

Ethyl 2-[2-(methylamino)ethoxy]ethyl carbonate hydrochloride

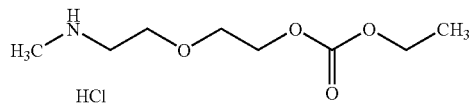

To a mixture of 2-(2-aminoethoxy)ethanol (99.52 g) and ethyl acetate (200 mL) was dropwise added a mixture of di-tert-butyl dicarbonate (208.57 g) and ethyl acetate (50 mL) under ice-cooling. After stirring at room temperature for 60 hrs., the mixture was concentrated under reduced pressure. The residue was dissolved in ethyl acetate (500 mL), washed with water (200 mL), 1N hydrochloric acid (200 mL), water (300 mL) and saturated brine (300 mL), and dried over anhydrous sodium sulfate. Concentration under reduced pressure gave tert-butyl [2-(2-hydroxyethoxy)ethyl]carbamate (169.2 g) as a colorless oil.

$^1$H-NMR(CDCl$_3$): 1.45 (9H, s), 3.33 (2H, q, J=5.1 Hz), 3.54-3.59 (4H, m), 3.74 (2H, q, J=5.1 Hz), 4.88. (2H, bs).

To a mixture of tert-butyl [2-(2-hydroxyethoxy)ethyl]carbamate (53.93 g) obtained above and ethyl acetate (350 mL) were added pyridine (53.78 mL) and ethyl chlorocarbonate (70.57 g) under ice-cooling, and the mixture was stirred at room temperature for 96 hrs. Ethyl acetate (500 mL) was added to the reaction mixture, and the mixture was washed with water (500 mL), an aqueous copper sulfate solution (200 mL), water (300 mL) and saturated brine (300 mL) and dried over anhydrous sodium sulfate. Concentration under reduced pressure gave 2-[2-[(tert-butoxycarbonyl)amino]ethoxy]ethyl ethyl carbonate (93.19 g) as a colorless oil.

$^1$H-NMR(CDCl$_3$): 1.32 (3H, t, J=7.2 Hz), 1.44 (9H, s), 3.32 (2H,t, J=5.1 Hz), 3.54 (2H,t, J=5.1 Hz), 3.67-3.74 (2H, m), 4.21 (2H,q, J=7.2 Hz), 4.26-4.31 (2H, m), 4.91 (1H, bs).

To a solution (350 mL) of 2-[2-[(tert-butoxycarbonyl)amino]ethoxy]ethyl ethyl carbonate (93.15 g) obtained above and methyl iodide (83.6 mL) in N,N-dimethylformamide was added sodium hydride (60% in oil, 16.12 g) under ice-cooling. After stirring at room temperature for 24 hrs., the reaction mixture was poured into an ice-aqueous ammonium chloride solution, and extracted with diethyl ether (800 mL). The diethyl ether layer was washed with saturated brine (300 mL), and dried over anhydrous magnesium sulfate. After concentration under reduced pressure, the residue was purified by silica gel column chromatography (eluted with ethyl acetate: hexane=1:8). To the purified product was added a 4N hydrogen chloride-ethyl acetate solution (300 mL) was added, and the mixture was stirred at room temperature for 2 hrs. Diethyl ether (300 mL) was added, and the precipitated solid was collected by filtration. The solid was dried under reduced pressure to give the title compound (33.21 g) as a white solid.

$^1$H-NMR(DMSO-d$_6$): 1.21 (3H, t, J=7.2 Hz), 2.51 (3H, s), 3.02-3.09 (2H, m), 3.65-3.72 (4H, m), 4.12 (2H, q, J=7.2 Hz), 4.22 (2H, t, J=4.5 Hz), 9.06 (2H, br).

Reference Example 53

Ethyl 2-[methyl[[2-(methylamino)ethoxy]carbonyl]amino]ethyl carbonate hydrochloride

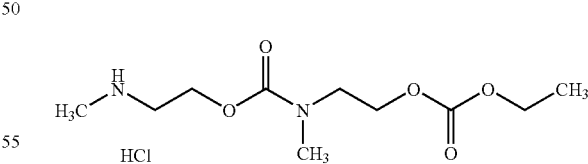

To a solution (100 mL) of bis(trichloromethyl)carbonate (11.87 g) in tetrahydrofuran was dropwise added a solution (20 mL) of pyridine (9.71 mL) in tetrahydrofuran under ice-cooling. After stirring under ice-cooling for 30 min., a solution (20 mL) of tert-butyl 2-hydroxyethyl(methyl)carbamate (17.52 g) obtained in Reference Example 1 in tetrahydrofuran was dropwise added and the mixture was stirred at room temperature for 15 hrs. After concentration under reduced pressure, water (500 mL) and anhydrous sodium sulfate were added to the residue. After filtration, the filtrate was concentrated under reduced pressure. To the obtained residue were added a solution (50 mL) of 2-(methylamino)ethanol (5.00 g) in ethyl acetate and triethylamine (10.0 mL) under ice-cooling and the mixture was stirred at room temperature for 15 hrs. Ethyl acetate (300 mL) was added to the reaction mixture, washed with water (150 mL) and saturated brine (200 mL) and dried over anhydrous sodium sulfate. After concentration under reduced pressure, to a mixture of the residue and ethyl acetate (100 mL) were added pyridine (2.91 mL) and ethyl chlorocarbonate (3.44 g) under ice-cooling, and the mixture was stirred at room temperature for 48 hrs. Ethyl acetate (200 mL) was added to the reaction mixture, washed with water (100 mL), an aqueous copper sulfate solution (50 mL), water (50 mL) and saturated brine (50 mL), and dried over anhydrous sodium sulfate. The mixture was concentrated under reduced pressure and the residue was purified by silica gel column chromatography (eluted with ethyl acetate:hexane=1:3). To the purified product was added a 4N hydrogen chloride-ethyl acetate solution (30 mL), and the mixture was stirred at room temperature for 3 hrs. Diethyl ether (100 mL) was added, and the precipitated solid was collected by filtration. The solid was dried under reduced pressure to give the title compound (2.90 g) as a white solid.

$^1$H-NMR(DMSO-$d_6$): 1.21 (3H, t, J=7.2 Hz), 2.57 (3H, bs), 2.86 (1.5H, s), 2.93 (1.5H, s), 3.16 (2H, bs), 3.34 (1H, bs), 3.48 (1H, t, J=5.1 Hz), 3.58 (1H, t, J=5.1 Hz), 4.12 (2H, q, J=7.2 Hz), 4.16-4.24 (4H, m), 8.94 (1H, br).

Reference Example 54

2-(Methylamino)ethyl 1-methylpiperidine-4-carboxylate dihydrochloride

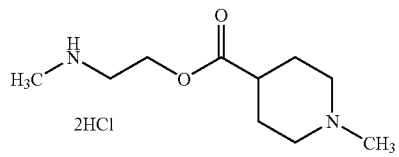

A mixture of ethyl piperidine-4-carboxylate (4.72 g), methyl iodide (2.24 mL), potassium carbonate (8.29 g) and acetonitrile (50 mL) was stirred at room temperature for 2 hrs. The reaction mixture was concentrated under reduced pressure and water (150 mL) was added. The mixture was extracted with ethyl acetate (150 mL). The ethyl acetate layer was washed with saturated brine (100 mL), dried over anhydrous magnesium sulfate, and concentrated under reduced pressure. A 1N aqueous sodium hydroxide solution (20 mL) was added to the residue (2.64 g), and the mixture was stirred overnight at room temperature. The reaction mixture was neutralized by adding 1N hydrochloric acid (20 mL) and the mixture was concentrated under reduced pressure. Ethanol was added to the residue, and the precipitate was filtered off. The filtrate was concentrated under reduced pressure. This step was repeated and ethanol and ethyl acetate were added to the residue for crystallization to give 1-methylpiperidine-4-carboxylic acid (1.79 g) as a colorless solid.

$^1$H-NMR(CD$_3$OD): 1.80-1.98 (2H, m), 2.00-2.14 (2H, m), 2.28-2.42 (1H, m), 2.78 (3H, s), 2.88-3.04 (2H.m), 3.32-3.44 (2H.m).

A mixture of 1-methylpiperidine-4-carboxylic acid (1.72 g) obtained above, tert-butyl 2-hydroxyethyl(methyl)carbamate (1.75 g) obtained in Reference Example 1, 1-ethyl-3-[3-(dimethylamino)propyl]carbodiimide hydrochloride (2.30 g), 4-dimethylaminopyridine (0.24 g) and acetonitrile (50 mL) was stirred at room temperature for 16 hrs. The reaction mixture was concentrated under reduced pressure and a saturated aqueous sodium hydrogen carbonate solution (50 mL) was added to the residue. The mixture was extracted with ethyl acetate (100 mL). The ethyl acetate layer was washed with saturated brine (50 mL), dried over anhydrous magnesium sulfate and concentrated under reduced pressure. The residue was purified by basic silica gel column chromatography (eluted with ethyl acetate:hexane=50:50, then 80:20). 1N Hydrochloric acid (25 mL) was added to the purified product (2.73 g), and the mixture was stirred overnight at room temperature. The reaction mixture was concentrated under reduced pressure and isopropanol was added. The mixture was again concentrated under reduced pressure and the precipitated solid was collected by filtration to give the title compound (1.72 g) as a colorless solid.

$^1$H-NMR(DMSO-$d_6$): 1.70-2.20 (4H, m), 2.40-3.50 (13H, m), 4.31 (2H, m), 9.25 (2H, br), 10.77 (1H, br).

Reference Example 55

2-[[4-(Aminocarbonyl)phenyl]amino]ethyl acetate

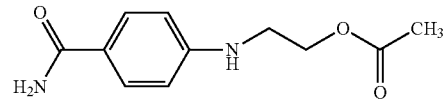 [SMILES: CC(=O)OCCNc1ccc(C(N)=O)cc1]

A mixture of 4-fluorobenzonitrile (6.06 g), 2-aminoethanol (3.71 g), potassium carbonate (8.29 g) and dimethyl sulfoxide (50 mL) was stirred at 100° C. overnight. Water (200 mL) was added to the reaction mixture and the mixture was extracted with ethyl acetate (200 mL×4). The ethyl acetate layer was washed with saturated brine (100 mL), dried over anhydrous magnesium sulfate and concentrated under reduced pressure. The residue was purified by silica gel column chromatography (eluted with ethyl acetate:hexane=30:70, then 50:50, then 80:20, then ethyl acetate) to give 4-[(2-hydroxyethyl)amino]benzonitrile (5.89 g) as a yellow solid.

$^1$H-NMR(CDCl$_3$): 2.04 (1H, t, J=4.8 Hz), 3.33 (2H, m), 3.86 (2H, q, J=4.8 Hz), 4.66 (1H, br), 6.58 (2H, d, J=8.7 Hz), 7.39 (2H, d, J=8.7 Hz).

A mixture of 4-[(2-hydroxyethyl)amino]benzonitrile (0.81 g) obtained above, potassium hydroxide (1.12 g) and tert-butanol (20 mL) was stirred at 100° C. for 1 hr. Water (100 mL) was added to the reaction mixture, and extracted with ethyl acetate (100 mL). The ethyl acetate layer was washed with saturated brine (80 mL), dried over anhydrous magnesium sulfate and concentrated under reduced pressure. To a solution (10 mL) of the residue (0.83 g), pyridine (0.49 mL) and 4-dimethylaminopyridine (0.061 g) in tetrahydrofuran was dropwise added a solution (1 mL) of acetic anhydride (0.57 mL) in tetrahydrofuran. The mixture was stirred at room temperature for 1 hr., water (80 mL) was added, and the mixture was extracted with ethyl acetate (100 mL). The ethyl acetate layer was washed with saturated brine (80 mL), dried over anhydrous magnesium sulfate and concentrated under reduced pressure. The residue was purified by silica gel column chromatography (eluted with ethyl acetate:hexane=30:70, then 60:40) to give the title compound (0.68 g) as a colorless solid.

$^1$H-NMR(CDCl$_3$): 2.08 (3H, s), 3.44 (2H, q, J=5.6 Hz), 4.29 (2H, t, J=5.4 Hz), 4.48 (1H, br), 6.59 (2H, d, J=8.9 Hz), 7.43 (2H, d, J=8.9 Hz).

Reference Example 56

2-(Methylamino)ethyl 1-methyl-4-piperidinyl carbonate dihydrochloride

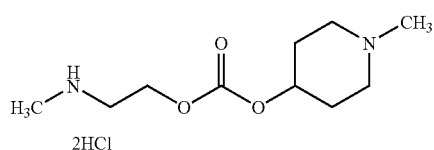

To a solution (40 mL) of N,N'-carbonyldiimidazole (3.36 g) in tetrahydrofuran was dropwise added slowly a solution (10 mL) of tert-butyl 2-hydroxyethyl(methyl)carbamate (3.30 g) obtained in Reference Example 1 in tetrahydrofuran under ice-cooling. The mixture was stirred under ice-cooling for 40 min. and at room temperature for 2 hrs. N,N'-Carbonyldiimidazole (0.31 g) was added and the mixture was further stirred for 3 days. The reaction mixture was concentrated under reduced pressure and ethyl acetate (150 mL) was added to the residue. The mixture was washed with saturated brine (100 mL×2), water (50 mL×3) and saturated brine (50 mL), dried over anhydrous magnesium sulfate and concentrated under reduced pressure to give 2-[(tert-butoxycarbonyl)(methyl)amino]ethyl 1H-imidazole-1-carboxylate (5.24 g) as a colorless oil.

$^1$H-NMR(CDCl$_3$): 1.39 (9H×0.5,s), 1.42 (9H×0.5,s), 2.94 (3H, m), 3.63 (2H, m), 4.51 (2H, t, J=5.3 Hz), 7.06 (1H, m), 7.42 (1H, m), 8.13 (1H, s).

A mixture of 2-[(tert-butoxycarbonyl)(methyl)amino]ethyl 1H-imidazole-1-carboxylate (1.35 g) obtained above, 1-methyl-4-piperidinol (1.38 g) and acetonitrile (20 mL) was stirred overnight at room temperature. 1-Methyl-4-piperidinol (0.92 g) was added and the mixture was stirred overnight. The reaction mixture was concentrated under reduced pressure and a saturated aqueous sodium hydrogen carbonate solution (50 mL) was added to the residue. The mixture was extracted with ethyl acetate (100 mL). The ethyl acetate layer was washed with saturated brine (50 mL), dried over anhydrous magnesium sulfate and concentrated under reduced pressure. 1N Hydrochloric acid (12 mL) was added to the residue (1.60 g), and the mixture was stirred overnight at room temperature. The reaction mixture was concentrated under reduced pressure, water, isopropanol and ethyl acetate were added, and the precipitated solid was collected by filtration to give the title compound (1.09 g) as a colorless solid.

$^1$H-NMR(DMSO-d$_6$): 1.85-2.20 (4H, m), 2.55 (3H, s), 2.70 (3H×0.5,s), 2.73 (3H×0.5,s), 2.90-3.50 (6H, m), 4.38 (2H, m), 4.65-5.00 (1H, m), 9.21 (2H, br), 11.10 (1H, br).

Synthetic Example 1

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl acetate

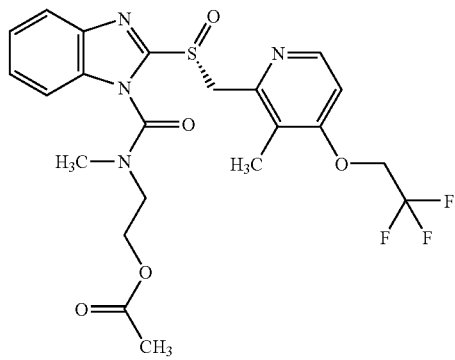

To a solution (30 mL) of bis(trichloromethyl)carbonate (0.50 g) in tetrahydrofuran was dropwise added a solution (1 mL) of pyridine (0.40 mL) in tetrahydrofuran under ice-cooling. After stirring under ice-cooling for 30 min., 2-(methylamino)ethyl acetate hydrochloride (0.77 g) obtained in Reference Example 2 was added. A solution (1 mL) of triethylamine (0.70 mL) in tetrahydrofuran was dropwise added and the mixture was stirred at room temperature for 1 hr. After concentration under reduced pressure, water (50 mL) was added to the residue. The mixture was extracted with ethyl acetate (50 mL). The ethyl acetate layer was washed with saturated brine (50 mL) and dried over anhydrous magnesium sulfate. The mixture was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.11 g), triethylamine (0.84 mL) and 4-dimethylaminopyridine (catalytic amount) were added, and the mixture was stirred at 60° C. overnight. After concentration under reduced pressure, water (50 mL) was added to the residue. The mixture was extracted with ethyl acetate (50 mL). The ethyl acetate layer was washed with saturated brine (50 mL) and dried over anhydrous magnesium sulfate. After concentration under reduced pressure, the residue was purified by basic silica gel column chromatography (eluted with ethyl acetate:hexane=1:1, then ethyl acetate), and further by silica gel column chromatography (eluted with ethyl acetate:hexane=2:1, then ethyl acetate, then acetone:ethyl acetate=1:4, then 1:1) to give the title compound (1.13 g) as a yellow amorphous solid.

$^1$H-NMR(CDCl$_3$): 2.10 (3H, s), 2.24 (3H, s), 3.09 (3H, bs), 3.60-4.00 (2H, br), 4.25-4.50 (4H, m), 4.89 (1H, d, J=13.3

Hz), 5.05 (1H, d, J=13.3 Hz), 6.65 (1H, d, J=5.5 Hz), 7.35-7.51 (3H, m), 7.80-7.90 (1H, m), 8.35 (1H, d, J=5.5 Hz).

Synthetic Example 2

2-[Methyl[[(R)-2-[[[(3-methyl-4-(2,2,2-trifluoroethoxy)-2-pyridyl]methyl]sulfinyl]-1H-benzimidazol-1-yl]carbonyl]amino]ethyl trimethylacetate

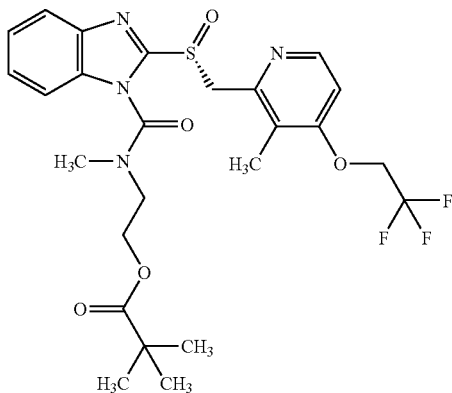 [SMILES: Cc1c(OCC(F)(F)F)ccnc1C[S@@](=O)c1nc2ccccc2n1C(=O)N(C)CCOC(=O)C(C)(C)C]

To a solution (30 mL) of bis(trichloromethyl)carbonate (0.50 g) in tetrahydrofuran was dropwise added a solution (1 mL) of pyridine (0.40 mL) in tetrahydrofuran under ice-cooling. After stirring under ice-cooling for 1 hr., 2-(methylamino)ethyl trimethylacetate hydrochloride (0.98 g) obtained in Reference Example 3 was added. A solution (1 mL) of triethylamine (0.70 mL) in tetrahydrofuran was dropwise added, and the mixture was stirred overnight at room temperature. After concentration under reduced pressure, water (50 mL) was added to the residue. The mixture was extracted with ethyl acetate (50 mL). The ethyl acetate layer was washed with saturated brine (50 mL), and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.11 g), triethylamine (0.84 mL) and 4-dimethylaminopyridine (0.037 g) were added, and the mixture was stirred overnight at 60° C. After concentration under reduced pressure, water (50 mL) was added to the residue. The mixture was extracted with ethyl acetate (50 mL). The ethyl acetate layer was washed with saturated brine (50 mL) and dried over anhydrous magnesium sulfate. After concentration under reduced pressure, the residue was purified by flash silica gel column chromatography (eluted with acetone:hexane=1:3, then 3:2). Crystallization from acetone-diisopropyl ether and recrystallization from acetone-diisopropyl ether gave the title compound (1.01 g) as a colorless solid.

$^1$H-NMR(CDCl$_3$): 1.23 (9H, s), 2.23 (3H, s), 3.08 (3H, bs), 3.40-4.30 (2H, br), 4.30-4.50 (4H, m), 4.80-5.20 (2H, br), 6.64 (1H, d, J=5.7 Hz), 7.35-7.50 (3H, m), 7.78-7.88 (1H, m), 8.35 (1H, d, J=5.7 Hz).

Synthetic Example 3

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl cyclohexanecarboxylate

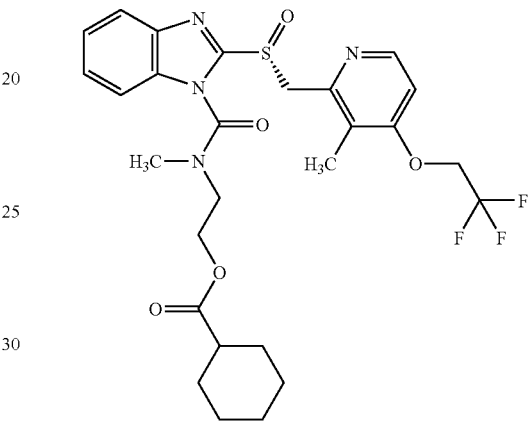

To a solution (30 mL) of bis(trichloromethyl)carbonate (0.50 g) in tetrahydrofuran was dropwise added a solution (1 mL) of pyridine (0.40 mL) in tetrahydrofuran under ice-cooling. After stirring under ice-cooling for 30 min., 2-(methylamino)ethyl cyclohexane carboxylate hydrochloride (1.11 g) obtained in Reference Example 4 was added. A solution (1 mL) of triethylamine (0.70 mL) in tetrahydrofuran was dropwise added, and the mixture was stirred at room temperature for 1 hr. After concentration under reduced pressure, water (50 mL) was added to the residue. The mixture was extracted with ethyl acetate (50 mL). The ethyl acetate layer was washed with saturated brine (50 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.11 g), triethylamine (0.84 mL) and 4-dimethylaminopyridine (0.037 g) were added, and the mixture was stirred overnight at 60° C. After concentration under reduced pressure, water (50 mL) was added to the residue. The mixture was extracted with ethyl acetate (50 mL). The ethyl acetate layer was washed with saturated brine (50 mL) and dried over anhydrous magnesium sulfate. After concentration under reduced pressure, the residue was purified by flash silica gel column chromatography (eluted with acetone:hexane=1:3, then 3:2). Crystallization from acetone-diisopropyl ether and recrystallization from acetone-diisopropyl ether gave the title compound (1.11 g) as a colorless solid.

$^1$H-NMR(CDCl$_3$): 1.10-1.55 (5H, m), 1.55-1.82 (3H, m), 1.84-1.98 (2H, m), 2.23 (3H, s), 2.27-2.40 (1H, m), 3.08 (3H, bs), 3.40-4.30 (2H, br), 4.30-4.50 (4H, m), 4.80-5.15 (2H, br), 6.64 (1H, d, J=5.4 Hz), 7.35-7.48 (3H, m), 7.84 (1H, d, J=6.9 Hz), 8.34 (1H, d, J=5.4 Hz).

Synthetic Example 4

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl benzoate

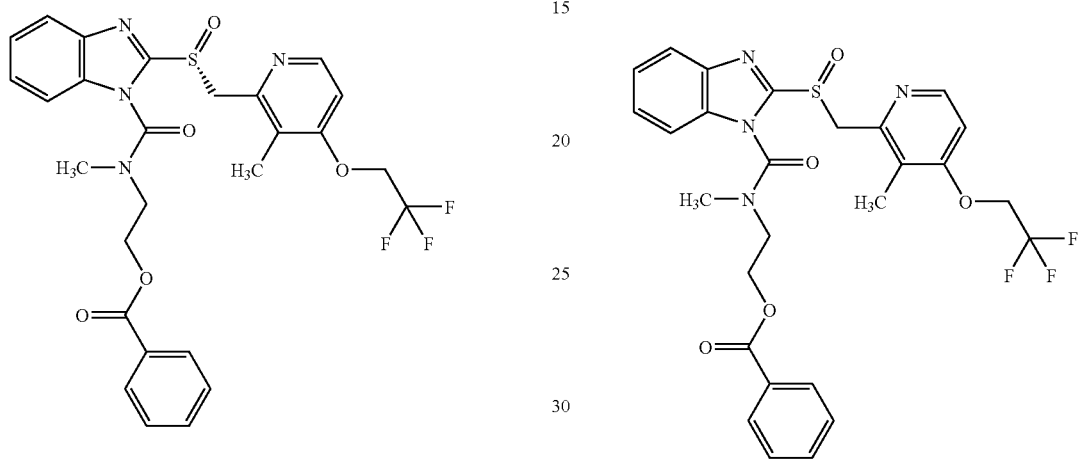

To a solution (30 mL) of bis(trichloromethyl)carbonate (0.50 g) in tetrahydrofuran was dropwise added a solution (1 mL) of pyridine (0.40 mL) in tetrahydrofuran under ice-cooling. After stirring under ice-cooling for 1 hr., 2-(methylamino)ethyl benzoate hydrochloride (1.08 g) obtained in Reference Example 5 was added. A solution (1 mL) of triethylamine (0.70 mL) in tetrahydrofuran was dropwise added, and the mixture was stirred overnight at room temperature. After concentration under reduced pressure, water (50 mL) was added to the residue. The mixture was extracted with ethyl acetate (50 mL). The ethyl acetate layer was washed with saturated brine (50 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.11 g), triethylamine (0.84 mL) and 4-dimethylaminopyridine (0.037 g) were added, and the mixture was stirred overnight at 60° C. After concentration under reduced pressure, water (50 mL) was added to the residue. The mixture was extracted with ethyl acetate (50 mL). The ethyl acetate layer was washed with saturated brine (50 mL) and dried over anhydrous magnesium sulfate. After concentration under reduced pressure, the residue was purified by flash silica gel column chromatography (eluted with acetone:hexane=1:3, then 3:2). Crystallization from acetone-diethyl ether and recrystallization from acetone-diethyl ether gave the title compound (1.09 g) as a colorless solid.

$^1$H-NMR(CDCl$_3$): 2.22 (3H, s), 3.12 (3H, bs), 3.50-4.30 (2H, br), 4.37 (2H, q, J=7.8 Hz), 4.68 (2H, m), 4.80-5.20 (2H, br), 6.63 (1H, d, J=5.7 Hz), 7.26-7.48 (5H, m), 7.53-7.61 (1H, m), 7.82 (1H, d, J=8.1 Hz), 8.04 (2H, d, J=7.2 Hz), 8.33 (1H, d, J=5.7 Hz).

Synthetic Example 5

2-[Methyl[[2-[[[3-methyl-4-(2,2,2-trifluoroethoxy)-2-pyridyl]methyl]sulfinyl]-1H-benzimidazol-1-yl]carbonyl]amino]ethyl benzoate To a solution (30 mL) of bis(trichloromethyl)carbonate (0.99 g) in tetrahydrofuran was dropwise added a solution (2 mL) of pyridine (0.81 mL) in tetrahydrofuran under ice-cooling. After stirring under ice-cooling for 30 min., 2-(methylamino)ethyl benzoate hydrochloride (2.16 g) obtained in Reference Example 5 was added. After addition of a solution (2 mL) of triethylamine (1.39 mL) in tetrahydrofuran, the mixture was stirred at room temperature for 1 hr. After concentration under reduced pressure, ethyl acetate (100 mL) and water (100 mL) were added to the residue, and the mixture was stirred. The ethyl acetate layer was separated and taken, washed with saturated brine (50 mL) and dried over anhydrous magnesium sulfate. After concentration under reduced pressure, the residue was dissolved in tetrahydrofuran (40 mL). 2-[[[3-Methyl-4-(2,2,2-trifluoroethoxy)-2-pyridyl]methyl]sulfinyl]-1H-benzimidazole (2.90 g), triethylamine (2.20 mL) and 4-dimethylaminopyridine (0.096 g) were added, and the mixture was stirred at 60° C. for 2 hr. After concentration under reduced pressure, ethyl acetate (150 mL) and water (80 mL) were added to the residue, and the mixture was stirred. The ethyl acetate layer was separated and taken, washed with saturated brine (50 mL) and dried over anhydrous magnesium sulfate. After concentration under reduced pressure, the residue was purified by silica gel column chromatography (eluted with ethyl acetate:hexane=1:1, then ethyl acetate). Recrystallization from acetone gave the title compound (2.62 g) as a colorless solid.

$^1$H-NMR(CDCl$_3$): 2.22 (3H, s), 3.13 (3H, bs), 3.68-3.98 (2H,bm), 4.38 (2H, q, J=7.8 Hz), 4.69 (2H, m), 4.80-5.10

(2H,bm), 6.64 (1H, d, J=5.7 Hz), 7.27-7.48 (5H, m), 7.59 (1H, m), 7.83 (1H, m), 8.06 (2H, d, J=6.0 Hz), 8.35 (1H, d, J=5.7 Hz).

Synthetic Example 6

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl 4-methoxybenzoate

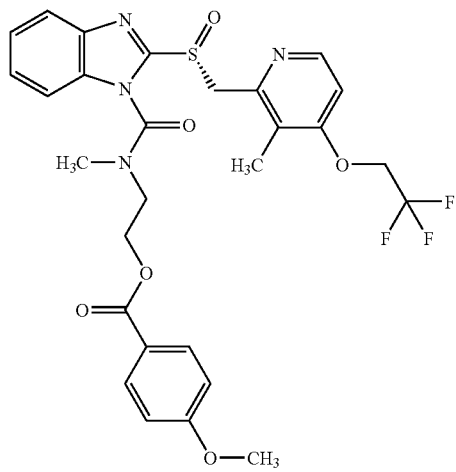 [SMILES: COc1ccc(C(=O)OCCN(C)C(=O)n2c([S@](=O)Cc3nccc(OCC(F)(F)F)c3C)nc3ccccc32)cc1]

To a solution (18 mL) of bis(trichloromethyl)carbonate (0.584 g) in tetrahydrofuran was dropwise added a solution (1 mL) of pyridine (0.49 mL) in tetrahydrofuran under ice-cooling. After stirring under ice-cooling for 40 min., 2-(methylamino)ethyl 4-methoxybenzoate hydrochloride (1.48 g) obtained in Reference Example 6 was added. A solution (1 mL) of triethylamine (0.84 mL) in tetrahydrofuran was added and the mixture was stirred at room temperature for 80 min. After concentration under reduced pressure, ethyl acetate (80 mL) and water (50 mL) were added to the residue and the mixture was stirred. The ethyl acetate layer was separated and taken, washed with saturated brine (30 mL) and dried over anhydrous magnesium sulfate. After concentration under reduced pressure, the residue was dissolved in tetrahydrofuran (25 mL). (R)-2-[[[3-Methyl-4-(2,2,2-trifluoroethoxy)-2-pyridyl]methyl]sulfinyl]-1H-benzimidazole (1.55 g), triethylamine (1.17 mL) and 4-dimethylaminopyridine (0.051 g) were added, and the mixture was stirred at 60° C. for 3 hrs. After concentration under reduced pressure, ethyl acetate (150 mL) and water (50 mL) were added to the residue, and the mixture was stirred. The ethyl acetate layer was separated and taken, washed with saturated brine (50 mL) and dried over anhydrous magnesium sulfate. After concentration under reduced pressure, the residue was purified by silica gel column chromatography (eluted with ethyl acetate:hexane=1:1, then ethyl acetate). Recrystallization from ethyl acetate-hexane gave the title compound (1.08 g) as a colorless solid.

$^1$H-NMR(CDCl$_3$): 2.22 (3H, s), 3.11 (3H, bs), 3.68-3.90 (2H,bm), 3.85 (3H, s), 4.37 (2H, q, J=7.9 Hz), 4.58-4.72 (2H, m), 4.82-5.14 (2H,bm), 6.63 (1H, d, J=5.7 Hz), 6.91 (2H, d, J=9.0 Hz), 7.27-7.40 (3H, m), 7.82 (1H, m), 7.99 (2H, d, J=9.0 Hz), 8.33 (1H, d, J=5.7 Hz).

Synthetic Example 7

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl 3-chlorobenzoate

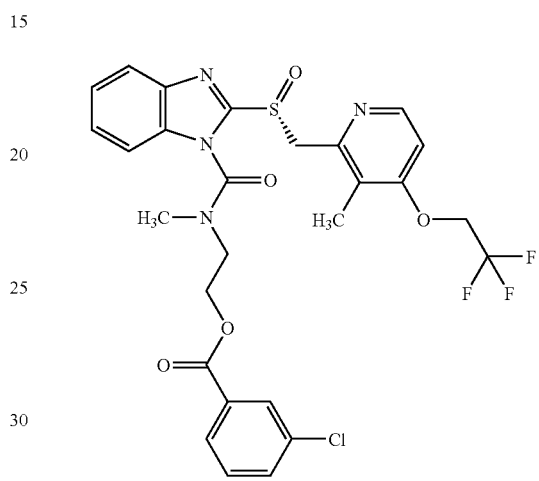

To a solution (20 mL) of bis(trichloromethyl)carbonate (0.582 g) in tetrahydrofuran was dropwise added a solution (1 mL) of pyridine (0.49 mL) in tetrahydrofuran under ice-cooling. After stirring under ice-cooling for 30 min., 2-(methylamino)ethyl 3-chlorobenzoate hydrochloride (1.50 g) obtained in Reference Example 7 was added. A solution (1 mL) of triethylamine (0.84 mL) in tetrahydrofuran was added and the mixture was stirred at room temperature for 2 hrs. After concentration under reduced pressure, ethyl acetate (80 mL) and water (40 mL) were added to the residue and the mixture was stirred. The ethyl acetate layer was separated and taken, washed with saturated brine (25 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.44 g), triethylamine (1.09 mL) and 4-dimethylaminopyridine (0.048 g) were added, and the mixture was stirred at 60° C. for 3 hrs. After concentration under reduced pressure, ethyl acetate (80 mL) and water (40 mL) were added to the residue and the mixture was stirred. The ethyl acetate layer was separated and taken, washed with saturated brine (30 mL) and dried over anhydrous magnesium sulfate. After concentration under reduced pressure, the residue was purified by basic silica gel column chromatography (eluted with ethyl acetate:hexane=1:2, then 1:1) to give the title compound (0.84 g) as colorless syrup.

$^1$H-NMR(CDCl$_3$): 2.21 (3H, s), 3.12 (3H, bs), 3.78-4.08 (2H,bm), 4.38 (2H, q, J=7.8 Hz), 4.64-5.08 (4H,bm), 6.64

(1H, d, J=5.2 Hz), 7.34-7.42 (4H, m), 7.56 (1H, m), 7.82 (1H, m), 7.94 (1H, d, J=7.6 Hz), 8.02 (1H, s), 8.34 (1H, d, J=5.2 Hz).

Synthetic Example 8

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl 3,4-difluorobenzoate

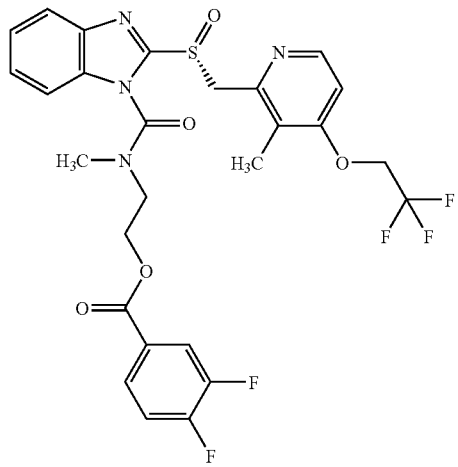 [SMILES: Cc1c(OCC(F)(F)F)ccnc1C[S@@](=O)c1nc2ccccc2n1C(=O)N(C)CCOC(=O)c1ccc(F)c(F)c1]

To a solution (20 mL) of bis(trichloromethyl)carbonate (0.582 g) in tetrahydrofuran was dropwise added a solution (1 mL) of pyridine (0.49 mL) in tetrahydrofuran under ice-cooling. After stirring under ice-cooling for 30 min., 2-(methylamino)ethyl 3,4-difluorobenzoate hydrochloride (1.51 g) obtained in Reference Example 8 was added. A solution (1 mL) of triethylamine (0.84 mL) in tetrahydrofuran was added and the mixture was stirred at room temperature for 3 hrs. After concentration under reduced pressure, ethyl acetate (80 mL) and water (50 mL) were added to the residue and the mixture was stirred. The ethyl acetate layer was separated and taken, washed with saturated brine (30 mL) and dried over anhydrous magnesium sulfate. The layer was concentrated under reduced pressure, and the residue was dissolved in tetrahydrofuran (25 mL). (R)-2-[[[3-Methyl-4-(2,2,2-trifluoroethoxy)-2-pyridyl]methyl]sulfinyl]-1H-benzimidazole (1.71 g), triethylamine (1.29 mL) and 4-dimethylaminopyridine (0.056 g) were added, and the mixture was stirred at 60° C. for 17 hrs. After concentration under reduced pressure, ethyl acetate (100 mL) and water (50 mL) were added to the residue, and the mixture was stirred. The ethyl acetate layer was separated and taken, and the aqueous layer was extracted with ethyl acetate (20 mL). Ethyl acetate layers were combined, washed with saturated brine (30 mL) and dried over anhydrous magnesium sulfate. After concentration under reduced pressure, the residue was purified by silica gel column chromatography (eluted with ethyl acetate:hexane=1:1, then 2:1), and by basic silica gel column chromatography (eluted with ethyl acetate:hexane=1:1). Crystallization from acetone-diisopropyl ether and recrystallization from ethyl acetate-hexane gave the title compound (1.37 g) as a colorless solid.

$^1$H-NMR(CDCl$_3$): 2.21 (3H, s), 3.11 (3H, bs), 3.82-4.08 (2H,bm), 4.38 (2H, q, J=7.8 Hz), 4.60-5.14 (4H,bm), 6.63 (1H, d, J=5.7 Hz), 7.20 (1H, m), 7.33-7.41 (3H, m), 7.78-7.92 (3H, m), 8.33 (1H, d, J=5.7 Hz).

Synthetic Example 9

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl 4-trifluoromethoxybenzoate

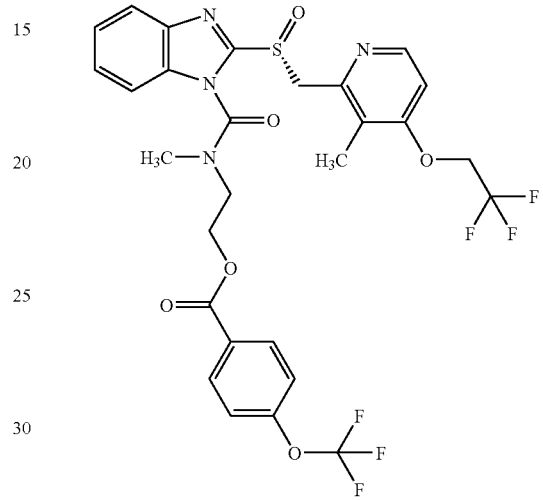

To a solution (20 mL) of bis(trichloromethyl)carbonate (0.582 g) in tetrahydrofuran was dropwise added a solution (1 mL) of pyridine (0.49 mL) in tetrahydrofuran under ice-cooling. After stirring under ice-cooling for 30 min., 2-(methylamino)ethyl 4-trifluoromethoxybenzoate hydrochloride (1.79 g) obtained in Reference Example 9 was added. A solution (1 mL) of triethylamine (0.84 mL) in tetrahydrofuran was added and the mixture was stirred at room temperature for 1.5 hrs. After concentration under reduced pressure, ethyl acetate (80 mL) and water (50 mL) were added to the residue and the mixture was stirred. The ethyl acetate layer was separated and taken, washed with saturated brine (30 mL) and dried over anhydrous magnesium sulfate. After concentration under reduced pressure, the residue was dissolved in tetrahydrofuran (25 mL). (R)-2-[[[3-Methyl-4-(2,2,2-trifluoroethoxy)-2-pyridyl]methyl]sulfinyl]-1H-benzimidazole (1.57 g), triethylamine (1.18 mL) and 4-dimethylaminopyridine (0.052 g) were added, and the mixture was stirred at 60° C. for 4.5 hrs. After concentration under reduced pressure, ethyl acetate (100 mL) and water (50 mL) were added to the residue, and the mixture was stirred. The ethyl acetate layer was separated and taken, and the aqueous layer was extracted with ethyl acetate (30 mL). The ethyl acetate layers were combined, washed with saturated brine (30 mL) and dried over anhydrous magnesium sulfate. After concentration under reduced pressure, the residue was purified by silica gel column chromatography (eluted with ethyl acetate:hexane=1:1), and further by basic silica gel column chromatography (eluted with ethyl acetate:hexane=1:1) to give the title compound (1.44 g) as colorless syrup.

$^1$H-NMR(CDCl$_3$): 2.22 (3H, s), 3.11 (3H, bs), 3.85-4.05 (2H,bm), 4.38 (2H, q, J=7.8 Hz), 4.60-5.12 (4H,bm), 6.64

(1H, d, J=5.7 Hz), 7.24 (2H, d, J=8.7 Hz), 7.25-7.40 (3H, m), 7.82 (1H, d, J=7.2 Hz), 8.09 (2H, d, J=8.7 Hz), 8.33 (1H, d, J=5.7 Hz).

Synthetic Example 10

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl 4-fluorobenzoate

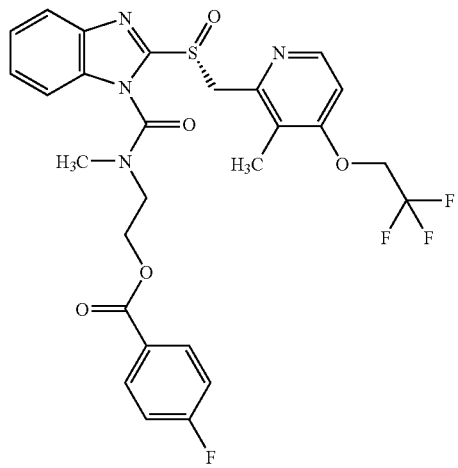 [SMILES: Cc1c(OCC(F)(F)F)ccnc1C[S@@](=O)c1nc2ccccc2n1C(=O)N(C)CCOC(=O)c1ccc(F)cc1]

To a solution (20 mL) of bis(trichloromethyl)carbonate (0.582 g) in tetrahydrofuran was dropwise added a solution (1 mL) of pyridine (0.49 mL) in tetrahydrofuran under ice-cooling. After stirring under ice-cooling for 30 min., 2-(methylamino)ethyl 4-fluorobenzoate hydrochloride (1.40 g) obtained in Reference Example 10 was added. A solution (1 mL) of triethylamine (0.84 mL) in tetrahydrofuran was added and the mixture was stirred at room temperature for 2 hrs. After concentration under reduced pressure, ethyl acetate (80 mL) and water (40 mL) were added to the residue and the mixture was stirred. The ethyl acetate layer was separated and taken, washed with saturated brine (30 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.32 g), triethylamine (1.00 mL) and 4-dimethylaminopyridine (0.049 g) were added, and the mixture was stirred at 60° C. for 14.5 hrs. After concentration under reduced pressure, ethyl acetate (150 mL) and water (50 mL) were added to the residue, and the mixture was stirred. The ethyl acetate layer was separated and taken, washed with saturated brine (30 mL) and dried over anhydrous magnesium sulfate. After concentration under reduced pressure, the residue was crystallized from ethyl acetate:hexane=1:1 and collected by filtration. Recrystallization from acetone gave the title compound (1.39 g) as a colorless solid.

$^1$H-NMR(CDCl$_3$): 2.22 (3H, s), 3.12 (3H, bs), 3.78-4.20 (2H,bm), 4.38 (2H, q, J=7.8 Hz), 4.58-5.08 (4H,bm), 6.65 (1H, d, J=5.6 Hz), 7.11 (2H, t, J=8.4 Hz), 7.28-7.44 (3H, m), 7.81-7.86 (1H, m), 8.03-8.11 (2H, m), 8.35 (1H, d, J=5.6 Hz).

Synthetic Example 11

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl 3,4,5-trimethoxybenzoate

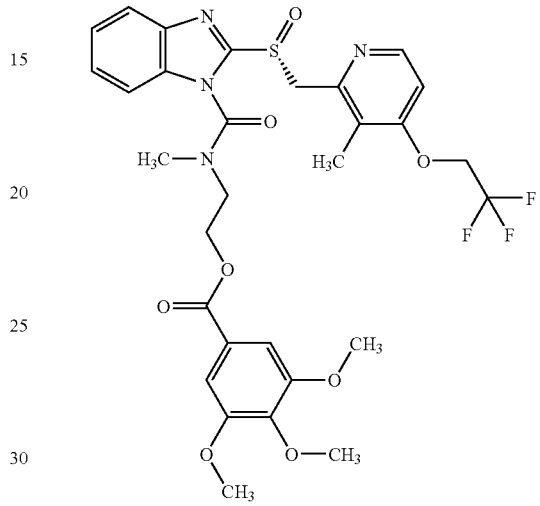

To a solution (30 mL) of bis(trichloromethyl)carbonate (0.60 g) in tetrahydrofuran was dropwise added a solution (1 mL) of pyridine (0.49 mL) in tetrahydrofuran under ice-cooling. After stirring under ice-cooling for 10 min., 2-(methylamino)ethyl 3,4,5-teimethoxybenzoate hydrochloride (1.22 g) obtained in Reference Example 11 was added. A solution (1 mL) of triethylamine (0.84 mL) in tetrahydrofuran was dropwise added and the mixture was stirred at room temperature for 1 hr. After concentration under reduced pressure, water (50 mL) was added to the residue. The mixture was extracted with ethyl acetate (50 mL). The ethyl acetate layer was washed with dilute hydrochloric acid (20 mL) and saturated brine (50 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.11 g), triethylamine (0.84 mL) and 4-dimethylaminopyridine (0.037 g) were added, and the mixture was stirred at 60° C. for 3 hrs. and at room temperature for 2 days. After concentration under reduced pressure, water (50 mL) was added to the residue. The mixture was extracted with ethyl acetate (50 mL). The ethyl acetate layer was washed with saturated brine (50 mL) and dried over anhydrous magnesium sulfate. After concentration under reduced pressure, the residue was purified by flash silica gel column chromatography (eluted with acetone:hexane=1:3, then 3:2) to give the title compound (1.56 g) as a yellow amorphous solid.

$^1$H-NMR (CDCl$_3$): 2.21 (3H, s), 3.12 (3H, bs), 3.50-4.30 (2H, br), 3.83 (6H, s), 3.90 (3H, s), 4.38 (2H, q, J=7.8 Hz), 4.67 (2H, m), 4.80-5.15 (2H, br), 6.64 (1H, d, J=5.7 Hz), 7.25-7.40 (5H, m), 7.78-7.86 (1H, m), 8.33 (1H, d, J=5.7 Hz).

Synthetic Example 12

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl 2-pyridinecarboxylate

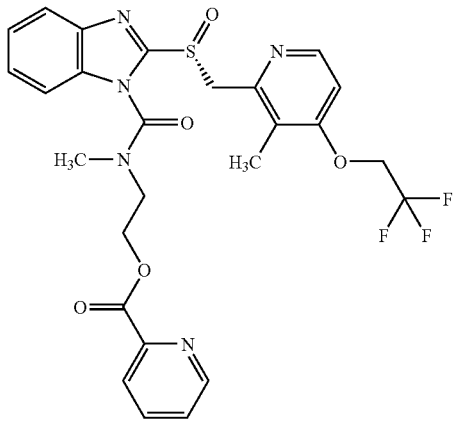 [SMILES: Cc1c(OCC(F)(F)F)ccnc1C[S@@](=O)c1nc2ccccc2n1C(=O)N(C)CCOC(=O)c1ccccn1]

To a solution (30 mL) of bis(trichloromethyl)carbonate (0.422 g) in tetrahydrofuran was dropwise added pyridine (0.345 mL) under ice-cooling. After stirring under ice-cooling for 30 min., 2-(methylamino)ethyl 2-pyridinecarboxylate dihydrochloride (1.08 g) obtained in Reference Example 12 was added. After dropwise addition of triethylamine (1.19 mL), the mixture was stirred at room temperature for 2 hrs. The precipitated solid was filtered off and the filtrate was concentrated under reduced pressure. The residue was dissolved in tetrahydrofuran (10 mL), and (R)-2-[[[3-methyl-4-(2,2,2-trifluoroethoxy)-2-pyridyl]methyl]sulfinyl]-1H-benzimidazole (1.31 g), triethylamine (0.99 mL) and 4-dimethylaminopyridine (0.043 g) were added. The mixture was stirred at 60° C. for 24 hrs. Ethyl acetate (100 mL) was added to the reaction mixture, and the mixture was washed with water (100 mL) and saturated brine (100 mL), dried over anhydrous sodium sulfate, and concentrated under reduced pressure. The residue was purified by basic silica gel column chromatography (eluted with ethyl acetate:hexane=4:1). Crystallization from acetone-diethyl ether gave the title compound (0.9 g) as a white solid.

$^1$H-NMR(CDCl$_3$): 2.22 (3H, s), 3.16 (3H, s), 3.80-4.20 (2H, m), 4.38 (2H, q, J=7.8 Hz), 4.60-5.10 (4H, m), 6.64 (1H, d, J=5.8 Hz), 7.29-7.40 (2H, m), 7.47-7.52 (2H, m), 7.81-7.89 (2H, m), 8.14 (1H, d, J=7.8 Hz), 8.34 (1H, d, J=5.8 Hz), 8.75-8.79 (1H, m).

Synthetic Example 13

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl methoxyacetate

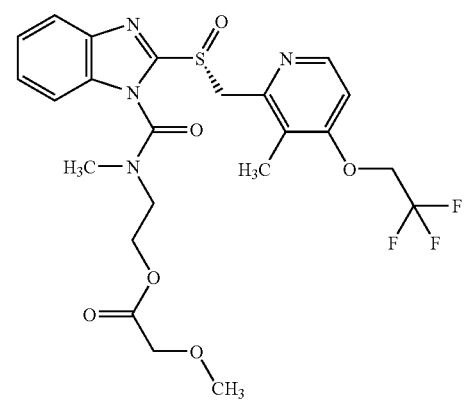 [SMILES: COCC(=O)OCCN(C)C(=O)n1c([S@](=O)Cc2nccc(OCC(F)(F)F)c2C)nc2ccccc21]

To a solution (15 mL) of bis(trichloromethyl)carbonate (0.652 g) in tetrahydrofuran was dropwise added a solution (1 mL) of pyridine (0.55 mL) in tetrahydrofuran under ice-cooling. After stirring under ice-cooling for 30 min., 2-(methylamino)ethyl methoxyacetate (0.99 g) obtained in Reference Example 13 was added. The mixture was stirred at room temperature for 3 hrs. After concentration under reduced pressure, ethyl acetate (80 mL) and water (50 mL) were added to the residue and the mixture was stirred. The ethyl acetate layer was separated and taken, washed with saturated brine (30 mL) and dried over anhydrous magnesium sulfate. After concentration under reduced pressure, the residue was dissolved in tetrahydrofuran (15 mL). (R)-2-[[[3-Methyl-4-(2,2,2-trifluoroethoxy)-2-pyridyl]methyl]sulfinyl]-1H-benzimidazole (1.13 g), triethylamine (0.86 mL) and 4-dimethylaminopyridine (0.037 g) were added, and the mixture was stirred at 60° C. for 4 days. After concentration under reduced pressure, ethyl acetate (80 mL) and water (30 mL) were added to the residue, and the mixture was stirred. The ethyl acetate layer was separated and taken, and the ethyl acetate layer was washed with a saturated aqueous sodium hydrogen carbonate solution (30 mL) and water (30 mL), and dried over anhydrous magnesium sulfate. After concentration under reduced pressure, the residue was purified by silica gel column chromatography (eluted with ethyl acetate, then acetone:ethyl acetate=1:3), and further by basic silica gel column chromatography (eluted with ethyl acetate:hexane=1:1, then 3:1) to give the title compound (0.588 g) as colorless syrup.

$^1$H-NMR(CDCl$_3$): 2.32 (3H, s), 2.68 (3H, s), 3.48 (3H, s), 3.69-4.02 (4H, m), 4.38 (2H, q, J=7.8 Hz), 4.67 (2H, t, J=6.6

Hz), 4.99 (1H, d, J=13.9 Hz), 5.12 (1H, d, J=13.9 Hz), 6.63 (1H, d, J=5.7 Hz), 7.29-7.46 (2H, m), 7.62 (1H, m), 7.81 (1H, m), 8.25 (1H, d, J=5.7 Hz).

Synthetic Example 14

Ethyl 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate

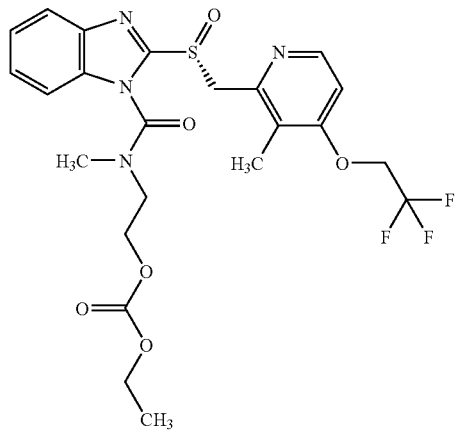 [SMILES: CCOC(=O)OCCN(C)C(=O)n1c([S@](=O)Cc2nccc(OCC(F)(F)F)c2C)nc2ccccc21]

To a solution (40 mL) of bis(trichloromethyl)carbonate (1.31 g) in tetrahydrofuran was dropwise added a solution (2 mL) of pyridine (1.07 mL) in tetrahydrofuran under ice-cooling. After stirring under ice-cooling for 10 min., ethyl 2-(methylamino)ethyl carbonate hydrochloride (2.02 g) obtained in Reference Example 14 was added. A solution (2 mL) of triethylamine (1.84 mL) in tetrahydrofuran was dropwise added and the mixture was stirred at room temperature for 1 hr. After concentration under reduced pressure, water (100 mL) was added to the residue, and the mixture was extracted with ethyl acetate (100 mL). The ethyl acetate layer was washed with 0.2N hydrochloric acid (50 mL) and saturated brine (100 mL) and dried over anhydrous magnesium sulfate. After concentration under reduced pressure, the residue was dissolved in tetrahydrofuran (50 mL). (R)-2-[[[3-Methyl-4-(2,2,2-trifluoroethoxy)-2-pyridyl]methyl]sulfinyl]-1H-benzimidazole (3.69 g), triethylamine (2.09 mL) and 4-dimethylaminopyridine (0.12 g) were added, and the mixture was stirred at 60° C. for 6 hrs. and at room temperature for 8 hrs. After concentration under reduced pressure, water (100 mL) was added to the residue, and the mixture was extracted with ethyl acetate (100 mL). The ethyl acetate layer was washed with saturated brine (100 mL) and dried over anhydrous magnesium sulfate. After concentration under reduced pressure, the residue was purified by basic silica gel column chromatography (eluted with ethyl acetate:hexane=3:7, then ethyl acetate). Crystallization from diethyl ether and recrystallization from diethyl ether gave the title compound (3.84 g) as a colorless solid.

$^{1}$H-NMR(CDCl$_{3}$): 1.32 (3H, t, J=7.2 Hz), 2.23 (3H, s), 3.10 (3H, bs), 3.50-4.20 (2H, br), 4.22 (2H, q, J=7.2 Hz), 4.39 (2H, q, J=7.9 Hz), 4.45 (2H, m), 4.80-5.15 (2H, br), 6.65 (1H, d, J=5.6 Hz), 7.36-7.50 (3H, m), 7.84 (1H, d, J=7.8 Hz), 8.35 (1H, d, J=5.6 Hz).

Synthetic Example 15

Isopropyl 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate

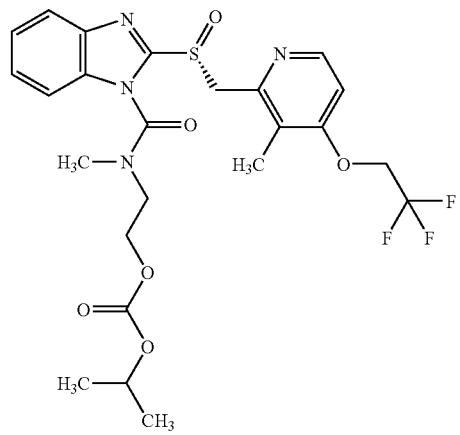 [SMILES: Cc1c(OCC(F)(F)F)ccnc1C[S@@](=O)c1nc2ccccc2n1C(=O)N(C)CCOC(=O)OC(C)C]

To a solution (30 mL) of bis(trichloromethyl)carbonate (0.50 g) in tetrahydrofuran was dropwise added a solution (1 mL) of pyridine (0.40 mL) in tetrahydrofuran under ice-cooling. After stirring under ice-cooling for 1 hr., isopropyl 2-(methylamino)ethyl carbonate hydrochloride (0.99 g) obtained in Reference Example 15 was added. A solution (1 mL) of triethylamine (0.70 mL) in tetrahydrofuran was dropwise added and the mixture was stirred at room temperature for 1 hr. Bis(trichloromethyl)carbonate (0.50 g), a solution (1 mL) of pyridine (0.40 mL) in tetrahydrofuran and a solution (1 mL) of triethylamine (0.70 mL) in tetrahydrofuran were successively added and the mixture was stirred at room temperature for 1 hr. After concentration under reduced pressure, water (50 mL) was added to the residue. The mixture was extracted with ethyl acetate (50 mL). The ethyl acetate layer was washed with saturated brine (50 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.11 g), triethylamine (0.84 mL) and 4-dimethylaminopyridine (0.037 g) were added, and the mixture was stirred at 60° C. for 12 hrs. and at room temperature for 3 days. After concentration under reduced pressure, water (50 mL) was added to the residue. The mixture was extracted with ethyl acetate (50 mL). The ethyl acetate layer was washed with saturated brine (50 mL) and dried over anhydrous magnesium sulfate. After concentration under reduced pressure, the residue was purified by flash silica gel column chromatography (eluted with acetone:hexane=1:3, then 3:2), and further by basic silica gel column chromatography (eluted with ethyl acetate:hexane=3:7, then ethyl acetate). Crystallization from diethyl ether and recrystallization from acetone-diisopropyl ether gave the title compound (0.58 g) as a colorless solid.

$^{1}$H-NMR(CDCl$_{3}$): 1.31 (6H, d, J=6.3 Hz), 2.23 (3H, s), 3.08 (3H, bs), 3.40-4.30 (2H, br), 4.37 (2H, q, J=7.9 Hz), 4.32-4.53 (2H, m), 4.80-5.20 (3H, m), 6.63 (1H, d, J=5.7 Hz), 7.35-7.50 (3H, m), 7.83 (1H, d, J=7.2 Hz), 8.34 (1H, d, J=5.7 Hz).

Synthetic Example 16

Isopropyl 2-[methyl[[2-[[[3-methyl-4-(2,2,2-trifluoroethoxy)-2-pyridyl]methyl]sulfinyl]-1H-benzimidazol-1-yl]carbonyl]amino]ethyl carbonate

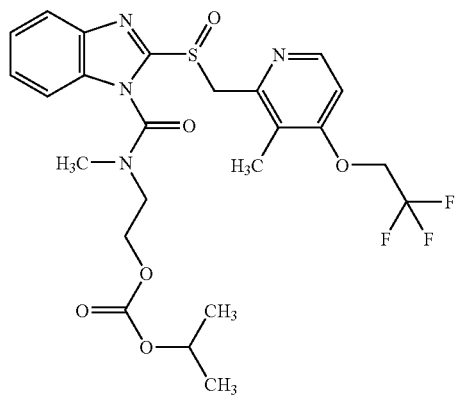 [SMILES: Cc1c(OCC(F)(F)F)ccnc1CS(=O)c1nc2ccccc2n1C(=O)N(C)CCOC(=O)OC(C)C]

To a solution (20 mL) of bis(trichloromethyl)carbonate (0.582 g) in tetrahydrofuran was dropwise added a solution (1 mL) of pyridine (0.49 mL) in tetrahydrofuran under ice-cooling. After stirring under ice-cooling for 30 min., isopropyl 2-(methylamino)ethyl carbonate hydrochloride (1.18 g) obtained in Reference Example 15 was added. A solution (1 mL) of triethylamine (0.84 mL) in tetrahydrofuran was added and the mixture was stirred at room temperature for 2 hrs. After concentration under reduced pressure, ethyl acetate (80 mL) and water (30 mL) were added to the residue, and the mixture was stirred. The ethyl acetate layer was separated and taken, washed with saturated brine (30 mL) and dried over anhydrous magnesium sulfate. After concentration under reduced pressure, the residue was dissolved in tetrahydrofuran (25 mL). 2-[[[3-Methyl-4-(2,2,2-trifluoroethoxy)-2-pyridyl]methyl]sulfinyl]-1H-benzimidazole (1.73 g), triethylamine (1.31 mL) and 4-dimethylaminopyridine (0.057 g) were added, and the mixture was stirred at 60° C. for 5 hrs. After concentration under reduced pressure, ethyl acetate (100 mL) and water (50 mL) were added to the residue, and the mixture was stirred. The ethyl acetate layer was separated and taken, washed with saturated brine (50 mL) and dried over anhydrous magnesium sulfate. After concentration under reduced pressure, the residue was purified by basic silica gel column chromatography (eluted with ethyl acetate: hexane=1:1), and further by silica gel column chromatography (eluted with ethyl acetate:hexane=1:1, then 2:1). Crystallization from diisopropyl ether-hexane and recrystallization from diisopropyl ether gave the title compound (1.20 g) as a colorless solid.

$^1$H-NMR(CDCl$_3$): 1.31 (6H, d, J=6.6 Hz), 2.23 (3H, s), 3.08 (3H, bs), 3.50-3.90 (2H,bm), 4.38 (2H, q, J=7.8 Hz), 4.36-4.58 (2H,bm), 4.79-5.15 (3H, m), 6.64 (1H, d, J=5.7 Hz), 7.35-7.48 (3H, m), 7.83 (1H, d, J=7.5 Hz), 8.34 (1H, d, J=5.7 Hz).

Synthetic Example 17

Benzyl 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate

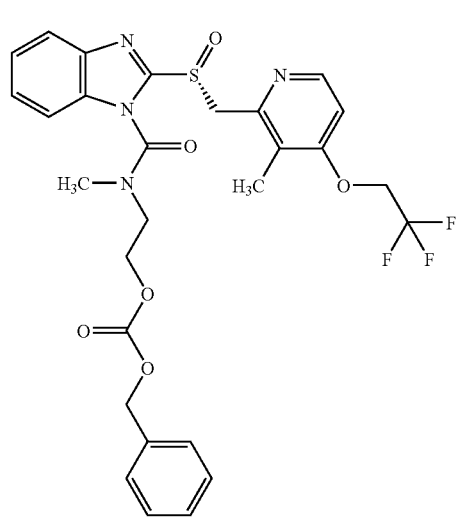 [SMILES: Cc1c(OCC(F)(F)F)ccnc1C[S@@](=O)c1nc2ccccc2n1C(=O)N(C)CCOC(=O)OCc1ccccc1]

To a solution (30 mL) of bis(trichloromethyl)carbonate (0.50 g) in tetrahydrofuran was dropwise added a solution (1 mL) of pyridine (0.40 mL) in tetrahydrofuran under ice-cooling. After stirring under ice-cooling for 1 hr., benzyl 2-(methylamino)ethyl carbonate hydrochloride (1.08 g) obtained in Reference Example 16 was added. A solution (1 mL) of triethylamine (0.70 mL) in tetrahydrofuran was dropwise added, and the mixture was stirred overnight at room temperature. After concentration under reduced pressure, water (50 mL) was added to the residue. The mixture was extracted with ethyl acetate (50 mL). The ethyl acetate layer was washed with saturated brine (50 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.11 g), triethylamine (0.84 mL) and 4-dimethylaminopyridine (0.037 g) were added, and the mixture was stirred overnight at 60° C. After concentration under reduced pressure, water (50 mL) was added to the residue. The mixture was extracted with ethyl acetate (50 mL). The ethyl acetate layer was washed with saturated brine (50 mL) and dried over anhydrous magnesium sulfate. After concentration under reduced pressure, the residue was purified by flash silica gel column chromatography (eluted with acetone:hexane=1:3, then 3:2). Crystallization from acetone-diethyl ether and recrystallization from acetone-diethyl ether gave the title compound (1.17 g) as a colorless solid.

$^1$H-NMR(CDCl$_3$): 2.22 (3H, s), 3.05 (3H, bs), 3.50-4.20 (2H, br), 4.37 (2H, q, J=7.8 Hz), 4.46 (2H, m), 4.80-5.10 (2H, br), 5.17 (2H, s), 6.62 (1H, d, J=5.6 Hz), 7.26-7.48 (8H, m), 7.77-7.88 (1H, m), 8.33 (1H, d, J=5.6 Hz).

Synthetic Example 18

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl tetrahydropyran-4-yl carbonate

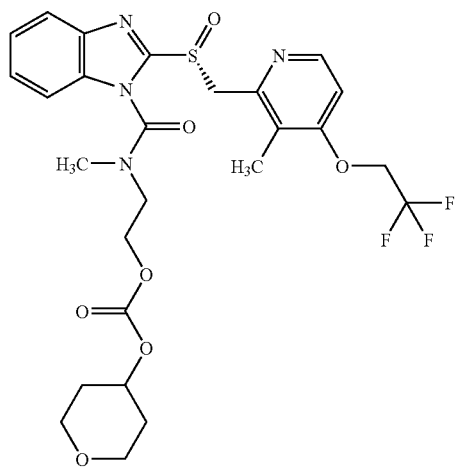 [SMILES: Cc1c(OCC(F)(F)F)ccnc1C[S@@](=O)c1nc2ccccc2n1C(=O)N(C)CCOC(=O)OC1CCOCC1]

To a solution (20 mL) of bis(trichloromethyl)carbonate (0.48 g) in tetrahydrofuran was dropwise added a solution (1 mL) of pyridine (0.39 mL) in tetrahydrofuran under ice-cooling. After stirring under ice-cooling for 20 min., 2-(methylamino)ethyl tetrahydropyran-4-yl carbonate hydrochloride (0.96 g) obtained in Reference Example 17 was added. A solution (1 mL) of triethylamine (0.67 mL) in tetrahydrofuran was dropwise added, and the mixture was stirred at room temperature for 2 hrs. After concentration under reduced pressure, water (50 mL) was added to the residue. The mixture was extracted with ethyl acetate (50 mL). The ethyl acetate layer was washed with 0.2N hydrochloric acid (20 mL) and saturated brine (50 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.26 g), triethylamine (0.71 mL) and 4-dimethylaminopyridine (0.042 g) were added, and the mixture was stirred at 60° C. for 6 hrs. and at room temperature for 8 hrs. After concentration under reduced pressure, water (50 mL) was added to the residue. The mixture was extracted with ethyl acetate (50 mL). The ethyl acetate layer was washed with saturated brine (50 mL) and dried over anhydrous magnesium sulfate. After concentration under reduced pressure, the residue was purified by basic silica gel column chromatography (eluted with ethyl acetate:hexane=3:7, then ethyl acetate). Crystallization from diethyl ether and recrystallization from acetone-diisopropyl ether gave the title compound (1.45 g) as a colorless solid.

$^1$H-NMR(CDCl$_3$): 1.64-1.81 (2H, m), 1.92-2.03 (2H, m), 2.23 (3H, s), 3.09 (3H, bs), 3.40-4.30 (2H, br), 3.45-3.57 (2H, m), 3.87-3.97 (2H, m), 4.38 (2H, q, J=7.8 Hz), 4.45 (2H, m), 4.77-5.15 (3H, m), 6.64 (1H, d, J=5.7 Hz), 7.35-7.50 (3H, m), 7.83 (1H, d, J=6.9 Hz), 8.35 (1H, d, J=5.7 Hz).

Synthetic Example 19

2-Methoxyethyl 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate

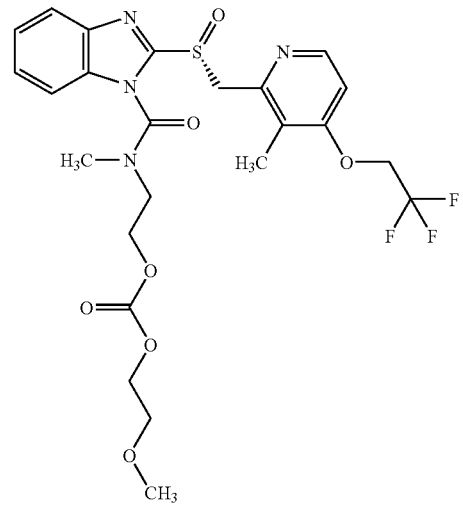 [SMILES: COCCOC(=O)OCCN(C)C(=O)n1c([S@](=O)Cc2nccc(OCC(F)(F)F)c2C)nc2ccccc21]

To a solution (20 mL) of bis(trichloromethyl)carbonate (0.59 g) in tetrahydrofuran was dropwise added a solution (1 mL) of pyridine (0.49 mL) in tetrahydrofuran under ice-cooling. After stirring under ice-cooling for 10 min., 2-methoxyethyl 2-(methylamino)ethyl carbonate hydrochloride (1.07 g) obtained in Reference Example 18 was added. A solution (1 mL) of triethylamine (0.84 mL) in tetrahydrofuran was dropwise added and the mixture was stirred at room temperature for 1 hr. After concentration under reduced pressure, water (50 mL) was added to the residue. The mixture was extracted with ethyl acetate (50 mL). The ethyl acetate layer was washed with 0.2N hydrochloric acid (20 mL) and saturated brine (50 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.85 g), triethylamine (1.05 mL) and 4-dimethylaminopyridine (0.061 g) were added, and the mixture was stirred at 60° C. for 6 hrs. and at room temperature for 8 hrs. After concentration under reduced pressure, water (50 mL) was added to the residue. The mixture was extracted with ethyl acetate (50 mL). The ethyl acetate layer was washed with saturated brine (50 mL) and dried over anhydrous magnesium sulfate. After concentration under reduced pressure, the residue was purified by basic silica gel column chromatography (eluted with ethyl acetate:hexane=3:7, then ethyl acetate). Crystallization from ethyl acetate-diethyl ether and recrystallization from ethyl acetate-diisopropyl ether gave the title compound (1.39 g) as a colorless solid.

$^1$H-NMR(CDCl$_3$): 2.23 (3H, s), 3.09 (3H, bs), 3.37 (3H, s), 3.50-4.20 (2H, br), 3.59-3.65 (2H, m), 4.28-4.33 (2H, m), 4.38 (2H, q, J=7.8 Hz), 4.46 (2H, m), 4.80-5.15 (2H, br), 6.64 (1H, d, J=5.7 Hz), 7.35-7.47 (3H, m), 7.83 (1H, d, J=7.8 Hz), 8.34 (1H, d, J=5.7 Hz).

Synthetic Example 20

2-[Ethyl[[(R)-2-[[[3-methyl-4-(2,2,2-trifluoroethoxy)-2-pyridyl]methyl]sulfinyl]-1H-benzimidazol-1-yl]carbonyl]amino]ethyl acetate

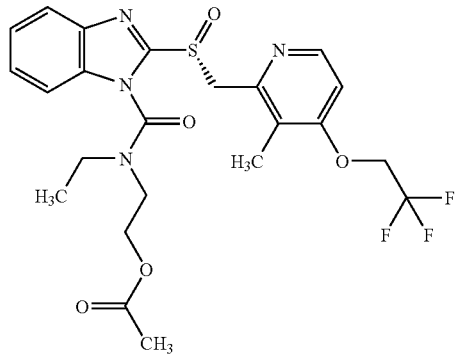 [SMILES: CCN(CCOC(C)=O)C(=O)n1c([S@](=O)Cc2nccc(OCC(F)(F)F)c2C)nc2ccccc21]

To a solution (30 mL) of bis(trichloromethyl)carbonate (0.59 g) in tetrahydrofuran was dropwise added a solution (1 mL) of pyridine (0.49 mL) in tetrahydrofuran under ice-cooling. After stirring under ice-cooling for 10 min., 2-(ethylamino)ethyl acetate hydrochloride (0.67 g) obtained in Reference Example 20 was added. A solution (1 mL) of triethylamine (0.84 mL) in tetrahydrofuran was dropwise added and the mixture was stirred at room temperature for 1 hr. After concentration under reduced pressure, water (50 mL) was added to the residue. The mixture was extracted with ethyl acetate (50 mL). The ethyl acetate layer was washed with saturated brine (50 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl] methyl]sulfinyl]-1H-benzimidazole (1.11 g), triethylamine (0.84 mL) and 4-dimethylaminopyridine (0.037 g) were added, and the mixture was stirred overnight at 60° C. After concentration under reduced pressure, water (50 mL) was added to the residue. The mixture was extracted with ethyl acetate (50 mL). The ethyl acetate layer was washed with saturated brine (50 mL) and dried over anhydrous magnesium sulfate. After concentration under reduced pressure, the residue was purified by basic silica gel column chromatography (eluted with ethyl acetate:hexane=3:7, then ethyl acetate) to give the title compound (1.58 g) as a yellow amorphous solid.

$^1$H-NMR(CDCl$_3$): 1.25 (3H, m), 2.08 (3H, s), 2.23 (3H, s), 3.30-4.10 (4H, br), 4.23-4.45 (2H, m), 4.38 (2H, q, J=7.8 Hz), 4.75-5.20 (2H, br), 6.64 (1H, d, J=5.7 Hz), 7.35-7.46 (3H, m), 7.84 (1H, d, J=6.9 Hz), 8.36 (1H, d, J=5.7 Hz).

Synthetic Example 21

2-[Isopropyl[[(R)-2-[[[3-methyl-4-(2,2,2-trifluoroethoxy)-2-pyridyl]methyl]sulfinyl]-1H-benzimidazol-1-yl]carbonyl]amino]ethyl acetate

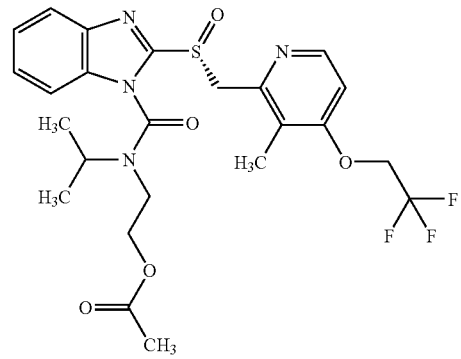 [SMILES: CC(=O)OCCN(C(=O)n1c([S@](=O)Cc2nccc(OCC(F)(F)F)c2C)nc2ccccc21)C(C)C]

To a solution (10 mL) of bis(trichloromethyl)carbonate (0.543 g) in tetrahydrofuran was dropwise added a solution (5 mL) of pyridine (0.445 mL) in tetrahydrofuran under ice-cooling, and the mixture was stirred at 0° C. for 30 min. 2-(Isopropylamino)ethyl acetate hydrochloride (1.0 g) obtained in Reference Example 22 was added. A solution (5 mL) of triethylamine (0.805 mL) in tetrahydrofuran was dropwise added, and the mixture was stirred at room temperature for 30 min. The reaction mixture was concentrated under reduced pressure, water (30 mL) was added to the residue. The mixture was extracted with ethyl acetate (50 mL). The ethyl acetate layer was washed with saturated brine (30 mL), dried over anhydrous sodium sulfate, and concentrated under reduced pressure. The obtained oil was dissolved in tetrahydrofuran (5 mL), and added to a solution (20 mL) of (R)-2-[[[3-methyl-4-(2,2,2-trifluoroethoxy)-2-pyridyl]methyl] sulfinyl]-1H-benzimidazole (1.73 g), triethylamine (1.53 mL) and 4-dimethylaminopyridine (0.134 g) in tetrahydrofuran. The mixture was stirred at 40° C. for 12 hrs. The reaction mixture was concentrated under reduced pressure and water (30 mL) was added to the residue. The mixture was extracted with ethyl acetate (50 mL). The ethyl acetate layer was washed with saturated brine (30 mL), dried over anhydrous sodium sulfate, and concentrated under reduced pressure. The residue was purified by silica gel column chromatography (eluted with ethyl acetate:hexane=2:1, then ethyl acetate) to give the title compound (1.50 g) as a pale-yellow amorphous solid.

$^1$H-NMR(CDCl$_3$): 1.20-1.40 (6H, m), 2.05 (3H×0.4,s), 2.11 (3H×0.6,s), 2.18 (3H×0.6,s), 2.27 (3H×0.4,s), 3.40-3.60

(1H, m), 3.70-4.60 (6H, m), 4.70-5.25 (2H, m), 6.65 (1H, d, J=5.8 Hz), 7.30-7.50 (3H, m), 7.75-7.90 (1H, m), 8.37 (1H, d, J=5.8 Hz).

Synthetic Example 22

Ethyl 2-[isopropyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate

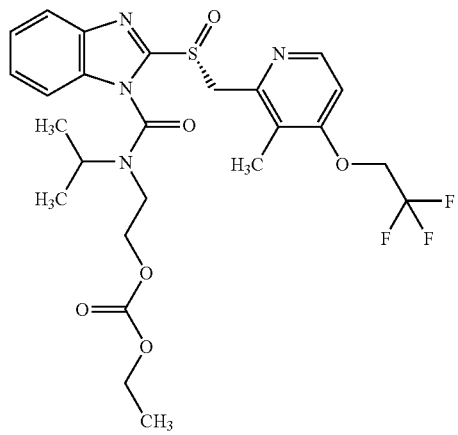 [SMILES: CCOC(=O)OCCN(C(=O)n1c([S@](=O)Cc2nccc(OCC(F)(F)F)c2C)nc2ccccc21)C(C)C]

To a solution (10 mL) of bis(trichloromethyl)carbonate (0.467 g) in tetrahydrofuran was dropwise added a solution (5 mL) of pyridine (0.381 mL) in tetrahydrofuran under ice-cooling, and the mixture was stirred at 0° C. for 30 min. Ethyl 2-(isopropylamino)ethyl carbonate hydrochloride (1.0 g) obtained in Reference Example 23 was added to the reaction mixture. A solution (5 mL) of triethylamine (0.69 mL) in tetrahydrofuran was dropwise added, and the mixture was stirred at 0° C. for 15 min. and at room temperature for 30 min. The reaction mixture was concentrated under reduced pressure and water (30 mL) was added to the residue. The mixture was extracted with ethyl acetate (50 mL). The ethyl acetate layer was washed with saturated brine (30 mL), dried over anhydrous sodium sulfate, and concentrated under reduced pressure. The obtained oil was dissolved in tetrahydrofuran (5 mL), and added to a solution (20 mL) of (R)-2-[[[3-methyl-4-(2,2,2-trifluoroethoxy)-2-pyridyl]methyl]sulfinyl]-1H-benzimidazole (1.48 g), triethylamine (1.32 mL) and 4-dimethylaminopyridine (0.115 g) in tetrahydrofuran, and the mixture was stirred at 40° C. for 12 hrs. The reaction mixture was concentrated under reduced pressure and water (30 mL) was added to the residue. The mixture was extracted with ethyl acetate (50 mL). The ethyl acetate layer was washed with saturated brine (30 mL), dried over anhydrous sodium sulfate, and concentrated under reduced pressure. The residue was purified by silica gel column chromatography (eluted with ethyl acetate:hexane=2:1, then ethyl acetate) to give the title compound (1.20 g) as a pale-yellow amorphous solid.

$^1$H-NMR(CDCl$_3$): 1.20-1.40 (9H, m), 2.17 (3H×0.6,s), 2.27 (3H×0.4,s), 3.40-3.70 (1H, m), 3.75-4.65 (8H, m), 4.70-5.30 (2H, m), 6.64 (1H, d, J=5.8 Hz), 7.35-7.55 (3H, m), 7.75-7.90 (1H, m), 8.38 (1H, d, J=5.8 Hz).

Synthetic Example 23

2-[Cyclohexyl[[(R)-2-[[[3-methyl-4-(2,2,2-trifluoroethoxy)-2-pyridyl]methyl]sulfinyl]-1H-benzimidazol-1-yl]carbonyl]amino]ethyl acetate

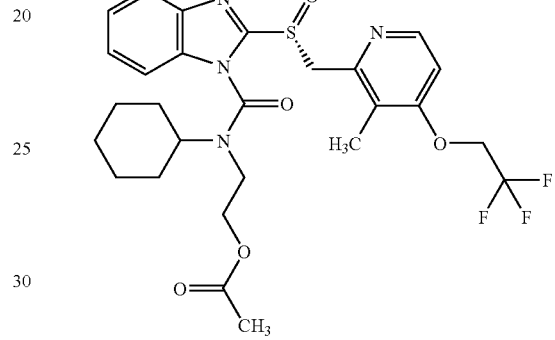

To a solution (10 mL) of bis(trichloromethyl)carbonate (0.593 g) in tetrahydrofuran was dropwise added pyridine (0.485 mL) under ice-cooling. After stirring under ice-cooling for 30 min., 2-(cyclohexylamino)ethyl acetate hydrochloride (1.33 g) obtained in Reference Example 25 was added. Triethylamine (0.84 mL) was dropwise added, and the mixture was stirred at room temperature for 2 hrs. Ethyl acetate (50 mL) was added to the reaction mixture and the mixture was washed with water (50 mL) and saturated brine (50 mL), dried over anhydrous magnesium sulfate and concentrated under reduced pressure. The residue was dissolved in tetrahydrofuran (20 mL), and (R)-2-[[[3-methyl-4-(2,2,2-trifluoroethoxy)-2-pyridyl]methyl]sulfinyl]-1H-benzimidazole (1.61 g), triethylamine (1.21 mL) and 4-dimethylaminopyridine (0.053 g) were added. The mixture was stirred at 60° C. for 24 hrs. Ethyl acetate (50 mL) was added to the reaction mixture, and the mixture was washed with water (20 mL) and saturated brine (50 mL), dried over anhydrous sodium sulfate, and concentrated under reduced pressure. The residue was purified by flash silica gel column chromatography (eluted with ethyl acetate:hexane=1:4, then ethyl acetate) to give the title compound (2.12 g) as a pale-yellow amorphous solid.

$^1$H-NMR(CDCl$_3$): 1.00-2.42 (16H, m), 3.30-3.70 (2H, m), 3.80-4.00 (1H, m), 4.27-4.42 (2H, m), 4.40 (2H, q, J=8.2 Hz), 4.78 (1H×0.5, d, J=13.2 Hz), 4.97 (2H×0.5,s), 5.20 (1H×0.5, d, J=13.2 Hz), 6.67 (1H, d, J=5.8 Hz), 7.36-7.46 (3H, m), 7.81-7.91 (1H, m), 8.39 (1H, d, J=5.8 Hz).

Synthetic Example 29

2-[Cyclohexyl[[(R)-2-[[[3-methyl-4-(2,2,2-trifluoro-ethoxy)-2-pyridyl]methyl]sulfinyl]-1H-benzimidazol-1-yl]carbonyl]amino]ethyl ethyl carbonate

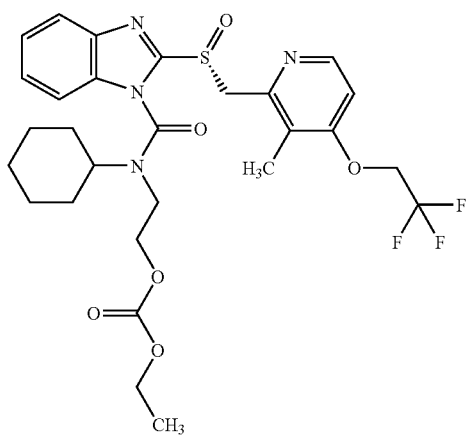 [SMILES: CCOC(=O)OCCN(C(=O)n1c([S@](=O)Cc2nccc(OCC(F)(F)F)c2C)nc2ccccc21)C1CCCCC1]

To a solution (10 mL) of bis(trichloromethyl)carbonate (0.238 g) in tetrahydrofuran was dropwise added pyridine (0.20 mL) under ice-cooling. After stirring under ice-cooling for 30 min., 2-(cyclohexylamino)ethyl ethyl carbonate hydrochloride (0.605 g) obtained in Reference Example 26 was added. Triethylamine (0.335 mL) was dropwise added, and the mixture was stirred at room temperature for 2 hrs. Ethyl acetate (50 mL) was added to the reaction mixture, and the mixture was washed with water (50 mL) and saturated brine (50 mL), dried over anhydrous magnesium sulfate and concentrated under reduced pressure. The residue was dissolved in tetrahydrofuran (10 mL), and (R)-2-[[[3-methyl-4-(2,2,2-trifluoroethoxy)-2-pyridyl]methyl]sulfinyl]-1H-benzimidazole (0.60 g), triethylamine (0.45 mL) and 4-dimethylaminopyridine (0.02 g) were added. The mixture was stirred at 60° C. for 24 hrs. Ethyl acetate (50 mL) was added to the reaction mixture, and the mixture was washed with water (20 mL) and saturated brine (50 mL), dried over anhydrous sodium sulfate, and concentrated under reduced pressure. The residue was purified by flash silica gel column chromatography (eluted with ethyl acetate:hexane=1:4, then ethyl acetate) to give the title compound (0.92 g) as a pale-yellow amorphous solid.

$^1$H-NMR(CDCl$_3$): 1.02-2.27 (16H, m), 3.40-4.60 (9H, m), 4.78 (1H×0.5, d, J=13.2 Hz), 4.97 (2H×0.5,s), 5.44 (1H×0.5, d, J=13.2 Hz), 6.69 (1H, d, J=5.6 Hz), 7.32-7.54 (3H, m), 7.80-7.91 (1H, m), 8.38 (1H, d, J=5.6 Hz).

Synthetic Example 25

2-[[[(R)-2-[[[3-Methyl-4-(2,2,2-trifluoroethoxy)-2-pyridyl]methyl]sulfinyl]-1H-benzimidazol-1-yl]carbonyl](phenyl)amino]ethyl acetate

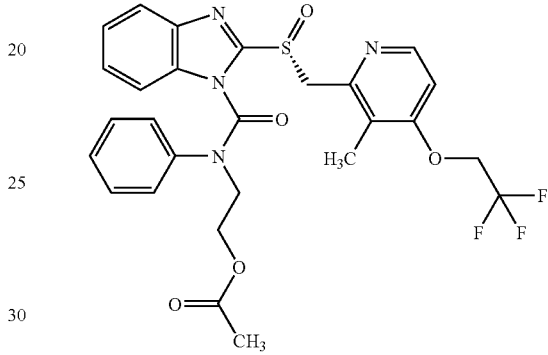

To a solution (350 mL) of bis(trichloromethyl)carbonate (13.4 g) in tetrahydrofuran was dropwise added pyridine (10.38 mL) under ice-cooling. After stirring under ice-cooling for 30 min., 2-anilinoethyl acetate hydrochloride (25.9 g) obtained in Reference Example 27 was added. Triethylamine (18.4 mL) was dropwise added, and the mixture was stirred at room temperature for 2 hrs. After concentration under reduced pressure, ethyl acetate (500 mL) and water (500 mL) were added to the residue, and the mixture was stirred. The ethyl acetate layer was separated and taken, washed with saturated brine (500 mL), dried over anhydrous magnesium sulfate and concentrated under reduced pressure to give 2-[(chlorocarbonyl)(phenyl)amino]ethyl acetate. This was dissolved in tetrahydrofuran (300 mL), (R)-2-[[[3-methyl-4-(2,2,2-trifluoroethoxy)-2-pyridyl]methyl]sulfinyl]-1H-benzimidazole (41.2 g), triethylamine (15.6 mL) and 4-dimethylaminopyridine (1.363 g) were added, and the mixture was stirred at 60° C. for 3 hrs. Ethyl acetate (800 mL) was added to the reaction mixture, and the mixture was washed twice with water (800 mL) and with saturated brine (800 mL), dried over anhydrous sodium sulfate, and concentrated under reduced pressure. The residue was purified by basic silica gel column chromatography (eluted with ethyl acetate:hexane=3:7, then 1:1). Crystallization from diethyl ether gave the title compound (54.1 g) as a white solid.

$^1$H-NMR(CDCl$_3$): 2.00 (3H, s), 2.25 (3H, s), 4.15-4.48 (6H, m), 4.83 (1H, d, J=13.6 Hz), 5.05 (1H, d, J=13.6 Hz), 6.67 (1H, d, J=5.4 Hz), 7.03-7.45 (8H, m), 7.64-7.69 (1H, m), 8.40 (1H, d, J=5.4 Hz).

Synthetic Example 26

2-[[[2-[[[3-Methyl-4-(2,2,2-trifluoroethoxy)-2-pyridyl]methyl]sulfinyl]-1H-benzimidazol-1-yl]carbonyl](phenyl)amino]ethyl acetate

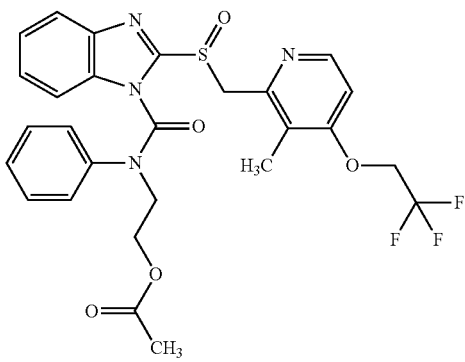 [SMILES: CC(=O)OCCN(C(=O)n1c(S(=O)Cc2nccc(OCC(F)(F)F)c2C)nc2ccccc21)c1ccccc1]

To a solution (10 mL) of 2-[(chlorocarbonyl)(phenyl)amino]ethyl acetate (0.58 g) prepared in the same manner as in Synthetic Example 25 in tetrahydrofuran were added 2-[[[3-methyl-4-(2,2,2-trifluoroethoxy)-2-pyridyl]methyl]sulfinyl]-1H-benzimidazole (0.739 g), triethylamine (0.558 mL) and 4-dimethylaminopyridine (0.024 g), and the mixture was stirred at 60° C. for 15 hrs. Ethyl acetate (30 mL) was added to the reaction mixture, and the mixture was washed with water (50 mL) and saturated brine (50 mL), dried over anhydrous sodium sulfate, and concentrated under reduced pressure. The residue was purified by flash silica gel column chromatography (eluted with acetone:hexane=1:4, then 3:2). Crystallization from diethyl ether gave the title compound (0.779 g) as a white solid.

$^1$H-NMR(CDCl$_3$): 1.99 (3H, s), 2.25 (3H, s), 4.20-4.48 (6H, m), 4.83 (1H, d, J=13.6 Hz), 5.05 (1H, d, J=13.6 Hz), 6.67 (1H, d, J=5.8 Hz), 7.03-7.45 (8H, m), 7.64-7.69 (1H, m), 8.40 (1H, d, J=5.8 Hz).

Synthetic Example 27 tert-Butyl [2-[methyl[[(R)-2-[[[3-methyl-4-(2,2,2-trifluoroethoxy)-2-pyridyl]methyl]sulfinyl]-1H-benzimidazol-1-yl]carbonyl]amino]-3-pyridyl]methyl carbonate

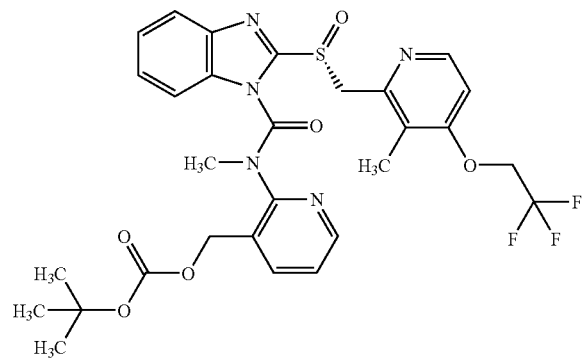 [SMILES: Cc1c(OCC(F)(F)F)ccnc1C[S@@](=O)c1nc2ccccc2n1C(=O)N(C)c1ncccc1COC(=O)OC(C)(C)C]

To a solution (20 mL) of bis(trichloromethyl)carbonate (0.30 g) in tetrahydrofuran was dropwise added pyridine (0.24 mL) under ice-cooling. After stirring under ice-cooling for 30 min., tert-butyl [2-(methylamino)-3-pyridyl]methyl carbonate (0.71 g) obtained in Reference Example 28 was added, and the mixture was stirred at room temperature for 2 hrs. The precipitated solid was filtered off and the filtrate was concentrated under reduced pressure. The residue was dissolved in tetrahydrofuran (20 mL), (R)-2-[[[3-methyl-4-(2,2,2-trifluoroethoxy)-2-pyridyl]methyl]sulfinyl]-1H-benzimidazole (0.92 g), triethylamine (0.70 mL) and 4-dimethylaminopyridine (0.031 g) were added, and the mixture was stirred at 60° C. for 1 hr. Water (50 mL) was added to the reaction mixture and the mixture was extracted twice with ethyl acetate (50 mL). The ethyl acetate layer was washed with saturated brine (50 mL), dried over anhydrous sodium sulfate, and concentrated under reduced pressure. The residue was purified by flash silica gel column chromatography (eluted with acetone:hexane=1:2), and further by basic silica gel column chromatography (eluted with ethyl acetate) to give the title compound (0.38 g) as a pale-yellow amorphous solid.

$^1$H-NMR(CDCl$_3$): 1.46 (9H, s), 2.25 (3H, s), 3.54 (3H, s), 4.37 (2H, q, J=8.0 Hz), 4.95 (2H, s), 5.15 (1H, d, J=14.0 Hz), 5.27 (1H, d, J=14.0 Hz), 6.63 (1H, d, J=5.4 Hz), 7.26-7.45 (3H, m), 7.69-7.87 (3H, m), 8.33 (1H, d, J=5.4 Hz), 8.44-8.46 (1H, m).

Synthetic Example 28

2-[Methyl[[(R)-2-[[[3-methyl-4-(2,2,2-trifluoroethoxy)-2-pyridyl]methyl]sulfinyl]-1H-benzimidazol-1-yl]carbonyl]amino]benzyl acetate

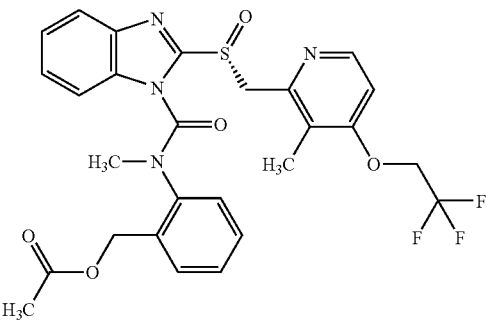 [SMILES: CC(=O)OCc1ccccc1N(C)C(=O)n1c([S@](=O)Cc2nccc(OCC(F)(F)F)c2C)nc2ccccc21]

To a solution (30 mL) of bis(trichloromethyl)carbonate (1.46 g) in tetrahydrofuran was dropwise added pyridine (1.16 mL) under ice-cooling. After stirring under ice-cooling for 30 min., 2-(methylamino)benzyl acetate (2.57 g) obtained in Reference Example 29 was added. The mixture was stirred at room temperature for 3 hrs. The precipitated solid was filtered off and the filtrate was concentrated under reduced pressure. The residue was dissolved in tetrahydrofuran (40 mL), (R)-2-[[[3-methyl-4-(2,2,2-trifluoroethoxy)-2-pyridyl]methyl]sulfinyl]-1H-benzimidazole (4.41 g), triethylamine (3.33 mL) and 4-dimethylaminopyridine (0.15 g) were added, and the mixture was stirred at 60° C. for 18 hrs. Water (100 mL) was added to the reaction mixture, and the mixture was extracted with ethyl acetate (100 mL). The ethyl acetate layer was washed with saturated brine (100 mL), dried over anhydrous sodium sulfate, and concentrated under reduced pressure. The residue was purified by flash silica gel column chromatography (eluted with acetone:hexane=1:4, then 1:2). Crystallization from ethyl acetate-diethyl ether-hexane gave the title compound (2.76 g) as a white solid.

$^1$H-NMR(CDCl$_3$): 2.10 (3H, s), 2.00-2.30 (3H, br), 3.20-3.50 (3H, br), 4.38 (2H, q, J=7.6 Hz), 4.70-5.20 (2H, m), 5.20-5.50 (2H, m), 6.65 (1H, d, J=5.4 Hz), 7.10-7.82 (8H, m), 8.38 (1H, d, J=5.4 Hz).

Synthetic Example 29

2-[[2-(Acetyloxy)ethyl][[(R)-2-[[[3-methyl-4-(2,2,2-trifluoroethoxy)-2-pyridyl]methyl]sulfinyl]-1H-benzimidazol-1-yl]carbonyl]amino]ethyl acetate

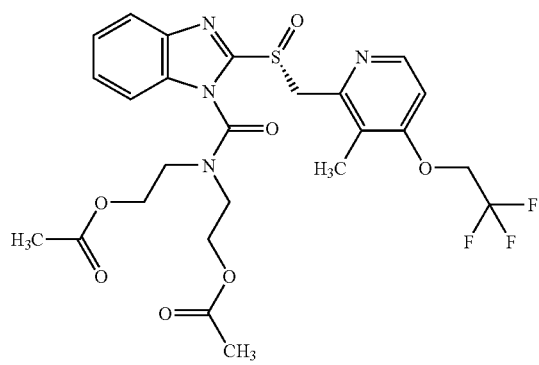 [SMILES: CC(=O)OCCN(CCOC(C)=O)C(=O)n1c([S@](=O)Cc2nccc(OCC(F)(F)F)c2C)nc2ccccc21]

To a solution (30 mL) of bis(trichloromethyl)carbonate (0.50 g) in tetrahydrofuran was dropwise added a solution (1 mL) of pyridine (0.40 mL) in tetrahydrofuran under ice-cooling. After stirring under ice-cooling for 10 min., 2-[(2-acetyloxyethyl)amino]ethyl acetate hydrochloride (1.13 g) obtained in Reference Example 30 was added. A solution (1 mL) of triethylamine (0.70 mL) in tetrahydrofuran was dropwise added, and the mixture was stirred at room temperature for 2 hrs. The precipitated solid was filtered off and the filtrate was concentrated under reduced pressure. Ethyl acetate (20 mL) was added to the residue, the precipitated solid was filtered off and the filtrate was concentrated under reduced pressure. The residue was dissolved in tetrahydrofuran (30 mL). (R)-2-[[[3-Methyl-4-(2,2,2-trifluoroethoxy)-2-pyridyl]methyl]sulfinyl]-1H-benzimidazole (1.48 g), triethylamine (1.12 mL) and 4-dimethylaminopyridine (catalytic amount) were added, and the mixture was stirred at 60° C. overnight. After concentration under reduced pressure, water (50 mL) was added to the residue. The mixture was extracted with ethyl acetate (50 mL). The ethyl acetate layer was washed with saturated brine (50 mL) and dried over anhydrous magnesium sulfate. After concentration under reduced pressure, the residue was purified by silica gel column chromatography (eluted with ethyl acetate:hexane=1:1, then ethyl acetate), and further by basic silica gel column chromatography (eluted with ethyl acetate:hexane=1:1, then ethyl acetate). The resulting product was dissolved in ethyl acetate (20 mL), activated carbon was added and the mixture was stirred overnight. The activated carbon was filtered off and the filtrate was concentrated under reduced pressure to give the title compound (1.60 g) as a yellow amorphous solid.

$^1$H-NMR(CDCl$_3$): 2.06 (3H, s), 2.08 (3H, s), 2.24 (3H, s), 3.40-4.45 (8H, m), 4.39 (2H, q, J=7.9 Hz), 4.88 (1H, d, J=13.2 Hz), 5.05 (1H, d, J=13.2 Hz), 6.66 (1H, d, J=5.6 Hz), 7.38-7.50 (3H, m), 7.87 (1H, d, J=6.9 Hz), 8.36 (1H, d, J=5.6 Hz).

Synthetic Example 30

[(2S)-1-[[(R)-2-[[[3-Methyl-4-(2,2,2-trifluoroethoxy)-2-pyridyl]methyl]sulfinyl]-1H-benzimidazol-1-yl]carbonyl]-2-pyrrolidinyl]methyl acetate

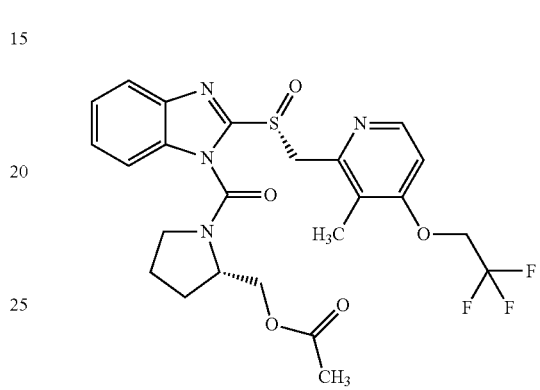

To a solution (30 mL) of bis(trichloromethyl)carbonate (0.50 g) in tetrahydrofuran was dropwise added a solution (1 mL) of pyridine (0.40 mL) in tetrahydrofuran under ice-cooling. After stirring under ice-cooling for 1 hr., (S)-2-pyrrolidinylmethyl acetate hydrochloride (0.90 g) obtained in Reference Example 31 was added. A solution (1 mL) of triethylamine (0.70 mL) in tetrahydrofuran was dropwise added, and the mixture was stirred at room temperature for 2 hrs. After concentration under reduced pressure, water (50 mL) was added to the residue, and the mixture was extracted with ethyl acetate (50 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.11 g), triethylamine (0.84 mL) and 4-dimethylaminopyridine (0.037 g) were added, and the mixture was stirred at 60° C. for 1 day and at room temperature for 2 days. After concentration under reduced pressure, water (50 mL) was added to the residue and the mixture was extracted with ethyl acetate (50 mL). The ethyl acetate layer was washed with saturated brine (50 mL) and dried over anhydrous magnesium sulfate. After concentration under reduced pressure, the residue was purified by basic silica gel column chromatography (eluted with ethyl acetate:hexane=1:1, then ethyl acetate) and further by silica gel column chromatography (eluted with ethyl acetate:hexane=3:1, then ethyl acetate, then acetone:ethyl acetate=1:4, then 2:3) to give the title compound (0.80 g) as a pale-yellow amorphous solid.

$^1$H-NMR(CDCl$_3$): 1.80-2.30 (4H, m), 2.09 (3H, s), 2.30 (3H, s), 3.39 (1H, m), 3.50-3.62 (1H, m), 4.20-4.45 (4H, m), 4.58 (1H, m), 4.89 (1H, d, J=13.5 Hz), 4.96 (1H, d, J=13.5

Hz), 6.65 (1H, d, J=5.9 Hz), 7.36-7.48 (3H, m), 7.89 (1H, d, J=8.7 Hz), 8.38 (1H, d, J=5.9 Hz).

Synthetic Example 31

Ethyl [methyl[[(R)-2-[[[3-methyl-4-(2,2,2-trifluoro-ethoxy)-2-pyridyl]methyl]sulfinyl]-1H-benzimida-zol-1-yl]carbonyl]amino]acetate

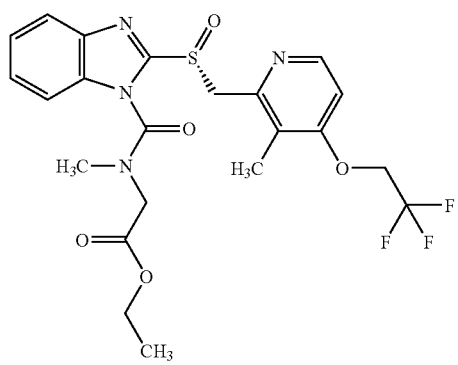 [SMILES: CCOC(=O)CN(C)C(=O)n1c([S@](=O)Cc2nccc(OCC(F)(F)F)c2C)nc2ccccc21]

To a solution (30 mL) of bis(trichloromethyl)carbonate (0.50 g) in tetrahydrofuran was dropwise added a solution (1 mL) of pyridine (0.40 mL) in tetrahydrofuran under ice-cooling. After stirring under ice-cooling for 30 min., sarcosine ethyl ester hydrochloride (0.77 g) was added. A solution (1 mL) of triethylamine (0.70 mL) in tetrahydrofuran was dropwise added and the mixture was stirred at room temperature for 1 hr. The precipitated solid was filtered off and the filtrate was concentrated under reduced pressure. Water (50 mL) was added to the residue, and the mixture was extracted with ethyl acetate (50 mL). The ethyl acetate layer was washed with saturated brine (50 mL) and dried over anhydrous magnesium sulfate. After concentration under reduced pressure, the residue was dissolved in tetrahydrofuran (33 mL). (R)-2-[[[3-Methyl-4-(2,2,2-trifluoroethoxy)-2-pyridyl]methyl]sulfinyl]-1H-benzimidazole sodium (1.37 g) and 4-dimethylaminopyridine (catalytic amount) were added, and the mixture was stirred at 60° C. overnight. After concentration under reduced pressure, water (50 mL) was added to the residue and the mixture was extracted with ethyl acetate (50 mL). The ethyl acetate layer was washed with saturated brine (50 mL) and dried over anhydrous magnesium sulfate. After concentration under reduced pressure, the residue was purified by basic silica gel column chromatography (eluted with ethyl acetate:hexane=1:1, then ethyl acetate) to give the title compound (0.40 g) as a yellow amorphous solid.

$^1$H-NMR(CDCl$_3$): 1.33 (3H, t, J=7.1 Hz), 2.24 (3H, s), 3.10 (3H, bs), 3.70-4.30 (2H, br), 4.28 (2H, q, J=7.1 Hz), 4.38 (2H, q, J=7.8 Hz), 4.82-5.10 (2H, br), 6.63 (1H, d, J=5.5 Hz), 7.34-7.52 (2H, m), 7.70-7.90 (2H, m), 8.32 (1H, d, J=5.5 Hz).

Synthetic Example 32

2-[[[5-Methoxy-2-[[(4-methoxy-3,5-dimethyl-2-pyridyl)methyl]sulfinyl]-1H-benzoimidazol-1-yl]carbonyl](methyl)amino]ethyl benzoate

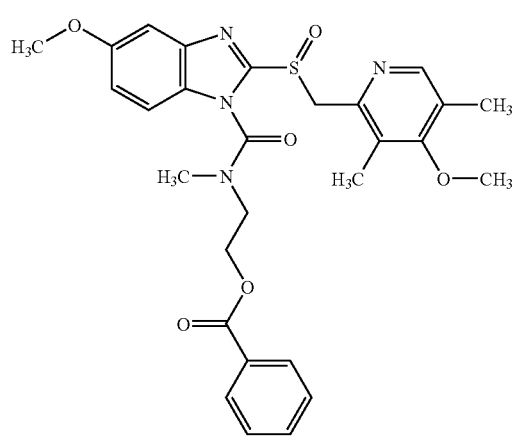

To a solution (10 mL) of bis(trichloromethyl)carbonate (0.344 g) in tetrahydrofuran was dropwise added a solution (5 mL) of pyridine (0.281 mL) in tetrahydrofuran under ice-cooling, and the mixture was stirred at 0° C. for 30 min. 2-(Methylamino)ethyl benzoate hydrochloride (0.750 g) obtained in Reference Example 5 was added. A solution (5 mL) of triethylamine (0.485 mL) in tetrahydrofuran was added, and the mixture was stirred at 0° C. for 1 hr. and at room temperature for 30 min. The reaction mixture was concentrated under reduced pressure and water (30 mL) was added to the residue. The mixture was extracted with ethyl acetate (50 mL). The ethyl acetate layer was washed with saturated brine (30 mL), dried over anhydrous sodium sulfate, and concentrated under reduced pressure. The obtained oil was dissolved in tetrahydrofuran (5 mL), added to a solution (10 mL) of 5-methoxy-2-[[(4-methoxy-3,5-dimethyl-2-pyridyl)methyl]sulfinyl]-1H-benzoimidazole (1.0 g), triethylamine (0.808 mL) and 4-dimethylaminopyridine (0.071 g) in tetrahydrofuran, and the mixture was stirred at 40° C. for 18 hrs. The reaction mixture was concentrated under reduced pressure and water (30 mL) was added to the residue. The mixture was extracted with ethyl acetate (50 mL). The ethyl acetate layer was washed with saturated brine (30 mL), dried over anhydrous sodium sulfate, and concentrated under reduced pressure. The residue was purified by silica gel column chromatography (eluted with ethyl acetate:hexane=1:1, then ethyl acetate) to give a 1:1 mixture (1.50 g) of the title compound and 2-[[[6-methoxy-2-[[(4-methoxy-3,5-dimethyl-2-pyridyl)methyl]sulfinyl]-1H-benzoimidazol-1-yl]carbonyl](methyl)amino]ethyl benzoate as a pale-yellow amorphous solid.

¹H-NMR(CDCl₃): 2.05-2.35 (6H, m), 3.00-3.30 (3H, br), 3.60-4.40 (8H, m), 4.60-5.10 (4H, m), 6.80-7.00 (2H, m), 7.20-7.70 (4H, m), 7.95-8.25 (3H, m).

Synthetic Example 33

3-[Methyl[[(R)-2-[[[3-methyl-4-(2,2,2-trifluoroethoxy)-2-pyridyl]methyl]sulfinyl]-1H-benzimidazol-1-yl]carbonyl]amino]propyl benzoate

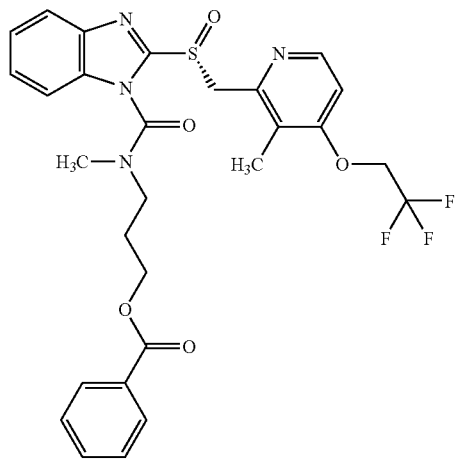 [SMILES: Cc1c(OCC(F)(F)F)ccnc1C[S@@](=O)c1nc2ccccc2n1C(=O)N(C)CCCOC(=O)c1ccccc1]

To a solution (20 mL) of bis(trichloromethyl)carbonate (0.582 g) in tetrahydrofuran was dropwise added a solution (1 mL) of pyridine (0.485 mL) in tetrahydrofuran under ice-cooling. After stirring under ice-cooling for 1 hr., 3-(methylamino)propyl benzoate hydrochloride (1.38 g) obtained in Reference Example 32 was added. A solution (1 mL) of triethylamine (0.84 mL) in tetrahydrofuran was dropwise added, and the mixture was stirred at room temperature for 2 hrs. After concentration under reduced pressure, water (40 mL) was added to the residue, and the mixture was extracted with ethyl acetate (80 mL). The ethyl acetate layer was washed with saturated brine (25 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.63 g), triethylamine (1.23 mL) and 4-dimethylaminopyridine (0.054 g) were added, and the mixture was stirred at 60° C. for 4 hrs. After concentration under reduced pressure, water (40 mL) was added to the residue, and the mixture was extracted with ethyl acetate (80 mL). The ethyl acetate layer was washed with saturated brine (30 mL) and dried over anhydrous magnesium sulfate. After concentration under reduced pressure, the residue was purified by basic silica gel column chromatography (eluted with ethyl acetate:hexane=1:2, then 1:1) to give the title compound (1.26 g) as a yellow amorphous solid.

¹H-NMR(CDCl₃): 2.21 (3H, s), 2.20-2.30 (2H,bm), 3.06 (3H, bs), 3.60-3.75 (2H,bm), 4.36 (2H, q, J=7.8 Hz), 4.30-4.50 (2H,bm), 4.80-5.15 (2H,bm), 6.62 (1H, d, J=5.7 Hz), 7.26-7.44 (5H, m), 7.54 (1H, m), 7.81 (1H, m), 7.93-8.03 (2H,bm), 8.35 (1H, d, J=5.7 Hz).

Synthetic Example 34

2-[Methyl[[2-[[[3-methyl-4-(2,2,2-trifluoroethoxy)-2-pyridyl]methyl]sulfinyl]-1H-benzimidazol-1-yl]carbonyl]amino]ethyl tetrahydropyran-4-yl carbonate

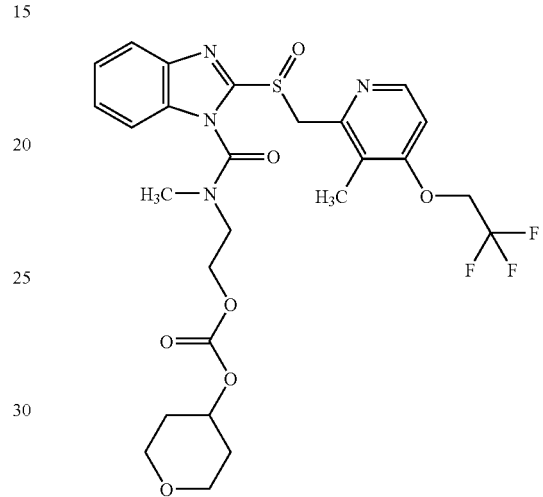

To a solution (20 mL) of bis(trichloromethyl)carbonate (0.582 g) in tetrahydrofuran was dropwise added a solution (1 mL) of pyridine (0.485 mL) in tetrahydrofuran under ice-cooling. After stirring under ice-cooling for 20 min., 2-(methylamino)ethyl tetrahydropyran-4-yl carbonate hydrochloride (1.43 g) obtained in Reference Example 17 was added. A solution (1 mL) of triethylamine (0.84 mL) in tetrahydrofuran was dropwise added, and the mixture was stirred at room temperature for 3 hrs. After concentration under reduced pressure, water (30 mL) was added to the residue, and the mixture was extracted with ethyl acetate (80 mL). The ethyl acetate layer was washed with saturated brine (20 mL), dried over anhydrous magnesium sulfate and concentrated under reduced pressure. The residue was dissolved in tetrahydrofuran (20 mL). 2-[[[3-Methyl-4-(2,2,2-trifluoroethoxy)-2-pyridyl]methyl]sulfinyl]-1H-benzimidazole (1.63 g), triethylamine (1.23 mL) and 4-dimethylaminopyridine (0.027 g) were added, and the mixture was stirred at 60° C. for 17.5 hrs. After concentration under reduced pressure, water (50 mL) was added to the residue, and the mixture was extracted with ethyl acetate (120 mL). The ethyl acetate layer was washed with saturated brine (30 mL) and dried over anhydrous magnesium sulfate. After concentration under reduced pressure, the residue was purified by basic silica gel column chromatography (eluted with ethyl acetate:hexane=1:2, then 1:1), then by silica gel column chromatography (eluted with ethyl acetate:hexane=1:1, then 2:1). Crystallization from diethyl ether gave the title compound (1.23 g) as a colorless solid.

¹H-NMR(CDCl₃): 1.64-1.81 (2H, m), 1.92-2.03 (2H, m), 2.23 (3H, s), 3.10 (3H, bs), 3.40-4.30 (2H, br), 3.46-3.59 (2H, m), 3.87-3.99 (2H, m), 4.39 (2H, q, J=7.9 Hz), 4.45 (2H, m), 4.77-5.15 (3H, m), 6.65 (1H, d, J=5.4 Hz), 7.35-7.50 (3H, m), 7.85 (1H, m), 8.36 (1H, d, J=5.4 Hz).

Synthetic Example 35

Ethyl 2-[methyl[[2-[[[3-methyl-4-(2,2,2-trifluoroethoxy)-2-pyridyl]methyl]sulfinyl]-1H-benzimidazol-1-yl]carbonyl]amino]ethyl carbonate

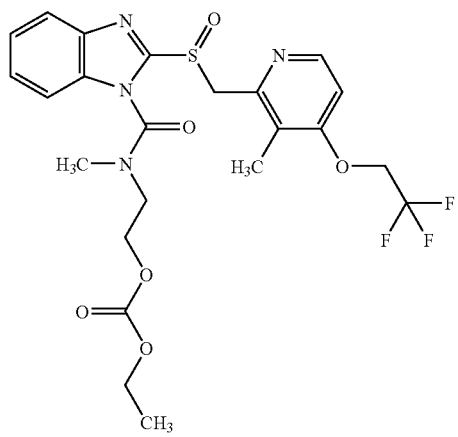

To a solution (20 mL) of bis(trichloromethyl)carbonate (0.582 g) in tetrahydrofuran was dropwise added a solution (1 mL) of pyridine (0.485 mL) in tetrahydrofuran under ice-cooling. After stirring under ice-cooling for 30 min., ethyl 2-(methylamino)ethyl carbonate hydrochloride (1.10 g) obtained in Reference Example 14 was added. A solution (1 mL) of triethylamine (0.84 mL) in tetrahydrofuran was dropwise added, and the mixture was stirred at room temperature for 3 hrs. After concentration under reduced pressure, water (30 mL) was added to the residue, and the mixture was extracted with ethyl acetate (80 mL). The ethyl acetate layer was washed with saturated brine (30 mL) and dried over anhydrous magnesium sulfate. The layer was concentrated under reduced pressure, and the residue was dissolved in tetrahydrofuran (20 mL). 2-[[[3-Methyl-4-(2,2,2-trifluoroethoxy)-2-pyridyl]methyl]sulfinyl]-1H-benzimidazole (1.63 g), triethylamine (1.23 mL), 4-dimethylaminopyridine (0.054 g) was added, and the mixture was stirred at 60° C. for 14 hrs. After concentration under reduced pressure, water (40 mL) was added to the residue, and the mixture was extracted with ethyl acetate (100 mL). The ethyl acetate layer was washed with saturated brine (30 mL), and dried over anhydrous magnesium sulfate. After concentration under reduced pressure, the residue was purified by basic silica gel column chromatography (eluted with ethyl acetate:hexane=1:2, then 1:1), and then by silica gel column chromatography (eluted with ethyl acetate:hexane=1:1, then 2:1) to give the title compound (1.27 g) as a yellow amorphous solid.

$^1$H-NMR(CDCl$_3$): 1.32 (3H, t, J=7.1 Hz), 2.23 (3H, s), 3.09 (3H, bs), 3.50-4.76 (4H, br), 4.21 (2H, q, J=7.1 Hz), 4.38 (2H, q, J=7.9 Hz), 4.84-5.14 (2H, m), 6.64 (1H, d, J=5.6 Hz), 7.36-7.46 (3H, m), 7.83 (1H, d, J=7.2 Hz), 8.34 (1H, d, J=5.6 Hz).

Synthetic Example 36

Ethyl 2-[methyl[[(S)-2-[[[3-methyl-4-(2,2,2-trifluoroethoxy)-2-pyridyl]methyl]sulfinyl]-1H-benzimidazol-1-yl]carbonyl]amino]ethyl carbonate

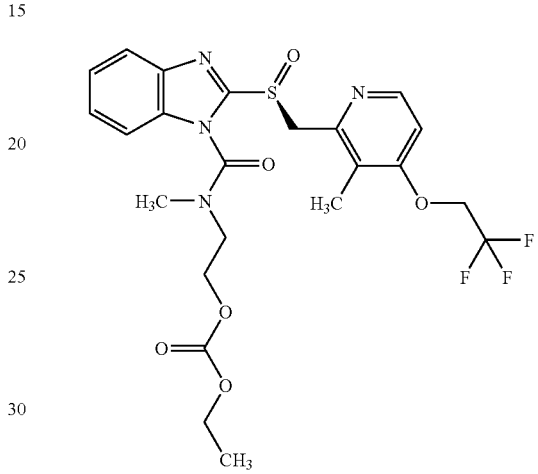

To a solution (20 mL) of bis(trichloromethyl)carbonate (0.582 g) in tetrahydrofuran was dropwise added a solution (1 mL) of pyridine (0.485 mL) in tetrahydrofuran under ice-cooling. After stirring under ice-cooling for 1 hr., ethyl 2-(methylamino)ethyl carbonate hydrochloride (1.10 g) obtained in Reference Example 14 was added. A solution (1 mL) of triethylamine (0.84 mL) in tetrahydrofuran was dropwise added, and the mixture was stirred at room temperature for 2 hrs. After concentration under reduced pressure, water (30 mL) was added to the residue, and the mixture was extracted with ethyl acetate (80 mL). The ethyl acetate layer was washed with saturated brine (30 mL), and dried over anhydrous magnesium sulfate. The layer was concentrated under reduced pressure, and the residue was dissolved in tetrahydrofuran (20 mL). (S)-2-[[[3-Methyl-4-(2,2,2-trifluoroethoxy)-2-pyridyl]methyl]sulfinyl]-1H-benzimidazole (1.15 g), triethylamine (0.87 mL) and 4-dimethylaminopyridine (0.035 g) were added, and the mixture was stirred at 60° C. for 12 hrs. After concentration under reduced pressure, water (30 mL) was added to the residue, and the mixture was extracted with ethyl acetate (100 mL). The ethyl acetate layer was washed with saturated brine (30 mL), and dried over anhydrous magnesium sulfate. After concentration under reduced pressure, the residue was purified by basic silica gel column chromatography (eluted with ethyl acetate:hexane=1:2, then 1:1). Crystallization from diethyl ether gave the title compound (0.40 g) as a colorless solid.

$^1$H-NMR(CDCl$_3$): 1.32 (3H, t, J=7.2 Hz), 2.23 (3H, s), 3.10 (3H, bs), 3.50-4.56 (4H, br), 4.22 (2H, q, J=7.2 Hz), 4.38

(2H, q, J=7.9 Hz), 4.84-5.14 (2H, m), 6.65 (1H, d, J=5.6 Hz), 7.34-7.50 (3H, m), 7.85 (1H, m), 8.36 (1H, d, J=5.6 Hz).

Synthetic Example 37

Ethyl 2-[[[5-methoxy-2-[[(4-methoxy-3,5-dimethyl-2-pyridyl)methyl]sulfinyl]-3H-imidazo[4,5-b]pyridin-3-yl]carbonyl](methyl)amino]ethyl carbonate

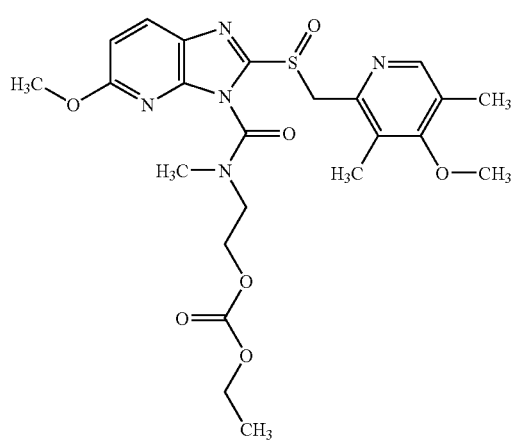

To a solution (20 mL) of bis(trichloromethyl)carbonate (0.582 g) in tetrahydrofuran was dropwise added a solution (1 mL) of pyridine (0.485 mL) in tetrahydrofuran under ice-cooling. After stirring under ice-cooling for 30 min., ethyl 2-(methylamino)ethyl carbonate hydrochloride (1.10 g) obtained in Reference Example 14 was added. A solution (1 mL) of triethylamine (0.84 mL) in tetrahydrofuran was dropwise added, and the mixture was stirred at room temperature for 2.5 hrs. After concentration under reduced pressure, water (30 mL) was added to the residue, and the mixture was extracted with ethyl acetate (80 mL). The ethyl acetate layer was washed with saturated brine (30 mL) and dried over anhydrous magnesium sulfate. The layer was concentrated under reduced pressure, and the residue was dissolved in tetrahydrofuran (20 mL). 5-Methoxy-2-[[(4-methoxy-3,5-dimethyl-2-pyridyl)methyl]sulfinyl]-1H-imidazo[4,5-b]pyridine (1.44 g) synthesized by the method described in JP-A-63-146882, triethylamine (1.16 mL) and 4-dimethylaminopyridine (0.049 g) were added, and the mixture was stirred at 60° C. for 6 hrs. After concentration under reduced pressure, water (30 mL) was added to the residue, and the mixture was extracted with ethyl acetate (100 mL). The ethyl acetate layer was washed with saturated brine (30 mL) and dried over anhydrous magnesium sulfate. After concentration under reduced pressure, the residue was purified by basic silica gel column chromatography (eluted with ethyl acetate:hexane=1:2, then 1:1). Crystallization from diethyl ether gave the title compound (0.721 g) as a colorless solid.

¹H-NMR(CDCl₃): 1.25-1.34 (3H, m), 2.23 (6H, s), 3.15, 3.32 (total 3H, s), 3.72 (3H, s), 3.90-4.53 (9H, m), 4.86 (1H, d, J=13.4 Hz), 4.95 (1H, d, J=13.4 Hz), 6.79 (1H, d, J=8.7 Hz), 7.95 (1H, d, J=8.7 Hz), 8.22 (1H, s).

Synthetic Example 38

2-[[[5-Methoxy-2-[[(4-methoxy-3,5-dimethyl-2-pyridyl)methyl]sulfinyl]-3H-imidazo[4,5-b]pyridin-3-yl]carbonyl](methyl)amino]ethyl acetate

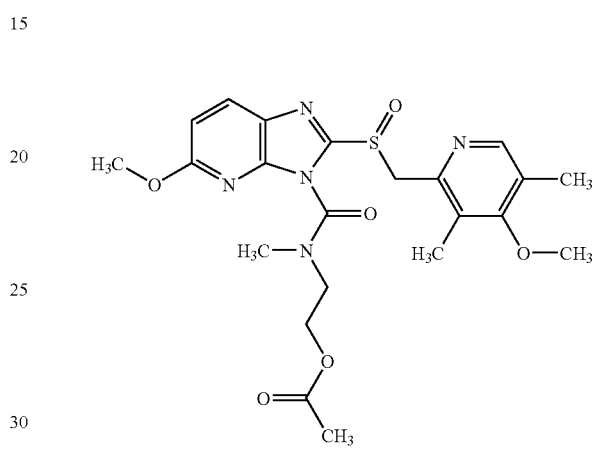

To a solution (20 mL) of bis(trichloromethyl)carbonate (0.582 g) in tetrahydrofuran was dropwise added a solution (1 mL) of pyridine (0.485 mL) in tetrahydrofuran under ice-cooling. After stirring under ice-cooling for 30 min., 2-(methylamino)ethyl acetate hydrochloride (0.922 g) obtained in Reference Example 2 was added. A solution (1 mL) of triethylamine (0.84 mL) in tetrahydrofuran was dropwise added, and the mixture was stirred at room temperature for 2 hrs. After concentration under reduced pressure, water (30 mL) was added to the residue, and the mixture was extracted with ethyl acetate (80 mL). The ethyl acetate layer was washed with saturated brine (30 mL) and dried over anhydrous magnesium sulfate. After concentration under reduced pressure, the residue was dissolved in tetrahydrofuran (10 mL). 5-Methoxy-2-[[(4-methoxy-3,5-dimethyl-2-pyridyl)methyl]sulfinyl]-1H-imidazo[4,5-b]pyridine (0.85 g) synthesized by the method described in JP-A-63-146882, triethylamine (0.70 mL) and 4-dimethylaminopyridine (0.025 g) were added, and the mixture was stirred at 60° C. for 5 hrs. After concentration under reduced pressure, water (30 mL) was added to the residue, and the mixture was extracted with ethyl acetate (90 mL). The ethyl acetate layer was washed with saturated brine (30 mL) and dried over anhydrous magnesium sulfate. After concentration under reduced pressure, the residue was purified by basic silica gel column chromatography (eluted with ethyl acetate:hexane=1:2, then 1:1). Crystallization from diethyl ether gave the title compound (0.173 g) as a colorless solid.

¹H-NMR(CDCl₃): 2.04, 2.09 (total 3H, s), 2.24 (6H, s), 3.13, 3.30 (total 3H, s), 3.45-3.97 (2H, m), 3.72 (3H, s), 3.97

(3H, s), 4.15-4.50 (2H, m), 4.85 (1H, d, J=13.1 Hz), 4.96 (1H, d, J=13.1 Hz), 6.80 (1H, d, J=8.9 Hz), 7.96 (1H, d, J=8.9 Hz), 8.22 (1H, s).

Synthetic Example 39

2-[[[5-Methoxy-2-[[(4-methoxy-3,5-dimethyl-2-pyridyl)methyl]sulfinyl]-3H-imidazo[4,5-b]pyridin-3-yl]carbonyl](phenyl)amino]ethyl acetate

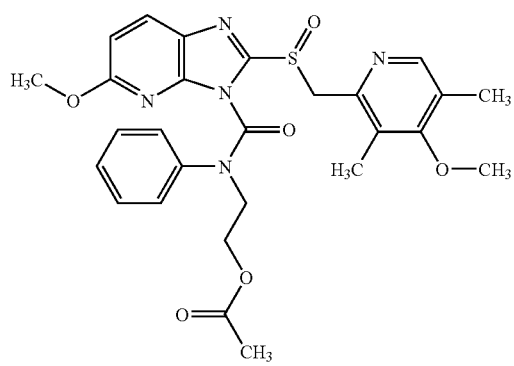

To a solution (10 mL) of bis(trichloromethyl)carbonate (0.291 g) in tetrahydrofuran was dropwise added a solution (1 mL) of pyridine (0.243 mL) in tetrahydrofuran under ice-cooling. After stirring under ice-cooling for 30 min., 2-anilinoethyl acetate hydrochloride (0.647 g) obtained in Reference Example 27 was added. A solution (1 mL) of triethylamine (0.419 mL) in tetrahydrofuran was dropwise added, and the mixture was stirred at room temperature for 3 hrs. After concentration under reduced pressure, water (20 mL) was added to the residue, and the mixture was extracted with ethyl acetate (50 mL). The ethyl acetate layer was washed with saturated brine (15 mL) and dried over anhydrous magnesium sulfate. After concentration under reduced pressure, the residue was dissolved in tetrahydrofuran (10 mL). 5-Methoxy-2-[[(4-methoxy-3,5-dimethyl-2-pyridyl)methyl]sulfinyl]-1H-imidazo[4,5-b]pyridine (0.867 g) synthesized by the method described in JP-A-63-146882, triethylamine (0.697 mL) and 4-dimethylaminopyridine (0.020 g) was added, and the mixture was stirred at 60° C. for 10 hrs. After concentration under reduced pressure, water (20 mL) was added to the residue, and the mixture was extracted with ethyl acetate (50 mL). The ethyl acetate layer was washed with saturated brine (15 mL) and dried over anhydrous magnesium sulfate. After concentration under reduced pressure, the residue was purified by basic silica gel column chromatography (eluted with ethyl acetate:hexane=1:1). Crystallization from diethyl ether gave the title compound (0.311 g) as a colorless solid.

$^1$H-NMR(CDCl$_3$): 1.96 (3H, s), 2.23 (3H, s), 2.25 (3H, s), 3.72 (3H, s), 4.01 (3H, s), 4.12-4.52 (4H, m), 4.78-5.22 (2H, m), 6.62 (1H, d, J=8.7 Hz), 7.02-7.18 (3H, m), 7.32-7.48 (2H, m), 7.73 (1H, d, J=8.7 Hz), 8.26 (1H, s).

Synthetic Example 40

4-[Methyl[[(R)-2-[[[3-methyl-4-(2,2,2-trifluoroethoxy)-2-pyridyl]methyl]sulfinyl]-1H-benzimidazol-1-yl]carbonyl]amino]butyl acetate

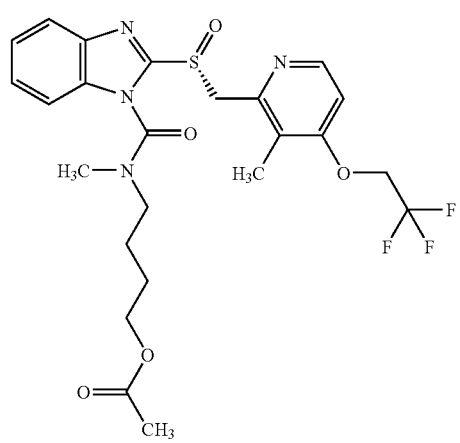 [SMILES: CC(=O)OCCCCN(C)C(=O)n1c([S@](=O)Cc2nccc(OCC(F)(F)F)c2C)nc2ccccc21]

To a solution (20 mL) of bis(trichloromethyl)carbonate (0.59 g) in tetrahydrofuran was dropwise added a solution (1 mL) of pyridine (0.49 mL) in tetrahydrofuran under ice-cooling. After stirring under ice-cooling for 30 min., 4-(methylamino)butyl acetate hydrochloride (1.08 g) obtained in Reference Example 37 was added. A solution (1 mL) of triethylamine (0.84 mL) in tetrahydrofuran was dropwise added, and the mixture was stirred at room temperature for 3 hrs. After concentration under reduced pressure, water (50 mL) was added to the residue and the mixture was extracted with ethyl acetate (50 mL). The ethyl acetate layer was washed with saturated brine (50 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.02 g), triethylamine (0.77 mL) and 4-dimethylaminopyridine (catalytic amount) were added, and the mixture was stirred at 60° C. overnight. After concentration under reduced pressure, water (50 mL) was added to the residue and the mixture was extracted with ethyl acetate (50 mL). The ethyl acetate layer was washed with saturated brine (50 mL) and dried over anhydrous magnesium sulfate. After concentration under reduced pressure, the residue was purified by basic silica gel column chromatography (eluted with ethyl acetate:hexane=1:2, then 1:1) to give the title compound (0.93 g) as a yellow amorphous solid.

$^1$H-NMR(CDCl$_3$): 1.65-1.85 (4H, m), 2.03 (3H, s), 2.23 (3H, s), 3.02 (3H, bs), 3.45-3.63 (2H, m), 4.03-4.13 (2H, m), 4.37 (2H, q, J=7.8 Hz), 4.85-5.13 (2H, m), 6.64 (1H, d, J=5.6 Hz), 7.36-7.46 (3H, m), 7.84 (1H, d, J=8.4 Hz), 8.35 (1H, d, J=5.6 Hz).

Synthetic Example 41

Ethyl 4-[methyl[[(R)-2-[[[3-methyl-4-(2,2,2-trifluoroethoxy)-2-pyridyl]methyl]sulfinyl]-1H-benzimidazol-1-yl]carbonyl]amino]butyl carbonate

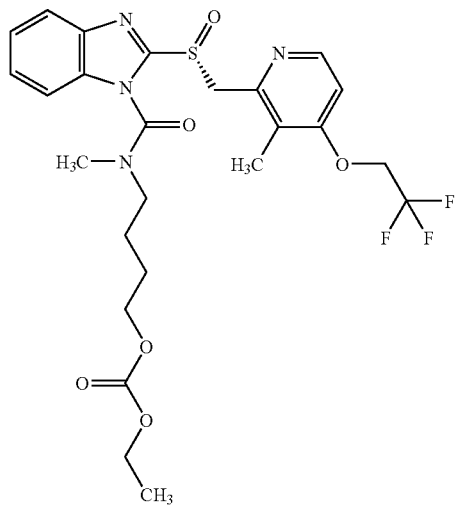 [SMILES: CCOC(=O)OCCCCN(C)C(=O)n1c([S@](=O)Cc2nccc(OCC(F)(F)F)c2C)nc2ccccc21]

To a solution (20 mL) of bis(trichloromethyl)carbonate (0.59 g) in tetrahydrofuran was dropwise added a solution (1 mL) of pyridine (0.49 mL) in tetrahydrofuran under ice-cooling. After stirring under ice-cooling for 30 min., ethyl 4-(methylamino)butyl carbonate hydrochloride (1.27 g) obtained in Reference Example 39 was added. A solution (1 mL) of triethylamine (0.84 mL) in tetrahydrofuran was dropwise added, and the mixture was stirred at room temperature for 3 hrs. After concentration under reduced pressure, water (50 mL) was added to the residue and the mixture was extracted with ethyl acetate (50 mL). The ethyl acetate layer was washed with saturated brine (50 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.26 g), triethylamine (0.95 mL) and 4-dimethylaminopyridine (catalytic amount) were added, and the mixture was stirred at 60° C. overnight. After concentration under reduced pressure, water (50 mL) was added to the residue and the mixture was extracted with ethyl acetate (50 mL). The ethyl acetate layer was washed with saturated brine (50 mL) and dried over anhydrous magnesium sulfate. After concentration under reduced pressure, the residue was purified by basic silica gel column chromatography (eluted with ethyl acetate:hexane=1:2; then 1:1) to give the title compound (1.08 g) as a yellow amorphous solid.

$^1$H-NMR(CDCl$_3$): 1.31 (3H, t, J=7.2 Hz), 1.73-1.91 (4H, m), 2.23 (3H, s), 3.01 (3H, bs), 3.50-3.62 (2H, m), 4.15-4.22 (4H, m), 4.38 (2H, q, J=7.8 Hz), 4.87-5.13 (2H, m), 6.64 (1H, d, J=5.4 Hz), 7:35-7.46 (3H, m), 7.83 (1H, d, J=7.8 Hz), 8.35 (1H, d, J=5.4 Hz).

Synthetic Example 42

Ethyl 3-[methyl[[(R)-2-[[[3-methyl-4-(2,2,2-trifluoroethoxy)-2-pyridyl]methyl]sulfinyl]-1H-benzimidazol-1-yl]carbonyl]amino]propyl carbonate

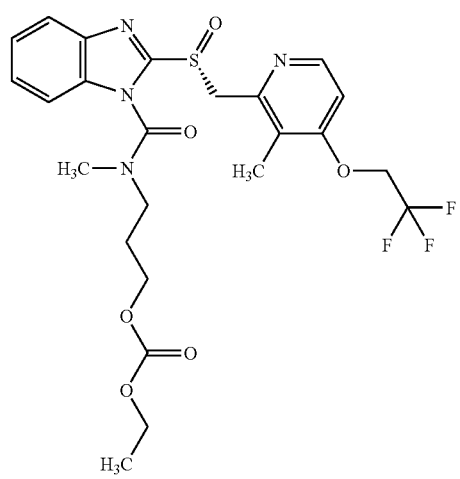 [SMILES: CCOC(=O)OCCCN(C)C(=O)n1c([S@](=O)Cc2nccc(OCC(F)(F)F)c2C)nc2ccccc21]

To a solution (20 mL) of bis(trichloromethyl)carbonate (0.59 g) in tetrahydrofuran was dropwise added a solution (1 mL) of pyridine (0.49 mL) in tetrahydrofuran under ice-cooling. After stirring under ice-cooling for 30 min., ethyl 3-(methylamino)propyl carbonate hydrochloride (1.18 g) obtained in Reference Example 44 was added. A solution (1 mL) of triethylamine (0.84 mL) in tetrahydrofuran was dropwise added, and the mixture was stirred at room temperature for 3 hrs. After concentration under reduced pressure, water (50 mL) was added to the residue and the mixture was extracted with ethyl acetate (50 mL). The ethyl acetate layer was washed with saturated brine (50 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.10 g), triethylamine (0.83 mL) and 4-dimethylaminopyridine (catalytic amount) were added, and the mixture was stirred at 60° C. overnight. After concentration under reduced pressure, water (50 mL) was added to the residue and the mixture was extracted with ethyl acetate (50 mL). The ethyl acetate layer was washed with saturated brine (50 mL) and dried over anhydrous magnesium sulfate. After concentration under reduced pressure, the residue was purified by basic silica gel column chromatography (eluted with ethyl acetate:hexane=1:2, then 1:1) to give the title compound (0.88 g) as a yellow amorphous solid.

$^1$H-NMR(CDCl$_3$): 1.29 (3H, t, J=7.2 Hz), 2.10-2.20 (2H, m), 2.22 (3H, s), 3.02 (3H, bs), 3.55-3.77 (2H, m), 4.14-4.30

(4H, m), 4.37 (2H, q, J=7.8 Hz), 4.83-5.13 (2H, m), 6.64 (1H, d, J=5.6 Hz), 7.35-7.46 (3H, m), 7.82 (1H, d, J=8.1 Hz), 8.35 (1H, d, J=5.6 Hz).

Synthetic Example 43

3-[Methyl[[(R)-2-[[[3-methyl-4-(2,2,2-trifluoroethoxy)-2-pyridyl]methyl]sulfinyl]-1H-benzimidazol-1-yl]carbonyl]amino]propyl acetate

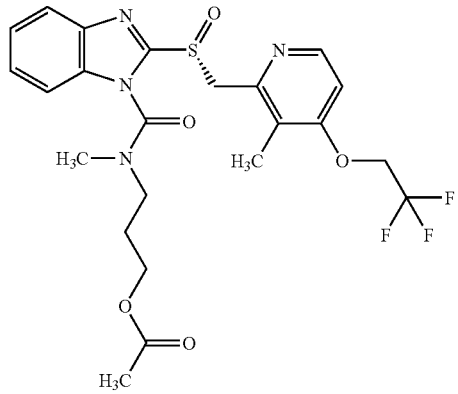 [SMILES: CC(=O)OCCCN(C)C(=O)n1c([S@](=O)Cc2nccc(OCC(F)(F)F)c2C)nc2ccccc21]

To a solution (40 mL) of bis(trichloromethyl)carbonate (1.19 g) in tetrahydrofuran was dropwise added a solution (2 mL) of pyridine (0.95 mL) in tetrahydrofuran under ice-cooling. After stirring under ice-cooling for 30 min., 3-(methylamino)propyl acetate hydrochloride (1.90 g) obtained in Reference Example 42 was added. A solution (2 mL) of triethylamine (1.68 mL) in tetrahydrofuran was dropwise added, and the mixture was stirred at room temperature for 3 hrs. After concentration under reduced pressure, water (100 mL) was added to the residue, and the mixture was extracted with ethyl acetate (100 mL). The ethyl acetate layer was washed with saturated brine (100 mL) and dried over anhydrous magnesium sulfate. After concentration under reduced pressure, the residue was dissolved in tetrahydrofuran (40 mL). (R)-2-[[[3-Methyl-4-(2,2,2-trifluoroethoxy)-2-pyridyl]methyl]sulfinyl]-1H-benzimidazole (1.99 g), triethylamine (1.50 mL) and 4-dimethylaminopyridine (catalytic amount) were added, and the mixture was stirred at 60° C. overnight. After concentration under reduced pressure, water (100 mL) was added to the residue, and the mixture was extracted with ethyl acetate (100 mL). The ethyl acetate layer was washed with saturated brine (100 mL) and dried over anhydrous magnesium sulfate. After concentration under reduced pressure, the residue was purified by basic silica gel column chromatography (eluted with ethyl acetate:hexane=1:2, then 1:1) to give the title compound (1.22 g) as a yellow amorphous solid.

$^1$H-NMR(CDCl$_3$): 1.97 (3H, s), 2.05-2.15 (2H, m), 2.22 (3H, s), 3.03 (3H, bs), 3.42-3.72 (2H, m), 4.10-4.22 (2H, m), 4.37 (2H, q, J=7.8 Hz), 4.85-5.13 (2H, m), 6.64 (1H, d, J=5.6 Hz), 7.24-7.44 (3H, m), 7.83 (1H, d, J=7.5 Hz), 8.35 (1H, d, J=5.6 Hz).

Synthetic Example 44

3-[Methyl[[(R)-2-[[[3-methyl-4-(2,2,2-trifluoroethoxy)-2-pyridyl]methyl]sulfinyl]-1H-benzimidazol-1-yl]carbonyl]amino]propane-1,2-diyl diacetate

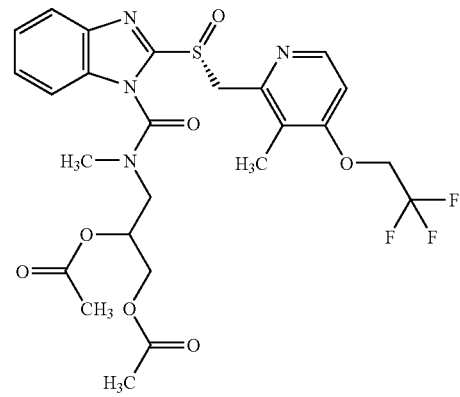 [SMILES: CC(=O)OCC(CN(C)C(=O)n1c([S@](=O)Cc2nccc(OCC(F)(F)F)c2C)nc2ccccc21)OC(C)=O]

To a solution (20 mL) of bis(trichloromethyl)carbonate (0.59 g) in tetrahydrofuran was dropwise added a solution (1 mL) of pyridine (0.49 mL) in tetrahydrofuran under ice-cooling. After stirring under ice-cooling for 30 min., 3-(methylamino)propane-1,2-diyl diacetate hydrochloride (1.35 g) obtained in Reference Example 46 was added. A solution (1 mL) of triethylamine (0.84 mL) in tetrahydrofuran was dropwise added, and the mixture was stirred at room temperature for 3 hrs. After concentration under reduced pressure, water (50 mL) was added to the residue and the mixture was extracted with ethyl acetate (50 mL). The ethyl acetate layer was washed with saturated brine (50 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.27 g), triethylamine (0.96 mL) and 4-dimethylaminopyridine (catalytic amount) were added, and the mixture was stirred at 60° C. overnight. After concentration under reduced pressure, water (50 mL) was added to the residue and the mixture was extracted with ethyl acetate (50 mL). The ethyl acetate layer was washed with saturated brine (50 mL) and dried over anhydrous magnesium sulfate. After concentration under reduced pressure, the residue was purified by basic silica gel column chromatography (eluted with ethyl acetate:hexane=1:2, then 1:1) to give the title compound (0.64 g) as a yellow amorphous solid.

$^1$H-NMR(CDCl$_3$): 2.05 (3H, s), 2.13 (3H, s), 2.23 (3H, s), 3.07 (3H, bs), 3.42-3.95 (2H, m), 4.06-4.43 (2H, m), 4.38

(2H, q, J=7.8 Hz), 4.85-5.05 (2H, m), 5.42-5.50 (1H, m), 6.63-6.66 (1H, m), 7.38-7.51 (3H, m), 7.78-7.85 (1H, m), 8.33-8.36 (1H, m).

Synthetic Example 45

Diethyl 3-[methyl[[(R)-2-[[[3-methyl-4-(2,2,2-trifluoroethoxy)-2-pyridyl]methyl]sulfinyl]-1H-benzimidazol-1-yl]carbonyl]amino]propane-1,2-diyl bis-carbonate

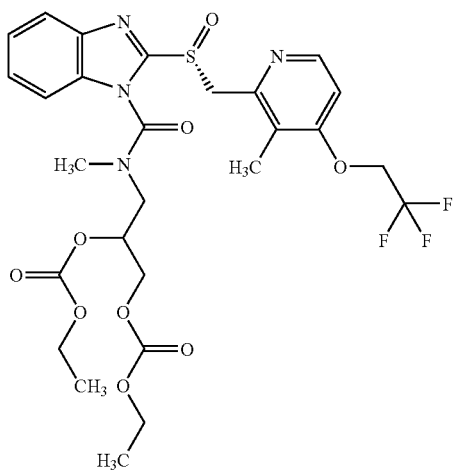 [SMILES: CCOC(=O)OCC(CN(C)C(=O)n1c([S@](=O)Cc2nccc(OCC(F)(F)F)c2C)nc2ccccc21)OC(=O)OCC]

To a solution (20 mL) of bis(trichloromethyl)carbonate (0.59 g) in tetrahydrofuran was dropwise added a solution (1 mL) of pyridine (0.49 mL) in tetrahydrofuran under ice-cooling. After stirring under ice-cooling for 30 min., diethyl 3-(methylamino)propane-1,2-diyl biscarbonate hydrochloride (1.71 g) obtained in Reference Example 47 was added. A solution (1 mL) of triethylamine (0.84 mL) in tetrahydrofuran was dropwise added, and the mixture was stirred at room temperature for 3 hrs. After concentration under reduced pressure, water (50 mL) was added to the residue and the mixture was extracted with ethyl acetate (50 mL). The ethyl acetate layer was washed with saturated brine (50 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.53 g), triethylamine (1.16 mL) and 4-dimethylaminopyridine (catalytic amount) were added, and the mixture was stirred at 60° C. overnight. After concentration under reduced pressure, water (50 mL) was added to the residue and the mixture was extracted with ethyl acetate (50 mL). The ethyl acetate layer was washed with saturated brine (50 mL) and dried over anhydrous magnesium sulfate. After concentration under reduced pressure, the residue was purified by basic silica gel column chromatography (eluted with ethyl acetate:hexane=1:2, then 1:1) to give the title compound (1.42 g) as a yellow amorphous solid.

$^1$H-NMR(CDCl$_3$): 1.28-1.34 (6H, m), 2.22 (3H, s), 3.07 (3H, bs), 3.42-4.60 (10H, m), 4.85-5.08 (2H, m), 5.30-5.42 (1H, m), 6.62-6.64 (1H, m), 7.37-7.42 (3H, m), 7.80-7.83 (1H, m), 8.32-8.35 (1H, m).

Synthetic Example 46

2-[[[5-Methoxy-2-[[(4-methoxy-3,5-dimethyl-2-pyridyl)methyl]sulfinyl]-3H-imidazo[4,5-b]pyridin-3-yl]carbonyl](methyl)amino]ethyl 3-chlorobenzoate

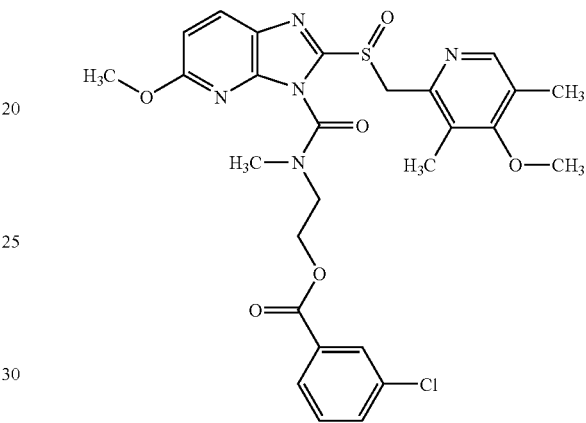

To a solution (7 mL) of bis(trichloromethyl)carbonate (0.194 g) in tetrahydrofuran was dropwise added a solution (1 mL) of pyridine (0.162 mL) in tetrahydrofuran under ice-cooling. After stirring under ice-cooling for 30 min., 2-(methylamino)ethyl 3-chlorobenzoate hydrochloride (0.50 g) obtained in Reference Example 7 was added. A solution (1 mL) of triethylamine (0.279 mL) in tetrahydrofuran was dropwise added, and the mixture was stirred at room temperature for 2.5 hrs. After concentration under reduced pressure, water (15 mL) was added to the residue, and the mixture was extracted with ethyl acetate (50 mL). The ethyl acetate layer was washed with saturated brine (15 mL) and dried over anhydrous magnesium sulfate. After concentration under reduced pressure, the residue was dissolved in tetrahydrofuran (10 mL). 5-Methoxy-2-[[(4-methoxy-3,5-dimethyl-2-pyridyl)methyl]sulfinyl]-1H-imidazo[4,5-b]pyridine (0.445 g) synthesized by the method described in JP-A-63-146882, triethylamine (0.357 mL) and 4-dimethylaminopyridine (0.012 g) were added, and the mixture was stirred at 60° C. for 14 hrs. After concentration under reduced pressure, water (30 mL) was added to the residue, and the mixture was extracted with ethyl acetate (70 mL). The ethyl acetate layer was washed with saturated brine (20 mL) and dried over anhydrous magnesium sulfate. After concentration under reduced pressure, the residue was purified by basic silica gel column chromatography (eluted with ethyl acetate:hexane=1:2, then 1:1) to give the title compound (0.360 g) as a colorless amorphous solid.

$^1$H-NMR(CDCl$_3$): 2.21 (3H, s), 2.23 (3H, s), 3.32, 3.38 (total 3H, s), 3.72 (3H, s), 3.81 (3H, s), 3.92-4.09 (2H, m), 4.50-4.73 (2H, m), 4.87 (1H, d, J=13.4 Hz), 4.94 (1H, d, J=13.4 Hz), 6.77 (1H, d, J=8.8 Hz), 7.36 (1H, m), 7.52 (1H, m), 7.80-8.03 (3H, m) 8.20 (1H, s).

Synthetic Example 47

2-[Methyl[[2-[[[3-methyl-4-(2,2,2-trifluoroethoxy)-2-pyridyl]methyl]sulfinyl]-1H-benzimidazol-1-yl]carbonyl]amino]ethyl acetate

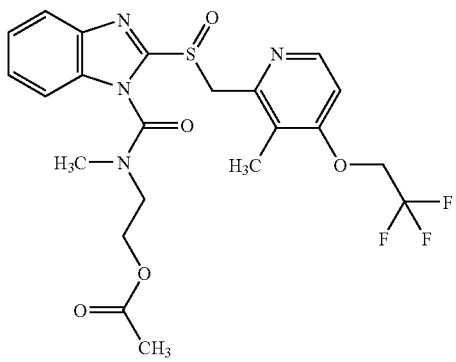 [SMILES: CC(=O)OCCN(C)C(=O)n1c(S(=O)Cc2nccc(OCC(F)(F)F)c2C)nc2ccccc21]

To a solution (20 mL) of bis(trichloromethyl)carbonate (0.582 g) in tetrahydrofuran was dropwise added a solution (1 mL) of pyridine (0.485 mL) in tetrahydrofuran under ice-cooling. After stirring under ice-cooling for 1 hr., 2-(methylamino)ethyl acetate hydrochloride (0.922 g) obtained in Reference Example 2 was added. A solution (1 mL) of triethylamine (0.84 mL) in tetrahydrofuran was dropwise added, and the mixture was stirred at room temperature for 2.5 hrs. After concentration under reduced pressure, water (40 mL) was added to the residue, and the mixture was extracted with ethyl acetate (80 mL). The ethyl acetate layer was washed with saturated brine (25 mL) and dried over anhydrous magnesium sulfate. After concentration under reduced pressure, the residue was dissolved in tetrahydrofuran (15 mL). 2-[[[3-Methyl-4-(2,2,2-trifluoroethoxy)-2-pyridyl]methyl]sulfinyl]-1H-benzimidazole (1.10 g), triethylamine (0.84 mL) and 4-dimethylaminopyridine (0.036 g) were added, and the mixture was stirred at 60° C. for 4.5 hrs. After concentration under reduced pressure, water (40 mL) was added to the residue, and the mixture was extracted with ethyl acetate (80 mL). The ethyl acetate layer was washed with saturated brine (30 mL) and dried over anhydrous magnesium sulfate. After concentration under reduced pressure, the residue was purified by silica gel column chromatography (eluted with ethyl acetate:hexane=1:1, then 2:1) to give the title compound (1.18 g) as a colorless solid.

$^1$H-NMR(CDCl$_3$): 2.10 (3H, s), 2.24 (3H, s), 3.09 (3H, bs), 3.60-4.00 (2H, br), 4.25-4.50 (2H, m), 4.38 (2H, q, J=7.8 Hz), 4.84-5.18 (2H, m), 6.64 (1H, d, J=5.6 Hz), 7.36-7.48 (3H, m), 7.85 (1H, d, J=7.8 Hz), 8.35 (1H, d, J=5.6 Hz).

Synthetic Example 48

Ethyl 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate

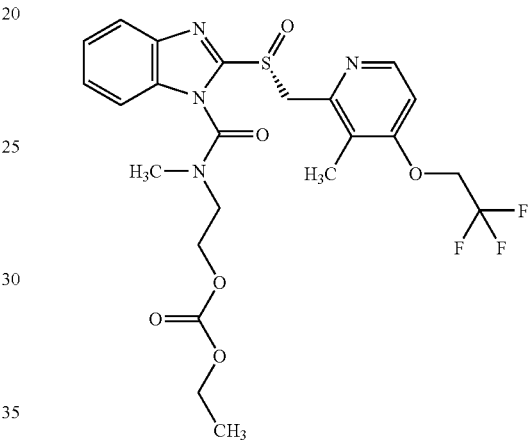

A solution of (R)-2-[[[3-methyl-4-(2,2,2-trifluoroethoxy)-2-pyridyl]methyl]sulfinyl]-1H-benzimidazole (130 g), triethylamine (63.8 mL), 4-dimethylaminopyridine (0.86 g) and 2-[(chlorocarbonyl)(methyl)amino]ethyl ethyl carbonate (84.8 g) obtained in Reference Example 34 in tetrahydrofuran (813 mL) was stirred at 45-50° C. for 18 hrs. The reaction mixture was concentrated under reduced pressure and water (300 mL) was added to the residue, and the mixture was extracted with ethyl acetate (700 mL). The ethyl acetate layer was washed 3 times with saturated brine (300 mL), and anhydrous magnesium sulfate (130 g) and activated carbon (13 g) were added. The mixture was stirred at room temperature for 30 min. and filtrated. The filtrate was concentrated under reduced pressure and the residue was dissolved in diethyl ether (600 mL) containing triethylamine (0.49 mL), and the mixture was concentrated under reduced pressure. This step was further repeated twice. The obtained oily substance was dissolved in ethanol (200 mL) containing triethylamine (2.45 mL) and water (120 mL) was dropwise added under ice-cooling. The precipitated crystals were collected by filtration, washed 3 times with ice-cooled ethanol-water (volume ratio 1:1, 150 mL) and dried to give the title compound (172.2 g) as

Synthetic Example 49

2-Ethoxyethyl 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate

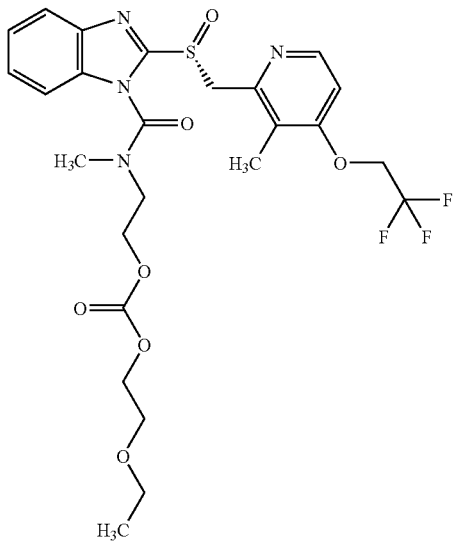 [SMILES: CCOCCOC(=O)OCCN(C)C(=O)n1c([S@](=O)Cc2nccc(OCC(F)(F)F)c2C)nc2ccccc21]

To a solution (20 mL) of bis(trichloromethyl)carbonate (0.43 g) in tetrahydrofuran was dropwise added a solution (1 mL) of pyridine (0.35 mL) in tetrahydrofuran under ice-cooling. After stirring under ice-cooling for 10 min., 2-ethoxyethyl 2-(methylamino)ethyl carbonate hydrochloride (0.82 g) obtained in Reference. Example 48 was added. A solution (1 mL) of triethylamine (0.60 mL) in tetrahydrofuran was dropwise added, and the mixture was stirred at room temperature for 3 days. After concentration under reduced pressure, water (50 mL) was added to the residue and the mixture was extracted with ethyl acetate (50 mL). The ethyl acetate layer was washed with 0.2N hydrochloric acid (20 mL) and saturated brine (50 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.11 g), triethylamine (0.63 mL) and 4-dimethylaminopyridine (0.037 g) were added, and the mixture was stirred at 60° C. for 6 hrs. and at room temperature for 11 hrs. After concentration under reduced pressure, water (50 mL) was added to the residue and the mixture was extracted with ethyl acetate (50 mL). The ethyl acetate layer was washed with saturated brine (50 mL) and dried over anhydrous magnesium sulfate. After concentration under reduced pressure, the residue was purified by basic silica gel column chromatography (eluted with ethyl acetate:hexane=3:7, then ethyl acetate:hexane=7:3) to give the title compound (1.39 g) as a yellow amorphous solid.

$^1$H-NMR(CDCl$_3$): 1.19 (3H, t, J=6.9 Hz), 2.23 (3H, s), 3.09 (3H, bs), 3.40-4.20 (2H, br), 3.53 (2H, q, J=6.9 Hz), 3.63-3.69 (2H, m), 4.27-4.34 (2H, m), 4.39 (2H, q, J=7.8 Hz), 4.47 (2H, m), 4.80-5.20 (2H, m), 6.65 (1H, d, J=5.6 Hz), 7.30-7.52 (3H, m), 7.84 (1H, d, J=7.5 Hz), 8.35 (1H, d, J=5.6 Hz).

Synthetic Example 50

3-Methoxypropyl 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate

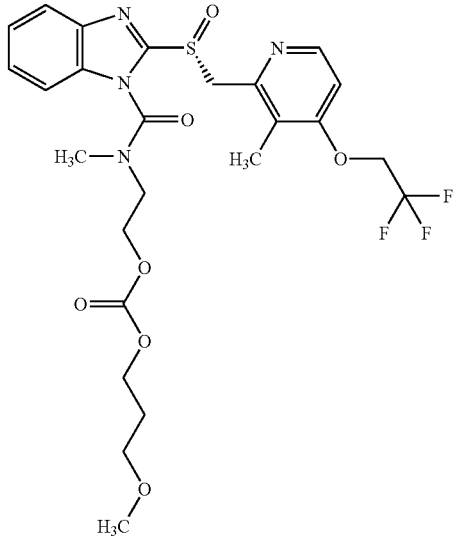 [SMILES: COCCCOC(=O)OCCN(C)C(=O)n1c([S@](=O)Cc2nccc(OCC(F)(F)F)c2C)nc2ccccc21]

To a solution (20 mL) of bis(trichloromethyl)carbonate (0.53 g) in tetrahydrofuran was dropwise added a solution (1 mL) of pyridine (0.44 mL) in tetrahydrofuran under ice-cooling. After stirring under ice-cooling for 5 min., 3-methoxypropyl 2-(methylamino)ethyl carbonate hydrochloride (0.82 g) obtained in Reference Example 49 was added. A solution (1 mL) of triethylamine (0.75 mL) in tetrahydrofuran was dropwise added and the mixture was stirred at room temperature for 1 hr. After concentration under reduced pressure, water (50 mL) was added to the residue and the mixture was extracted with ethyl acetate (50 mL). The ethyl acetate layer was washed with 0.2N hydrochloric acid (20 mL) and saturated brine (50 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.11 g), triethylamine (0.63 mL) and 4-dimethylaminopyridine (0.037 g) were added, and the mixture was stirred at 60° C. for 6 hrs. and at room temperature for 6 hrs. After concentration under reduced pressure, water (50 mL) was added to the residue and the mixture was extracted with ethyl acetate (50 mL). The ethyl acetate layer was washed with saturated brine (50 mL) and dried over anhydrous magnesium sulfate. After concentration under reduced pressure, the residue was purified by basic silica gel column chromatography (eluted with ethyl acetate:hexane=3:7, then ethyl acetate:hexane=7:3). Crystallization from diethyl ether gave the title compound (0.70 g) as a colorless solid. $^1$H-NMR(CDCl$_3$) showed the same chart as with the compound obtained in Synthetic Example 14.

$^1$H-NMR(CDCl$_3$): 1.94 (2H,quintet, J=6.2 Hz), 2.23 (3H, s), 3.09 (3H, bs), 3.31 (3H, s), 3.40-4.20 (2H, br), 3.44 (2H, t, J=6.2 Hz), 4.25 (2H, t, J=6.5 Hz), 4.38 (2H, q, J=7.8 Hz), 4.44

(2H, m), 4.80-5.20 (2H, m), 6.64 (1H, d, J=5.6 Hz), 7.35-7.48 (3H, m), 7.83 (1H, d, J=7.8 Hz), 8.34 (1H, d, J=5.6 Hz).

Synthetic Example 51

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl N,N-dimethylglycinate

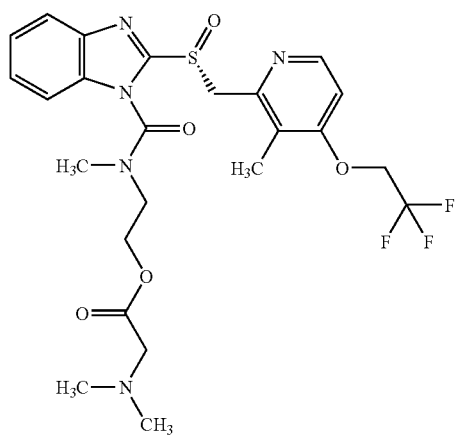 [SMILES: Cc1c(OCC(F)(F)F)ccnc1C[S@@](=O)c1nc2ccccc2n1C(=O)N(C)CCOC(=O)CN(C)C]

2-(Methylamino)ethyl N,N-dimethylglycinate dihydrochloride (1.06 g) obtained in Reference Example 50 was added to tetrahydrofuran (40 mL) and the mixture was stirred for a while, to which bis(trichloromethyl)carbonate (0.77 g) was added. After ice-cooling, a solution (5 mL) of triethylamine (2.17 mL) in tetrahydrofuran was dropwise added and the mixture was stirred at room temperature for 3 hrs. The precipitated solid was filtered off and ethyl acetate (80 mL) was added. The mixture was washed with an ice-cooled aqueous sodium hydrogen carbonate solution (50 mL) and saturated brine (50 mL×2) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.11 g), triethylamine (0.63 mL) and 4-dimethylaminopyridine (0.037 g) were added, and the mixture was stirred at 60° C. for 6 hrs. and at room temperature for 3 days. 4-Dimethylaminopyridine (0.037 g) was added, and the mixture was further stirred at 60° C. for 6 hrs. After concentration under reduced pressure, an aqueous sodium hydrogen carbonate solution (50 mL) was added to the residue, and the mixture was extracted with ethyl acetate (50 mL). The ethyl acetate layer was washed With saturated brine (50 mL) and dried over anhydrous magnesium sulfate. After concentration under reduced pressure, the residue was purified by basic silica gel column chromatography (eluted with ethyl acetate:hexane=1:1, then ethyl acetate, then methanol:ethyl acetate=1:19). Crystallization from diethyl ether gave the title compound (0.41 g) as a colorless solid.

$^1$H-NMR(CDCl$_3$): 2.23 (3H, s), 2.35 (6H, s), 3.08 (3H, bs), 3.21 (2H, s), 3.50-4.20 (2H, br), 4.38 (2H, q, J=7.8 Hz), 4.44

(2H, m), 4.80-5.18 (2H, m), 6.64 (1H, d, J=5.6 Hz), 7.36-7.48 (3H, m), 7.84 (1H, d, J=6.9 Hz), 8.35 (1H, d, J=5.6 Hz).

Synthetic Example 52

S-[2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl]thioacetate

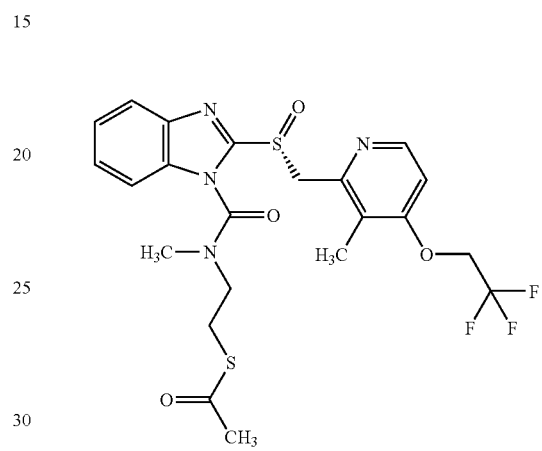

S-[2-(Methylamino)ethyl]thioacetate hydrochloride (0.75 g) obtained in Reference Example 51 was added to tetrahydrofuran (30 mL) and the mixture was stirred for a while, to which bis(trichloromethyl)carbonate (0.66 g) was added. After ice-cooling, a solution (10 mL) of triethylamine (1.85 mL) in tetrahydrofuran was dropwise added and the mixture was stirred under ice-cooling for 30 min. and at room temperature for 30 min. The precipitated solid was filtered off and ethyl acetate (50 mL) was added to the filtrate. The mixture was washed with ice-cooled 0.2N hydrochloric acid (20 mL) and saturated brine (50 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (0.96 g), triethylamine (0.54 mL) and 4-dimethylaminopyridine (0.032 g) were added, and the mixture was stirred at 60° C. for 6 hrs. and at room temperature for 8 hrs. After concentration under reduced pressure, water (50 mL) was added to the residue and the mixture was extracted with ethyl acetate (50 mL). The ethyl acetate layer was washed with saturated brine (50 mL) and dried over anhydrous magnesium sulfate. After concentration under reduced pressure, the residue was purified by silica gel column chromatography (eluted with acetone:hexane=3:7, then acetone:hexane=7:3) to give the title compound (1.19 g) as a yellow amorphous solid.

$^1$H-NMR(CDCl$_3$): 2.23 (3H, s), 2.34 (3H, s), 3.10 (3H, bs), 3.22 (2H, t, J=6.6 Hz), 3.67 (2H, m), 4.38 (2H, q, J=7.8 Hz), 4.80-5.20 (2H, m), 6.64 (1H, d, J=5.7 Hz), 7.35-7.50 (3H, m), 7.83 (1H, d, J=6.9 Hz), 8.35 (1H, d, J=5.7 Hz).

Synthetic Example 53

Ethyl 2-[2-[methyl[[(R)-2-[[[3-methyl-4-(2,2,2-trifluoroethoxy)-2-pyridyl]methyl]sulfinyl]-1H-benzimidazol-1-yl]carbonyl]amino]ethoxy]ethyl carbonate

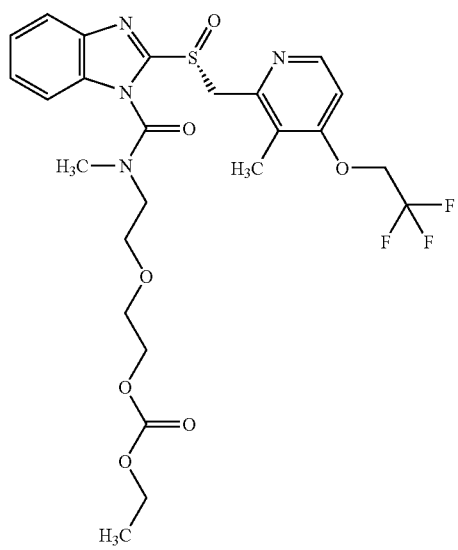 [SMILES: CCOC(=O)OCCOCCN(C)C(=O)n1c([S@](=O)Cc2nccc(OCC(F)(F)F)c2C)nc2ccccc21]

To a solution (40 mL) of bis(trichloromethyl)carbonate (1.19 g) in tetrahydrofuran was dropwise added a solution (2 mL) of pyridine (0.95 mL) in tetrahydrofuran under ice-cooling. After stirring under ice-cooling for 30 min., ethyl 2-[2-(methylamino)ethoxy]ethyl carbonate hydrochloride (2.73 g) obtained in Reference Example 52 was added. A solution (2 mL) of triethylamine (1.68 mL) in tetrahydrofuran was dropwise added, and the mixture was stirred at room temperature for 3 hrs. After concentration under reduced pressure, water (100 mL) was added to the residue, and the mixture was extracted with ethyl acetate (100 mL). The ethyl acetate layer was washed with saturated brine (100 mL) and dried over anhydrous magnesium sulfate. After concentration under reduced pressure, the residue was dissolved in tetrahydrofuran (40 mL). (R)-2-[[[3-Methyl-4-(2,2,2-trifluoroethoxy)-2-pyridyl]methyl]sulfinyl]-1H-benzimidazole (2.80 g), triethylamine (2.11 mL) and 4-dimethylaminopyridine (catalytic amount) were added, and the mixture was stirred at 60° C. overnight. After concentration under reduced pressure, water (100 mL) was added to the residue, and the mixture was extracted with ethyl acetate (100 mL). The ethyl acetate layer was washed with saturated brine (100 mL) and dried over anhydrous magnesium sulfate. After concentration under reduced pressure, the residue was purified by basic silica gel column chromatography (eluted with ethyl acetate:hexane=1:2, then 1:1) to give the title compound (2.19 g) as a yellow amorphous solid.

$^1$H-NMR(CDCl$_3$): 1.28 (3H, t, J=7.2 Hz), 2.24 (3H, s), 3.10 (3H, bs), 3.38-3.80 (6H, m), 4.18 (2H, q, J=7.2 Hz), 4.27-4.34 (2H, m), 4.38 (2H, q, J=8.4 Hz), 4.83-5.30 (2H, m), 6.65 (1H, d, J=5.7 Hz), 7.35-7.50 (3H, m), 7.84 (1H, d, J=7.8 Hz), 8.36 (1H, d, J=5.7 Hz).

Synthetic Example 54

Ethyl 2-[methyl[[2-[methyl[[(R)-2-[[[3-methyl-4-(2,2,2-trifluoroethoxy)-2-pyridyl]methyl]sulfinyl]-1H-benzimidazol-1-yl]carbonyl]amino]ethoxy]carbonyl]amino]ethyl carbonate

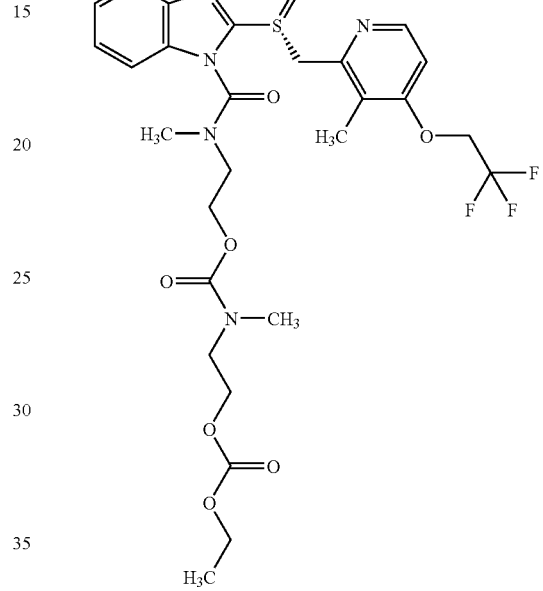

To a solution (20 mL) of bis(trichloromethyl)carbonate (0.59 g) in tetrahydrofuran was dropwise added a solution (1 mL) of pyridine (0.49 mL) in tetrahydrofuran under ice-cooling. After stirring under ice-cooling for 30 min., ethyl 2-[methyl[[2-(methylamino)ethoxy]carbonyl]amino]ethyl carbonate hydrochloride (1.71 g) obtained in Reference Example 53 was added. A solution (1 mL) of triethylamine (0.84 mL) in tetrahydrofuran was dropwise added and the mixture was stirred at room temperature for 3 hrs. After concentration under reduced pressure, water (50 mL) was added to the residue and the mixture was extracted with ethyl acetate (50 mL). The ethyl acetate layer was washed with saturated brine (50 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.59 g), triethylamine (1.20 mL) and 4-dimethylaminopyridine (catalytic amount) were added, and the mixture was stirred at 60° C. overnight. After concentration under reduced pressure, water (50 mL) was added to the residue and the mixture was extracted with ethyl acetate (50 mL). The ethyl acetate layer was washed with saturated brine (50 mL) and dried over anhydrous magnesium sulfate. After concentration under reduced pressure, the residue was purified by basic silica gel column chromatography (eluted with ethyl acetate:hexane=1:2, then 1:1) to give the title compound (1.62 g) as a yellow amorphous solid.

$^1$H-NMR(CDCl$_3$): 1.24-1.31 (3H, m), 2.24 (3H, bs), 2.97-2.99 (3H, m), 3.10 (3H, bs), 3.55-3.58 (2H, m), 4.09-4.50

(10H, m), 4.88-5.08 (2H, m), 6.65 (1H, t, J=5.7 Hz), 7.36-7.48 (3H, m), 7.85 (1H, d, J=6.9 Hz), 8.36 (1H, d, J=5.7 Hz).

Synthetic Example 55

Ethyl 2-[[[5-methoxy-2-[[(4-methoxy-3,5-dimethyl-2-pyridyl)methyl]sulfinyl]-1H-benzimidazol-1-yl]carbonyl](methyl)amino]ethyl carbonate

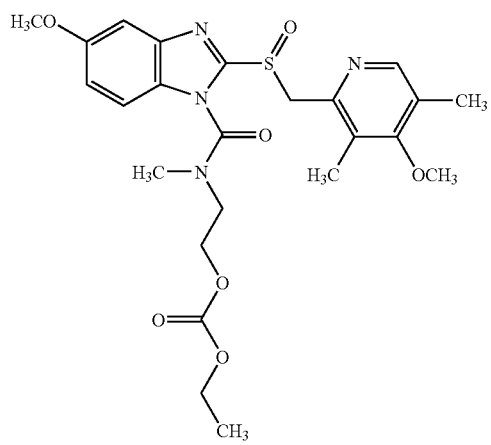 [SMILES: CCOC(=O)OCCN(C)C(=O)n1c(S(=O)Cc2ncc(C)c(OC)c2C)nc2cc(OC)ccc21]

To a solution (10 mL) of bis(trichloromethyl)carbonate (0.291 g) in tetrahydrofuran was dropwise added a solution (1 mL) of pyridine (0.243 mL) in tetrahydrofuran under ice-cooling. After stirring under ice-cooling for 1 hr., ethyl 2-(methylamino)ethyl carbonate hydrochloride (0.551 g) obtained in Reference Example 14 was added. A solution (1 mL) of triethylamine (0.418 mL) in tetrahydrofuran was dropwise added, and the mixture was stirred at room temperature for 2 hrs. After concentration under reduced pressure, water (15 mL) was added to the residue, and the mixture was extracted with ethyl acetate (50 mL). The ethyl acetate layer was washed with saturated brine (15 mL) and dried over anhydrous magnesium sulfate. After concentration under reduced pressure, the residue was dissolved in tetrahydrofuran (10 mL). 5-Methoxy-2-[[(4-methoxy-3,5-dimethyl-2-pyridyl)methyl]sulfinyl]-1H-benzimidazole (0.817 g), triethylamine (0.661 mL) and 4-dimethylaminopyridine (0.012 g) were added, and the mixture was stirred at 60° C. for 12 hrs. After concentration under reduced pressure, water (20 mL) was added to the residue, and the mixture was extracted with ethyl acetate (50 mL). The ethyl acetate layer was washed with saturated brine (15 mL) and dried over anhydrous magnesium sulfate. After concentration under reduced pressure, the residue was purified by basic silica gel column chromatography (eluted with ethyl acetate:hexane=1:2, then 1:1) to give a 3:2 mixture (0.92 g) of the title compound and ethyl 2-[[[6-methoxy-2-[[(4-methoxy-3,5-dimethyl-2-pyridyl)methyl]sulfinyl]-1H-benzimidazol-1-yl]carbonyl](methyl)amino]ethyl carbonate as a pale-yellow amorphous solid.

$^1$H-NMR(CDCl$_3$): 1.27-1.34 (3H, m), 2.10-2.30 (3H, m), 2.23 (3H, s), 2.99-3.23 (3H, m), 3.40-3.85 (2H, m), 3.69 (6/5H, s), 3.71 (9/5H, s), 3.86 (6/5H, s), 3.88 (9/5H, s), 4.14-4.25 (2H, m), 4.38-4.60 (2H, m), 4.82-5.06 (2H, m), 6.92-7.08 (7/5H, m), 7.33 (3/5H, d, J=9.0 Hz), 7.66 (1H, m), 8.21 (1H, s).

Synthetic Example 56

2-[[[5-Methoxy-2-[[(4-methoxy-3,5-dimethyl-2-pyridyl)methyl]sulfinyl]-1H-benzimidazol-1-yl]carbonyl](phenyl)amino]ethyl acetate

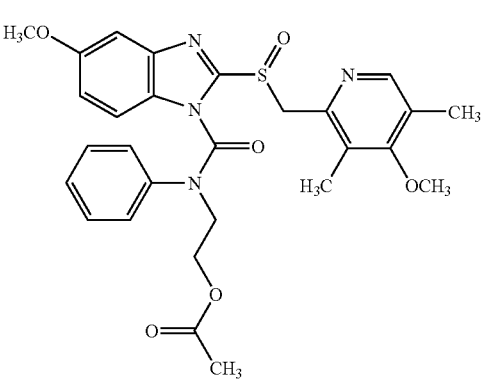 [SMILES: COc1ccc2c(c1)nc(S(=O)Cc1ncc(C)c(OC)c1C)n2C(=O)N(CCOC(C)=O)c1ccccc1]

To a solution (10 mL) of bis(trichloromethyl)carbonate (0.291 g) in tetrahydrofuran was dropwise added a solution (1 mL) of pyridine (0.243 mL) in tetrahydrofuran under ice-cooling. After stirring under ice-cooling for 30 min., 2-anilinoethyl acetate hydrochloride (0.647 g) obtained in Reference Example 27 was added. A solution (1 mL) of triethylamine (0.419 mL) in tetrahydrofuran was dropwise added, and the mixture was stirred at room temperature for 3 hrs. After concentration under reduced pressure, water (20 mL) was added to the residue, and the mixture was extracted with ethyl acetate (50 mL). The ethyl acetate layer was washed with saturated brine (15 mL) and dried over anhydrous magnesium sulfate. After concentration under reduced pressure, the residue was dissolved in tetrahydrofuran (10 mL). 5-Methoxy-2-[[(4-methoxy-3,5-dimethyl-2-pyridyl)methyl]sulfinyl]-1H-benzimidazole (0.829 g), triethylamine (0.669 mL) and 4-dimethylaminopyridine (0.012 g) were added, and the mixture was stirred at 60° C. for 14 hrs. After concentration under reduced pressure, water (40 mL) was added to the residue, and the mixture was extracted with ethyl acetate (80 mL). The ethyl acetate layer was washed with saturated brine (15 mL) and dried over anhydrous magnesium sulfate. After concentration under reduced pressure, the residue was purified by basic silica gel column chromatography (eluted with ethyl acetate:hexane=1:2) to give a 1:1 mixture (1.10 g) of the title compound and 2-[[[6-methoxy-2-[[(4-methoxy-3,5-dimethyl-2-pyridyl)methyl]sulfinyl]-1H-benzimidazol-1-yl]carbonyl](phenyl)amino]ethyl acetate as a colorless amorphous solid.

$^1$H-NMR(CDCl$_3$): 1.99 (3H, s), 2.19 (1.5H.s), 2.21 (1.5H, s), 2.25 (3H, s), 3.70 (1.5H, s), 3.71 (3H, s), 3.78 (1.5H, s), 3.84 (1.5H, s), 4.15-4.56 (4H, m), 4.74-4.80 (1H, m), 4.91-

4.98 (1H, m), 6.83-6.91 (1.5H, m), 7.04-7.19 (3.5H, m), 7.25-7.53 (2.5H, m), 7.51 (0.5H, d, J=8.7 Hz), 8.25 (1H, s).

Synthetic Example 57

Ethyl 2-[[[(S)-5-methoxy-2-[[(4-methoxy-3,5-dimethyl-2-pyridyl)methyl]sulfinyl]-1H-benzimidazol-1-yl]carbonyl](methyl)amino]ethyl carbonate

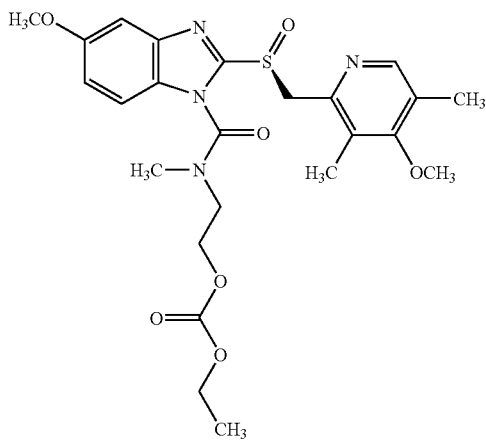 [SMILES: CCOC(=O)OCCN(C)C(=O)n1c([S@@](=O)Cc2ncc(C)c(OC)c2C)nc2cc(OC)ccc21]

To a solution (10 mL) of (S)-5-methoxy-2-[[(4-methoxy-3,5-dimethyl-2-pyridyl)methyl]sulfinyl]-1H-benzimidazole (1.34 g) synthesized by the method described in Synthetic Example 1 of Japanese Patent Application under PCT laid-open under kohyo No. 10-504290 in tetrahydrofuran were added 2-[(chlorocarbonyl)(methyl)amino]ethyl ethyl carbonate (0.9 mL) obtained in Reference Example 34, triethylamine (1.08 mL) and 4-dimethylaminopyridine (0.010 g), and the mixture was stirred at 60° C. for 6 hrs. After concentration under reduced pressure, water (30 mL) was added to the residue and the mixture was extracted with ethyl acetate (50 mL). The ethyl acetate layer was washed with saturated brine (15 mL) and dried over anhydrous magnesium sulfate. After concentration under reduced pressure, the residue was purified by basic silica gel column chromatography (eluted with ethyl acetate:hexane=1:2, then 1:1) to give a 3:2 mixture (0.92 g) of the title compound and ethyl 2-[[[(S)-6-methoxy-2-[[(4-methoxy-3,5-dimethyl-2-pyridyl)methyl]sulfinyl]-1H-benzimidazol-1-yl]carbonyl](methyl)amino]ethyl carbonate as a pale-yellow amorphous solid.

$^1$H-NMR(CDCl$_3$): 1.25-1.34 (3H, m), 2.10-2.30 (3H, m), 2.23 (3H, s), 2.99-3.23 (3H, m), 3.40-3.85 (2H, m), 3.69 (6/5H, s), 3.71 (9/5H, s), 3.86 (6/5H, s), 3.88 (9/5H, s), 4.14-4.25 (2H, m), 4.38-4.60 (2H, m), 4.79-5.05 (2H, m), 6.92-7.08 (7/5H, m), 7.33 (3/5H, d, J=9.3 Hz), 7.65 (1H, m), 8.21 (1H, s)

Synthetic Example 58

Ethyl 2-[[[2-[[[4-(3-methoxypropoxy)-3-methyl-2-pyridyl]methyl]sulfinyl]-1H-benzimidazol-1-yl]carbonyl](methyl)amino]ethyl carbonate

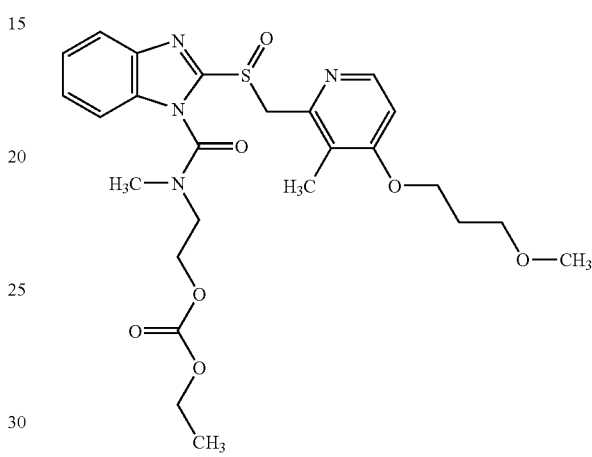

To a solution (10 mL) of bis(trichloromethyl)carbonate (0.291 g) in tetrahydrofuran was dropwise added a solution (1 mL) of pyridine (0.243 mL) in tetrahydrofuran under ice-cooling. After stirring under ice-cooling for 30 min., ethyl 2-(methylamino)ethyl carbonate hydrochloride (0.551 g) obtained in Reference Example 14 was added. A solution (1 mL) of triethylamine (0.418 mL) in tetrahydrofuran was dropwise added, and the mixture was stirred at room temperature for 2.5 hrs. After concentration under reduced pressure, water (15 mL) was added to the residue, and the mixture was extracted with ethyl acetate (50 mL). The ethyl acetate layer was washed with saturated brine (15 mL) and dried over anhydrous magnesium sulfate. After concentration under reduced pressure, the residue was dissolved in tetrahydrofuran (10 mL). 2-[[[4-(3-Methoxypropoxy)-3-methyl-2-pyridyl]methyl]sulfinyl]-1H-benzimidazole (0.723 g), triethylamine (0.528 mL) and 4-dimethylaminopyridine (0.012 g) were added, and the mixture was stirred at 60° C. for 17 hrs. After concentration under reduced pressure, water (40 mL) was added to the residue, and the mixture was extracted with ethyl acetate (80 mL). The ethyl acetate layer was washed with saturated brine (15 mL) and dried over anhydrous magnesium sulfate. After concentration under reduced pressure, the residue was purified by basic silica gel column chromatography (eluted with ethyl acetate:hexane=1:2), then by silica gel column chromatography (eluted with ethyl acetate:hexane=1:1, then ethyl acetate) to give the title compound (0.44 g) as a colorless amorphous solid.

$^1$H-NMR(CDCl$_3$): 1.31 (3H, t, J=7.1 Hz), 2.05 (2H, m), 2.18 (3H, s), 3.08 (3H, bs), 3.34 (3H, s), 3.54 (2H, t, J=6.1 Hz), 3.61-4.01 (2H, m), 4.08 (2H, t, J=6.3 Hz), 4.21 (2H, t,

J=7.1 Hz), 4.38-4.54 (2H, m), 4.81-5.12 (2H, m), 6.68 (1H, d, J=5.6 Hz), 7.34-7.48 (3H, m), 7.83 (1H, d, J=7.8 Hz), 8.27 (1H, d, J=5.6 Hz).

Synthetic Example 59

2-[[[2-[[[4-(3-Methoxypropoxy)-3-methyl-2-pyridyl]methyl]sulfinyl]-1H-benzimidazol-1-yl]carbonyl](phenyl)amino]ethyl acetate

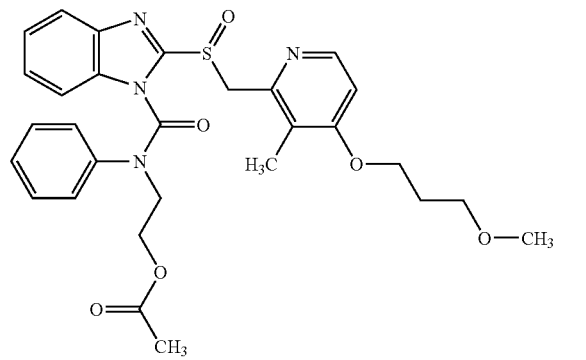 [SMILES: COCCCOc1ccnc(CS(=O)c2nc3ccccc3n2C(=O)N(CCOC(C)=O)c2ccccc2)c1C]

To a solution (10 mL) of bis(trichloromethyl)carbonate (0.291 g) in tetrahydrofuran was dropwise added a solution (1 mL) of pyridine (0.243 mL) in tetrahydrofuran under ice-cooling. After stirring under ice-cooling for 30 min., 2-anilinoethyl acetate hydrochloride (0.647 g) obtained in Reference Example 27 was added. A solution (1 mL) of triethylamine (0.419 mL) in tetrahydrofuran was dropwise added, and the mixture was stirred at room temperature for 3 hrs. After concentration under reduced pressure, water (20 mL) was added to the residue, and the mixture was extracted with ethyl acetate (50 mL). The ethyl acetate layer was washed with saturated brine (15 mL) and dried over anhydrous magnesium sulfate. After concentration under reduced pressure, the residue was dissolved in tetrahydrofuran (10 mL). 2-[[[4-(3-Methoxypropoxy)-3-methyl-2-pyridyl]methyl]sulfinyl]-1H-benzimidazole (0.877 g), triethylamine (0.641 mL) and 4-dimethylaminopyridine (0.012 g) were added, and the mixture was stirred at 60° C. for 16 hrs. After concentration under reduced pressure, water (40 mL) was added to the residue, and the mixture was extracted with ethyl acetate (80 mL). The ethyl acetate layer was washed with saturated brine (15 mL) and dried over anhydrous magnesium sulfate. After concentration under reduced pressure, the residue was purified by basic silica gel column chromatography (eluted with ethyl acetate:hexane=1:2), then by silica gel column chromatography (eluted with ethyl acetate) to give the title compound (0.93 g) as a colorless amorphous solid.

$^1$H-NMR(CDCl$_3$): 1.99 (3H, s), 2.07 (3H.s), 2.19 (3H, s), 3.35 (3H, s), 3.54 (2H, t, J=6.2 Hz), 4.09 (2H, t, J=6.2 Hz), 4.14-4.40 (4H, m), 4.80 (1H, d, J=13.7 Hz), 5.00 (1H, d, J=13.7 Hz), 6.71 (1H, d, J=5.7 Hz), 7.03-7.34 (7H, m), 7.38 (1H, m), 7.65 (1H, m), 8.32 (1H, d, J=5.7 Hz).

Synthetic Example 60

2-[[[5-(Difluoromethoxy)-2-[[(3,4-dimethoxy-2-pyridyl)methyl]sulfinyl]-1H-benzimidazol-1-yl]carbonyl](methyl)amino]ethyl ethyl carbonate

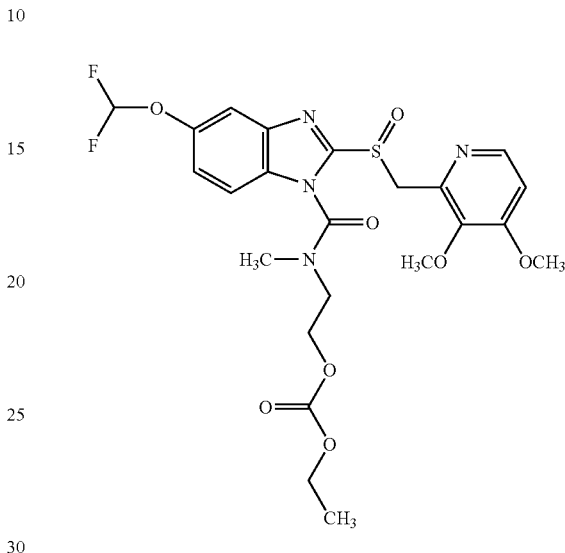

To a solution (8 mL) of bis(trichloromethyl)carbonate (0.174 g) in tetrahydrofuran was dropwise added a solution (1 mL) of pyridine (0.146 mL) in tetrahydrofuran under ice-cooling. After stirring under ice-cooling for 1 hr., ethyl 2-(methylamino)ethyl carbonate hydrochloride (0.330 g) obtained in Reference Example 14 was added. A solution (1 mL) of triethylamine (0.250 mL) in tetrahydrofuran was dropwise added, and the mixture was stirred at room temperature for 3 hrs. After concentration under reduced pressure, water (10 mL) was added to the residue, and the mixture was extracted with ethyl acetate (30 mL). The ethyl acetate layer was washed with saturated brine (10 mL) and dried over anhydrous magnesium sulfate. After concentration under reduced pressure, the residue was dissolved in tetrahydrofuran (8 mL). 5-(Difluoromethoxy)-2-[[(3,4-dimethoxy-2-pyridyl)methyl]sulfinyl]-1H-benzimidazole (0.432 g), triethylamine (0.279 mL) and 4-dimethylaminopyridine (0.008 g) were added, and the mixture was stirred at 60° C. for 17.5 hrs. After concentration under reduced pressure, water (20 mL) was added to the residue, and the mixture was extracted with ethyl acetate (50 mL). The ethyl acetate layer was washed with saturated brine (10 mL) and dried over anhydrous magnesium sulfate. After concentration under reduced pressure, the residue was purified by basic silica gel column chromatography (eluted with ethyl acetate:hexane=1:2, then 1:1), then by silica gel column chromatography (eluted with ethyl acetate:hexane=2:1, then ethyl acetate) to give a 1:1 mixture (0.09 g) of the title compound and 2-[[[6-(difluoromethoxy)-2-[[(3,4-dimethoxy-2-pyridyl)methyl]sulfinyl]-1H-benzimidazol-1-yl]carbonyl]methylamino]ethyl ethyl carbonate as a pale-yellow amorphous solid.

$^1$H-NMR(CDCl$_3$): 1.31 (3H, t, J=7.2 Hz), 3.06 (3H, s), 3.42-3.98 (2H, m), 3.87 (3H, s), 3.90 (3H, s), 4.21 (2H, q, J=7.2 Hz), 4.36-4.54 (2H, m), 4.90 (1H, d, J=13.2 Hz), 4.98 (1H, d, J=13.2 Hz), 6.54 (0.5H, t, J=73.5 Hz), 6.61 (0.5H, t,

J=73.5 Hz), 6.78 (1H, d, J=5.3 Hz), 7.15-7.25 (1.5H, m), 7.44 (0.5H, d, J=9.0 Hz), 7.59 (0.5H, s), 7.80 (0.5H, d, J=9.0 Hz), 8.17 (1H, d, J=5.3 Hz).

Synthetic Example 61

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl 1-methylpiperidine-4-carboxylate

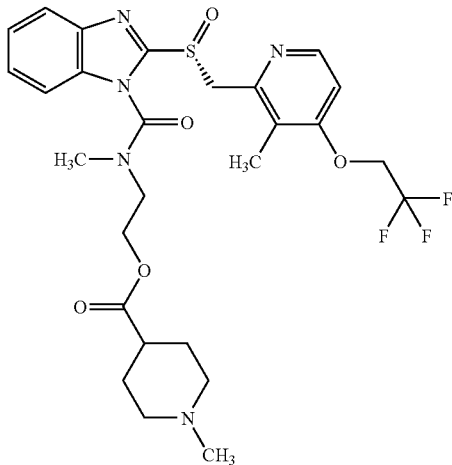 [SMILES: Cc1c(OCC(F)(F)F)ccnc1C[S@@](=O)c1nc2ccccc2n1C(=O)N(C)CCOC(=O)C1CCN(C)CC1]

2-(Methylamino)ethyl 1-methylpiperidine-4-carboxylate dihydrochloride (0.98 g) obtained in Reference Example 54 was added to tetrahydrofuran (50 mL) and the mixture was stirred for a while, to which bis(trichloromethyl)carbonate (0.53 g) was added. After ice-cooling, a solution (50 mL) of triethylamine (2.01 mL) in tetrahydrofuran was dropwise added and the mixture was stirred at room temperature for 3 hrs. Ethyl acetate (100 mL) was added and the mixture was washed with an aqueous sodium hydrogen carbonate solution (100 mL) and saturated brine (80 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (0.74 g), triethylamine (0.56 mL) and 4-dimethylaminopyridine (0.049 g) were added, and the mixture was stirred at 60° C. overnight. After concentration under reduced pressure, an aqueous sodium hydrogen carbonate solution (50 mL) was added to the residue, and the mixture was extracted with ethyl acetate (50 mL). The ethyl acetate layer was washed with saturated brine (50 mL) and dried over anhydrous magnesium sulfate. After concentration under reduced pressure, the residue was purified by basic silica gel column chromatography (eluted with ethyl acetate:hexane=7:3, then ethyl acetate, then methanol:ethyl acetate=1:19) to give the title compound (0.78 g) as a yellow-green amorphous solid.

$^1$H-NMR(CDCl$_3$): 1.65-2.05 (6H, m), 2.23 (3H, s), 2.25 (3H, s), 2.24-2.38 (1H, m), 2.75-2.85 (2H, m), 3.07 (3H, bs), 3.40-4.10 (2H, br), 4.38 (2H, q, J=7.8 Hz), 4.40 (2H, m), 4.80-5.10 (2H, br), 6.64 (1H, d, J=5.6 Hz), 7.36-7.47 (3H, m), 7.84 (1H, d, J=7.8 Hz), 8.35 (1H, d, J=5.6 Hz).

Synthetic Example 62

2-[[4-(Aminocarbonyl)phenyl][[(R)-2-[[[3-methyl-4-(2,2,2-trifluoroethoxy)-2-pyridyl]methyl]sulfinyl]-1H-benzimidazol-1-yl]carbonyl]amino]ethyl acetate

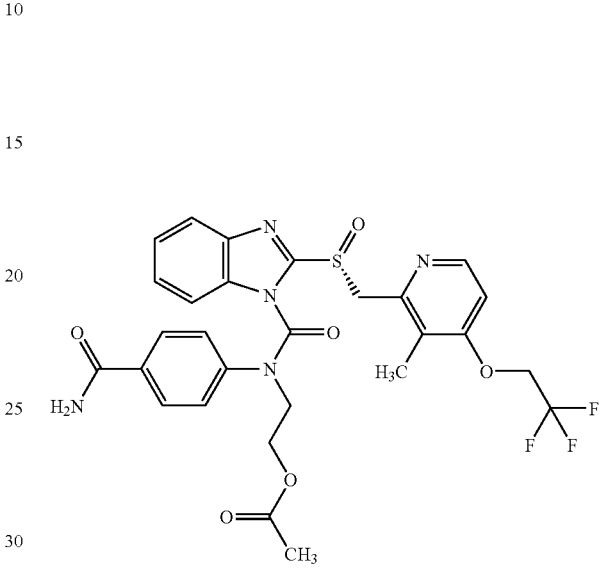

To a solution (20 mL) of bis(trichloromethyl)carbonate (0.45 g) in tetrahydrofuran was dropwise added a solution (10 mL) of 2-[[4-(aminocarbonyl)phenyl]amino]ethyl acetate (0.67 g) obtained in Reference Example 55 and triethylamine (0.63 mL) in tetrahydrofuran under ice-cooling, and the mixture was stirred at room temperature for 1 hr. After concentration under reduced pressure, water (50 mL) was added to the residue and the mixture was extracted with ethyl acetate (50 mL). The ethyl acetate layer was washed with 0.2N hydrochloric acid (20 mL) and saturated brine (50 mL) and dried over anhydrous magnesium sulfate. After concentration under reduced pressure, the residue was dissolved in tetrahydrofuran (30 mL). (R)-2-[[[3-Methyl-4-(2,2,2-trifluoroethoxy)-2-pyridyl]methyl]sulfinyl]-1H-benzimidazole (1.11 g), triethylamine (0.63 mL) and 4-dimethylaminopyridine (0.037 g) were added, and the mixture was stirred at 60° C. for 30 min. and at room temperature overnight. After concentration under reduced pressure, an aqueous sodium hydrogen carbonate solution (50 mL) was added to the residue, and the mixture was extracted with ethyl acetate (50 mL). The ethyl acetate layer was washed with saturated brine (50 mL) and dried over anhydrous magnesium sulfate. After concentration under reduced pressure, the residue was purified by basic silica gel column chromatography (eluted with ethyl acetate:hexane=4:6, then 6:4, then 8:2) to give the title compound (1.26 g) as a yellow amorphous solid.

$^1$H-NMR(CDCl$_3$): 1.99 (3H, s), 2.26 (3H, s), 4.15-4.55 (4H, m), 4.41 (2H, q, J=7.9 Hz), 4.80-5.20 (2H, br), 6.69 (1H, d, J=5.7 Hz), 7.26-7.38 (3H, m), 7.48 (2H, d, J=8.9 Hz), 7.54 (2H, d, J=8.9 Hz), 7.66-7.73 (1H, m), 8.39 (1H, d, J=5.7 Hz).

Synthetic Example 63

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl 1-methyl-4-piperidinyl carbonate

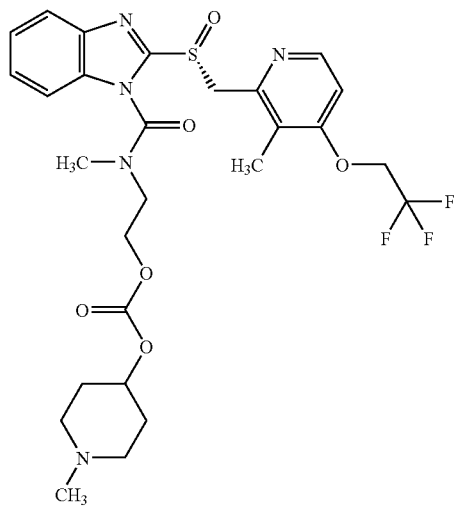

2-(Methylamino)ethyl 1-methyl-4-piperidinyl carbonate dihydrochloride (1.01 g) obtained in Reference Example 56 was added to tetrahydrofuran (30 mL) and, after stirring for a while, ice-cooled. Bis(trichloromethyl)carbonate (0.69 g) was added and a solution (10 mL) of triethylamine (1.95 mL) in tetrahydrofuran was dropwise added. After stirring under ice-cooling for 1 hr. and at room temperature for 1 hr., the precipitated solid was filtered off. After concentration under reduced pressure, ethyl acetate (50 mL) was added, and the mixture was washed with an ice-cooled aqueous sodium hydrogen carbonate solution (50 mL) and saturated brine (50 mL), and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.11 g), triethylamine (0.63 mL) and 4-dimethylaminopyridine (0.037 g) were added, and the mixture was stirred at 60° C. overnight. After concentration under reduced pressure, an aqueous sodium hydrogen carbonate solution (50 mL) was added to the residue, and the mixture was extracted with ethyl acetate (50 mL). The ethyl acetate layer was washed with saturated brine (50 mL) and dried over anhydrous magnesium sulfate. After concentration under reduced pressure, the residue was purified by basic silica gel column chromatography (eluted with ethyl acetate:hexane=1:1, then ethyl acetate, then methanol:ethyl acetate=1:19) to give the title compound (0.70 g) as a yellow amorphous solid.

$^1$H NMR(CDCl$_3$): 1.70-1.86 (2H, m), 1.90-2.04 (2H, m), 2.23 (3H, s), 2.28 (3H, s), 2.10-2.35 (2H, m), 2.60-2.72 (2H, m), 3.08 (3H, bs), 3.40-4.20 (2H, br), 4.39 (2H, q, J=7.9 Hz), 4.44 (2H, m), 4.60-4.74 (1H, m), 4.80-5.15 (2H, br), 6.65 (1H, d, J=5.9 Hz), 7.35-7.52 (3H, m), 7.84 (1H, d, J=7.5 Hz), 8.35 (1H, d, J=5.9 Hz).

Synthetic Example 64

2-[[4-(Aminocarbonyl)phenyl][[2-[[[3-methyl-4-(2,2,2-trifluoroethoxy)-2-pyridyl]methyl]sulfinyl]-1H-benzimidazol-1-yl]carbonyl]amino]ethyl acetate

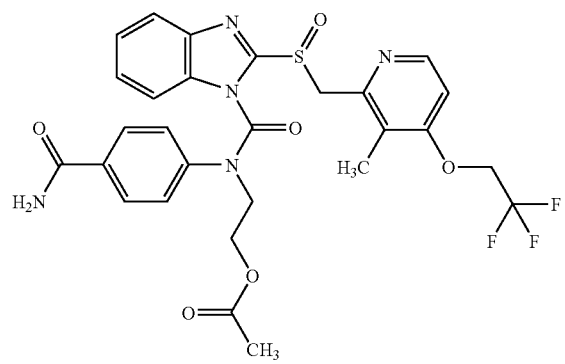 [SMILES: CC(=O)OCCN(C(=O)n1c([S@](=O)Cc2nccc(OCC(F)(F)F)c2C)nc2ccccc21)c1ccc(C(N)=O)cc1]

To a solution (5 mL) of bis(trichloromethyl)carbonate (0.12 g) in tetrahydrofuran was dropwise added a solution (5 mL) of 2-[[4-(aminocarbonyl)phenyl]amino]ethyl acetate (0.22 g) obtained in Reference Example 55 and triethylamine (0.17 mL) in tetrahydrofuran under ice-cooling, and the mixture was stirred at room temperature for 30 min. Water (20 mL) was added, and the mixture was extracted with ethyl acetate (30 mL). The ethyl acetate layer was washed with saturated brine (20 mL) and dried over anhydrous magnesium sulfate. After concentration under reduced pressure, the residue was dissolved in tetrahydrofuran (10 mL). 2-[[[3-Methyl-4-(2,2,2-trifluoroethoxy)-2-pyridyl]methyl]sulfinyl]-1H-benzimidazole (0.37 g), triethylamine (0.28 mL) and 4-dimethylaminopyridine (0.012 g) were added, and the mixture was stirred at 60° C. for 1 hr. After concentration under reduced pressure, an aqueous sodium hydrogen carbonate solution (20 mL) was added to the residue, and the mixture was extracted with ethyl acetate (30 mL). The ethyl acetate layer was washed with saturated brine (20 mL) and dried over anhydrous magnesium sulfate. After concentration under reduced pressure, the residue was purified by basic silica gel column chromatography (eluted with ethyl acetate:hexane=3:7, then 5:5, then 8:2) to give the title compound (0.34 g) as a pale-yellow amorphous solid.

$^1$H-NMR(CDCl$_3$): 1.99 (3H, s), 2.26 (3H, s), 4.15-4.55 (4H, m), 4.41 (2H, q, J=7.9 Hz), 4.80-5.20 (2H, br), 6.69 (1H, d, J=5.9 Hz), 7.26-7.40 (3H, m), 7.47 (2H, d, J=8.8 Hz), 7.54 (2H, d, J=8.8 Hz), 7.65-7.74 (1H, m), 8.38 (1H, d, J=5.9 Hz).

Synthetic Example 65

(−)-Ethyl 2-[[[5-methoxy-2-[[(4-methoxy-3,5-dimethyl-2-pyridyl)methyl]sulfinyl]-3H-imidazo[4,5-b]pyridin-3-yl]carbonyl](methyl)amino]ethyl carbonate

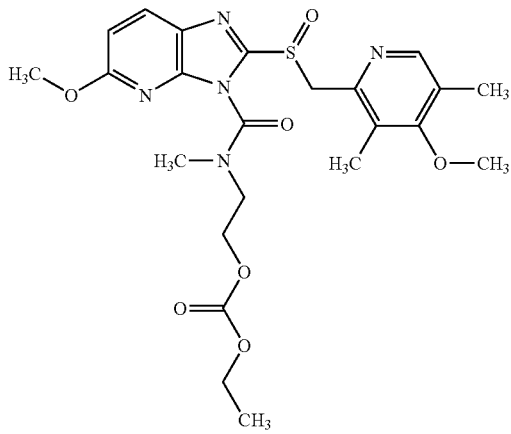

5-Methoxy-2-[[(4-methoxy-3,5-dimethyl-2-pyridyl)methyl]sulfinyl]-1H-imidazo[4,5-b]pyridine synthesized according to the method described in JP-A-63-146882 was subjected to preparative HPLC for optical resolution to give a (−) enantiomeric form (0.10 g) thereof. To a solution (5 mL) of this form in tetrahydrofuran were added 2-[(chlorocarbonyl)(methyl)amino]ethyl ethyl carbonate (0.081 g) obtained in Reference Example 34, triethylamine (0.080 mL) and 4-dimethylaminopyridine (0.007 g) and the mixture was stirred at 50° C. for 18 hrs. After concentration under reduced pressure, water (30 mL) was added to the residue and the mixture was extracted with ethyl acetate (50 mL). The ethyl acetate layer was washed with saturated brine (30 mL) and dried over anhydrous sodium sulfate. After concentration under reduced pressure, the residue was purified by basic silica gel column chromatography (eluted with ethyl acetate:hexane=2:1) to give the title compound (0.053 g) as a colorless oil.

$^1$H-NMR(CDCl$_3$): 1.30 (3H, t, J=7.1 Hz), 2.24 (6H, s), 3.15, 3.32 (total 3H, s), 3.73 (3H, s), 3.90-4.55 (9H, m), 4.85 (1H, d, J=13.2 Hz), 4.97 (1H, d, J=13.2 Hz), 6.80 (1H, d, J=8.8 Hz), 7.96 (1H, d, J=8.8 Hz), 8.23 (1H, s).

Synthetic Example 66

(+)-Ethyl 2-[[[5-methoxy-2-[[(4-methoxy-3,5-dimethyl-2-pyridyl)methyl]sulfinyl]-3H-imidazo[4,5-b]pyridin-3-yl]carbonyl](methyl)amino]ethyl carbonate

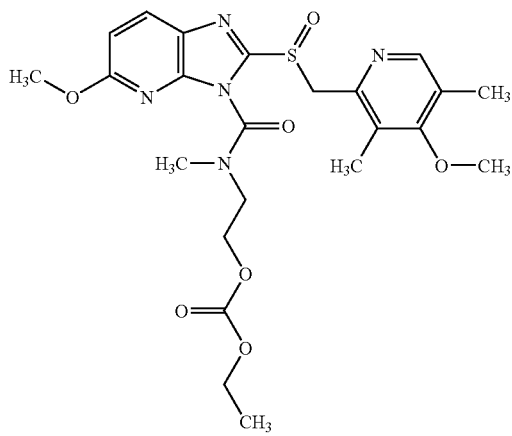

5-Methoxy-2-[[(4-methoxy-3,5-dimethyl-2-pyridyl)methyl]sulfinyl]-1H-imidazo[4,5-b]pyridine synthesized according to the method described in JP-A-63-146882 was subjected to preparative HPLC for optical resolution to give a (+) enantiomeric form (0.10 g) thereof. To a solution (5 mL) of this form in tetrahydrofuran were added 2-[(chlorocarbonyl)(methyl)amino]ethyl ethyl carbonate (0.081 g) obtained in Reference Example 34, triethylamine (0.080 mL) and 4-dimethylaminopyridine (0.007 g) and the mixture was stirred at 50° C. for 18 hrs. After concentration under reduced pressure, water (30 mL) was added to the residue and the mixture was extracted with ethyl acetate (50 mL). The ethyl acetate layer was washed with saturated brine (30 mL) and dried over anhydrous sodium sulfate. After concentration under reduced pressure, the residue was purified by basic silica gel column chromatography (eluted with ethyl acetate:hexane=2:1) to give a 2:1 mixture (0.115 g) of the title compound and (+)-ethyl 2-[[[5-methoxy-2-[[(4-methoxy-3,5-dimethyl-2-pyridyl)methyl]sulfinyl]-1H-imidazo[4,5-b]pyridin-1-yl]carbonyl](methyl)amino]ethyl carbonate as a colorless oil.

$^1$H-NMR(CDCl$_3$): 1.20-1.38 (3H, m), 2.24 (6H, s), 3.08, 3.15, 3.33 (total 3H, s), 3.73 (3H, s), 3.88-4.55 (9H, m), 4.78-5.05 (2H, m), 6.80, 6.86 (1H, d, J=8.8 Hz), 7.76, 7.96 (1H, d, J=8.8 Hz), 8.21, 8.22 (total 1H, s).

Example 1

Among the components described below, 247.7 g of lansoprazole R-isomer (hereinafter, referred to as 'Compound A'), 184.6 g of magnesium carbonate, 492.2 g of purified sucrose, 299.9 g of corn starch and 329.6 g of low substituted hydroxypropyl cellulose were mixed well to obtain a dusting powder. 880 g of sucrose starch spheres (trade name: Nonpareil-101, produced by Freund Industrial Co., Ltd.) were charged in a centrifugal fluid-bed granulator (CF-360, manufactured by Freund Industrial Co., Ltd.) and the above dusting powder was coated on the sucrose.starch spheres while spraying a hydroxypropyl cellulose solution (2 w/w %), thereby producing spherical granules. The spherical granules were dried at 40° C. for 16 hrs under vacuum and passed through a round sieve to give granules of 710 μm-1400 μm.
Composition in 300.0 mg of the Granules

| | |
|---|---|
| sucrose.starch spheres | 110.0 mg |
| Compound A | 30.0 mg |
| magnesium carbonate | 22.4 mg |
| purified sucrose | 59.8 mg |
| corn starch | 36.4 mg |
| low substituted hydroxypropyl cellulose | 40.0 mg |
| hydroxypropyl cellulose | 1.4 mg |
| total | 300.0 mg |

Example 2

25 g of Macrogol 6000 and 10 g of Polysorbate 80 were dissolved in 1206 g of purified water, and 78 g of talc, 25 g of titanium oxide and 866.7 g of methacrylic acid copolymer LD (260 g as solid content) were dispersed into the resulting solution to obtain an enteric coating solution. The granules obtained in Example 1 were coated with the above enteric coating solution using an agitation fluidized bed granulator (SPIR-A-FLOW, manufactured by Freund Industrial Co., Ltd.) under the condition of inlet air temperature: 45° C., rotor revolution speed: 200 rpm, coating solution spray rate: 3.8 g/min. and spray air pressure: 1.0 kg/cm², followed by drying as it was and passing through a round sieve to give enteric-coated granules of 710 μm-1400 μm having following composition. The obtained spherical granules were dried at 40° C. for 16 hrs under vacuum.
Composition in 369.2 mg of the Enteric-Coated Granules

| | |
|---|---|
| granules of Example 1 | 300.0 mg |
| methacrylic acid copolymer LD | 148.7 mg (44.6 mg as solid content) |
| talc | 13.8 mg |
| Macrogol 6000 | 4.4 mg |
| titanium oxide | 4.4 mg |
| Polysorbate 80 | 2.0 mg |
| total | 369.2 mg |

Example 3

36 g of methacrylic acid copolymer S, 12 g of methacrylic acid copolymer L and 4.8 g of triethyl citrate were dissolved in a mixed solution of purified water (69.12 g) and absolute ethanol (622.08 g), and 24 g of talc was dispersed into the resulting solution to obtain a coating solution. 100 g of the enteric-coated granules obtained in Example 2 was coated with the above coating solution using an agitation fluidized bed granulator (SPIR-A-FLOW, manufactured by Freund Industrial Co., Ltd.) under the condition of inlet air temperature: 30° C., rotor revolution speed: 150 rpm, coating solution spray rate: 3.3 g/min. and spray air pressure: 1.0 kg/cm² to give controlled release granules having the following composition which is coated with release-controlled coating-layer being soluble pH-dependently (releasing an active ingredient under the circumstances of more than a certain pH value). The resulting spherical granules were passed through a round sieve to give controlled release granules of 710 μm-1400 μm. Then the obtained spherical granules were dried at 40° C. for 16 hrs under vacuum.
Composition in 605.5 mg of the Controlled Release Granules

| | |
|---|---|
| enteric-coated granules of Example 2 | 369.2 mg |
| methacrylic acid copolymer S | 110.8 mg |
| methacrylic acid copolymer L | 36.9 mg |
| talc | 73.8 mg |
| triethyl citrate | 14.8 mg |
| total | 605.5 mg |

Example 4

24 g of methacrylic acid copolymer S, 24 g of methacrylic acid copolymer L and 4.8 g of triethyl citrate were dissolved in a mixed solution of purified water (69.12 g) and absolute ethanol (622.08 g), and 24 g of talc was dispersed into the resulting solution to obtain coating solution. 100 g of the enteric-coated granules obtained in Example 2 was coated with the above coating solution using an agitation fluidized bed granulator (SPIR-A-FLOW, manufactured by Freund Industrial Co., Ltd.) under the condition of inlet air temperature: 30° C., rotor revolution speed: 150 rpm, coating solution spray rate: 3.3 g/min. and spray air pressure: 1.0 kg/cm² to give controlled release granules having the following composition which is coated with release-controlled coating-layer being soluble pH-dependently (releasing an active ingredient under the circumstances of more than a certain pH value). The resulting spherical granules were passed through a round sieve to give controlled release granules of 710 μm-1400 μm. Then the obtained spherical granules were dried at 40° C. for 16 hrs under vacuum.
Composition in 605.5 mg of the Controlled Release Granules

| | |
|---|---|
| enteric-coated granules of Example 2 | 369.2 mg |
| methacrylic acid copolymer S | 73.85 mg |
| methacrylic acid copolymer L | 73.85 mg |
| talc | 73.8 mg |
| triethyl citrate | 14.8 mg |
| total | 605.5 mg |

Example 5

104 mg of enteric-coated granules obtained in Example 2 and 500 mg of controlled release granules obtained in Example 3 were mixed and thereto 205 mg of polyethylene oxide (trade name: Polyox WSR Coagulant, produced by Dow Chemical Co., Ltd.) was added to obtain a mixture. Two geratin capsules #0 were filled with the resulting mixture to obtain a capsule.

Example 6

104 mg of enteric-coated granules obtained in Example 2 and 500 mg of controlled release granules obtained in Example 4 were mixed and thereto 205 mg of polyethylene oxide (trade name: Polyox WSR Coagulant, produced by Dow Chemical Co., Ltd.) was added to obtain a mixture. Two geratin capsules #0 were filled with the resulting mixture to obtain a capsule.

Example 7

300 g of Compound A, 105 g of magnesium carbonate, 195 g of purified sucrose and 75 g of low substituted hydroxypropyl cellulose were mixed well to obtain a dusting powder for active ingredient layer. 75 g of purified sucrose, 48.8 g of titanium oxide and 18.8 g of low substituted hydroxypropyl cellulose were mixed well to obtain a dusting powder for intermediate layer. 375 g of sucrose.starch spheres (trade name: Nonpareil-101, produced by Freund Industrial Co., Ltd.) were charged in a centrifugal fluid-bed granulator (CF-360, manufactured by Freund Industrial Co., Ltd.) and the sucrose.starch spheres were coated with the above dusting powder for active ingredient layer while spraying a hydroxypropyl cellulose solution (2 w/w %), thereby producing spherical granules. Then, the resulting spherical granules were coated with the above dusting powder for intermediate layer while spraying a hydroxypropyl cellulose solution (2 w/w %) to obtain spherical granules. The obtained spherical granules were dried at 40° C. for 16 hrs under vacuum and passed through a round sieve to give granules of 710 μm-1400 μm.

Composition in 120.0 mg of the Granules

| | |
|---|---|
| sucrose.starch spheres | 37.5 mg |
| hydroxypropyl cellulose | 0.75 mg |
| dusting powder for active ingredient layer | |
| Compound A | 30.0 mg |
| magnesium carbonate | 10.5 mg |
| purified sucrose | 19.5 mg |
| low substituted hydroxypropyl cellulose | 7.5 mg |
| dusting powder for intermediate layer | |
| purified sucrose | 7.5 mg |
| low substituted hydroxypropyl cellulose | 1.875 mg |
| titanium oxide | 4.875 mg |
| total | 120.0 mg |

Example 8

25 g of Macrogol 6000 and 10 g of Polysorbate 80 were dissolved in 1206 g of purified water, and 78 g of talc, 25 g of titanium oxide and 866.7 g of methacrylic acid copolymer LD (260 g as solid content) were dispersed into the resulting solution to obtain an enteric coating solution. The granules obtained in Example 7 were coated with the above enteric coating solution using an agitation fluidized bed granulator (SPIR-A-FLOW, manufactured by Freund Industrial Co., Ltd.) under the condition of inlet air temperature: 45° C., rotor revolution speed: 200 rpm, coating solution spray rate: 3.8 g/min. and spray air pressure: 1.0 kg/cm², followed by drying as it was and passing through a round sieve to give enteric-coated granules of 710 μm-1400 μm having the following composition. The obtained spherical granules were dried at 40° C. for 16 hrs under vacuum.

Composition in 149.86 mg of the Enteric-Coated Granules

| | |
|---|---|
| granules of Example 7 | 120.00 mg |
| methacrylic acid copolymer LD | 65 mg (19.5 mg as solid content) |
| talc | 5.85 mg |
| Macrogol 6000 | 1.88 mg |
| titanium oxide | 1.88 mg |
| Polysorbate 80 | 0.75 mg |
| total | 149.86 mg |

Example 9

36 g of methacrylic acid copolymer S, 12 g of methacrylic acid copolymer L and 4.8 g of triethyl citrate were dissolved in a mixed solution of purified water (69.12 g) and absolute ethanol (622.08 g), and 24 g of talc was dispersed into the resulting solution to obtain a coating solution. 100 g of the enteric-coated granules obtained in Example 8 was coated with the above coating solution using an agitation fluidized bed granulator (SPIR-A-FLOW, manufactured by Freund Industrial Co., Ltd.) under the condition of inlet air temperature: 30° C., rotor revolution speed: 150 rpm, coating solution spray rate: 3.3 g/min. and spray air pressure: 1.0 kg/cm² to give controlled release granules having the following composition which is coated with a release-controlled coating-layer being soluble pH-dependently (releasing an active ingredient under the circumstances of more than a certain pH value). The resulting spherical granules were passed through a round sieve to give controlled release granules of 710 μm-1400 μm. Then the obtained spherical granules were dried at 40° C. for 16 hrs under vacuum.

Composition in 245.86 mg of the Controlled Release Granules

| | |
|---|---|
| enteric-coated granules of Example 8 | 149.86 mg |
| methacrylic acid copolymer S | 45.00 mg |
| methacrylic acid copolymer L | 15.00 mg |
| talc | 30.00 mg |
| triethyl citrate | 6.00 mg |
| total | 245.86 mg |

Example 10

24 g of methacrylic acid copolymer S, 24 g of methacrylic acid copolymer L and 4.8 g of triethyl citrate were dissolved in a mixed solution of purified water (69.12 g) and absolute ethanol (622.08 g), and 24 g of talc was dispersed into the resulting solution to obtain a coating solution. 100 g of the enteric-coated granules obtained in Example 8 was coated with the above coating solution using an agitation fluidized bed granulator (SPIR-A-FLOW, manufactured by Freund Industrial Co., Ltd.) under the condition of inlet air temperature: 30° C., rotor revolution speed: 150 rpm, coating solution spray rate: 3.3 g/min. and spray air pressure: 1.0 kg/cm² to give controlled release granules having the following composition which is coated with a release-controlled coating-layer being soluble pH-dependently (releasing an active ingredient under the circumstances of more than a certain pH value). The resulting spherical granules were passed through a round sieve to give controlled release granules of 710 μm-1400 μm. Then the obtained spherical granules were dried at 40° C. for 16 hrs under vacuum.

Composition in 245.86 mg of the Controlled Release Granules

| enteric-coated granules of Example 8 | 149.86 mg |
|---|---|
| methacrylic acid copolymer S | 30.0 mg |
| methacrylic acid copolymer L | 30.0 mg |
| talc | 30.0 mg |
| triethyl citrate | 6.0 mg |
| total | 245.86 mg |

Example 11

35.5 mg of enteric-coated granules obtained in Example 8 and 175 mg of controlled release granules obtained in Example 9 were mixed and thereto 70.2 mg of polyethylene oxide (trade name: Polyox WSR Coagulant, produced by Dow Chemical Co., Ltd.) was added to obtain a mixture. One capsule #1 was filled with the resulting mixture to obtain a capsule (correspond to 30 mg of Compound A).

Example 12

35.5 mg of enteric-coated granules obtained in Example 8 and 175 mg of controlled release granules obtained in Example 10 were mixed and thereto 70.2 mg of polyethylene oxide (trade name: Polyox WSR Coagulant, produced by Dow Chemical Co., Ltd.) was added to obtain a mixture. One capsule #1 was filled with the resulting mixture to obtain a capsule (correspond to 30 mg of Compound A).

Experiment Example 1

A capsule obtained in Example 5 was administered orally with 30 ml of water to a fasting beagle dog. Each plasma concentration of Compound A at 1 hr, 2 hrs, 4 hrs, 6 hrs, 7 hrs, 8 hrs and 10 hrs after administration was 186 ng/mL, 132 ng/mL, 107 ng/mL, 303 ng/mL, 355 ng/mL, 216 ng/mL and 113 ng/mL, respectively.

Experiment Example 2

A capsule obtained in Example 6 was administered orally with 30 ml of water to a fasting beagle dog. Each plasma concentration of Compound A at 1 hr, 2 hrs, 4 hrs, 6 hrs, 7 hrs, 8 hrs and 10 hrs after administration was 192 ng/mL, 137 ng/mL, 473 ng/mL, 478 ng/mL, 364 ng/mL, 257 ng/mL and 28 ng/mL, respectively.

Experiment Example 3

A capsule obtained in Example 11 was administered orally with 30 ml of water to a fasting beagle dog. Each plasma concentration of Compound A at 1 hr, 2 hrs, 4 hrs, 6 hrs, 7 hrs, 8 hrs and 10 hrs after administration was 308 ng/mL, 245 ng/mL, 323 ng/mL, 81 ng/mL, 39 ng/mL, 26 ng/mL and 0 ng/mL, respectively.

Experiment Example 4

A capsule obtained in Example 12 was administered orally with 30 ml of water to a fasting beagle dog. Each plasma concentration of Compound A at 1 hr, 2 hrs, 4 hrs, 6 hrs, 7 hrs, 8 hrs and 10 hrs after administration was 160 ng/mL, 319 ng/mL, 631 ng/mL, 371 ng/mL, 230 ng/mL, 144 ng/mL and 25 ng/mL, respectively.

Example 13

36 g of methacrylic acid copolymer S, 12 g of methacrylic acid copolymer L and 4.8 g of triethyl citrate, were dissolved in a mixed solution of purified water (69.12 g) and absolute ethanol (622.08 g), and 24 g of talc was dispersed into the resulting solution to obtain a coating solution. 100 g of the enteric-coated granules obtained in Example 8 was coated with the above coating solution using an agitation fluidized bed granulator (SPIR-A-FLOW, manufactured by Freund Industrial Co., Ltd.) under the condition of inlet air temperature: 30° C., rotor revolution speed: 150 rpm, coating solution spray rate: 3.3 g/min. and spray air pressure: 1.0 kg/cm² to give controlled release granules having the following composition which is coated with a release-controlled coating-layer being soluble pH-dependently (releasing an active ingredient under the circumstances of more than a certain pH value). The resulting spherical granules were passed through a round sieve to give controlled release granules of 710 μm-1400 μm. Then the obtained spherical granules were dried at 40° C. for 16 hrs under vacuum.

Composition in 221.86 mg of the Controlled Release Granules

| enteric-coated granules of Example 8 | 149.86 mg |
|---|---|
| methacrylic acid copolymer S | 33.75 mg |
| methacrylic acid copolymer L | 11.25 mg |
| talc | 22.5 mg |
| triethyl citrate | 4.5 mg |
| total | 221.86 mg |

Example 14

24 g of methacrylic acid copolymer S, 24 g of methacrylic acid copolymer L and 4.8 g of triethyl citrate were dissolved in a mixed solution of purified water (69.12 g) and absolute ethanol (622.08 g), and 24 g of talc was dispersed into the resulting solution to obtain a coating solution. 100 g of the enteric-coated granules obtained in Example 8 was coated with the above coating solution using an agitation fluidized bed granulator (SPIR-A-FLOW, manufactured by Freund Industrial Co., Ltd.) under the condition of inlet air temperature: 30° C., rotor revolution speed: 150 rpm, coating solution spray rate: 3.3 g/min. and spray air pressure: 1.0 kg/cm² to give controlled release granules having the following composition which is coated with a release-controlled coating-layer being soluble pH-dependently (releasing an active ingredient under the circumstances of more than a certain pH value). The resulting spherical granules were passed through a round sieve to give controlled release granules of 710 μm-1400 μm. Then the obtained spherical granules were dried at 40° C. for 16 hrs under vacuum.

Composition in 221.86 mg of the Controlled Release Granules

| enteric-coated granules of Example 8 | 149.86 mg |
|---|---|
| methacrylic acid copolymer S | 22.5 mg |
| methacrylic acid copolymer L | 22.5 mg |

-continued

| talc | 22.5 mg |
|---|---|
| triethyl citrate | 4.5 mg |
| total | 221.86 mg |

Example 15

35.5 mg of enteric-coated granules obtained in Example 8 and 168 mg of controlled release granules obtained in Example 13 were mixed and thereto 68.2 mg of polyethylene oxide (trade name: Polyox WSR Coagulant, produced by Dow Chemical Co., Ltd.) was added to obtain a mixture. One capsule #1 was filled with the resulting mixture to obtain a capsule (correspond to 30 mg of Compound A).

Example 16

35.5 mg of enteric-coated granules obtained in Example 8 and 168 mg of controlled release granules obtained in Example 14 were mixed and thereto 68.2 mg of polyethylene oxide (trade name: Polyox WSR Coagulant, produced by Dow Chemical Co., Ltd.) was added to obtain a mixture. One capsule #1 was filled with the resulting mixture to obtain a capsule (correspond to 30 mg of Compound A).

Example 17

35.5 mg of enteric-coated granules obtained in Example 8 and 168 mg of controlled release granules obtained in Example 13 were mixed and the resulting mixture was filled in one capsule #3 to give a capsule (correspond to 30 mg of Compound A).

Example 18

35.5 mg of enteric-coated granules obtained in Example 8 and 168 mg of controlled release granules obtained in Example 14 were mixed and the resulting mixture was filled in one capsule #3 to give a capsule (correspond to 30 mg of Compound A).

Experiment Example 5

A capsule obtained in Example 14 was administered orally with 30 ml of water to a fasting beagle dog. Each plasma concentration of Compound A at 1 hr, 2 hrs, 4 hrs, 6 hrs, 7 hrs, 8 hrs and 10 hrs after administration was 403 ng/mL, 687 ng/mL, 803 ng/mL, 463 ng/mL, 329 ng/mL, 217 ng/mL and 65 ng/mL, respectively.

Example 19

100 g of the granules obtained in Example 1 was charged in a centrifugal fluid-bed granulator (CF-mini, manufactured by Freund Industrial Co., Ltd.) and Ac-Di-Sol that is a disintegrant were coated on the granules by a ratio of 32 w/w % based on the granules while spraying a solution of hydroxypropyl cellulose dissolved in isopropyl alcohol (8 w/w %), thereby producing spherical granules. The spherical granules were dried at 40° C. for 16 hrs under vacuum and passed through a round sieve to give granules of 1400 μm or less.

Example 20

24 g of aminoalkyl methacrylate copolymer RS was dissolved in acetone (120 g) and isopropyl alcohol (288 g), and 48 g of talc was dispersed into the resulting solution to obtain a coating solution. 100 g of the granules obtained in Example 19 was coated with the above coating solution using an agitation fluidized bed granulator (SPIR-A-FLOW, manufactured by Freund Industrial Co., Ltd.) under the condition of inlet air temperature: 30° C., rotor revolution speed: 150 rpm, coating solution spray rate: 3.1 g/min. and spray air pressure: 1.0 kg/cm² to give controlled release granules having the following composition. The resulting spherical granules were passed through a round sieve to give controlled release granules of 710 μm-1700 μm. Then the obtained spherical granules were dried at 40° C. for 16 hrs under vacuum.

Composition in 130.0 mg of the Controlled Release Granules

| granules of Example 19 | 100 mg |
|---|---|
| aminoalkyl methacrylate copolymer RS | 10.0 mg |
| talc | 20.0 mg |
| total | 130.0 mg |

Example 21

104 mg of enteric-coated granules obtained in Example 2 and 420 mg of controlled release granules obtained in Example 20 were mixed and thereto 175 mg of polyethylene oxide (trade name: Polyox WSR Coagulant, produced by Dow Chemical Co., Ltd.) was added to obtain a mixture. Two gelatin capsules #0 were filled with the resulting mixture to obtain a capsule (correspond to 30 mg of Compound A).

Example 22

104 mg of enteric-coated granules obtained in Example 2 and 420 mg of controlled release granules obtained in Example 20 were mixed and the resulting mixture was filled in two gelatin capsules #0 to give a capsule (correspond to 30 mg of Compound A).

Experiment Example 6

A capsule obtained in Example 21 was administered orally with 30 ml of water to a fasting beagle dog. Each plasma concentration of Compound A at 1 hr, 2 hrs, 4 hrs, 6 hrs, 7 hrs, 8 hrs and 10 hrs after administration was 657 ng/mL, 406 ng/mL, 223 ng/mL, 504 ng/mL, 399 ng/mL, 228 ng/mL and 50 ng/mL, respectively.

Example 23

36 g of methacrylic acid copolymer S, 12 g of methacrylic acid copolymer L and 4.8 g of triethyl citrate were dissolved in a mixed solution of purified water (69.12 g) and absolute ethanol (622.08 g), and 24 g of talc was dispersed into the resulting solution to obtain a coating solution. 100 g of the granules obtained in Example 19 was coated with the above coating solution using an agitation fluidized bed granulator (SPIR-A-FLOW, manufactured by Freund Industrial Co., Ltd.) under the condition of inlet air temperature: 30° C., rotor revolution speed: 150 rpm, coating solution spray rate: 3.3 g/min. and spray air pressure: 1.0 kg/cm² to give controlled release granules having the following composition. The resulting spherical granules were passed through a round sieve to give controlled release granules of 710 μm-1700 μm. Then the obtained spherical granules were dried at 40° C. for 16 hrs under vacuum.

Composition in 164.0 mg of the Controlled Release Granules

| | |
|---|---|
| granules of Example 19 | 100 mg |
| methacrylic acid copolymer S | 30.0 mg |
| methacrylic acid copolymer L | 10.0 mg |
| talc | 20.0 mg |
| triethyl citrate | 4.0 mg |
| total | 164.0 mg |

Example 24

104 mg of enteric-coated granules obtained in Example 2 and 614 mg of controlled release granules obtained in Example 23 were mixed and thereto 239 mg of polyethylene oxide (trade name: Polyox WSR Coagulant, produced by Dow Chemical Co., Ltd.) was added to obtain a mixture. Two gelatin capsules #0 were filled with the resulting mixture to obtain a capsule (correspond to 30 mg of Compound A).

Example 25

104 mg of enteric-coated granules obtained in Example 2 and 614 mg of controlled release granules obtained in Example 23 were mixed and the resulting mixture was filled in two gelatin capsules #0 to obtain a capsule (correspond to 30 mg of Compound A).

Experiment Example 7

A capsule obtained in Example 24 was administered orally with 30 ml of water to a fasting beagle dog. Each plasma concentration of Compound A at 1 hr, 2 hrs, 4 hrs, 6 hrs, 7 hrs, 8 hrs and 10 hrs after administration was 106 ng/mL, 135 ng/mL, 639 ng/mL, 129 ng/mL, 49 ng/mL, 16 ng/mL and 0 ng/mL, respectively.

Comparison Example 1

One gelatin capsule #0 obtained in Example 2, which was filled with 414 mg of enteric-coated granules, was administered orally with 30 ml of water to a fasting beagle dog. Each plasma concentration of Compound A at 1 hr, 2 hrs, 4 hrs, 6 hrs, 7 hrs, 8 hrs and 10 hrs after administration was 2,068 ng/mL, 689 ng/mL, 70 ng/mL, 0 ng/mL, 0 ng/mL, 0 ng/mL and 0 ng/mL, respectively.

Example 26

150 g of Compound A, 50 g of magnesium carbonate, 25 g of low substituted hydroxypropyl cellulose and 25 g of hydroxypropyl cellulose were suspended in 1420 g of purified water to obtain a spraying solution. 200 g of crystalline cellulose (sphere) was charged in an agitation fluidized bed granulator (SPIR-A-FLOW, manufactured by Freund Industrial Co., Ltd.) and was sprayed with the above spraying solution under the condition of inlet air temperature: 62° C., rotor revolution speed: 300 rpm, coating solution spray rate: 10 g/min. and spray air pressure: 1.0 kg/cm² to give spherical granules having the following composition. The resulting spherical granules were dried at 40° C. for 16 hrs under vacuum and passed through a round sieve to give controlled release granules of 500 μm-1400 μm.

Composition in 41.24 mg of the Granules

| | |
|---|---|
| crystalline cellulose (sphere) | 22.5 mg |
| Compound A | 11.25 mg |
| magnesium carbonate | 3.75 mg |
| low substituted hydroxypropyl cellulose | 10.0 mg |
| hydroxypropyl cellulose | 1.87 mg |
| total | 41.24 mg |

Example 27

90 g of Compound A, 31.5 g of magnesium carbonate, 58.5 g of purified sucrose and 22.5 g of low substituted hydroxypropyl cellulose were mixed well to obtain a dusting powder of active ingredient layer. 110 g of the granules obtained in Example 26 was charged in a centrifugal fluid-bed granulator (CF-mini, manufactured by Freund Industrial Co., Ltd.) and was coated with the above dusting powder of active ingredient layer while spraying a hydroxypropyl cellulose solution (2 w/w %), thereby producing spherical granules having the following composition. The obtained spherical granules were dried at 40° C. for 16 hrs under vacuum and passed through a round sieve to give granules of 710 μm-1400 μm.

Composition in 118.03 mg of the Granules

| | |
|---|---|
| granules of Example 26 | 41.25 mg |
| Compound A | 33.75 mg |
| magnesium carbonate | 11.81 mg |
| purified sucrose | 21.94 mg |
| low substituted hydroxypropyl cellulose | 8.44 mg |
| hydroxypropyl cellulose | 0.84 mg |
| total | 118.03 mg |

Example 28

The granules obtained in Example 27 were coated with a coating solution for intermediate layer using an agitation fluidized bed granulator (SPIR-A-FLOW, manufactured by Freund Industrial Co., Ltd.), and were dried intact to give granules having the following composition. The coating solution for intermediate layer was produced by dissolving 20.09 g of hydroxypropyl methylcellulose 2910 in 361.55 g of purified water and followed by dispersing 8.03 g of titanium oxide and 12.05 g of talc into the obtained solution. The coating operation was carried out under the condition of inlet air temperature: 62° C., rotor revolution speed: 200 rpm, coating solution spray rate: 3.0 g/min. and spray air pressure: 1.0 kg/cm². The resulting spherical granules were dried at 40° C. for 16 hrs under vacuum and passed through a round sieve to give granules of 710 μm-1400 μm.

Composition in 133.03 mg of the Granules Coated with an Intermediate Layer

| | |
|---|---|
| granules of Example 27 | 118.03 mg |
| hydroxypropyl methylcellulose 2910 | 7.5 mg |
| talc | 4.5 mg |
| titanium oxide | 3.0 mg |
| total | 133.03 mg |

Example 29

25 g of Macrogol 6000 and 10 g of Polysorbate 80 were dissolved in 1206 g of purified water, and 78 g of talc, 25 g of titanium oxide and 866.7 g of methacrylic acid copolymer LD (260 g as solid content) were dispersed into the resulting solution to obtain an enteric coating solution. The granules obtained in Example 28 were coated with the above enteric coating solution using an agitation fluidized bed granulator (SPIR-A-FLOW, manufactured by Freund Industrial Co., Ltd.) under the condition of inlet air temperature: 45° C., rotor revolution speed: 200 rpm, coating solution spray rate: 3.8 g/min. and spray air pressure: 1.0 kg/cm², followed by drying as it was and passing through a round sieve to give enteric-coated granules of 710 μm-1400 μm having the following composition. The obtained spherical granules were dried at 40° C. for 16 hrs under vacuum.

Composition in 165.18 mg of the Enteric-Coated Granules

| | |
|---|---|
| granules of Example 28 | 133.03 mg |
| methacrylic acid copolymer LD | 70 mg |
| | (21 mg as solid content) |
| talc | 6.30 mg |
| Macrogol 6000 | 2.02 mg |
| titanium oxide | 2.02 mg |
| Polysorbate 80 | 0.81 mg |
| total | 165.18 mg |

Example 30

36 g of methacrylic acid copolymer S, 12 g of methacrylic acid copolymer L and 4.8 g of triethyl citrate were dissolved in a mixed solution of purified water (69.12 g) and absolute ethanol (622.08 g), and 24 g of talc was dispersed into the resulting solution to obtain a coating solution. 100 g of the granules obtained in Example 28 was coated with the above coating solution using an agitation fluidized bed granulator (SPIR-A-FLOW, manufactured by Freund Industrial Co., Ltd.) under the condition of inlet air temperature: 30° C., rotor revolution speed: 100 rpm, coating solution spray rate: 3.0 g/min. and spray air pressure: 1.0 kg/cm² to give controlled release granules having the following composition which is coated with a release-controlled coating-layer being soluble pH-dependently (releasing an active ingredient under the circumstances of more than a certain pH value). The resulting spherical granules were passed through a round sieve to give controlled release granules of 1180 μm-1700 μm. Then the obtained spherical granules were dried at 40° C. for 16 hrs under vacuum.

Composition in 196.88 mg of the Controlled Release Granules

| | |
|---|---|
| granules of Example 28 | 133.03 mg |
| methacrylic acid copolymer S | 29.93 mg |
| methacrylic acid copolymer L | 9.98 mg |
| talc | 19.95 mg |
| triethyl citrate | 3.99 mg |
| total | 196.88 mg |

Example 31

24 g of methacrylic acid copolymer S, 24 g of methacrylic acid copolymer L and 4.8 g of triethyl citrate were dissolved in a mixed solution of purified water (69.12 g) and absolute ethanol (622.08 g), and 24 g of talc was dispersed into the resulting solution to obtain a coating solution. 100 g of the granules obtained in Example 28 was coated with the above coating solution using an agitation fluidized bed granulator (SPIR-A-FLOW, manufactured by Freund Industrial Co., Ltd.) under the condition of inlet air temperature: 30° C., rotor revolution speed: 100 rpm, coating solution spray rate: 3.0 g/min. and spray air pressure: 1.0 kg/cm² to give controlled release granules having the following composition which is coated with a release-controlled coating-layer being soluble pH-dependently (releasing an active ingredient under the circumstances of more than a certain pH value). The resulting spherical granules were passed through a round sieve to give controlled release granules of 1180 μm-1700 μm. Then the obtained spherical granules were dried at 40° C. for 16 hrs under vacuum.

Composition in 196.88 mg of the Controlled Release Granules

| | |
|---|---|
| granules of Example 28 | 133.03 mg |
| methacrylic acid copolymer S | 19.95 mg |
| methacrylic acid copolymer L | 19.95 mg |
| talc | 19.95 mg |
| triethyl citrate | 3.99 mg |
| total | 196.88 mg |

Example 32

28 mg of enteric-coated granules obtained in Example 29 and 98.7 mg of controlled release granules obtained in Example 30 were mixed and thereto 42.3 mg of polyethylene oxide (trade name: Polyox WSR Coagulant, produced by Dow Chemical Co., Ltd.) was added to obtain a mixture. One capsule #1 was filled with the resulting mixture to obtain a capsule (correspond to 30 mg of Compound A).

Example 33

28 mg of enteric-coated granules obtained in Example 29 and 98.7 mg of controlled release granules obtained in Example 31 were mixed and thereto 42.3 mg of polyethylene oxide (trade name: Polyox WSR Coagulant, produced by Dow Chemical Co., Ltd.) was added to obtain a mixture. One capsule #1 was filled with the resulting mixture to obtain a capsule (correspond to 30 mg of Compound A).

Example 34

56 mg of enteric-coated granules obtained in Example 29 and 197.4 mg of controlled release granules obtained in Example 30 were mixed and the resulting mixture was filled in one capsule #2 to give a capsule (correspond to 60 mg of Compound A).

Example 35

84 mg of enteric-coated granules obtained in Example 29 and 296.1 mg of controlled release granules obtained in Example 30 were mixed and the resulting mixture was filled in one capsule #1 to give a capsule (correspond to 90 mg of Compound A).

Example 36

42 mg of enteric-coated granules obtained in Example 29 and 148.05 mg of controlled release granules obtained in Example 30 were mixed and the resulting mixture was filled in one capsule #3 to give a capsule (correspond to 45 mg of Compound A).

Example 37

48 g of methacrylic acid copolymer S and 4.8 g of triethyl citrate were dissolved in a mixed solution of purified water (69.12 g) and absolute ethanol (622.08 g), and 24 g of talc was dispersed into the resulting solution to obtain a coating solution. 100 g of the granules obtained in Example 30 was coated with the above coating solution using an agitation fluidized bed granulator (SPIR-A-FLOW, manufactured by Freund Industrial Co., Ltd.) under the condition of inlet air temperature: 30° C., rotor revolution speed: 100 rpm, coating solution spray rate: 3.0 g/min. and spray air pressure: 1.0 kg/cm$^2$ to give controlled release granules having the following composition which is coated with a release-controlled coating-layer being soluble pH-dependently (releasing an active ingredient under the circumstances of more than a certain pH value). The resulting spherical granules were passed through a round sieve to give controlled release granules of 1180 μm-1700 μm. Then the obtained spherical granules were dried at 40° C. for 16 hrs under vacuum.

Composition in 207.52 mg of the Controlled Release Granules

| | |
|---|---|
| granules of Example 30 | 196.88 mg |
| methacrylic acid copolymer S | 6.65 mg |
| talc | 3.32 mg |
| triethyl citrate | 0.67 mg |
| total | 207.52 mg |

Example 38

48 g of methacrylic acid copolymer S and 4.8 g of triethyl citrate were dissolved in a mixed solution of purified water (69.12 g) and absolute ethanol (622.08 g), and 24 g of talc was dispersed into the resulting solution to obtain a coating solution. 100 g of the granules obtained in Example 31 was coated with the above coating solution using an agitation fluidized bed granulator (SPIR-A-FLOW, manufactured by Freund Industrial Co., Ltd.) under the condition of inlet air temperature: 30° C., rotor revolution speed: 100 rpm, coating solution spray rate: 3.0 g/min. and spray air pressure: 1.0 kg/cm$^2$ to give controlled release granules having the following composition which is coated with a release-controlled coating-layer being soluble pH-dependently (releasing an active ingredient under the circumstances of more than a certain pH value). The resulting spherical granules were passed through a round sieve to give controlled release granules of 1180 μm-1700 μm. Then the obtained spherical granules were dried at 40° C. for 16 hrs under vacuum.

Composition in 207.52 mg of the Controlled Release Granules

| | |
|---|---|
| granules of Example 31 | 196.88 mg |
| methacrylic acid copolymer S | 6.65 mg |
| talc | 3.32 mg |
| triethyl citrate | 0.67 mg |
| total | 207.52 mg |

Example 39

28 mg of enteric-coated granules obtained in Example 29 and 103.8 mg of controlled release granules obtained in Example 37 were mixed and thereto 43.9 mg of polyethylene oxide (trade name: Polyox WSR Coagulant, produced by Dow Chemical Co., Ltd.) was added to obtain a mixture. One capsule #1 was filled with the resulting mixture to obtain a capsule (correspond to 30 mg of Compound A).

Example 40

28 mg of enteric-coated granules obtained in Example 29 and 103.8 mg of controlled release granules obtained in Example 38 were mixed and thereto 43.9 mg of polyethylene oxide (trade name: Polyox WSR Coagulant, produced by Dow Chemical Co., Ltd.) was added to obtain a mixture. One capsule #1 was filled with the resulting mixture to obtain a capsule (correspond to 30 mg of Compound A).

Example 41

56 mg of enteric-coated granules obtained in Example 29 and 207.5 mg of controlled release granules obtained in Example 37 were mixed and the resulting mixture was filled in one capsule #2 to give a capsule (correspond to 60 mg of Compound A).

Example 42

84 mg of enteric-coated granules obtained in Example 29 and 311.3 mg of controlled release granules obtained in Example 37 were mixed and the resulting mixture was filled in one capsule #1 to give a capsule (correspond to 90 mg of Compound A).

Example 43

42 mg of enteric-coated granules obtained in Example 29 and 155.6 mg of controlled release granules obtained in Example 37 were mixed and the resulting mixture was filled in one capsule #3 to give a capsule (correspond to 45 mg of Compound A).

Example 44

300 g of Compound A, 105 g of magnesium carbonate, 195 g of purified sucrose and 75 g of low substituted hydroxypropyl cellulose were mixed well to obtain a dusting powder for active ingredient layer. 75 g of purified sucrose, 48.8 g of titanium oxide and 18.8 g of low substituted hydroxypropyl cellulose were mixed well to obtain a dusting powder for intermediate layer. 375 g of sucrose.starch spherical granules (trade name: Nonpareil-101, produced by Freund Industrial Co., Ltd.) were charged in a centrifugal fluid-bed granulator (CF-360, manufactured by Freund Industrial Co., Ltd.) and the sucrose.starch spheres were coated with the above dusting powder for active ingredient layer while spraying a hydroxypropyl cellulose solution (2 w/w %), thereby producing spherical granules. The obtained spherical granules were dried at 40° C. for 16 hrs under vacuum and passed through a round sieve to give granules of 710 μm-1400 μm.

Composition in 158.07 mg of the Granules

| | |
|---|---|
| sucrose.starch spheres | 56.25 mg |
| hydroxypropyl cellulose | 0.57 mg |
| dusting powder for active ingredient layer | |
| Compound A | 45.00 mg |
| magnesium carbonate | 15.75 mg |
| purified sucrose | 29.25 mg |
| low substituted hydroxypropyl cellulose | 11.25 mg |
| total | 158.07 mg |

Example 45

The granules obtained in Example 44 were coated with a coating solution for intermediate layer using an agitation fluidized bed granulator (SPIR-A-FLOW, manufactured by Freund Industrial Co., Ltd.), and were dried intact to give granules having the following composition. The coating solution for intermediate layer was produced by dissolving 20.09 g of hydroxypropyl methylcellulose 2910 in 361.55 g of purified water and followed by dispersing 8.03 g of titanium oxide and 12.05 g of talc into the obtained solution. The coating operation was carried out under the condition of inlet air temperature: 62° C., rotor revolution speed: 200 rpm, coating solution spray rate: 3.0 g/min. and spray air pressure: 1.0 kg/cm². The resulting spherical granules were dried at 40° C. for 16 hrs under vacuum and passed through a round sieve to give granules of 710 μm-1400 μm.

Composition in 188.07 mg of the Granules Coated with an Intermediate Layer

| | |
|---|---|
| granules of Example 44 | 158.07 mg |
| hydroxypropyl methylcellulose 2910 | 15.00 mg |
| talc | 9.00 mg |
| titanium oxide | 6.00 mg |
| total | 188.07 mg |

Example 46

36 g of methacrylic acid copolymer S, 12 g of methacrylic acid copolymer L and 4.8 g of triethyl citrate were dissolved in a mixed solution of purified water (69.12 g) and absolute ethanol (622.08 g), and 24 g of talc was dispersed into the resulting solution to obtain a coating solution. 100 g of the granules obtained in Example 45 was coated with the above coating solution using an agitation fluidized bed granulator (SPIR-A-FLOW, manufactured by Freund Industrial Co., Ltd.) under the condition of inlet air temperature: 30° C., rotor revolution speed: 100 rpm, coating solution spray rate: 3.0 g/min. and spray air pressure: 1.0 kg/cm² to give controlled release granules having the following composition which is coated with a release-controlled coating-layer being soluble pH-dependently (releasing an active ingredient under the circumstances of more than a certain pH value). The resulting spherical granules were passed through a round sieve to give controlled release granules of 1180 μm-1700 μm. Then the obtained spherical granules were dried at 40° C. for 16 hrs under vacuum.

Composition in 278.35 mg of the Controlled Release Granules

| | |
|---|---|
| granules of Example 45 | 188.07 mg |
| methacrylic acid copolymer S | 42.32 mg |
| methacrylic acid copolymer L | 14.11 mg |
| talc | 28.21 mg |
| triethyl citrate | 5.64 mg |
| total | 278.35 mg |

Example 47

35.5 mg of enteric-coated granules obtained in Example 8 and 139.2 mg of controlled release granules obtained in Example 46 were mixed and thereto 58.2 mg of polyethylene oxide (trade name: Polyox WSR Coagulant, produced by Dow Chemical Co., Ltd.) was added to obtain a mixture. One capsule #1 was filled with the resulting mixture to obtain a capsule (correspond to 30 mg of Compound A).

Example 48

71 mg of enteric-coated granules obtained in Example 8 and 278.35 mg of controlled release granules obtained in Example 46 were mixed and the resulting mixture was filled in one capsule #1 to give a capsule (correspond to 60 mg of Compound A).

Example 49

106.5 mg of enteric-coated granules obtained in Example 8 and 417.5 mg of controlled release granules obtained in Example 46 were mixed and the resulting mixture was filled in two capsules #2 to give a capsule (correspond to 90 mg of Compound A).

Example 50

53.3 mg of enteric-coated granules obtained in Example 8 and 208.8 mg of controlled release granules obtained in Example 46 were mixed and the resulting mixture was filled in one capsule #2 to give a capsule (correspond to 45 mg of Compound A).

Example 51

824.4 g of Compound A, 303.2 g of magnesium carbonate, 1062 g of purified sucrose and 228.2 g of low substituted hydroxypropyl cellulose were mixed well to obtain a dusting powder for active ingredient layer. 722.4 g of sucrose.starch spheres (trade name: Nonpareil-101, produced by Freund Industrial Co., Ltd.) were charged in a centrifugal fluid-bed granulator (CF-360, manufactured by Freund Industrial Co., Ltd.) and the sucrose.starch spheres were coated with the above dusting powder for active ingredient layer while spraying a hydroxypropyl cellulose solution (2 w/w %), thereby producing spherical granules. The obtained spherical granules were dried at 40° C. for 16 hrs under vacuum and passed through a round sieve to give granules of 710 μm-1400 μm.

Composition in 86.67 mg of the Granules

| | |
|---|---|
| sucrose.starch spheres | 20.64 mg |
| hydroxypropyl cellulose | 0.24 mg |
| dusting powder for active ingredient layer | |

| | |
|---|---|
| Compound A | 22.50 mg |
| magnesium carbonate | 8.25 mg |
| purified sucrose | 28.83 mg |
| low substituted hydroxypropyl cellulose | 6.21 mg |
| total | 86.67 mg |

Example 52

The granules obtained in Example 51 were coated with a coating solution for intermediate layer using a fluid-bed fluidized bed coating machine (MP-10, manufactured by Powrex Co., Ltd.), and were dried intact to give granules having the following composition. The coating solution for intermediate layer was produced by dissolving 270.0 g of hydroxypropyl methylcellulose 2910 in 4874 g of purified water and followed by dispersing 163.5 g of titanium oxide and 108 g of talc into the obtained solution. The coating operation was carried out under the condition of inlet air temperature: 67° C., inlet air volume: 1.5 m³/min., coating solution spray rate: 12.0 g/min., spray air pressure: 0.28 MPa and spray air volume: 90 Nl/hr. The resulting spherical granules were dried at 40° C. for 16 hrs under vacuum and passed through a round sieve to give granules of 710 μm-1400 μm.

Composition in 97.50 mg of the Granules Coated with an Intermediate Layer

| | |
|---|---|
| granules of Example 51 | 86.67 mg |
| hydroxypropyl methylcellulose 2910 | 5.40 mg |
| talc | 2.16 mg |
| titanium oxide | 3.27 mg |
| total | 97.50 mg |

Example 53

57.60 g of Macrogol 6000 and 26.40 g of Polysorbate 80 were dissolved in 2724 g of purified water, and 174 g of talc, 57.6 g of titanium oxide and 19323 g of methacrylic acid copolymer LD (579.6 g as solid content) were dispersed into the resulting solution to obtain an enteric coating solution. The granules obtained in Example 52 were coated with the above enteric coating solution using an agitation fluidized bed granulator (MP-10, manufactured by Powrex Co., Ltd.) under the condition of inlet air temperature: 65° C., inlet air volume: 1.5 m³/min., coating solution spray rate: 15.0 g/min. and spray air pressure: 0.30 MPa, and spray air volume: 90 Nl/hr. The resulting granules were dried as it was and passed through a round sieve to give enteric-coated granules of 710 μm-1400 μm having the following composition. The obtained spherical granules were dried at 40° C. for 16 hrs under vacuum, and to 1918 g of the granules were added 0.96 g of talc and 0.96 g of aerosil to give enteric-coated granules.

Composition in 120.0 mg of the Enteric-Coated Granules

| | |
|---|---|
| granules of Example 52 | 97.5 mg |
| methacrylic acid copolymer LD | 48.3 mg |
| | (14.49 mg as solid content) |
| talc | 4.35 mg |
| Macrogol 6000 | 1.44 mg |
| titanium oxide | 1.44 mg |
| Polysorbate 80 | 0.66 mg |
| talc | 0.06 mg |
| aerosil | 0.06 mg |
| total | 120.0 mg |

Example 54

1131 g of Compound A, 303.2 g of magnesium carbonate, 750.1 g of purified sucrose and 226.8 g of low substituted hydroxypropyl cellulose were mixed well to obtain a dusting powder for active ingredient layer. 720.0 g of sucrose.starch spheres (trade name: Nonpareil-101, produced by Freund Industrial Co., Ltd.) were charged in a centrifugal fluid-bed granulator (CF-360, manufactured by Freund Industrial Co., Ltd.) and the sucrose.starch spheres were coated with the above dusting powder for active ingredient layer while spraying a hydroxypropyl cellulose solution (2 w/w %), thereby producing spherical granules. The obtained spherical granules were dried at 40° C. for 16 hrs under vacuum and passed through a round sieve to give granules of 710 μm-1400 μm.

Composition in 189.0 mg of the Granules

| | |
|---|---|
| sucrose.starch spheres | 45.0 mg |
| hydroxypropyl cellulose | 0.54 mg |
| dusting powder for active ingredient layer | |
| Compound A | 67.5 mg |
| magnesium carbonate | 18.0 mg |
| purified sucrose | 44.46 mg |
| low substituted hydroxypropyl cellulose | 13.5 mg |
| total | 189.0 mg |

Example 55

The granules obtained in Example 54 were coated with a coating solution for intermediate layer using a fluid-bed fluidized bed coating machine (MP-10, manufactured by Powrex Co., Ltd.), and were dried intact to give granules having the following composition. The coating solution for intermediate layer was produced by dissolving 236.4 g of hydroxypropyl methylcellulose 2910 in 4255 g of purified water and followed by dispersing 141.6 g of titanium oxide and 94.8 g of talc into the obtained solution. The coating operation was carried out under the condition of inlet air temperature: 65° C., inlet air volume: 1.5 m³/min., coating solution spray rate: 12.0 g/min., spray air pressure: 0.26 MPa and spray air volume: 90 Nl/hr. The resulting spherical granules were dried at 40° C. for 16 hrs under vacuum and passed through a round sieve to give granules of 710 μm-1400 μm.

Composition in 212.64 mg of the Granules Coated with an Intermediate Layer

| | |
|---|---|
| granules of Example 54 | 189.0 mg |
| hydroxypropyl methylcellulose 2910 | 11.82 mg |
| talc | 4.74 mg |
| titanium oxide | 7.08 mg |
| total | 212.64 mg |

Example 56

382.8 g of methacrylic acid copolymer S, 127.7 g of methacrylic acid copolymer L and 50.88 g of triethyl citrate were dissolved in a mixed solution of purified water (734.8 g) and absolute ethanol (6614 g), and 255.1 g of talc was dispersed into the resulting solution to obtain a coating solution. The granules obtained in Example 55 was coated with the above coating solution using an agitation fluidized bed granulator (MP-10, manufactured by Powrex Co., Ltd.) under the condition of inlet air temperature: 65° C., inlet air volume: 1.5 m³/min., coating solution spray rate: 15.0 g/min., spray air pressure: 0.30 MPa and spray air volume: 90 Nl/hr to give controlled release granules having the following composition which is coated with a release-controlled coating-layer being soluble pH-dependently (releasing an active ingredient under the circumstances of more than a certain pH value). The resulting spherical granules were passed through a round sieve to give controlled release granules of 1180 μm-1700 μm. Then the obtained spherical granules were dried at 40° C. for 16 hrs under vacuum, and to 1101 g of the granules were added 0.525 g of talc and 0.525 g of aerosil to give enteric-coated granules.

Composition in 315.0 mg of the Controlled Release Granules

| | |
|---|---|
| granules of Example 55 | 212.64 mg |
| methacrylic acid copolymer S | 47.85 mg |
| methacrylic acid copolymer L | 15.96 mg |
| talc | 31.89 mg |
| triethyl citrate | 6.36 mg |
| talc | 0.15 mg |
| aerosil | 0.15 mg |
| total | 315.0 mg |

Example 57

120 mg of enteric-coated granules obtained in Example 53 and 315 mg of controlled release granules obtained in Example 56 were mixed and the resulting mixture was filled in one capsule #1 to give a capsule (correspond to 90 mg of Compound A).

Example 58

80 mg of enteric-coated granules obtained in Example 53 and 210 mg of controlled release granules obtained in Example 56 were mixed and the resulting mixture was filled in one capsule #2 to give a capsule (correspond to 60 mg of Compound A).

Example 59

40 mg of enteric-coated granules obtained in Example 53 and 105 mg of controlled release granules obtained in Example 56 were mixed and the resulting mixture was filled in one capsule #3 to give a capsule (correspond to 30 mg of Compound A).

Example 60

240 mg of enteric-coated granules obtained in Example 53 and 210 mg of controlled release granules obtained in Example 56 were mixed and the resulting mixture was filled in one capsule #1 to give a capsule (correspond to 90 mg of Compound A).

Example 61

160 mg of enteric-coated granules obtained in Example 53 and 280 mg of controlled release granules obtained in Example 56 were mixed and the resulting mixture was filled in one capsule #1 to give a capsule (correspond to 90 mg of Compound A).

Example 62

192 mg of enteric-coated granules obtained in Example 53 and 252 mg of controlled release granules obtained in Example 56 were mixed and the resulting mixture was filled in one capsule #1 to give a capsule (correspond to 90 mg of Compound A).

Example 63

160 mg of enteric-coated granules obtained in Example 53 and 210 mg of controlled release granules obtained in Example 56 were mixed and the resulting mixture was filled in one capsule #1 to give a capsule (correspond to 75 mg of Compound A).

Example 64

100 mg of enteric-coated granules obtained in Example 53 and 262.5 mg of controlled release granules obtained in Example 56 were mixed and the resulting mixture was filled in one capsule #1 to give a capsule (correspond to 75 mg of Compound A).

Example 65

133.3 mg of enteric-coated granules obtained in Example 53 and 233.3 mg of controlled release granules obtained in Example 56 were mixed and the resulting mixture was filled in one capsule #1 to give a capsule (correspond to 75 mg of Compound A).

Example 66

200 mg of enteric-coated granules obtained in Example 53 and 175 mg of controlled release granules obtained in Example 56 were mixed and the resulting mixture was filled in one capsule #1 to give a capsule (correspond to 75 mg of Compound A).

Example 67

106.7 mg of enteric-coated granules obtained in Example 53 and 186.7 mg of controlled release granules obtained in Example 56 were mixed and the resulting mixture was filled in one capsule #2 to give a capsule (correspond to 60 mg of Compound A).

Example 68

128 mg of enteric-coated granules obtained in Example 53 and 168 mg of controlled release granules obtained in Example 56 were mixed and the resulting mixture was filled in one capsule #2 to give a capsule (correspond to 60 mg of Compound A).

Example 69

160 mg of enteric-coated granules obtained in Example 53 and 140 mg of controlled release granules obtained in Example 56 were mixed and the resulting mixture was filled in one capsule #2 to give a capsule (correspond to 60 mg of Compound A).

Example 70

60 mg of enteric-coated granules obtained in Example 53 and 157.5 mg of controlled release granules obtained in Example 56 were mixed and the resulting mixture was filled in one capsule #2 to give a capsule (correspond to 45 mg of Compound A).

Example 71

120 mg of enteric-coated granules obtained in Example 53 and 105 mg of controlled release granules obtained in Example 56 were mixed and the resulting mixture was filled in one capsule #2 to give a capsule (correspond to 45 mg of Compound A).

Example 72

80 mg of enteric-coated granules obtained in Example 53 and 140 mg of controlled release granules obtained in Example 56 were mixed and the resulting mixture was filled in one capsule #2 to give a capsule (correspond to 45 mg of Compound A).

Example 73

96 mg of enteric-coated granules obtained in Example 53 and 126 mg of controlled release granules obtained in Example 56 were mixed and the resulting mixture was filled in one capsule #2 to give a capsule (correspond to 45 mg of Compound A).

Example 74

53.3 mg of enteric-coated granules obtained in Example 53 and 93.3 mg of controlled release granules obtained in Example 56 were mixed and the resulting mixture was filled in one capsule #3 to give a capsule (correspond to 30 mg of Compound A).

Example 75

64 mg of enteric-coated granules obtained in Example 53 and 84 mg of controlled release granules obtained in Example 56 were mixed and the resulting mixture was filled in one capsule #3 to give a capsule (correspond to 30 mg of Compound A).

Example 76

80 mg of enteric-coated granules obtained in Example 53 and 70 mg of controlled release granules obtained in Example 56 were mixed and the resulting mixture was filled in one capsule #3 to give a capsule (correspond to 30 mg of Compound A).

INDUSTRIAL APPLICABILITY

Since the controlled release preparation of the present invention can extend the therapeutic effective level by controlling the release of active ingredient over a long time, it can provide the effectiveness of treatment with a low dose and the reduction of side effects caused by the rise of blood level, as well as the reduction of administration times.

The invention claimed is:
1. A capsule comprising:
composition (i) comprising a tablet, granule or fine granule in which a release of an active ingredient is controlled; said tablet, granule or fine granule comprising a core particle containing an imidazole compound represented by formula (I'):

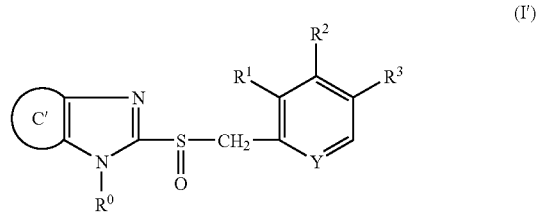

wherein ring C' is an optionally substituted benzene ring or an optionally substituted aromatic monocyclic heterocyclic ring, $R^0$ is a hydrogen atom, an optionally substituted aralkyl group, acyl group or acyloxy group, $R^1$, $R^2$ and $R^3$ are the same or different and are a hydrogen atom, an optionally substituted alkyl group, an optionally substituted alkoxy group or an optionally substituted amino group, and Y represents a nitrogen atom or CH; or a salt thereof or an optically active isomer thereof as the active ingredient, and a pH-dependently soluble release-controlled coating-layer which comprises one kind of polymeric substance or a mixture of two or more kinds of polymeric substances having different release properties selected from the group consisting of hydroxypropylmethyl cellulose phthalate, cellulose acetate phthalate, carboxymethylethyl cellulose, methyl methacrylate-methacrylic acid copolymer, methacrylic acid-ethyl acrylate copolymer, methacrylic acid-methyl acrylate-methyl methacrylate copolymer, hydroxypropyl cellulose acetate succinate, polyvinyl acetate phthalate and shellac, wherein the active ingredient is released at an elution rate of 10% or less for 5 hours in a solution of pH 6.0, and 5% or less for one hour and 60% or more for 8 hours in a solution of pH 6.8, and composition (ii) comprising a tablet, granule or fine granule comprising a core particle containing the active ingredient and enteric coat, such that the active ingredient is released in the pH range of no less than 5.0 to no more than 6.0, wherein the composition (i) and the composition (ii) in the capsule individually contain a sufficient amount of the imidazole compound represented by formula (I') to raise a plasma level of the imidazole compound represented by formula (I') in a mammal to whom the capsule is administered to at least 100 ng/ml.

2. The capsule according to claim 1, wherein the plasma level of at least 100 ng/ml in the mammal continues for at least 8 hours.

3. The capsule according to claim 1, wherein the composition (i) and the composition (ii) in the capsule individually contain a sufficient amount of the imidazole compound represented by formula (I') to raise the plasma level in the mammal to at least 300 ng/ml.

4. A capsule comprising:
composition (i) comprising a tablet, granule or fine granule in which a release of an active ingredient is controlled;

said tablet, granule or fine granule comprising a core particle containing an imidazole compound represented by formula (I'):

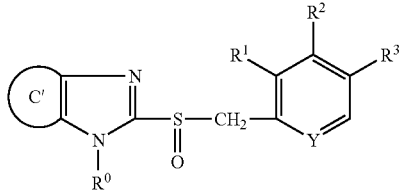

wherein ring C' is an optionally substituted benzene ring or an optionally substituted aromatic monocyclic heterocyclic ring, $R^0$ is a hydrogen atom, an optionally substituted aralkyl group, acyl group or acyloxy group, $R^1$, $R^2$ and $R^3$ are the same or different and are a hydrogen atom, an optionally substituted alkyl group, an optionally substituted alkoxy group or an optionally substituted amino group, and Y represents a nitrogen atom or CH; or a salt thereof or an optically active isomer thereof as the active ingredient, and a pH-dependently soluble release-controlled coating-layer which comprises one kind of polymeric substance or a mixture of two or more kinds of polymeric substances having different release properties, selected from the group consisting of hydroxypropylmethyl cellulose phthalate, cellulose acetate phthalate, carboxymethylethyl cellulose, methyl methacrylate-methacrylic acid copolymer, methacrylic acid-ethyl acrylate copolymer, methacrylic acid-methyl acrylate-methyl methacrylate copolymer, hydroxypropyl cellulose acetate succinate, polyvinyl acetate phthalate and shellac, wherein the active ingredient is released at an elution rate of 10% or less for 5 hours in a solution of pH 6.0, and 5% or less for one hour and 60% or more for 8 hours in a solution of pH 6.8, and composition (ii) comprising a tablet, granule or fine granule comprising a core particle containing the active ingredient and enteric coat, such that the active ingredient is released in the pH range of no less than 5.0 to no more than 6.0, wherein the imidazole compound represented by formula (I') contained in the composition (i) and the composition (ii) in the capsule is released from the capsule in a pulsatile manner, wherein the plasma level of the imidazole compound released from each of the composition (i) and the composition (ii) rises to at least 100 ng/ml in a mammal to whom the capsule is administered.

5. The capsule according to claim 4, wherein a plasma level of the imidazole compound released from each of the compositions (i) and the composition (ii) rises to at least 300 ng/ml in a mammal to whom the capsule is administered.

6. A capsule comprising:

composition (i) comprising a tablet, granule or fine granule in which a release of an active ingredient is controlled; said tablet, granule or fine granule comprising a core particle containing an imidazole compound represented by formula (I'):

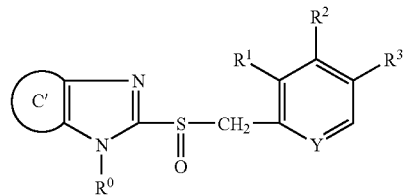

wherein ring C' is an optionally substituted benzene ring or an optionally substituted aromatic monocyclic heterocyclic ring, $R^0$ is a hydrogen atom, an optionally substituted aralkyl group, acyl group or acyloxy group, $R^1$, $R^2$ and $R^3$ are the same or different and are a hydrogen atom, an optionally substituted alkyl group, an optionally substituted alkoxy group or an optionally substituted amino group, and Y represents a nitrogen atom or CH; or a salt thereof or an optically active isomer thereof as the active ingredient, and a pH-dependently soluble release-controlled coating-layer which comprises one kind of polymeric substance or a mixture of two or more kinds of polymeric substances having different release properties selected from the group consisting of hydroxypropylmethyl cellulose phthalate, cellulose acetate phthalate, carboxymethylethyl cellulose, methyl methacrylate-methacrylic acid copolymer, methacrylic acid-ethyl acrylate copolymer, methacrylic acid-methyl acrylate-methyl methacrylate copolymer, hydroxypropyl cellulose acetate succinate, polyvinyl acetate phthalate and shellac, wherein the active ingredient is released at an elution rate of 10% or less for 5 hours in a solution of pH 6.0, and 5% or less for one hour and 60% or more for 8 hours in a solution of pH 6.8, and composition (ii) comprising a tablet, granule or fine granule comprising a core particle containing the active ingredient and enteric coat, such that the active ingredient is released in the pH range of no less than 5.0 to no more than 6.0, wherein an amount of the imidazole compound represented by formula (I') in the composition (i) is at least 50% more than an amount of the imidazole compound in the composition (ii), wherein the composition (i) and the composition (ii) in the capsule individually contain a sufficient amount of imidazole compound represented by formula (I') to raise the plasma level of the imidazole compound represented by formula (I') in a mammal to whom the capsule is administered to at least 100 ng/ml.

7. The capsule according to claim 6, wherein the amount of the imidazole compound contained in the composition (i) is at least twice the amount of the imidazole compound contained in the composition (ii).

8. The capsule according to claim 6, wherein the amount of the imidazole compound contained in the composition (i) is at least three times the amount of the imidazole compound contained in the composition (ii).

9. A capsule comprising:

composition (i) comprising a tablet, granule or fine granule in which a release of an active ingredient is controlled; said tablet, granule or fine granule comprising a core particle containing an imidazole compound represented by formula (I'):

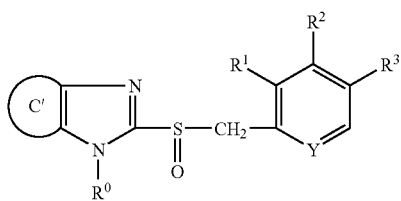 (I')

wherein ring C' is an optionally substituted benzene ring or an optionally substituted aromatic monocyclic heterocyclic ring, $R^0$ is a hydrogen atom, an optionally substituted aralkyl group, acyl group or acyloxy group, $R^1$, $R^2$ and $R^3$ are the same or different and are a hydrogen atom, an optionally substituted alkyl group, an optionally substituted alkoxy group or an optionally substituted amino group, and Y represents a nitrogen atom or CH; or a salt thereof or an optically active isomer thereof as the active ingredient, and a pH-dependently soluble release-controlled coating-layer which comprises one kind of polymeric substance or a mixture of two or more kinds of polymeric substances having different release properties selected from the group consisting of hydroxypropylmethyl cellulose phthalate, cellulose acetate phthalate, carboxymethylethyl cellulose, methyl methacrylate-methacrylic acid copolymer, methacrylic acid-ethyl acrylate copolymer, methacrylic acid-methyl acrylate-methyl methacrylate copolymer, hydroxypropyl cellulose acetate succinate, polyvinyl acetate phthalate and shellac, wherein the active ingredient is released at an elution rate of 10% or less for 5 hours in a solution of pH 6.0, and 5% or less for one hour and 60% or more for 8 hours in a solution of pH 6.8, and composition (ii) comprising a tablet, granule or fine granule comprising a core particle containing the active ingredient and enteric coat, such that the active ingredient is released in the pH range of no less than 5.0 to no more than 6.0, wherein a total amount of the imidazole compound represented by formula (I') in the composition (i) and the composition (ii) is between 5 mg and 150 mg, wherein the composition (i) and the composition (ii) in the capsule individually contain a sufficient amount of imidazole compound represented by formula (I') to raise the plasma level of the imidazole compound represented by formula (I') in a mammal to whom the capsule is administered to at least 100 ng/ml.

10. The capsule according to claim 9, wherein the total amount of the imidazole compound represented by formula (I') in the composition (i) and the composition (ii) is between 30 mg and 90 mg.

11. The capsule according to claim 4, wherein the capsule provides two plasma level peaks in a mammal to whom the capsule is administered and a plasma level lower than the plasma level peaks is present between the two plasma level peaks.

* * * * *